(12) United States Patent
Labrie et al.

(10) Patent No.: US 6,541,463 B1
(45) Date of Patent: Apr. 1, 2003

(54) INHIBITORS OF TYPE 5 AND TYPE 3 17β-HYDROXYSTEROID DEHYDROGENASE AND METHODS FOR THEIR USE

(75) Inventors: Fernand Labrie, Sainte-foy; Alain Belanger, Cap-Rouge; Sylvain Gauthier, Saint-Augustin-de-Desmaures; Van Luu-The, Charny; Yves Merand, Sainte-Foy; Donald Poirier, L'Ancienne-Lorette; Louis Provencher, Charny; Shankar M. Singh, Sainte-Foy, all of (CA)

(73) Assignee: Endorecherche, Inc., Quebec (CA)

( * ) Notice: Subject to any disclaimer, the term of this patent is extended or adjusted under 35 U.S.C. 154(b) by 0 days.

(21) Appl. No.: 09/265,807

(22) Filed: Mar. 10, 1999

Related U.S. Application Data

(60) Provisional application No. 60/077,510, filed on Mar. 11, 1998, and provisional application No. 60/095,623, filed on Aug. 7, 1998.

(51) Int. Cl.⁷ .......................... A61K 31/585; C07J 21/00
(52) U.S. Cl. ............................ 514/173; 540/41; 540/44
(58) Field of Search ...................... 540/41, 44; 514/173

(56) References Cited

U.S. PATENT DOCUMENTS

| | | | |
|---|---|---|---|
| 2,875,199 A | * 2/1959 | Cella | 260/239.57 |
| 3,917,657 A | 11/1975 | Van Kamp et al. | |
| 4,659,695 A | 4/1987 | Labrie et al. | |
| 4,666,885 A | 5/1987 | Labrie et al. | |
| 4,684,635 A | 8/1987 | Orentreich et al. | |
| 5,227,375 A | 7/1993 | Labrie et al. | |
| 5,434,146 A | 7/1995 | Labrie et al. | |

FOREIGN PATENT DOCUMENTS

| | | |
|---|---|---|
| BE | 898057 | 2/1984 |
| DE | 2059338 | 6/1972 |
| FR | 1405214 | 11/1965 |
| GB | 870286 | 6/1961 |
| GB | 2018591 | 10/1979 |
| GB | 2102287 | 2/1983 |
| WO | 8601105 | 2/1986 |
| WO | WO8601402 | 3/1986 |
| WO | 9010462 | 9/1990 |
| WO | 9100731 | 1/1991 |
| WO | 9100733 | 1/1991 |
| WO | 9426767 | 11/1994 |
| WO | WO9615794 | 5/1996 |
| WO | 9626201 | 8/1996 |
| WO | 9711162 | 3/1997 |

OTHER PUBLICATIONS

E.M. Coutinho et al., "Clinical Management of Leiomyomas with Medroxyprogesterone Acetate," Int. Congr. Symp. Semin. Ser., pp. 421–425 (1995).

J.R. Bierich, "Precocious and Retarded Puberty," Chemical Abstract No. 75:16982 (1970).
T. Machida, "Hormone Therapy for Male Genital," Chemical Abstract No. 108:16367 (1987).
J.E.F. Reynolds, Martindale, The Extra Pharmacopoeia, 1996, Royal Pharmaceutical Society, London, England, pp. 1495–1497, 525–526, 530–531 and 1476–1477.
K. Sudo et al., "Neovascularization Inhibitors Containing Steroid 17β–carboxylic Acid Defivatives," Chemical Abstract No. 116:99327.
H. Umeda et al., "Elimination of Luteinizing Hormone–releasing Hormone–induced Flare Reaction by Lead–in and Combination Therapies with Chlormadinone Acetate in Patients with Advanced Prostate Carcinoma—Comparison with Flutamide Treatment," Chemical Abstract No. 130:332443 (1998).
C. West et al., "Potential Role for Medroxyprogesterone Acetate as an Adjunct to Goserelin (Zoladex) in the Medical Management of Uterine Fibroids," Chemical Abstract No. 117:124808 (1992).
R. Wiechert et al., The Progestational Efficacy of 1–methyl and 1,2–α–methylene Steroids, Arzneimittel–Forsch 15(3):244–246 (1965).
Labrie, et al., *J. Androl.* 1: 209–228 (1980).
Qin, et al., *J. Steroid Biochem. Molec. Biol.* 46:673–679 (1993).
Karen, et al., In: *Current Protocols in Molecular Biology*, pp. 1.13.1–1.13.6 (1987).
Maniatis, et al., In: *Molecular cloning: lab manual*, Cold Spring Harbor Lab (1982).
Sanger, et al., *PNAS* 74:5453–5467 (1977).
Kingston, et al., In: *Current Protocols in Molecular Biology*, pp. 9.1.1–9.1.9 (1987).
Luu–The, et al., *Mol. Endocrinolo.* 4:268–275 (1990).
Lachance, et al., *J. Biol. Chem.* 265:20469–20475 (1990).
Luu–The, et al., *DNA & Cell Biol.*, 14:511–518 (1995).
Stanley, et al., *Cell* 10:35–44 (1977).
Rodbard, *Endocrinology* 94:1427–1431 (1974).
Kramer, *Biometrics* 12:307–310 (1956).
Simard, et al., *Endocrinology* 126:3223–3231 (1990).
Bradford, *Anal. Biochem.* 72:248–254 (1976).
Asselin, et al., *Endocrinology* 101:666–671 (1977).

(List continued on next page.)

*Primary Examiner*—Barbara P. Badio
(74) *Attorney, Agent, or Firm*—Ostrolenk, Faber, Gerb & Soffen, LLP

(57) ABSTRACT

Novel methods of medical treatment and/or inhibition of development of diseases are disclosed for diseases that are sensitive to androgenic or estrogenic activity. The treatments utilize inhibitors of type 5 and/or type 3 17β-hydroxysteroid dehydrogenase. Novel inhibitors of type 5 17β-hydroxysteroid dehydrogenase are also disclosed, as are novel inhibitors of type 3 17β-hydroxysteroid dehydrogenase.

18 Claims, 11 Drawing Sheets

(6 of 11 Drawing Sheet(s) Filed in Color)

OTHER PUBLICATIONS

Asselin, et al., *J. Steroid Biochem.* 9:1079–1082 (1978).
Pelletier, et al., *Steroids* 59:536–547 (1994).
Morrow and Hofer, *J. Med. Chem.* 9:249–51 (1966).
Doyle and Bryker, *J. Org. Chem.* 44:1572–1574 (1979).
Chemical Abstracts, vol. 103, Columbus, Ohio, US; abstract No. 27291, Shiseido Co., LTD., Japan: "Skin Lotion Containing Chlormadinone Acetate for Acne Treatment" XP002114855 abstract & JP 60 028926 A (Sheseido Co., Ltd., Japan) 1983.

Database WPI Section Ch., Week 8533, Derwent Publications Ltd., London, GB; Class B01. AN 85–200303 XP002114857 & JP 60 126214 A (Teikoku Hormone Mfg Co Ltd), Jul. 5, 1985, abstract.

Luu–The V. et al.: "Characteristics of Human Types 1, 2 and 3 17 Beta–Hydroxysteroid Dehydrogenase Activities: Oxidation/Reduction and Inhibition" Journal of Steroid Biochemistry and Molecular Biology, vol. 55, No. 5/06, Jan. 1, 1995, pp. 58–587, XP000196678 ISSN: 0960–0760, the whole document.

* cited by examiner

Human skin hybridized with type 5 17β-HSD cRNA probe
FIG.6a Antisense
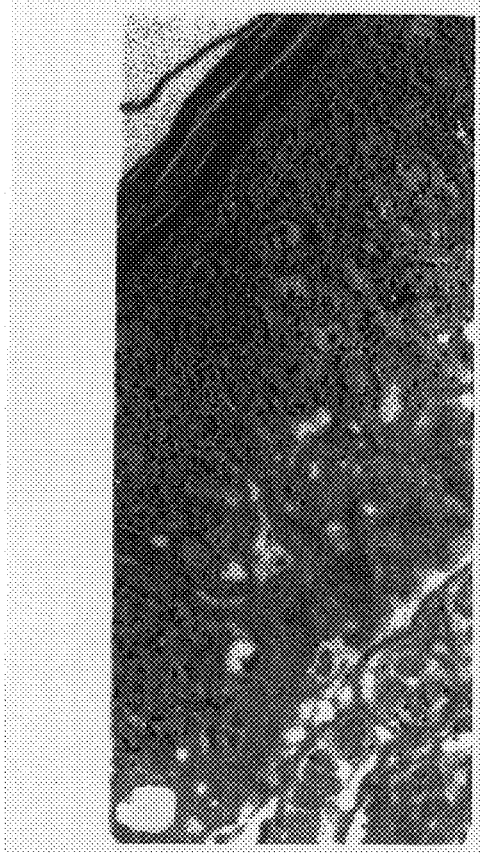
FIG.6b Sense
FIG.6c
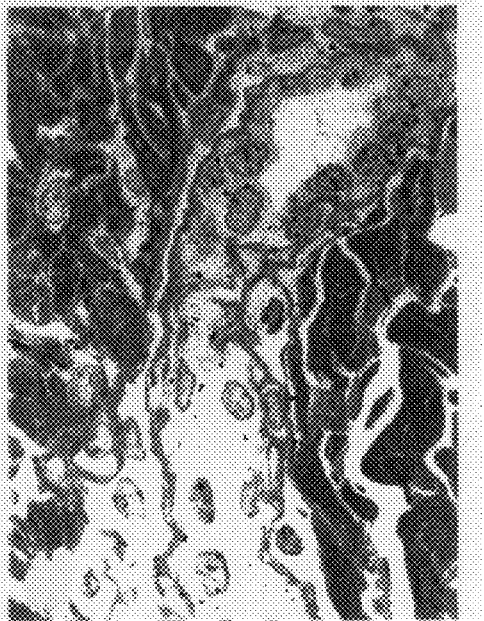
FIG.6d Monkey ovary hybridized with type 5 17β-HSD
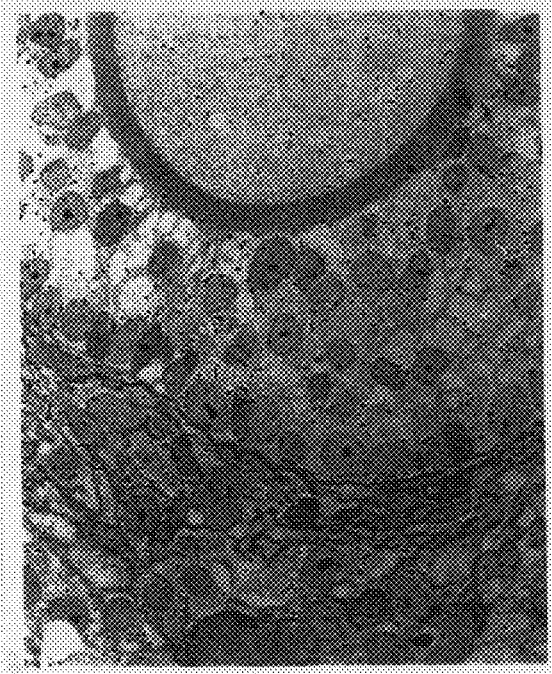
FIG.7a  Antisense
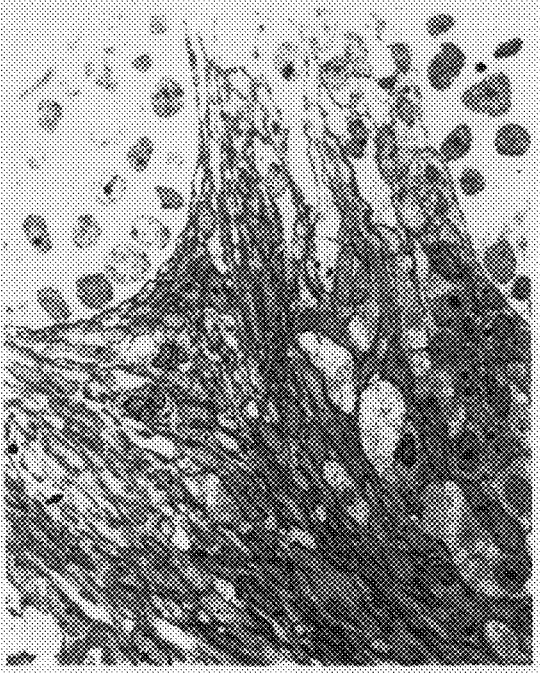
FIG.7b  Sense Biosynthetic pathway of active androgens in the prostate.

X, inhibition target.

INHIBITORS OF TYPE 5 AND TYPE 3 17β-HYDROXYSTEROID DEHYDROGENASE AND METHODS FOR THEIR USE

RELATED APPLICATION

This patent application is a regular, non-provisional application claiming priority of provisional application Serial No. 60/077,510, filed Mar. 11, 1998, the entire specification of which is incorporated by reference as though fully set forth herein. This application also claims priority of U.S. Provisional Application Serial No. 60/095,623, filed Aug. 7, 1998, the entire disclosure of which is incorporated by reference as though fully set forth herein.

FIELD OF THE INVENTION

The present invention relates to inhibitors of enzymes involved in the biosynthesis of sex steroids from natural precursors and to their use in the treatment of sex steroid dependent diseases. In particular, inhibitors are disclosed which suppress the activity of type 3 and type 5 17β-hydroxysteroid dehydrogenase, thus diminishing the production of androgens catalyzed by these two enzymes. Pharmaceutical use of the inhibitors may reduce the natural production of androgens such as testosterone and dihydrotestosterone, and thereby beneficially treat diseases whose onset or progress is aided by androgenic activity. Because androgens formed by reactions catalyzed by type 3 or type 5 enzyme are precursors to estrogens, the invention also has applicability to diseases whose onset or progress is aided by estrogenic activity.

BACKGROUND OF THE RELATED ART

Many androgen-sensitive diseases, i.e. diseases whose onset or progress is aided by androgenic activity, are known. They include but are not limited to prostate cancer, benign prostatic hyperplasia, acne, seborrhea, hirsutism, androgenic alopecia, precocious puberty, adrenal hyperplasia, and polycystic ovarian syndrome. Estrogen sensitive diseases, i.e. diseases whose onset or progress is aided by estrogenic activity are also known. They include but are not limited to breast cancer, endometriosis, leiomyoma, and precocious puberty.

Precocious puberty is usually associated with an excess of androgen secretion, usually of adrenal origin. The current treatments include blockade of adrenal secretion by glucocorticoids with its associated side effects. Blockade of type 5 17β-HSD would be an advantage, thus desirably reducing the dose or avoiding the use of glucocorticoids. Another treatment is the use of LHRH agonists to cause medical castration. A better controlled inhibition of androgen formation could be achieved with type 5 and 3 17β-HSD inhibitors.

Polycystic ovarian syndrome is associated with an excess of androgen secretion by the ovaries. LHRH agonists are used among other, as treatment, to cause medical castration. The use of an inhibitor of 17β-HSD would be advantageous.

Estrogen sensitive diseases may vary in their responses to androgens. They may, for example, respond favorably, unfavorably or not at all to androgens. Likewise, androgen-sensitive diseases may respond differently to estrogens. Thus, the treatment of sex steroid sensitive diseases may involve increasing or decreasing androgenic activity depending on whether the disease in question responds favorably or unfavorably to androgenic activity. Treatment may also involve increasing or decreasing estrogenic activity depending on whether the disease in question responds favorably or unfavorably to estrogenic activity. Breast cancer, for example, is known to respond favorably to androgenic activity and negatively to estrogenic activity. Benign prostatic hyperplasia is believed to respond negatively to both androgenic and estrogenic activity.

Androgenic and estrogenic activity may be suppressed by administering androgen receptor antagonists ("antiandrogens") or estrogen receptor antagonists ("antiestrogens"), respectively. See e.g. WO 94/26767 and WO 96/26201. Androgenic and estrogenic activity may also be reduced by suppressing androgen or estrogen biosynthesis using inhibitors of enzymes that catalyze one or more steps of such biosynthesis or by suppressing ovarian or testicular secretions by known methods. See e.g. WO 90/10462, WO 91/00731, WO 91/00733, and WO 86/01105. Type 5 17β-hydroxysteroid dehydrogenase is described in WO 97/11162.

Effective inhibitors of type 5 17β-hydroxysteroid dehydrogenase enzyme are provided by the present invention. The prior art is not believed to have provided compounds sufficiently effective at simultaneously (1) inhibiting type 5 or type 3 17β-hydroxysteroid dehydrogenase while (2) desirably failing to substantially inhibit other 17β-hydroxysteroid dehydrogenases or other catalysts of sex steroid degradation. Medroxyprogesterone acetate, megestrol acetate, and chlormadinone acetate which the prior art as used as pharmaceutical agents for other purposes are not believed to have been disclosed as inhibitors of type 5 17β-hydroxysteroid dehydrogenase, although applicants' research has now shown them to inhibit that type 5 enzyme.

SUMMARY OF THE INVENTION

It is accordingly an object of the present invention to more selectively and effectively inhibit type 3 and/or type 5 17β-hydroxysteroid dehydrogenase while preferably avoiding inhibition of other 17β-hydroxysteroid dehydrogenases, type 1 or 2 3α-hydroxysteroid dehydrogenases, or other androgen degradation enzymes.

It is another object to provide novel inhibitors of types 3 and 5 17β-hydroxysteroid dehydrogenase and pharmaceutical compositions thereof.

It is another object to provide treatment and prevention regimens for androgen and estrogen sensitive diseases which regimens include inhibiting activity of type 3 or type 5 17β-hydroxysteroid dehydrogenase.

In one embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

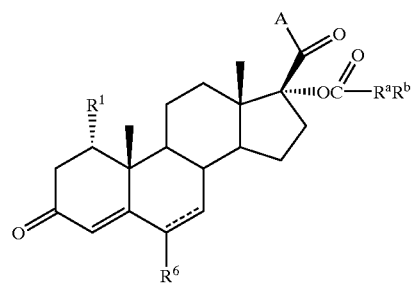

wherein the dotted line is optional pi bond;

wherein A is selected from the group consisting of straight or branched $C_1$–$C_4$ alkyl, —$OR^c$ ($R^c$ being a $C_1$–$C_8$ alkyl radical), and —$N(R^d)R^e$ ($R^d$ and $R^e$ being independently hydrogen or $C_1$–$C_8$ alkyl or aryl), and unsaturated analogs of any of the foregoing definitions for substituent A;

wherein $R^1$ is selected from the group consisting of hydrogen and methyl;

wherein $R^6$ is selected from the group consisting of hydrogen, and halogen, and $C_1$–$C_8$ alkyl;

wherein $R^a$ is selected from the group consisting of straight or branched $C_1$–$C_8$ alkylene, $C_3$–$C_7$ cycloalkylene; and $R^b$ is selected from the group consisting of hydrogen, substituted or unsubstituted phenyl, $C_2$–$C_{10}$ acyl, $C_2$–$C_{10}$ acyloxy, $C_2$–$C_{10}$ alkoxycarbonyl, and halogen;

provided that when A is methyl, $R^a$ and $R^b$ together have at least two carbon atoms, and $R^1$ is methyl.

It is preferred that the optional pi bond at 6 is present that $R^6$ is methyl, that $R^a$ is $C_1$–$C_6$ alkylene or that A is either methyl or —$N(R^d)R^e$.

It is also preferred when wherein A is —$N(R^d)R^e$ that $R^d$ is methyl or that $R^e$ is $C_1$–$C_6$ alkyl or $C_7$–$C_{12}$ phenyl alkyl.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

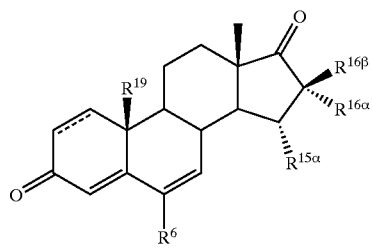

wherein the dotted line is an optional pi bond;

wherein $R^{16\beta}$ is selected from the group consisting of hydrogen, fluoro, chloro, $C_1$–$C_8$ alkyl, $C_1$–$C_8$ haloalkyl, a moiety which together with $R^{16\alpha}$ is $C_4$–$C_7$ spirocycloalkyl, $C_4$–$C_7$ halospirocycloalkyl, or =—$R'^{16}$ ($R'^{16}$ being $C_1$–$C_3$ alkyl) and unsaturated analogs of any of the foregoing definitions of $R^{16\beta}$;

wherein $R^{16\alpha}$ is selected from the group consisting of hydrogen, $C_1$–$C_8$ alkyl, $C_1$–$C_8$ haloalkyl, a moiety which together with $R^{16\beta}$ forms $C_4$–$C_7$ spirocycloalkyl, $C_4$–$C_7$ halospirocycloalkyl, or =—$R'^{16}$ ($R'^{16}$ being $C_1$–$C_3$ alkyl) and unsaturated analogs of any of the foregoing.;

wherein $R^{15\alpha}$ is selected from the group consisting of hydrogen, $C_1$–$C_4$ alkyl, $C_1$–$C_4$ alkenyl and $C_1$–$C_4$ alkynyl;

wherein $R^{19}$ is either —H or —$CH_3$; and wherein $R^6$ is selected from the group consisting of —H, $CH_3$, and halo;

provided that $R^{16\beta}$, $R^{16\alpha}$, and $R^{15\alpha}$ are not simultaneously hydrogen.

It is preferred that $R^{16\alpha}$ is a larger substituent than $R^{16\alpha}$, that $R^6$ is hydrogen, that the optional pi bond at position 1 is not present or that $R^{16\alpha}$ is a $C_3$–$C_5$ alkyl chain.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

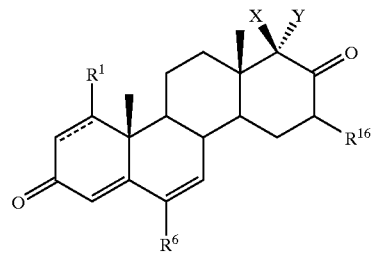

wherein the dotted line is optional pi bond
wherein X is $C_1$–$C_3$ alkyl;
wherein Y is hydrogen or an acyloxy moiety;
wherein $R^6$ is —H or —$CH_3$;
wherein $R^{16}$ is —H or halo;
wherein $R^1$ is —H or —$CH_3$.

It is preferred that $R^6$ is methyl that the optional pi bond at position 1 is present, that Y is a $C_3$–$C_6$ fluoroacyloxy or that X is methyl.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

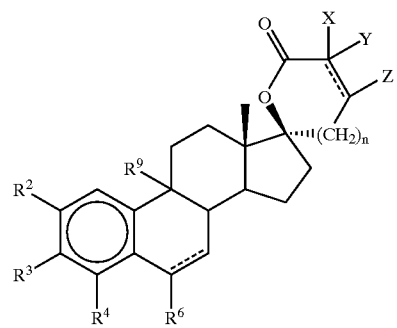

wherein n is an integer from 1–2;
wherein the dotted lines are optional double bonds;
wherein X and Y are independently selected from the group consisting of —H, ($C_1$–$C_3$)alkyl, ($C_2$–$C_3$) alkenyl, and methoxycarbonyl;
wherein Z is selected from the group consisting of —H and ($C_1$–$C_3$)alkyl;
wherein $R^3$ is selected from the group consisting of hydrogen, acyl, carboxyl, alkoxycarbonyl, substituted or unsubstituted carboxamide, cyano, alkoxy, alkoxyalkoxy, alkylthioalkoxy, acyloxy; hydroxy, halo, —O—$SO_2R^a$ ($R^a$ being selected from the group consisting of $C_1$–$C_6$ alkyl and $C_6$–$C_{10}$ aryl), and a moiety which, together with $R_2$, is a 5–6 member ring containing at least one oxygen and one nitrogen atom;
wherein $R^2$ is selected from the group consisting of hydrogen, amido, acyloxy, carboxyl, carboxamide, alkoxycarbonyl, cyano, halo, nitro, $C_1$–$C_8$ alkyl, and $CF_3$ and a moiety which, together with $R_3$, is a 5–6 member ring containing at least one oxygen and one nitrogen atom;

wherein $R^4$ is hydrogen or halo;

wherein $R^6$ is selected from the group consisting of hydrogen and oxo;

wherein $R^9$ is —H or —OH;

provided that X, Y, and Z are not all hydrogens when $R^3$ is methoxy.

It is preferred that $R^3$ is alkoxyalkoxy, carboxamide, carboxyl or alkoxyl, that at least one of X, Y or Z is methyl, that both X and Y are methyl, that n is 1 or that $R^6$ is oxo.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

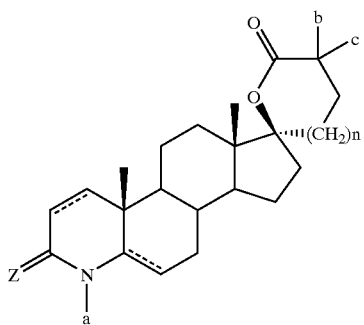

wherein the dotted lines are optional pi bonds;
wherein n=1 or 2; and
wherein a is either —H or —CH$_3$;
wherein b and c are independently hydrogen or methyl;
wherein Z is oxygen or sulfur.

It is preferred that n is 1, that at least one of b or c is methyl, both b and c are methyl or that Z is oxygen.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase selected from the group consisting of:

EM-1291

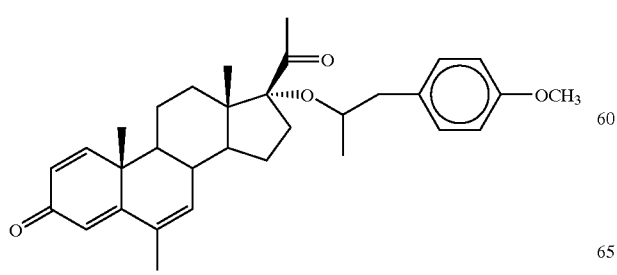

EM-1195-CS

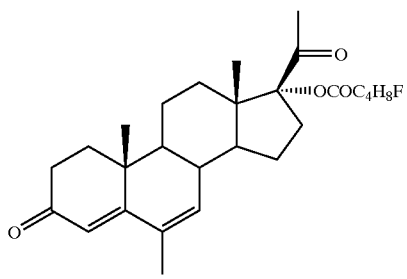

CS-243

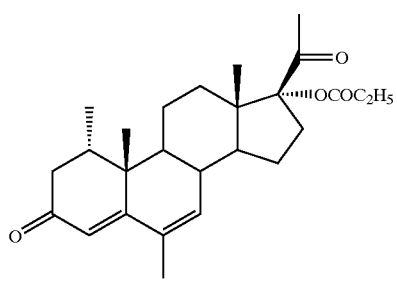

CS-245

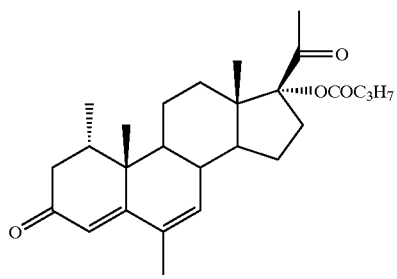

EM-1183

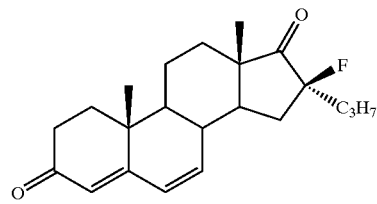

EM-1097

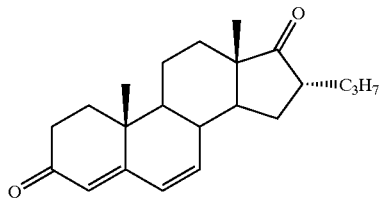

EM-1273-CS
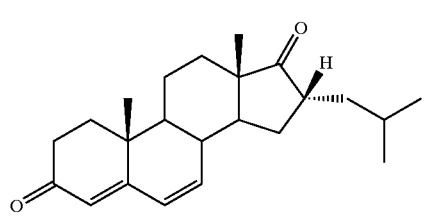
EM-1401
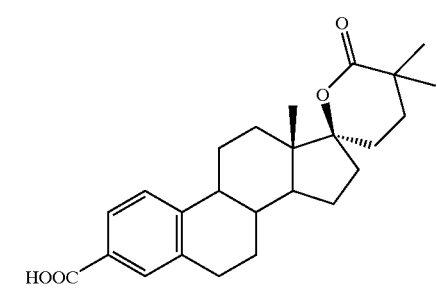
EM-1404
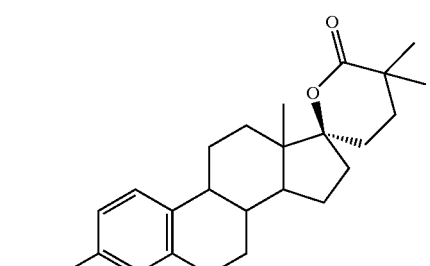
CS-237
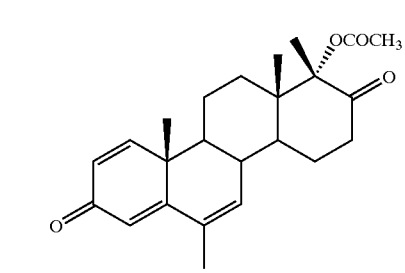
EM-1078
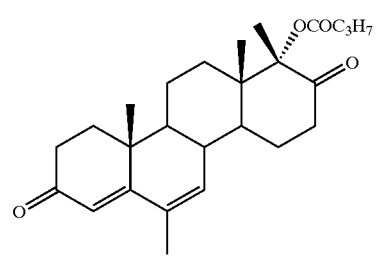
EM-1196-CS
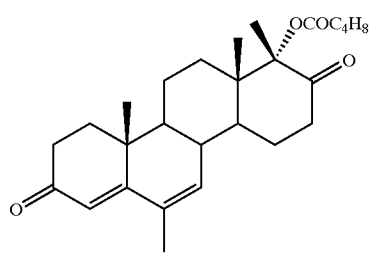
EM-1394
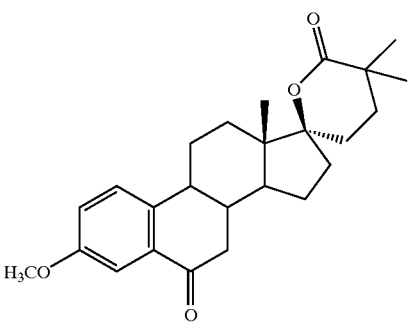
EM-1424-CS
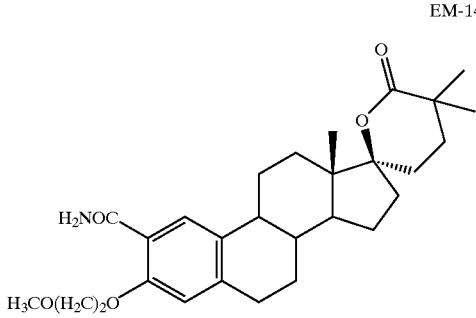
EM-1157-CS
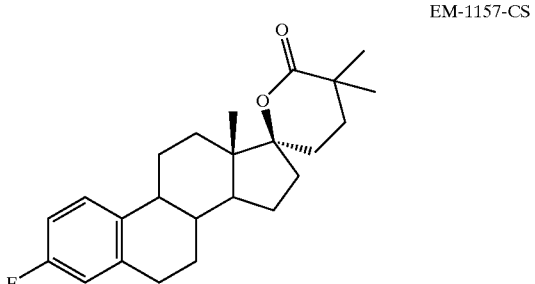
EM-1125
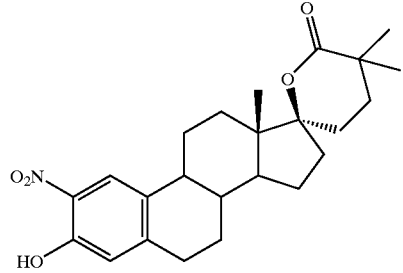
EM-1402-CS
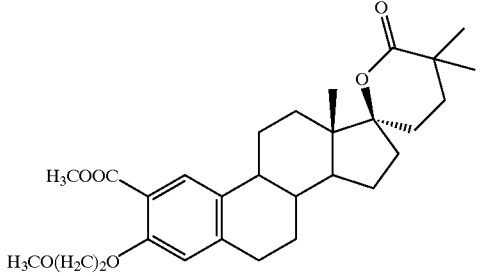

-continued

EM-1396
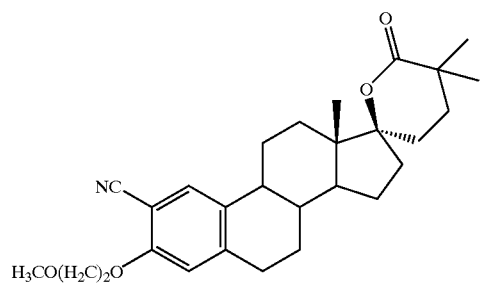

EM-1181
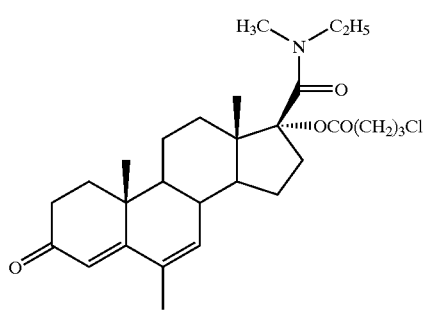

EM-1159
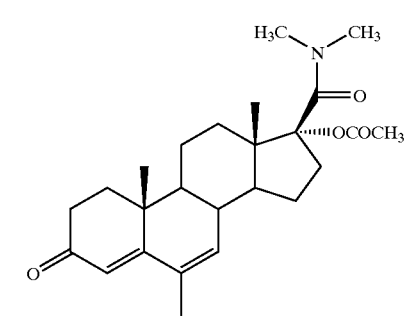

EM-1165
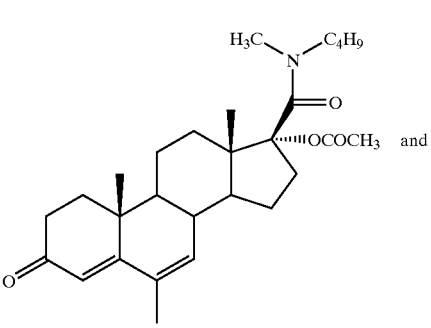

and

EM-122-CS
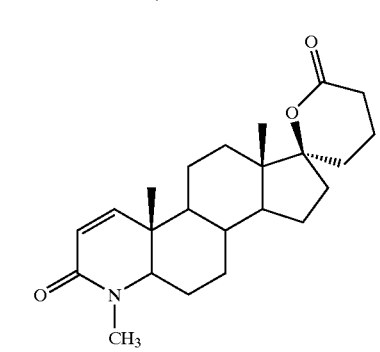

It is preferred that the type 5 inhibitor is selected from the group consisting of:

EM-1404
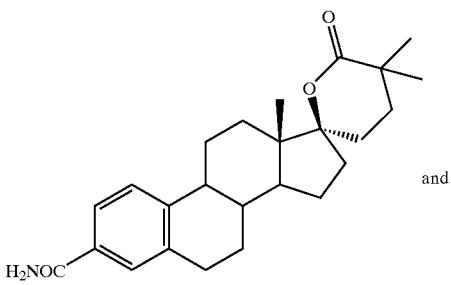

and

EM-1394
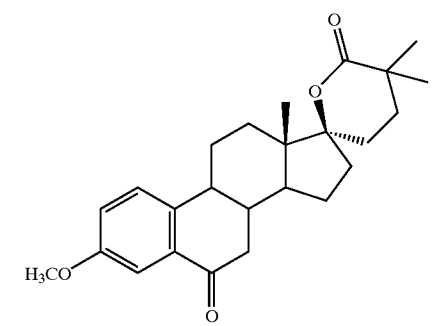

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase selected from the group consisting of:

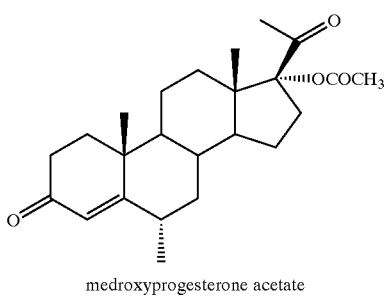

medroxyprogesterone acetate

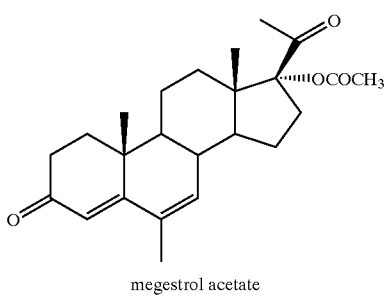

megestrol acetate

-continued

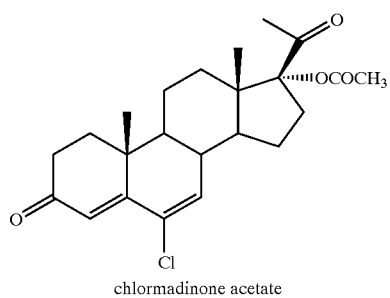

chlormadinone acetate

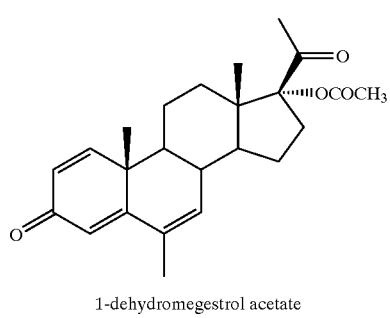

1-dehydromegestrol acetate

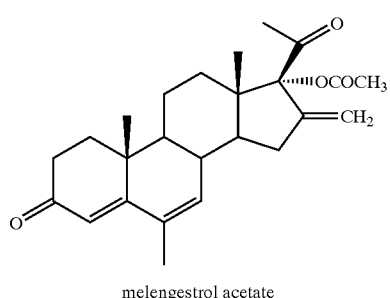

melengestrol acetate

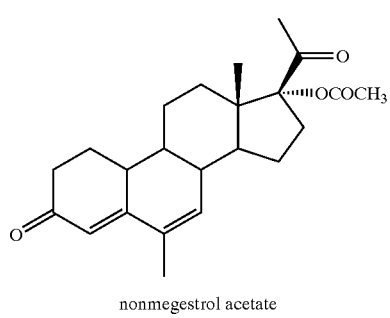

nonmegestrol acetate

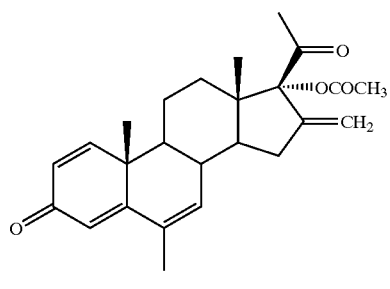

1-dehydromelengestrol acetate

-continued

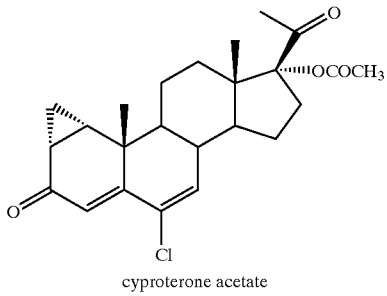

cyproterone acetate and compounds having the molecular structure:

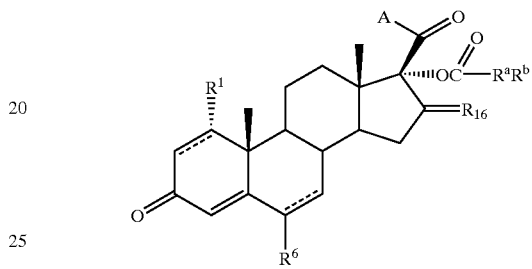

wherein the dotted lines are optional pi bonds;
wherein A is selected from the group consisting of straight or branched $C_1$–$C_4$ alkyl, —$OR^c$ ($R^c$ being a $C_1$–$C_4$ alkyl radical), and —$N(R^d)R^e$ ($R^d$ and $R^e$ being independently hydrogen or $C_1$–$C_8$ alkyl or aryl), and unsaturated analogs of any of the foregoing definitions for substituent A;
wherein $R^1$ is selected from the group consisting of hydrogens, and methyl;
wherein $R^6$ is selected from the group consisting of hydrogen, halogen, and $C_1$–$C_8$ alkyl;
wherein $R_{16}$ is selected from the group consisting of H,H and $CH_2$;
wherein $R^a$ is selected from the group consisting of straight or branched $C_1$–$C_8$ alkylene, $C_3$–$C_7$ cycloalkylene; and $R^b$ is selected from the group consisting of hydrogen, substituted or unsubstituted phenyl, $C_2$–$C_{10}$ acyl, $C_2$–$C_{10}$ acyloxy, $C_2$–$C_{10}$ alkoxycarbonyl, and halogen.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

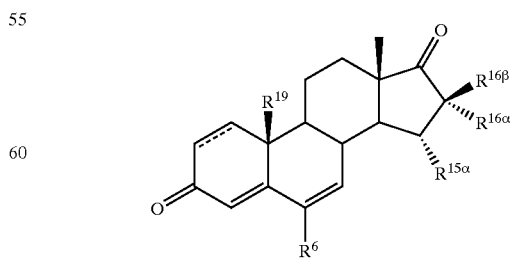

wherein the dotted line are optional pi bonds;

wherein $R^{16\beta}$ is selected from the group consisting of hydrogen, fluoro, chloro, $C_1$–$C_8$ alkyl, $C_1$–$C_8$ haloalkyl, a moiety which together with $R^{16\alpha}$ forms $C_4$–$C_7$ spirocycloalkyl, $C_4$–$C_7$ halospirocycloalkyl, or =—$R'^{16}$ ($R'^{16}$ being $C_1$–$C_3$ alkyl) and unsaturated analogs of any of the foregoing definitions of $R^{16\beta}$;

wherein $R^{16\alpha}$ is selected from the group consisting of hydrogen, $C_1$–$C_8$ alkyl, $C_1$–$C_8$ haloalkyl, a moiety which together with $R^{16\beta}$ forms $C_4$–$C_7$ spirocycloalkyl $C_4$–$C_7$ halospirocycloalkyl, or =—$R'^{16}$ ($R'^{16}$ being $C_1$–$C_3$ alkyl) and unsaturated analogs of any of the foregoing;

wherein $R^{15\alpha}$ is selected from the group consisting of hydrogen, $C_1$–$C_4$ alkyl, $C_1$–$C_4$ alkenyl and $C_1$–$C_4$ alkynyl;

wherein $R^{19}$ is either —H or $CH_3$; and wherein $R^6$ is selected from the group consisting of —H, —$CH_3$, and halo;

provided that $R^{16\beta}$, $R^{16\alpha}$, and $R^{15\alpha}$ are not simultaneously hydrogen.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

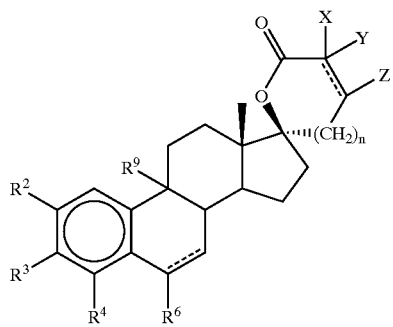

wherein n=1 or 2;

wherein the dotted lines are optional pi bonds;

wherein X and Y are independently selected from the group consisting of —H, ($C_1$–$C_3$)alkyl, ($C_2$–$C_3$) alkenyl, and methoxycarbonyl;

wherein Z is selected from the group consisting of —H and ($C_1$–$C_3$)alkyl;

wherein $R^3$ is selected from the group consisting of acyl, carboxyl, alkoxycarbonyl, substituted or unsubstituted carboxamide, cyano, alkoxy, alkoxyalkoxy, alkylthioalkoxy, acyloxy; hydroxy, halo, —O—$SO_2R^a$ ($R^a$ being selected from the group consisting of $C_1$–$C_6$ alkyl and $C_6$–$C_{10}$ aryl), and a moiety which, together with $R_2$, is a 5–6 member ring containing at least one oxygen and one nitrogen atom;

wherein $R^2$ is selected from the group consisting of amido, acyloxy, carboxyl, carboxamide, alkoxycarbonyl, cyano, halo, nitro, $C_1$–$C_8$ alkyl and $CF_3$ and a moiety which, together with $R_3$, is a 5–6 member ring containing at least one oxygen and one nitrogen atom;

wherein $R^4$ is hydrogen or halo;

wherein $R^6$ is selected from the group consisting of hydrogen and oxo;

wherein $R^9$ is —H or —OH;

provided that X, Y, and Z are not hydrogens when $R^3$ is methoxy.

It is preferred that $R^3$ is alkoxyalkoxy, carboxamide, carboxyl or alkoxyl, that at least one of X, Y or Z is methyl, that both X and Y are methyl, that n is 1 or that $R^6$ is oxo.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

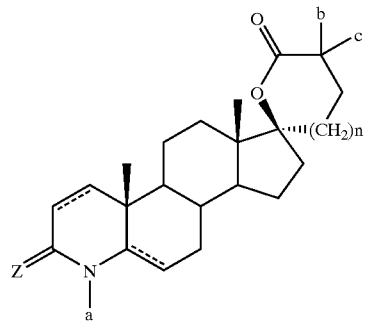

wherein the dotted lines are optional pi bonds;

wherein n=1 or 2; and wherein a is either —H or —$CH_3$;

wherein b and c are independently hydrogen or methyl;

wherein Z is oxygen or sulfur.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

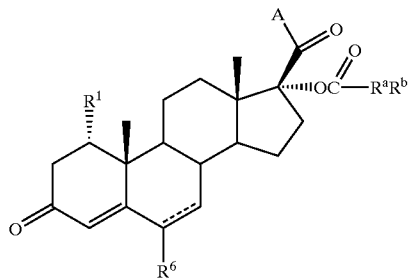

wherein the dotted line is an optional pi bond;

wherein A is selected from the group consisting of straight or branched $C_1$–$C_4$ alkyl, —$OR^c$ ($R^c$ being a $C_1$–$C_8$ alkyl radical), and —N($R^d$)$R^e$ ($R^d$ and $R^e$ being independently hydrogen or $C_1$–$C_8$ alkyl or aryl), and unsaturated analogs of any of the foregoing definitions for substituent A;

wherein $R^1$ is selected from the group consisting of hydrogen, methyl, and ethyl;

wherein $R^6$ is selected from the group consisting of hydrogen, halogen, and $C_1$–$C_8$ alkyl;

wherein $R^a$ is selected from the group consisting of straight or branched $C_1$–$C_8$ alkylene, $C_3$–$C_7$ cycloalkylene; and $R^b$ is selected from the group consisting of hydrogen, substituted or unsubstituted phenyl, $C_2$–$C_{10}$ acyl, $C_2$–$C_{10}$ acyloxy, $C_2$–$C_{10}$ alkoxycarbonyl, and halogen; provided that when A is methyl, $R^1$ is methyl.

In another embodiment, the invention provides a method of inhibiting activity of type 5 17β-hydroxysteroid dehydrogenase comprising administering to a patient in need of such treatment a therapeutically effective amount of an inhibitor of type 5 17β-hydroxysteroid dehydrogenase having the molecular structure:

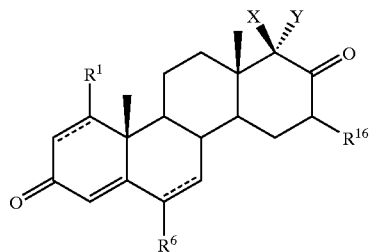

wherein the dotted lines are optional pi bonds
wherein X is $C_1$–$C_3$ alkyl;
wherein Y is hydrogen or an acyloxy moiety;
wherein $R^6$ is —H or —$CH_3$;
wherein $R^{16}$ is —H or halo;
wherein $R^1$ is —H or —$CH_3$.

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having the molecular structure:

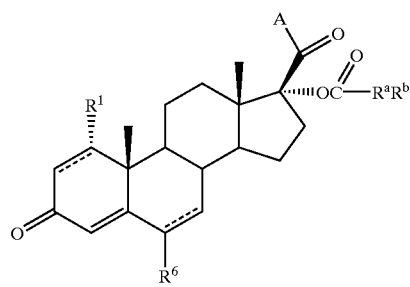

wherein the dotted lines are optional pi bonds;
wherein A is selected from the group consisting of straight or branched $C_1$–$C_4$ alkyl, —$OR^c$ ($R^c$ being a $C_1$–$C_8$ alkyl radical), and —$N(R^d)R^e$ ($R^d$ and $R^e$ being independently hydrogen or $C_1$–$C_8$ alkyl or aryl), and unsaturated analogs of any of the foregoing definitions for substituent A;
wherein $R^1$ is selected from the group consisting of hydrogen and methyl;
wherein $R^6$ is selected from the group consisting of hydrogen, halogen, and $C_1$–$C_8$ alkyl;
wherein $R^a$ is selected from the group consisting of straight or branched $C_1$–$C_8$ alkylene, $C_3$–$C_7$ cycloalkylene; and
$R^b$ is selected from the group consisting of hydrogen, substituted or unsubstituted phenyl, $C_2$–$C_{10}$ acyl, $C_2$–$C_{10}$ acyloxy, $C_2$–$C_{10}$ alkoxycarbonyl, and halogen; provided that when A is methyl, $R^a$ and $R^b$ together have at least two carbon atoms, and $R^1$ is methyl.

It is preferred that the optional pi bond at 6 is present, that $R^6$ is methyl, that $R^a$ is $C_1$–$C_6$ alkylene or that A is either methyl or —$N(R^d)R^e$.

It is also preferred when A is —$N(R^d)R^e$, that $R^d$ is methyl or that $R^e$ is $C_1$–$C_6$ alkyl or phenyl $C_1$–$C_6$ alkyl.

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having the molecular structure:

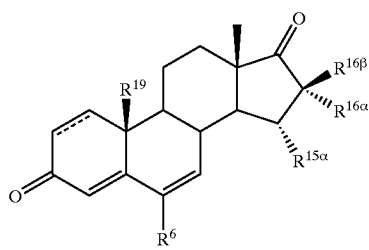

wherein the dotted line is an optional pi bond;
wherein $R^{16\beta}$ is selected from the group consisting of hydrogen, fluoro, chloro, $C_1$–$C_8$ alkyl, $C_1$–$C_8$ haloalkyl, a moiety which together with $R^{16\alpha}$ is $C_4$–$C_7$ spirocycloalkyl, $C_4$–$C_7$ halospirocycloalkyl, or =—$R'^{16}$ ($R'^{16}$ being $C_1$–$C_3$ alkyl) and unsaturated analogs of any of the foregoing definitions of $R^{16\beta}$;
wherein $R^{16\alpha}$ is selected from the group consisting of hydrogen, $C_1$–$C_8$ alkyl, $C_1$–$C_8$ haloalkyl, a moiety which together with $R^{16\beta}$ forms $C_4$–$C_7$ spirocycloalkyl, $C_4$–$C_7$ halospirocycloalkyl, or =—$R'^{16}$ ($R'^{16}$ being $C_1$–$C_3$ alkyl) and unsaturated analogs of any of the foregoings;
wherein $R^{15\alpha}$ is selected from the group consisting of hydrogen, $C_1$–$C_4$ alkyl, $C_1$–$C_4$ alkenyl and $C_1$–$C_4$ alkynyl;
wherein $R^{19}$ is either —H or —$CH_3$; and
wherein $R^6$ is selected from the group consisting of —H, —$CH_3$, and halo;
provided that $R^{16\beta}$, $R^{16\alpha}$, and $R^{15\alpha}$ are not simultaneously hydrogen.

It is preferred that $R^{16\alpha}$ is a larger substituent than $R^{16\beta}$ that $R^6$ is hydrogen, that the optional pi bond at position 1 is not present or that $R^{16\alpha}$ is a $C_3$–$C_5$ alkyl chain.

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having the molecular structure:

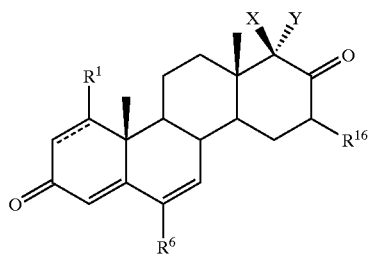

wherein the dotted line is an optional pi bond wherein X is $C_1$–$C_3$ alkyl;

wherein Y is hydrogen or an acyloxy moiety;

wherein $R^6$ is —H or —$CH_3$;

wherein $R^{16}$ is —H or halo;

wherein $R^1$ is —H or —$CH_3$.

It is preferred that $R^6$ is methyl, that the optional pi bond at position 1 is present, that Y is a $C_3$–$C_6$ fluoroacyloxy or that X is methyl.

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having the molecular structure:

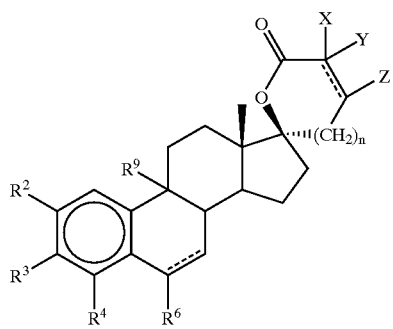

wherein n is an integer from 1–2;

wherein the dotted lines are optional pi bonds;

wherein X and Y are independently selected from the group consisting of —H, ($C_1$–$C_3$)alkyl, ($C_2$–$C_3$) alkenyl, and methoxycarbonyl;

wherein Z is selected from the group consisting of —H and ($C_1$–$C_3$)alkyl;

wherein $R^3$ is selected from the group consisting of hydrogen, acyl, carboxyl, alkoxycarbonyl, substituted or unsubstituted carboxamide, cyano, alkoxy, alkoxyalkoxy, alkythioalkoxy, acyloxy; hydroxy, halo, —O—$SO_2R^a$ ($R^a$ being selected from the group consisting of $C_1$–$C_6$ alkyl and $C_6$–$C_{10}$ aryl), and a moiety which, together with $R_2$, is a 5–6 member ring containing at least one oxygen and one nitrogen atom;

wherein $R^2$ is selected from the group consisting of hydrogen, amido, acyloxy, carboxyl, carboxamide, alkoxycarbonyl, cyano, halo, nitro, $C_1$–$C_8$ alkyl, and $CF_3$ and a moiety which, together with $R^3$, is a 5–6 member ring containing at least one oxygen and one nitrogen atom;

wherein $R^4$ is hydrogen or halo;

wherein $R^6$ is selected from the group consisting of hydrogen and oxo;

wherein $R^9$ is —H or —OH;

provided that X, Y, and Z are not all hydrogen when $R^3$ is methoxy.

It is preferred that $R^3$ is alkoxyalkoxy, carboxamide, carboxyl or alkoxyl, that at least one of X, Y or Z is methyl, that both X and Y are methyl, that n is 1 or that $R^6$ is oxo.

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having the molecular structure:

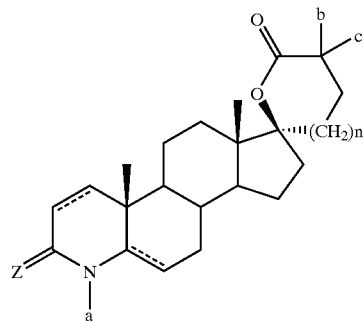

wherein the dotted lines are optional pi bonds;

wherein n=1 or 2; and wherein a is either —H or —$CH_3$;

wherein b and c are independently hydrogen or methyl;

wherein Z is oxygen or sulfur.

It is preferred that n is 1, that at least one of b or c is methyl, that both b and c are methyl or that Z is oxygen.

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having a molecular structure selected from the group consisting of:

EM-1291

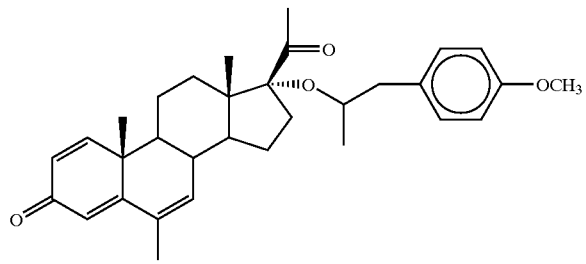

EM-1195-CS

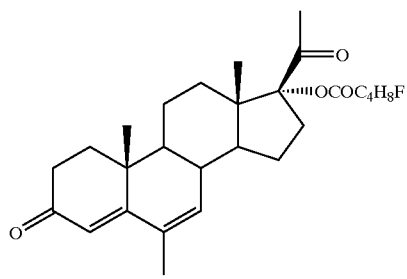

CS-243

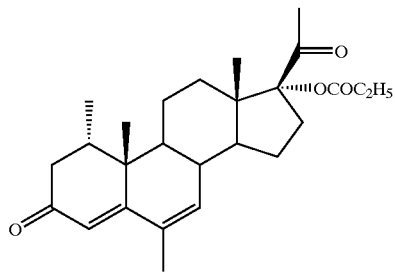

CS-245
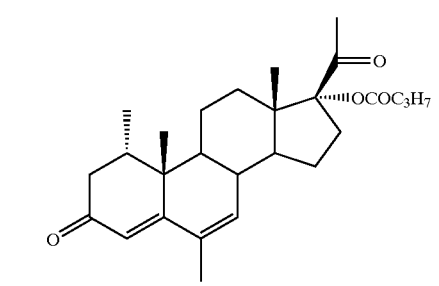
EM-1183
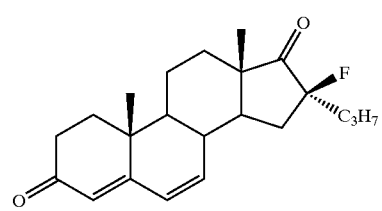
EM-1097
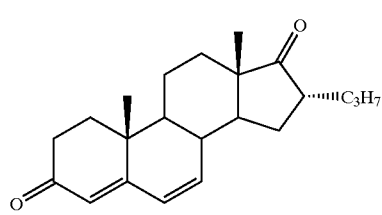
EM-1273-CS
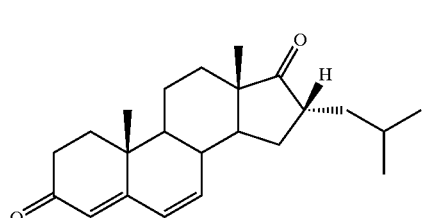
EM-1401
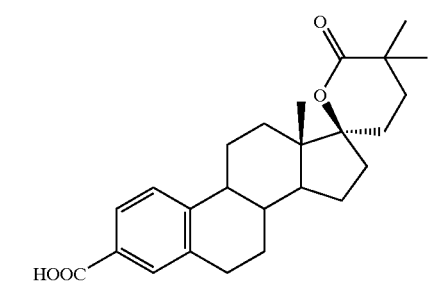
EM-1404
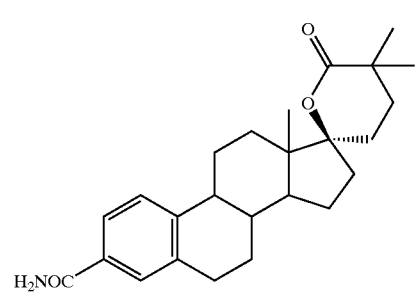
CS-237
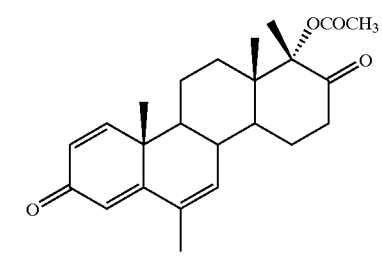
EM-1078
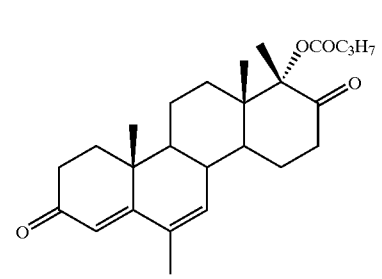
EM-1196-CS
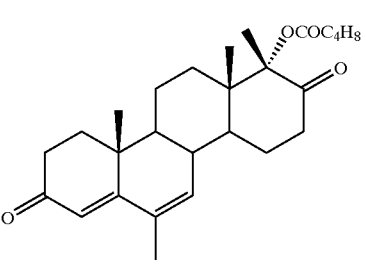
EM-1394
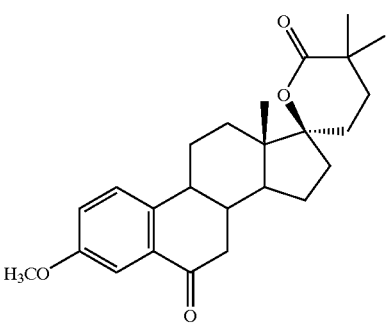
EM-1424-CS
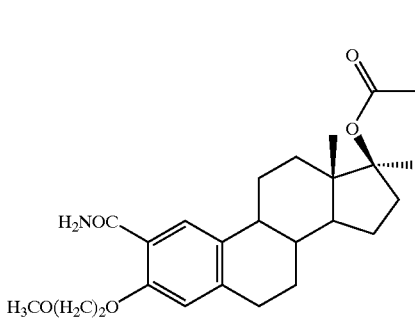

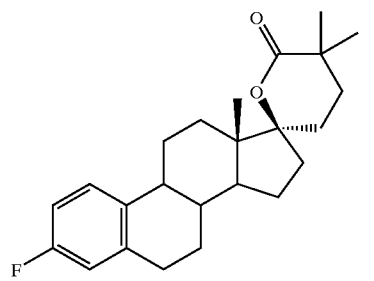
EM-1157-CS
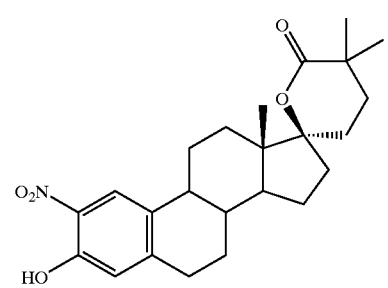
EM-1125
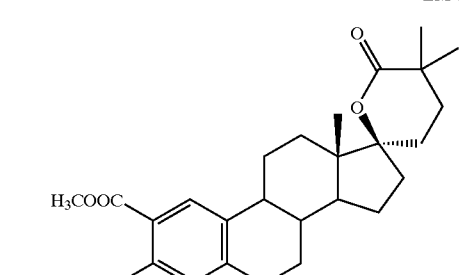
EM-1402-CS
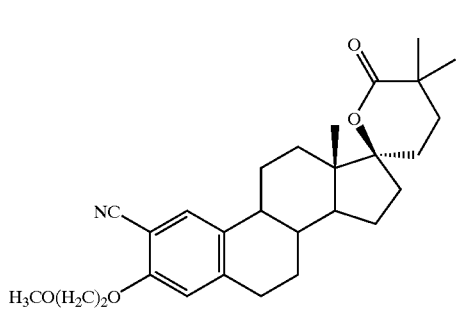
EM-1396
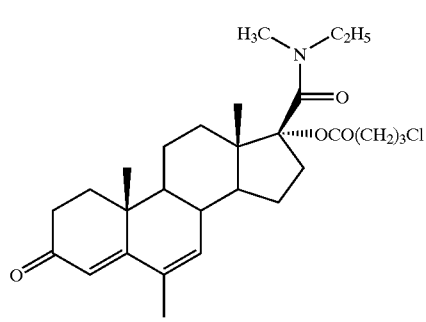
EM-1181
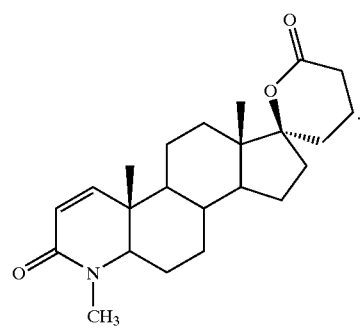
EM-1159
EM-1165
EM-1122-CS
It is preferred that the type 5 inhibitor is selected from the group consisting of:
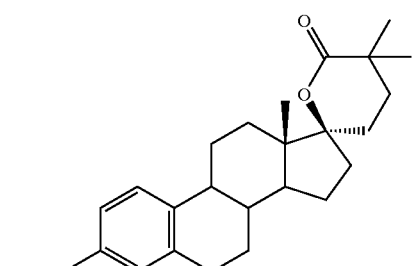
EM-1404
and

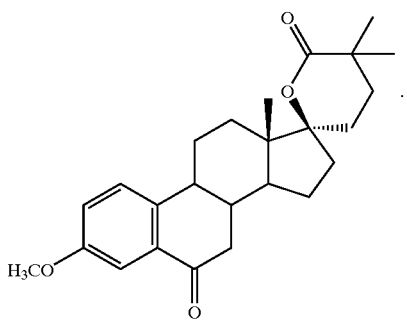

EM-1394

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having the molecular structure:

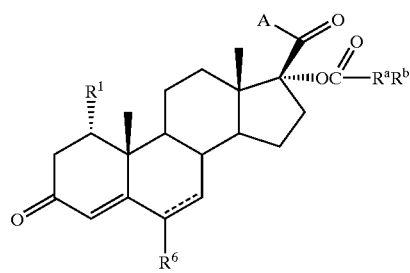

wherein the dotted line is an optional pi bond;

wherein A is selected from the group consisting of straight or branched $C_1$–$C_4$ alkyl, —$OR^c$ ($R^c$ being a $C_1$–$C_8$ alkyl radical), and —$N(R^d)R^e$ ($R^d$ and $R^e$ being independently hydrogen or $C_1$–$C_8$ alkyl or aryl), and unsaturated analogs of any of the foregoing definitions for substituent A;

wherein $R^1$ is selected from the group consisting of hydrogen and methyl;

wherein $R^6$ is selected from the group consisting of hydrogen, and halogen, and $C_1$–$C_8$ alkyl;

wherein $R^a$ is selected from the group consisting of straight or branched $C_1$–$C_8$ alkylene, $C_3$–$C_7$ cycloalkylene; and $R^b$ is selected from the group consisting of hydrogen, substituted or unsubstituted phenyl, $C_2$–$C_{10}$ acyl, $C_2$–$C_{10}$ acyloxy, $C_2$–$C_{10}$ alkoxycarbonyl, and halogen;

provided that when A is methyl, $R^1$ is methyl or ethyl.

In another embodiment, the invention provides a pharmaceutical composition comprising a pharmaceutically acceptable excipient, diluent or carrier and a therapeutically acceptable amount of an inhibitor of type 5 17β-hydroxysteroid dehydrogenase having the molecular structure:

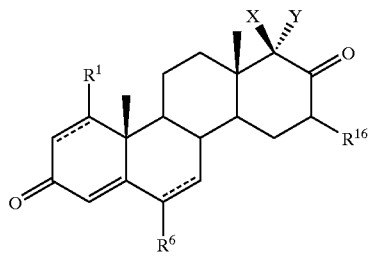

wherein the dotted lines are optional pi bonds wherein X is $C_1$–$C_3$ alkyl;

wherein Y is hydrogen or an acyloxy moiety;

wherein $R^6$ is —H or —$CH_3$;

wherein $R^{16}$ is —H or halo;

wherein $R^1$ is —H or —$CH_3$.

In another embodiment, the invention provides an inhibitor of type 5 17β-hydroxysteroid dehydrogenase having the molecular structure:

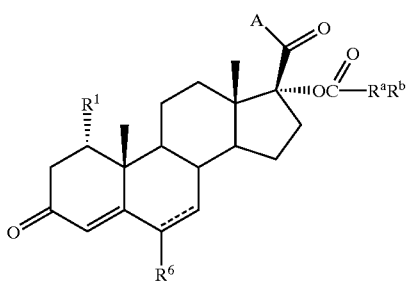

wherein the dotted line is optional pi bond;

wherein A is selected from the group consisting of straight or branched $C_1$–$C_4$ alkyl, —$OR^c$ ($R^c$ being a $C_1$–$C_8$ alkyl radical), and —$N(R^d)R^e$ ($R^d$ and $R^e$ being independently hydrogen or $C_1$–$C_8$ alkyl or aryl), and unsaturated analogs of any of the foregoing definitions for substituent A, wherein $R^1$ is selected from the group consisting of hydrogen and methyl;

wherein $R^6$ is selected from the group consisting of hydrogen, and halogen, and $C_1$–$C_8$ alkyl;

wherein $R^a$ is selected from the group consisting of straight or branched $C_1$–$C_8$ alkylene, $C_3$–$C_7$ cycloalkylene; and $R^b$ is selected from the group consisting of hydrogen, substituted or unsubstituted phenyl, $C_2$–$C_{10}$ acyl, $C_2$–$C_{10}$ acyloxy, $C_2$–$C_{10}$ alkoxycarbonyl, and halogen;

provided that when A is methyl, $R^a$ and $R^b$ together have at least two carbon atoms, and $R^1$ is methyl.

It is preferred that the optional pi bond at 6 is present, that $R^6$ is methyl; or that $R^a$ is $C_1$–$C_6$ alkylene.

It is preferred that A is either methyl or —$N(R^d)R^e$.

It is also preferred when A is $N(R^d)R^e$, that $R^d$ is methyl or that $R^e$ is $C_1$–$C_6$ alkyl or phenyl $C_1$–$C_6$ alkyl.

In another embodiment, the invention provides an inhibitor of type 5 17β-hydroxysteroid dehydrogenase having the molecular structure:

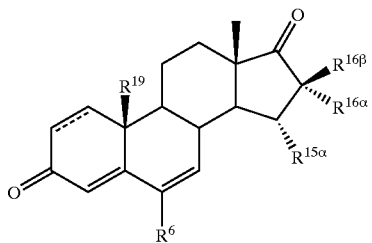

wherein the dotted line is an optional pi bond;

wherein $R^{16\beta}$ is selected from the group consisting of hydrogen, fluoro, chloro, $C_1$–$C_8$ alkyl, $C_1$–$C_8$ haloalkyl, a moiety which together with $R^{16\alpha}$ is $C_4$–$C_7$ spirocycloalkyl, $C_4$–$C_7$ halospirocycloalkyl, or =—$R'^{16}$ ($R'^{16}$ being $C_1$–$C_3$ alkyl) and unsaturated analogs of any of the foregoing definitions of $R^{16\beta}$;

wherein $R^{16\alpha}$ is selected from the group consisting of hydrogen, $C_1$–$C_8$ alkyl, $C_1$–$C_8$ haloalkyl and a moiety which together with $R^{16\beta}$ forms $C_4$–$C_7$ spirocycloalkyl, $C_4$–$C_7$ halospirocycloalkyl, or =—$R'^{16}$ ($R'^{16}$ being $C_1$–$C_3$ alkyl) and unsaturated analogs of any of the foregoings;

wherein $R^{15\alpha}$ is selected from the group consisting of hydrogen, $C_1$–$C_4$ alkyl, $C_1$–$C_4$ alkenyl and $C_1$–$C_4$ alkynyl;

wherein $R^{19}$ is either —H or —$CH_3$; and wherein $R^6$ is selected from the group consisting of —H, —$CH_3$, and halo;

provided that $R^{16\beta}$, $R^{16\alpha}$, and $R^{15\alpha}$ are not simultaneously hydrogen.

It is preferred that $R^{16\alpha}$ is a larger substituent than $R^{16\beta}$, that $R^6$ is hydrogen, that the optional pi bond at position 1 is not present or that $R^{16\alpha}$ is a $C_3$–$C_5$ alkyl chain.

In another embodiment, the invention provides an inhibitor of type 5 17β-hydroxysteroid dehydrogenase having the molecular structure:

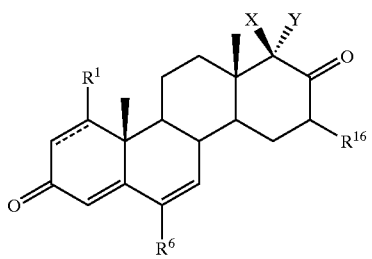

wherein the dotted line is optional pi bond wherein X is $C_1$–$C_3$ alkyl;

wherein Y is hydrogen or an acyloxy moiety;

wherein $R^6$ is —H or —$CH_3$;

wherein $R^{16}$ is —H or halo;

wherein R'is —H or —$CH_3$.

It is preferred that $R^6$ is methyl that the optional pi bond at position 1 is present, that Y is a $C_3$–$C_6$ fluoroacyloxy or that X is methyl.

In another embodiment, the invention provides an inhibitor of type 5 17β-hydroxysteroid dehydrogenase having the molecular structure:

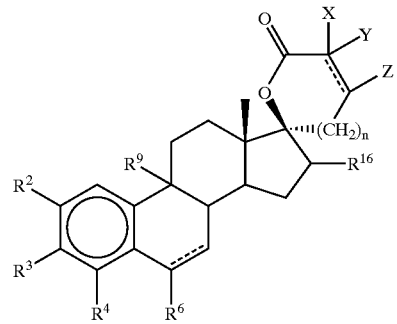

wherein n is an integer from 1–2;

wherein the dotted lines are optional pi bonds;

wherein X and Y are independently selected from the group consisting of —H, ($C_1$–$C_3$)alkyl, ($C_2$–$C_3$) alkenyl, and methoxycarbonyl;

wherein Z is selected from the group consisting of —H and ($C_1$–$C_3$)alkyl;

wherein $R^3$ is selected from the group consisting of hydrogen, acyl, carboxyl, alkoxycarbonyl, substituted or unsubstituted carboxamide, cyano, alkoxy, alkoxyalkoxy, alkythioalkoxy, acyloxy; hydroxy, halo, —O—$SO_2R^a$ ($R^a$ being selected from the group consisting of $C_1$–$C_6$ alkyl and $C_6$–$C_{10}$ aryl), and a moiety which, together with $R_2$, is a 5–6 member ring containing at least one oxygen and one nitrogen atom;

wherein $R^2$ is selected from the group consisting of hydrogen, amido, acyloxy, carboxyl, carboxamide, alkoxycarbonyl, cyano, halo, nitro, $C_1$–$C_8$ alkyl, and $CF_3$ and a moiety which, together with $R_3$, is a 5–6 member ring containing at least one oxygen and one nitrogen atom;

wherein $R^4$ is hydrogen or halo;

wherein $R^6$ is selected from the group consisting of hydrogen and oxo;

wherein $R^9$ is —H or —OH;

provided that X, Y, and Z are not hydrogen when $R^3$ is methoxy.

It is preferred that $R^3$ is alkoxyalkoxy; carboxamide, carboxyl or alkoxyl, that at least one of X, Y or Z is methyl, that X and Y are methyl, that n is 1 or $R^6$ is oxo.

In another embodiment, the invention provides an inhibitor of type 5 17β-hydroxysteroid dehydrogenase having the molecular structure:

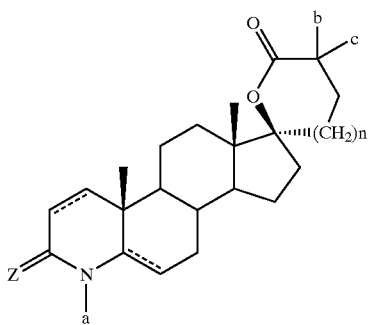

wherein the dotted lines are optional pi bonds;

wherein n=1 or 2; and wherein a is either —H or —$CH_3$;

wherein b and c are independently hydrogen or methyl;

wherein Z is oxygen or sulfur.

It is preferred that n is 1, that at least one of b or c is methyl, that both b and c are methyl or that Z is oxygen.

In another embodiment, the invention provides an inhibitor of type 5 17β-hydroxysteroid dehydrogenase having a molecular structure selected from the group consisting of:

EM-1291

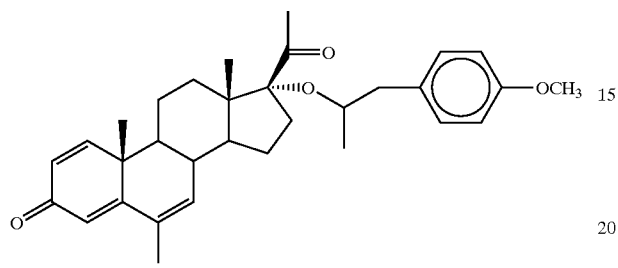

EM-1195-CS

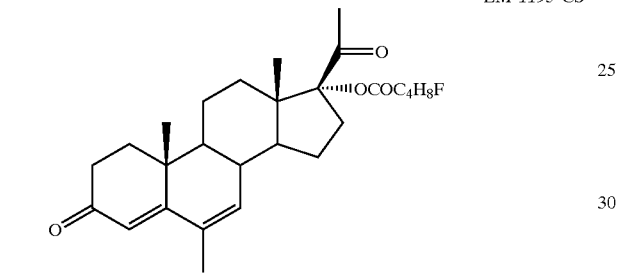

CS-243

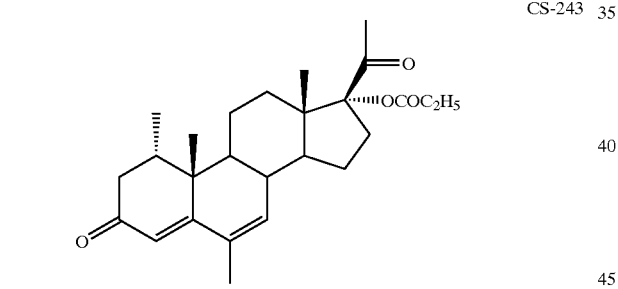

CS-245

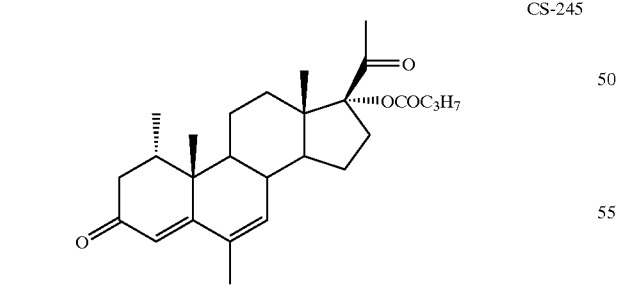

EM-1183

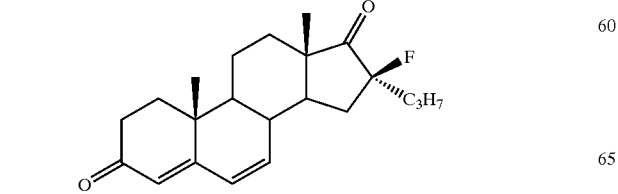

-continued

EM-1097

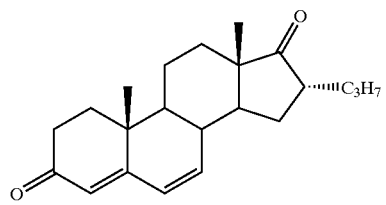

EM-1273-CS

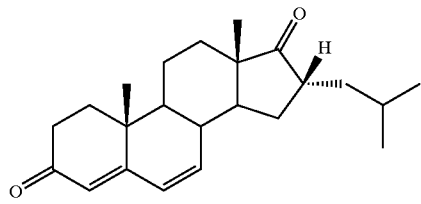

EM-1401

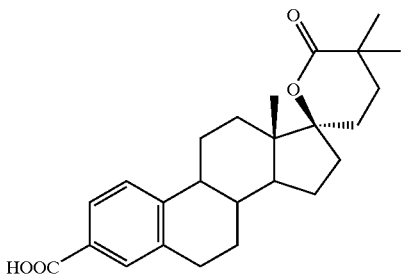

EM-1404

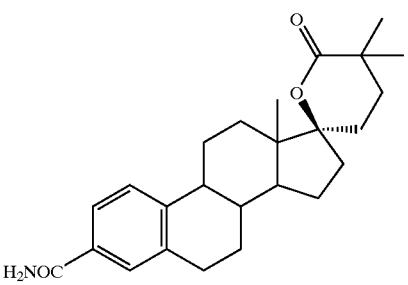

CS-237

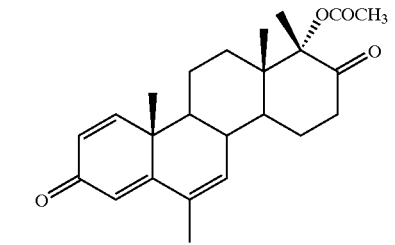

EM-1078

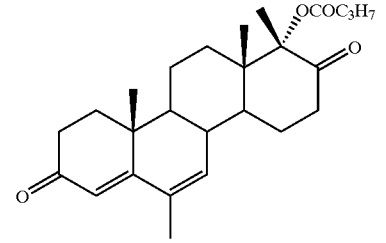

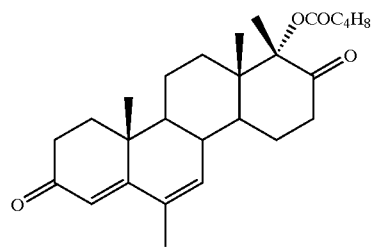
EM-1196-CS
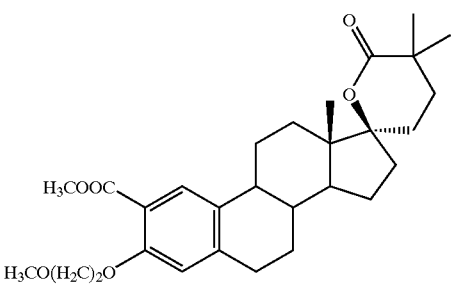
EM-1402-CS
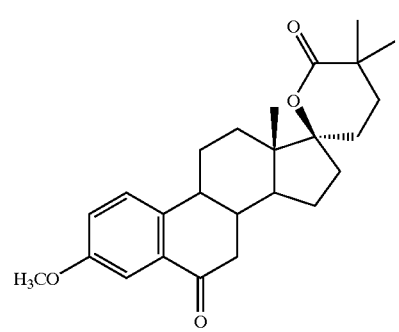
EM-1394
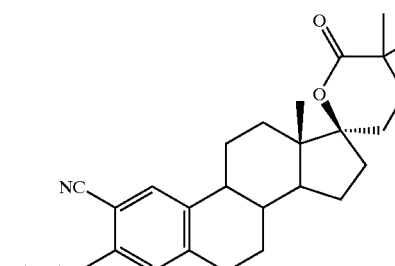
EM-1396
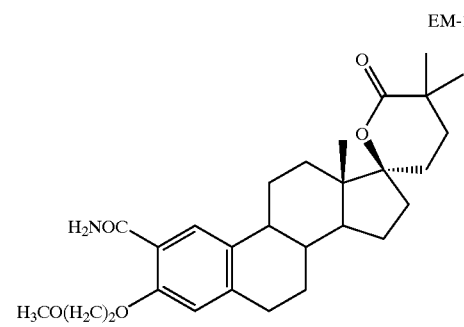
EM-1424-CS
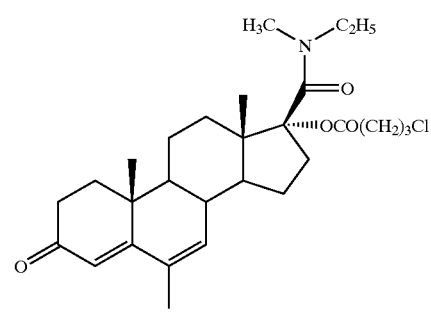
EM-1181
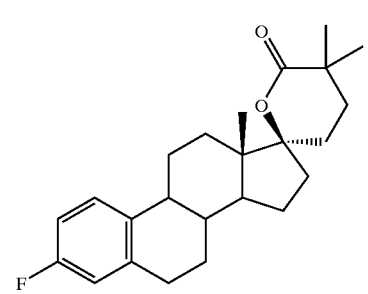
EM-1157-CS
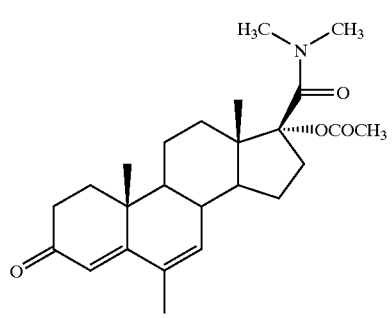
EM-1159
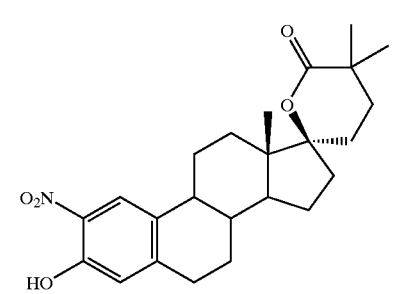
EM-1125
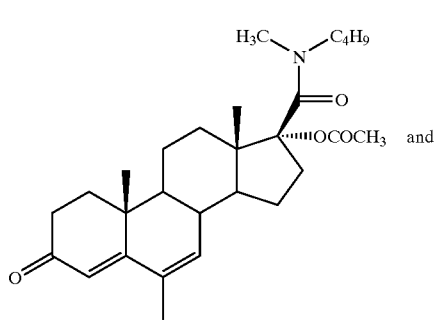
EM-1165
and

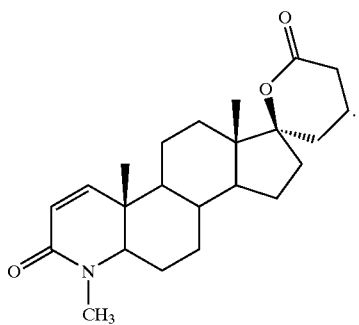
EM-122-CS

It is preferred that the type 5 inhibitor is selected from the group consisting of:

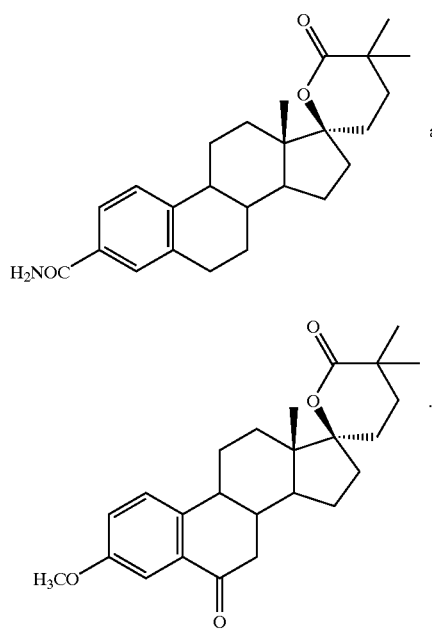
EM-1404 and

EM-1394

In another embodiment, the invention provides a method of inhibiting type 3 17β-hydroxysteroid dehydrogenase comprising administering to a patient in need of such treatment a therapeutically effective amount of an inhibitor of type 3 17β-hydroxysteroid dehydrogenase having the molecular structure:

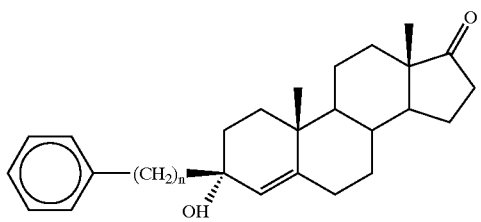

wherein R is selected from the group consisting of alkoxy, alkylthio, alkoxyalkoxy, alkoxyalkylthio, alkylthioalkoxy, and alkylthioalkylthio,

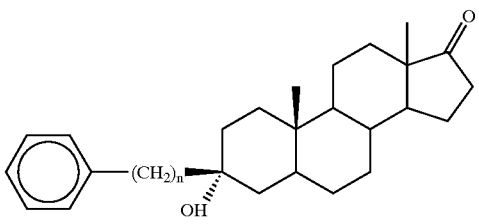

wherein n is an integer from 1 to 4.

It is preferred that the said type 3 inhibitor is selected from the group consisting of:

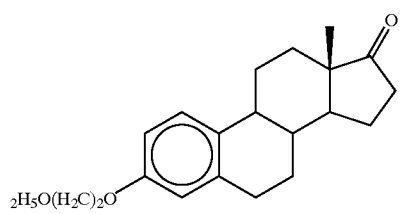
EM-1071

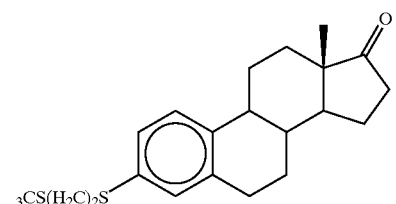
EM-1065

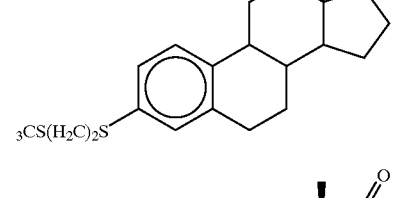
EM-1066

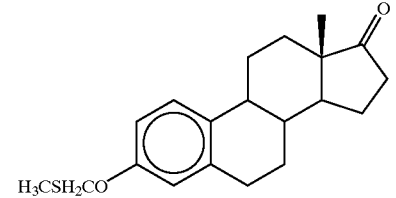
EM-1064

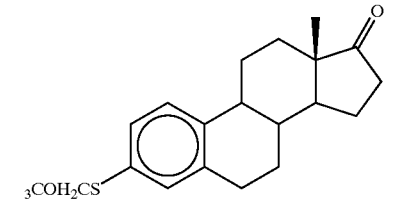
EM-1074

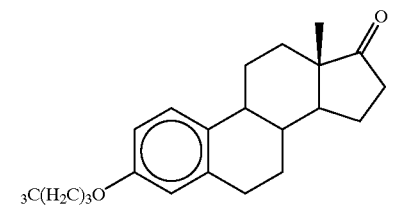
EM-1073

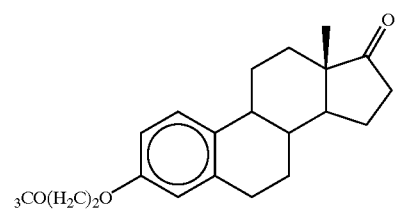

-continued

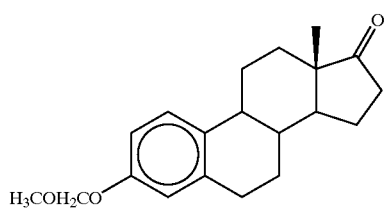
EM-1070

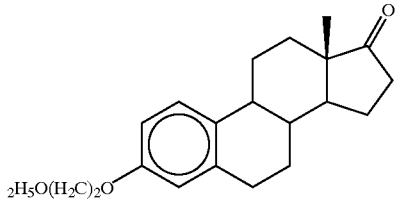
EM-1071

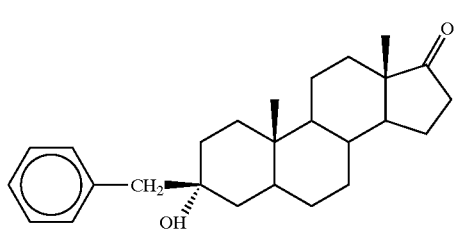
CS-213

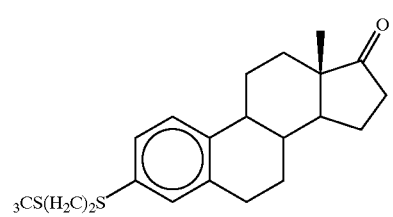
EM-1065

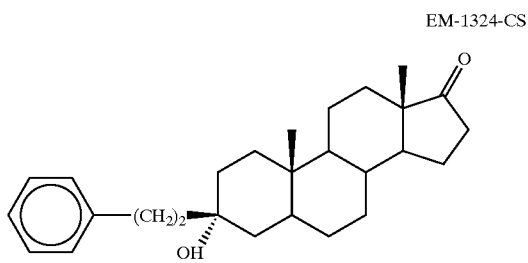
EM-1324-CS

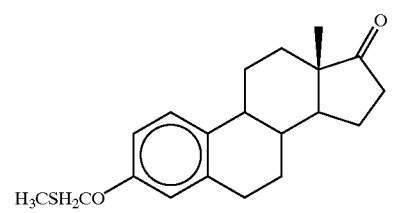
EM-1066

In another embodiment, the invention provides a pharmaceutical composition comprising a pharmaceutically acceptable excipient, diluent or carrier and a therapeutically acceptable amount of an inhibitor of type 3 17β-hydroxysteroid dehydrogenase having the molecular structure:

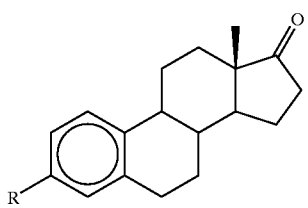

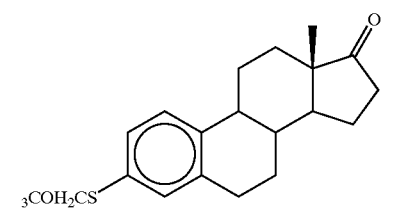
EM-1064 wherein R is selected from the group consisting of alkoxy, alkylthio, alkoxyalkoxy, alkoxyalkylthio, alkylthioalkoxy, and alkylthioalkylthio, or

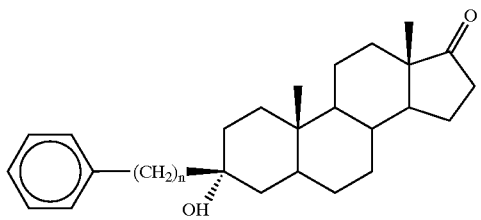

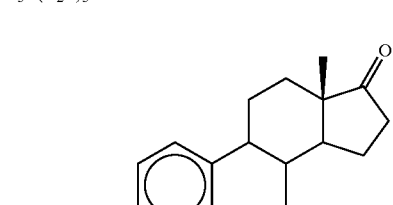
EM-1074

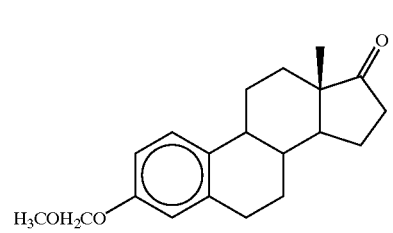
EM-1073 wherein n is an integer from 1 to 4.

It is preferred that the said type 3 inhibitor is selected from the group consisting of:

EM-1070

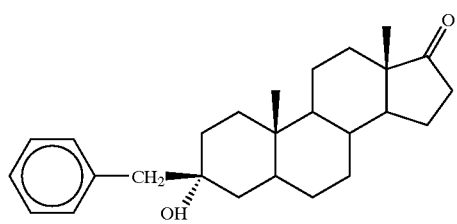
CS-213

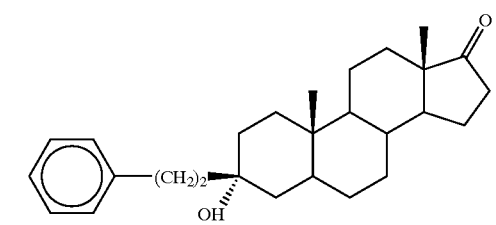
EM-1324-CS

In another embodiment, the invention provides an inhibitor of type 3 17β-hydroxysteroid dehydrogenase having the molecular structure:

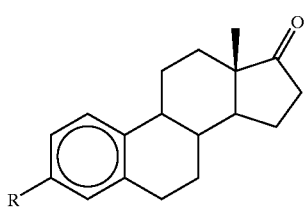

wherein R is selected from the group consisting of alkoxyethoxy, alkoxyalkylthio, alkylthioalkoxy, and alkylthioalkylthio, or

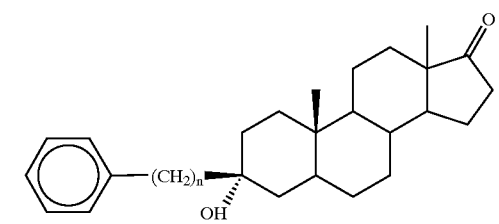

wherein n is an integer from 1 to 4.

It is preferred that the said type 3 inhibitor is selected from the group consisting of:

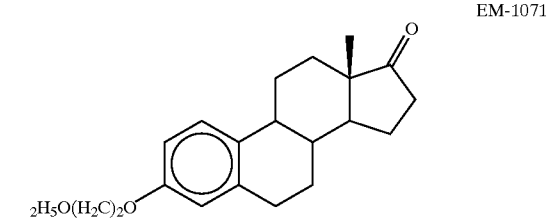
EM-1071

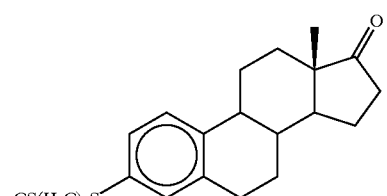
EM-1065

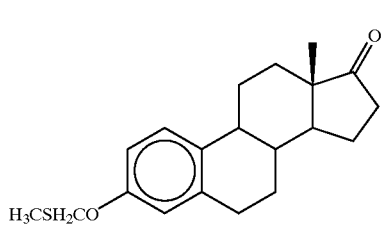
EM-1066

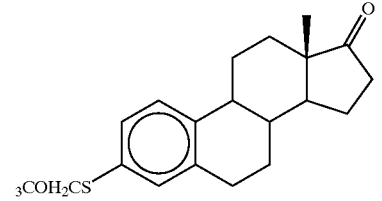
EM-1064

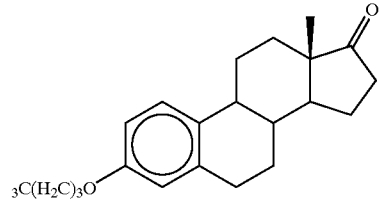
EM-1074

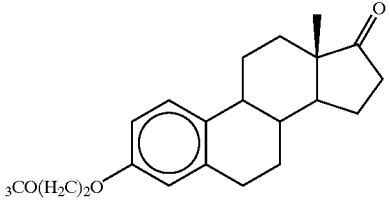
EM-1073

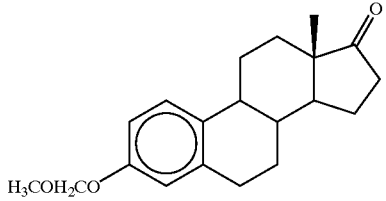
EM-1070

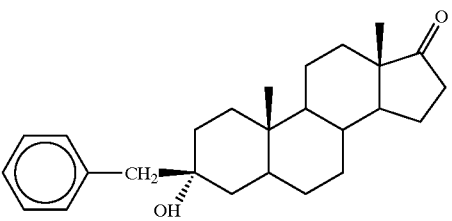
CS-213

-continued

EM-1324-CS

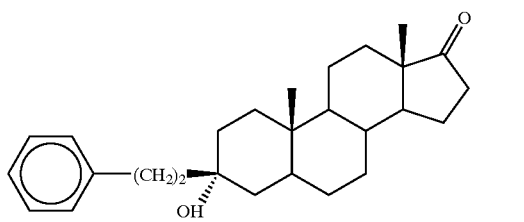

A patient in need of treatment or reducing the risk of onset of a given disease is one who has either been diagnosed with such disease or one who is particularly susceptible to acquiring such disease, for example, one at higher risk of acquiring the disease than the general population.

Except where otherwise stated, the preferred dosage of the active compounds of the invention is identical for both therapeutic and prophylactic purposes. The dosage for each active component discussed herein is the same regardless of the disease being treated (or prevented).

As used in the methods of medical treatment or methods of reduction of risk of onset of disease herein, an "inhibitor of type 5 or 3 17β-hydroxysteroid dehydrogenase" means a compound whose $IC_{50}$ of inhibition for the enzyme in question (computed in the same manner as described in connection with Table 1 herein) is no higher than 500 nM. It is preferred that such inhibitor be no higher than 20 nM, most preferably lower than 10 nM. In some embodiments of the type 5 or type 3 inhibitor, it is also preferred that $IC_{50}$ of undesirable inhibition of type 2 17β-hydroxysteroid dehydrogenase be more than 5 times that for inhibition of type 5, preferably more than 10 times, and most preferably more than 25 times. In some embodiments, it is preferred that the percentage of inhibition of the binding of [$^3$H]R1881 on the androgen receptor (as described in D-Androgen Receptor (AR) assays, supra), by the inhibitor of type 5 or 3 17β-hydroxysteroid dehydrogenase at the concentration of $10^{-6}$ M be less than 30% most preferably less than 20%.

Where two or more different active agents are discussed as part of a combination therapy herein (e.g. an enzyme inhibitor and an antiandrogen), a plurality of different compounds are administered rather than a single compound having multiple activities.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry, is appropriate for use herein, and the terms "ingredient", "diluent" or "carrier" include such non active ingredients as are typically, included together with active ingredients, used in such dosage form in the industry.

BRIEF DESCRIPTION OF THE DRAWINGS

The patent application file contains at least one drawing executed in color. Copies of this patent or patent application publication with color drawings will be provided by the office upon request and payment of the necessary fee.

FIG. 1a shows semithin Epon section (0.7 μm-thick) hybridized with the antisense probe. Epithelial cells lining the tube-alveoli as well as some of the surrounding stromal cells are labelled. In the epithelium, the dashed line approximately indicates the boundary between the basal and the luminal cells. The basal cells are intensively labelled in comparison with the luminal cells where only a few grains are seen. (×1000)

FIG. 1b shows similar area from the same prostate hybridized with the sense probe as a control. Only scattered silver grains can be detected. (×1000)

FIG. 1c shows the antisense probe generates strong radioautographic signals in the wall of blood vessels (arrows). (×600)

FIG. 1d shows similar blood vessels hybridized with the sense probe as a control. No significant labeling could be seen. (×600)

FIG. 3a shows the staining reaction is observed in basal cells (arrows) and in most of the stromal cells situated below. The luminal cells of the epithelium (above the basal cells) are not reactive.

FIG. 3b shows all epithelial cells are immunoreactive.

FIG. 3c shows the basal cells are not very well seen (thick arrows) but they are labelled as well as some luminal cells (thin arrows) of the tube-alveoli.

FIG. 3d shows an immunostained paraffin section of normal human prostate epithelial cells (PrEC 5500-1). The staining reaction can be seen in the cytoplasm of most of the cells.

FIG. 3e shows the same cultured cells as in FIG. 3d, but the antiserum was incubated with an excess of antigen. No staining reaction can be seen.

FIG. 4a shows all of the basal cells show a strong positive staining reaction (arrowheads). Note the absence of reaction in the luminal cells (L) while the fibroblasts of the stroma are stained (arrows) (×500).

FIG. 4b shows some of the luminal cells are immunoreactive (arrows) as well as basal cells (arrowheads) (×500).

FIG. 4c shows a section consecutive to that shown in FIG. 4a. Immunoabsorption of the antiserum with an excess of antigen completely prevents immunostaining (×500).

FIG. 4d shows, in the stroma, smooth muscle cells (arrows) are not labeled while the surrounding fibroblasts are stained (×800).

FIG. 4e shows the positive staining in the wall of a large vein (V). The endothelial cells of small blood vessels are well-labeled (arrows) (×800).

FIG. 4f shows the low magnification of an artery showing the labelling of endothelial cells (arrows) and of fibroblasts of the tunica adventitia (arrowheads) while smooth muscle cells of tunica media (m) are weakly labeled (×200).

FIG. 4g shows the high magnification of an artery which clearly demonstrates the labelling in the cytoplasm of endothelial cells (arrows) as well as of fibroblasts (arrow heads) while smooth muscle cells of the tunica media (m) are not labeled (×800).

FIGS. 5a and b show consecutive sections immunostained for type 5 17β-HSD (5a) and 3β-HSD (5b). Although the reaction for 3β-HSD is somewhat weaker than that obtained for type 5 17β-HSD, the distribution of the two enzymes in basal (arrowheads) and luminal cells (L) is similar.

FIG. 5c shows an androgen receptor immunoreactivity was found to be exclusively localized in the nuclei. In the epithelium, the reaction can be seen in the majority of the luminal cells (L) nuclei, but not in the nuclei of most basal cells (arrowheads).

FIG. 5d shows, in the fibromuscular stroma, most of the nuclei are labeled. Some smooth muscle cell nuclei are labeled (arrows) while others show not detectable reaction (arrowheads).

FIG. 5e shows the wall of the blood vessels shows labeled and unlabeled nuclei. Some of the nuclei of the endothelial cells lining the lumen of an arteriole are labeled (arrows), while others show no staining (arrowheads).

FIG. 6 shows human skin hybridized with type 5 17β-HSD cRNA probe.

FIG. 7 shows monkey ovary hybridized with type 5 17β-HSD.

DETAILED DESCRIPTION OF THE PREFERRED EMBODIMENTS

Figure 1A:
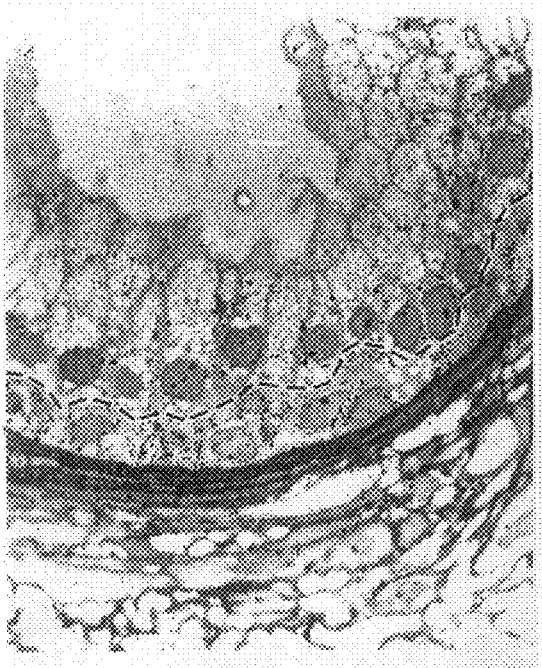
FIGS. 1a to 1d show autoradiographs of $^3$H-labelled type 5 17β-HSD antisense and sense riboprobes (35 base pairs) hybridized in situ to human benign prostatic hyperplasia (BPH) tissue.

There are several types of 17β-hydroxysteroid dehydrogenases. Of the various types of 17β-hydroxysteroid dehydrogenases, type 1 catalyzes conversion of estrone to estradiol. Types 2 and 4 catalyze the reverse reaction. Type 1 also catalyzes conversion of DHEA to 5-diol while type 4 catalyzes the reverse reaction. Types 3 and 5 catalyze conversion of 4-dione to testosterone while type 2 catalyzes the reverse reaction. Types 3 and 5, the primary concern of the present application, catalyze in vivo the biosynthesis of androgenic compounds, such as the biosynthesis of testosterone from androst4-ene-dione ("4-dione") or the conversion of androstanedione (A-dione) to DHT. The reaction catalyzed by type 3 or type 5 17β-hydroxysteroid dehydrogenase is a reversible reaction, and the reverse reaction can be catalyzed by type 2 17β-hydroxysteroid dehydrogenase, whose activity is preferably not inhibited. It is also desirable to avoid inhibition, for example, of type 4 17β-hydroxysteroid dehydrogenase which desirably (for androgen sensitive diseases) converts a different testosterone precursor to another compound.

For purposes of treating diseases which respond unfavorably to androgenic activity, it is desirable to inhibit androgen formation without hindering androgen degradation. Thus, in one aspect, the present invention endeavors to reduce the level of androgens by selectively inhibiting the type 3 and type 5 17β-hydroxysteroid dehydrogenases while desirably allowing the type 2 and type 4 enzymes to remain free of inhibition. Thus, the equilibrium of the reversible androgen (or androgen precursor) synthesis reactions is beneficially affected by inhibiting the forward androgen synthesis reactions while permitting any androgens or precursors that are synthesized (either locally or systemically) to be reconverted to their precursors by action of the type 2 and/or type 4 17β-hydroxysteroid dehydrogenases.

The type 5 enzyme is better inhibited by certain compounds discussed in more detail infra, while the type 3 enzyme is better inhibited by other compounds (also discussed infra). It is therefore possible to provide best inhibition of androgen synthesis by a combination therapy which includes administering both a type 5 inhibitor and a type 3 inhibitor.

Type 5 enzyme tends to predominate in liver, adrenal glands, prostate, and the peripheral tissues whereas type 3 enzyme tends to predominate in the testes. In the prior art, testicular androgens have been suppressed by either surgical or chemical castration, frequently by administration of an LHRH agonist. The present invention provides inhibitors of type 3 17β-hydroxysteroid dehydrogenase which, like the LHRH agonist of the prior art, reduce testicular androgen production. Thus, in some embodiments of the invention, the type 3 inhibitors of the invention may be used to inhibit testicular androgen secretion, either alone or in combination with prior art chemical or surgical castration. In some embodiments, antiandrogen and/or 5α-reductase inhibitor is also provided. In some embodiments, the inhibitors of the type 3 enzyme are used in addition to chemical castration by LHRH agonist. An undesirable initial upward spike of androgenic production and secretion by the testes occurs during the very early portion of treatment with LHRH agonist, prior to the beginning of the beneficial effect of androgen reduction caused by LHRH agonist. Using type 3 17β-hydroxysteroid dehydrogenase inhibitor in conjunction with LHRH agonist is expected to reduce that initial undesirable androgen elevation.

Both androgen-related and estrogen-related diseases may be treated with the 17β-hydroxysteroid dehydrogenase inhibitors of the present invention. Androgen-sensitive diseases are those whose onset or progress is aided by androgen activation of androgen receptors, and should respond favorably to treatment with the present invention because of the reduction of androgen biosynthesis that is achieved thereby. Estrogen-sensitive diseases (diseases whose onset or progress is aided by activation of the estrogen receptor) should also benefit because many androgens whose biosynthesis is suppressed by the present invention are precursors to estrogens, and the present invention may therefore reduce estrogen biosynthesis as well. Androgen-sensitive diseases include but are not limited to prostatic cancer, benign prostatic hyperplasia, acne, seborrhea, hirsutism, androgenic alopecia, and polycystic ovarian syndrome. Estrogen-sensitive diseases include but are not limited to breast cancer, endometrial cancer, endometriosis, and endometrial leiomyoma.

For the treatment of androgen-sensitive diseases, it is of course preferred that the inhibitors of 17β-hydroxysteroid dehydrogenase that are administered (whether type 5 or type 3 or both) do not possess inherent androgenic activity. However, breast cancer (and some other estrogen-sensitive diseases, e.g. ovarian cancer, uterine cancer, and endometrial cancer) respond favorably to androgens. Therefore, a compound which inhibits type 5 or type 3 17β-hydroxysteroid dehydrogenase, and which is also androgenic, can be especially useful for the treatment of breast cancer and other diseases which respond negatively to estrogen and positively to androgen.

Type 5 and/or type 3 inhibitors of 17β-hydroxysteroid dehydrogenase may, in accordance with the invention, be utilized as part of a combination therapy with other strategies (listed below) which, attack androgen- or estrogen-sensitive diseases through other mechanisms, thus providing synergistic combinations. These combination therapies include in addition to type 3 or type 5 inhibitors of 17β-hydroxysteroid dehydrogenase one or more of the following strategies:

Strategy 1: Suppression of testicular or ovarian hormonal secretion by chemical or surgical castration. This is useful in treatment of diseases which respond adversely to androgen or estrogen, respectively. When surgical or chemical castration is utilized, chemical castration is preferred utilizing either an LHRH-agonist, an LHRH antagonist or inhibitor of type 3 17β-hydroxysteroid dehydrogenase (as discussed herein). Suitable LHRH agonists are reported in U.S. Pat. No. 4,659,695, but any LHRH agonist showing the ability to induce chemical castration can be used since they all act through the same mechanisms as described (Labrie et al., J. Androl. 1: 209–228, 1980). Dosages are known in the art. Some suitable LHRH antagonists are reported in U.S. Pat. No. 4,666,885 but any LHRH antagonist is acceptable, if used according to the recommendation of the manufacturer.

Strategy 2: Utilizing androgen or estrogen receptor antagonists ("antiandrogens" or "antiestrogens") to prevent activation of androgen or estrogen receptors by androgens or estrogens. Strategy 2 is useful against diseases that respond adversely to androgenic or estrogenic activity, respectively. Antiandrogens, and dosages therefor, are known in the art (e.g. Flutamide (N-[4-nitro-3-(trifluoromethyl)phenyl)]-2-methyl propanamide) at a dosage of 250 mg, 2 or 3 times a day, Nilutamide at a dosage of 150 mg/day, Casodex at a dosage of 50 to 500 mg/day or EM-250 of the following structure:

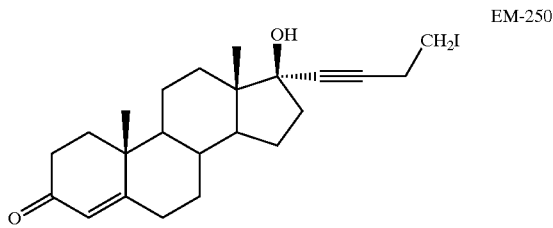

EM-250

Synthesized and used as reported in International Publication WO94/26767.

When antiestrogens are used in accordance with the invention, either alone or as part of one of the combination therapies described herein, the attending clinician should, at least initially, use the dosages recommended by the manufacturer. However, the attending clinician should monitor individual patient response and metabolism and adjust patient dosage accordingly. Indeed, that will be true of all of the strategies discussed herein. One preferred antiestrogen is EM-800 reported in PCT/CA96/00097 (WO 96/26201) The molecular structure of EM-800 is:

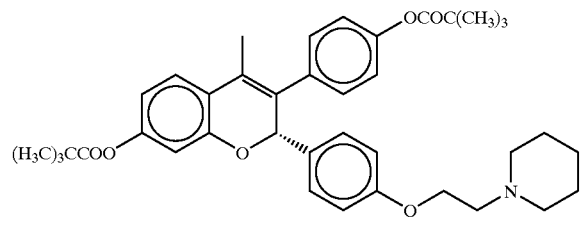

Other suitable antiestrogens include but are not limited to Tamoxifen ((Z)-2-[4-(1,2-diphenyl-1-butenyl)]-N,N-dimethylethanamine) and ICI 182780 (available from Zeneca, UK), Toremifene (available from Orion-Farmos Pharmaceuticla, Finland), Droloxifene (Pfizer Inc., USA), Raloxifene (Eli Lilly and Co., USA), LY 335563 and LY 353381 (Eli Lilly and Co., USA), lodoxifene (SmithKline Beecham, USA), Levormeloxifene (Novo Nordisk, A/S, Denmark). Any antiestrogen used as required for efficacy, as recommended by the manufacturer, can be used. Appropriate dosages are known in the art. Any other antiestrogen commercially available can be used according to the invention.

Strategy 3: Suppression of sex steroid biosynthesis by inhibition of 3β-hydroxysteroid dehydrogenase [e.g. Trilostane (2α-cyano-4α,5α-epoxy-17β-hydroxyandrostan-3-one), Sterling-Winthrop Research Institute, Renslaer, N.Y., USA] by administering such inhibitor at a dosage of 1 to 500 mg/day). Desirable serum levels of 3β-hydroxysteroid dehydrogenase inhibitor range from 5 ng/ml to 500 ng/ml, preferably 10 ng/ml to 100 ng/ml. Strategy 3 is useful against both (1) diseases that respond adversely to androgenic activity and (2) some diseases that respond adversely to estrogenic activity.

Strategy 4: Suppression of conversion of the androgen testosterone to the more potent androgen dihydrotestosterone (DHT) by inhibiting the activity of testosterone 5α-reductase (e.g. by administering Proscar, available from Merck Sharp and Dohme Canada, at the recommended dosage). Any other potent 5α-reductase inhibitor can be used. The dosage used can be 2 to 20 mg daily orally. The dosage should be the one recommended by the manufacturer. Strategy 4 is useful against diseases that respond adversely to androgenic activity.

Strategy 5: Utilizing an aromatase inhibitor to reduce estrogen production. Strategy 5 is useful against diseases that respond adversely to estrogenic activity or estrogen receptor-mediated exacerbation of the type of androgen-sensitive diseases that are also estrogen-sensitive diseases (e.g. benign prostatic hyperplasia). When aromatase inhibitors are used in accordance with the invention, either alone or as part of one of the combination therapies described herein, the attending clinician should initially use the dosage recommended by the manufacturer. When administered orally, the dosage which is usually effective to provide the desired serum levels is between 1.0 mg and 20 mg of active ingredient per day per 50 kg of body weight. For example, Arimidex (Zeneca) is taken at the oral dose of 1 mg daily. However, the attending clinician should monitor individual patient response and metabolism and adjust patient dosage accordingly. Aromatase inhibitors include those set forth in U.S. Pat. No. 5,227,375. Aromatase inhibition may also be achieved, for example, by administering Arimidex (2,2'-[5-(1H-1,2,4-triazol-1-ylmethyl)-1,3-phenylene bis (2-methylpropiononitrile)) available from Zeneca, UK, at a dosage of 1 mg/day. Any other aromatase inhibitor can be used according to the recommendations of the manufacturer.

Strategy 6: Administering an androgenic compound. Strategy 6 is useful against a disease which responds favorably to androgenic activity. Preferred androgens include but are not limited to medroxyprogesterone acetate, and megestrol acetate at a dosage of 5–200 mg/day. Desirable low dose and sustained release formulations of such androgens are described in U.S. Pat. No. 5,434,146.

Any of the above strategies useful against diseases that respond negatively to estrogenic activity may also be used to help alleviate estrogenic side effects that may result from treatment of purely androgen-sensitive diseases in accordance with the invention. For example, many androgen precursors are also estrogen precursors. Strategies which suppress formation of certain androgens may increase levels of precursors thereto which are also estrogen precursors thus undesirably increasing estrogen formation. For example, administering inhibitors of testosterone 5α-reductase to suppress conversion of testosterone to dihydrotestosterone may increase the conversion of testosterone to estradiol. In that case, strategy 5 may desirably reduce that unwanted estrogen production. Strategy 2 (estrogen antagonist aspect) and strategy 3 may also be helpful in that regard.

In general, for both androgen-sensitive diseases and estrogen-sensitive diseases, simultaneous treatment with inhibitors of sex steroid biosynthesis (inhibitors of enzymes which catalyze one or more steps of estrogen or androgen biosynthesis), and with estrogen receptor antagonists and/or androgen receptor antagonists, are believed to have additive rather than redundant effect because they are acting in a beneficial manner by a different mechanism. Likewise, the activity of two different enzyme inhibitors (enzymes which catalyze one or more different steps of sex steroid biosynthesis) are believed to provide additive effect, especially where the inhibitors affect more than one synthetic pathway. Such an approach permits to achieve a more complete effect.

Different sex steroid-dependent diseases respond differently to both androgen receptor activation and estrogen receptor activation. For example, breast cancer responds unfavorably to estrogen receptor activation, but favorably to androgen receptor activation. On the other hand, benign prostatic hyperplasia responds unfavorably to activation of either the estrogen or androgen receptor. The type 5 and/or type 3 inhibitors of the invention may be used in any combination with any of the strategies 1–6 above whose effect (increasing or decreasing androgenic or estrogenic activity) is consistent with desirable effect on the disease in question. With that in mind, set forth below are a list of representative diseases which may be treated, or risk of which may be reduced, in accordance with the present invention. Beneath each disease, is several preferred combination therapies for treatment, or risk reduction, of that particular disease. However, these combinations may be supplemented using one or more of the six strategies listed above, limited only by whether a particular disease responds favorably or adversely to estrogenic activity or to androgenic activity.

A) Prostate cancer (responds adversely to androgenic activity, favorably to estrogenic activity)

1. Inhibitor of type 5 17β-hydroxysteroid dehydrogenase+LHRH-agonist (or antagonist)
2. Inhibitor of type 5 17β-hydroxysteroid dehydrogenase+inhibitor of type 3 17β-hydroxysteroid dehydrogenase.
3. Inhibitor of type 5 17β-hydroxysteroid dehydrogenase+inhibitor of type 3 17β-hydroxysteroid dehydrogenase+LHRH agonist (or antagonist)
4. Inhibitor of type 5 17β-hydroxysteroid dehydrogenase+LHRH-agonist (or antagonist)+antiandrogen
5. Inhibitor of type 5 17β-hydroxysteroid dehydrogenase+inhibitor of type 3 17β-hydroxysteroid dehydrogenase+antiandrogen
6. Inhibitor of type 5 17β-hydroxysteroid dehydrogenase+inhibitor of type 3 17β-hydroxysteroid dehydrogenase+LHRH agonist (or antagonist)+antiandrogen
7. Inhibitor of type 5 17β-hydroxysteroid dehydrogenase+antiandrogen+5α-reductase inhibitor+LHRH agonist (or antagonist)
8. Inhibitor of type 5 17β-hydroxysteroid dehydrogenase+LHRH agonist+5α-reductase inhibitor
9. Inhibitor of type 5 17β-hydroxysteroid dehydrogenase+inhibitor of type 3 17β-hydroxysteroid dehydrogenase+5α-reductase inhibitor
10. Inhibitor of type 5 17β-hydroxysteroid dehydrogenase+inhibitor of type 3 17β-hydroxysteroid dehydrogenase+antiandrogen+5α-reductase inhibitor
11. Inhibitor of type 5 17β-hydroxysteroid dehydrogenase+inhibitor of type 3 17β-hydroxysteroid dehydrogenase+LHRH agonist (or antagonist)+antiandrogen+5α-reductase inhibitor B) Benign prostatic hyperplasia (responds adversely to both androgenic activity and estrogenic activity)

1. Inhibitor of type 5 17β-hydroxysteroid dehydrogenase
2. Inhibitor of type 5 17β-hydroxysteroid dehydrogenase+antiestrogen or aromatase inhibitor
3. Inhibitor of type 5 17β-hydroxysteroid dehydrogenase+antiandrogen
4. Inhibitor of type 5 17β-hydroxysteroid dehydrogenase+antiandrogen+5α-reductase inhibitor+antiestrogen or aromatase inhibitor
5. Inhibitor of type 5 17β-hydroxysteroid dehydrogenase+5α-reductase inhibitor
6. Inhibitor of type 5 17β-hydroxysteroid dehydrogenase+antiandrogen+5α-reductase inhibitor
7. Inhibitor of type 5 17β-hydroxysteroid dehydrogenase+5α-reductase inhibitor+antiestrogen or aromatase inhibitor C) Acne, seborrhea, hirsutism, androgenic alopecia (responds adversely to androgenic activity)

1. Inhibitor of type 5 17β-hydroxysteroid dehydrogenase
2. Inhibitor of type 5 17β-hydroxysteroid dehydrogenase+antiandrogen
3. Inhibitor of type 5 17β-hydroxysteroid dehydrogenase+5α-reductase inhibitor
4. Inhibitor of type 5 17β-hydroxysteroid dehydrogenase+5α-reductase inhibitor+antiandrogen D) Polycystic ovarian syndrome (responds adversely to androgenic stimulation)

1. Inhibitor of type 5 17β-hydroxysteroid dehydrogenase
2. Inhibitor of type 3 17β-hydroxysteroid dehydrogenase+Inhibitor of type 5 17β-hydroxysteroid dehydrogenase
3. Inhibitor of type 3 17β-hydroxysteroid dehydrogenase
4. Inhibitor of type 5 17β-hydroxysteroid dehydrogenase+antiandrogen
5. Inhibitor of type 3 17β-hydroxysteroid dehydrogenase+Inhibitor of type 5 17β-hydroxysteroid dehydrogenase+antiandrogen
6. Inhibitor of type 3 17β-hydroxysteroid dehydrogenase+antiandrogen E) Breast cancer (responds favorably to androgenic activity, adversely to estrogenic activity)

1. Inhibitor of type 5 17β-hydroxysteroid dehydrogenase+ antiestrogen
2. Inhibitor of type 5 17β-hydroxysteroid dehydrogenase+ antiestrogen+androgenic compound
3. Inhibitor of type 5 17β-hydroxysteroid dehydrogenase+ antiestrogen+LHRH agonist (or antagonist)
4. Inhibitor of type 5 17β-hydroxysteroid dehydrogenase+ antiestrogen+LHRH-agonist (or antagonist)+ androgenic compound F) Endometriosis, leiomyoma (responds adversely to estrogenic activity)
1. Inhibitor of type 5 17β-hydroxysteroid dehydrogenase
2. Inhibitor of type 5 17β-hydroxysteroid dehydrogenase+ antiestrogen or inhibitor of aromatase
3. Inhibitor of type 5 17β-hydroxysteroid dehydrogenase+ LHRH-agonist (or antagonist)
4. Inhibitor of type 5 17β-hydroxysteroid dehydrogenase+ LHRH-agonist (or antagonist)+antiestrogen or aromatase inhibitor G) Precocious puberty (male and female) (responding adversely to androgenic activity)
1. Inhibitor of type 5 17β-hydroxysteroid dehydrogenase
2. Inhibitor of type 5 17β-hydroxysteroid dehydrogenase+ LHRH agonist (or antagonist) (male only)
3. Inhibitor of type 5 17β-hydroxysteroid dehydrogenase+ antiandrogen
4. Inhibitor of type 5 17β-hydroxysteroid dehydrogenase+ antiandrogen+LHRH agonist (or antagonist) (male only)
5. Inhibitor of type 5 17β-hydroxysteroid dehydrogenase+ inhibitor of type 3 17β-hydroxysteroid dehydrogenase (male only)
6. Inhibitor of type 3 17β-hydroxysteroid dehydrogenase
7. Inhibitor of type 3 17β-hydroxysteroid dehydrogenase+ LHRH agonist (or antagonist) (male only)
8. Inhibitor of type 3 17β-hydroxysteroid dehydrogenase+ antiandrogen
9. Inhibitor of type 3 17β-hydroxysteroid dehydrogenase+ antiandrogen+LHRH agonist (or antagonist) (male only)

When type 5 17β-hydroxysteroid inhibitors are used in accordance with the invention, either alone or as part of one of the combination therapies described herein, the attending clinician desirably will target patient serum concentration of the type 5 inhibitor between 0.5 ng/ml and 100 ng/ml, preferably between 1 ng/ml and 20 ng/ml, and most preferably between 1 ng/ml and 10 ng/ml. Serum concentration may be measured by LC/MS. When administered orally, the dosage which is usually effective to provide the desired serum levels is between 1.0 mg and 1,000 mg of active ingredient per day per 50 kg of body weight, preferably between 10 mg and 500 mg and most preferably between 10 mg and 100 mg. However, dosage should vary with the bioavailability of the chosen inhibitor and with individual patient response. For example, when EM-1394, or EM-1404 are chosen, oral dosage is preferably between 5 mg and 500 mg per day per 50 kg body weight, more preferably between 10 mg/day and 300 mg/day, for example between 20 mg/day and 100 mg/day. The attending clinician should monitor individual patient response and metabolism and adjust patient dosage accordingly. When administered by injection, a lesser dosage is usually appropriate, e.g. 10 mg to 100 mg per day per 50 kg of body weight.

When type 3 17β-hydroxysteroid inhibitors are used in accordance with the invention, either alone or as part of one of the combination therapies described herein, the attending clinician desirably will target patient serum concentration of the type 3 inhibitor between 0.5 ng/ml and 100 ng/ml, preferably between 1 ng/ml and 20 ng/ml and most preferably between 1 ng/ml and 10 ng/ml. When administered orally, the dosage is preferably between 1.0 mg and 1,000 mg of active ingredient per day per 50 kg of body weight, preferably between 5 mg and 500 mg and most preferably between 10 mg and 100 mg. However, the attending clinician should monitor individual patient response and metabolism and adjust patient dosage accordingly.

All of the active ingredients used in any of the therapies discussed herein may be formulated in pharmaceutical compositions which include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example one or more active ingredients are to be formulated in a single pharmaceutical composition. In other embodiments of the invention, a kit is provided which includes at least two separate containers wherein, the contents of at least one container differs in whole or in part from the contents of at least one other container with respect to active ingredients contained therein. Two or more different containers are used in these combination therapies of the invention. Combination therapies discussed herein also include use of one active ingredient of the combination in the manufacture of a medicament for the treatment (or prevention) of the disease in question where the treatment or prevention further includes the other active ingredient(s) or strategy of the combination. Some embodiments of the methods of treating or preventing disease discussed herein, utilize the type 5 and/or type 3 inhibitors of 17β-hydroxysteroid dehydrogenase discussed herein (i.e. the molecular structures discussed herein).

It is believed that, in some situations, the desirability of using an inhibitor of type 5 17β-hydroxysteroid dehydrogenase implies the desirability of also using an inhibitor of type 3 17β-hydroxysteroid dehydrogenase and vice versa, depending upon the expression level of both types in implicated tissues. Type 3 17β-hydroxysteroid dehydrogenase is mainly expressed in the testis while type 5 17β-hydroxysteroid dehydrogenase is mainly expressed in liver, adrenal glands, prostate, ovary, skin, mammary gland, testis, and in a series of peripheral tissues. LHRH agonists and LHRH antagonists may be used interchangeably to suppress either testicular or ovarian hormonal secretions by known techniques, except where preferences are otherwise stated herein.

In other embodiment, pharmaceutical composition for combination therapy may contain one type 5 17β-hydroxysteroid dehydrogenase inhibitor and at least one of other active ingredients selected from the group consisting of type 3 17β-hydroxysteroid dehydrogenase inhibitor, antiestrogen, antiandrogen, aromatase inhibitor and 5α-reductase inhibitor.

In another embodiment, pharmaceutical composition for combination therapy contains one type 3 17β-hydroxysteroid dehydrogenase inhibitor and at least one of the other active ingredients selected from the group consisting of type 5 17β-hydroxysteroid dehydrogenase inhibitor, antiestrogen, antiandrogen, aromatase inhibitor and 5α-reductase inhibitor.

In another embodiment, kits for combination therapy may contain in two or more containers, one type 5 17β- hydroxysteroid dehydrogenase inhibitors and at least one of other active ingredients selected from the group consisting of type 3 17β-hydroxysteroid dehydrogenase inhibitor, antiestrogen, antiandrogen, aromatase inhibitor, 5α-reductase inhibitor, and an LHRH agonist or antagonist.

In another embodiment, kits for combination therapy may contain in two or more containers one type 3 17β-hydroxysteroid dehydrogenase inhibitors and at least one of other active ingredients selected from the group consisting of type 5 17β-hydroxysteroid dehydrogenase inhibitor, antiestrogen, antiandrogen, aromatase inhibitor, 5α-reductase inhibitor, and an LHRH agonist or antagonist.

It is desired that activation of glucocorticoid receptors be minimized when administering the active ingredients of the invention. In preferred embodiments, active ingredients have no more effect on glucocorticoid receptors than is provided by megestrol acetate.

Type 5 17β-HSD, 3β-HSD and AR in human prostate. In order to obtain precise information on the cellular distribution of type 5 17β-HSD and gain a better knowledge of the role of this enzyme in the human prostate, we performed in situ hybridization and immunocytochemical localization studies in human hyperplastic prostatic tissue (BPH). Normal human prostate tissue and the epithelial prostate cell line (PrEC) were also investigated by immunostaining. In the same series of experiments, the immunocytochemical localization of 3β-HSD was examined to compare the distribution of the two enzymes which are both involved in the biosynthesis of androgens from DHEA. In order to determine the site(s) of action of the locally produced androgens, we have also identified the immunocytochemical localization of the androgen receptor.

MATERIALS AND METHODS

Tissue preparation. Adult prostatic tissue was obtained from 12 patients with symptomatic benign prostatic hyperplasia (BPH) undergoing transurethral prostatectomy. The specimens were fixed by immersion in 2% glutaraldehyde, 4% formaldehyde and 3% dextran in 0.05 M phosphate buffer (pH 7.4). After 4 h, the specimens were processed and embedded in paraffin or frozen at −700° C. Four paraffin blocks of normal human prostate, fixed in 4% formaldehyde (age of patients between 37 and 73) were kindly provided by Dr. Bernard Tetu, Dep. of Pathology, Hotel-Dieu de Quebec.

Cultured cells. Normal prostate epithelial cells PrEC 5500-1 were cultured in PrEGM medium (Clonetics) and harvested after the third passage using a rubber policeman. The cells were then fixed in 2% glutaraldehyde, 4% formaldehyde and 3% dextran in 0.05M phosphate buffer for 20 min and centrifuged at 700 rpm for 5 min. After removing the supernatant, 2% agarose in 0.05 M phosphate buffer was added to the pellet at 55° C. (the volume of agarose was twice the volume of the pellet). After mixing the cells with agarose, the pellet was solidified at 4° C. and immersed in the same fixative for two hours, then washed, processed and paraffin embedded.

In situ hybridization. Two different procedures were used for in situ hybridization of BPH tissue. In the first one, 10 μm sections were cut from frozen tissue with a cryostat and processed. The second procedure will be described in detail elsewhere (El-Alfy et al, unpublished data). In brief, thick paraffin sections (20 μm) were cut and the unmounted sections were deparaffinized in toluene. The sections were subsequently rehydrated, postfixed in 2% glutaraldehyde, 4% formaldehyde and 3% dextran in 0.05M phosphate buffer and washed in the same buffer containing 7.5% glycine. Hybridization of the floating sections was performed overnight at 40° C. with a $^3$H-UTP riboprobe. Following hybridization, they were postfixed in osmium tetroxide, flat-embedded in Epon and cut at 0.7 μm with an ultramicrotome. Both frozen (10 μm) and semithin (0.7 μm) sections were coated with liquid photographic emulsion (Kodak NTB-2) and processed after 14 (semithin sections) or 28 days (frozen sections) of exposure.

Sense and antisense riboprobes were generated by in vitro transcription from the p-Bluescript phagemid containing a cDNA insert of 35 nucleotides of the human type 5 17β-HSD. [$^{35}$S]- and [$^3$H]-UTP riboprobes were used for hybridization with the frozen and floating deparaffinized sections, respectively.

Immunocytochemistry. Twelve paraffin-embedded BPH samples, four normal prostate specimens and PrEC cells in paraffin blocks were serially cut at 4 μm. Sections were incubated overnight at 4° C. with the human type 5 17β-HSD antiserum diluted at 1:1000 in Tris-saline, pH 7.6. The sections were then washed and incubated at room temperature for 4 h with peroxidase-labelled goat anti-rabbit γ-globulin (Hyclone, Logon, Utah.) diluted 1:500. Endogenous peroxidase activity was eliminated by preincubation with 3% $H_2O_2$ for 30 min and peroxidase was then revealed during incubation with 10 mg of 3,3-diaminobenzidine in 100 ml of Tris-saline buffer containing 0.03% $H_2O_2$. The intensity of staining was controlled under the microscope. The sections were then counterstained with hematoxylin. On other sections, immunostaining was performed using a commercial kit (Vectastain ABC Kit; Vector Laboratories, Burlingame, Calif.) and diaminobenzidine was used as the chromogen to visualize the biotin streptavidin-peroxidase complex. A microwave retrieval technique was applied for the androgen receptor staining Control experiments were performed on adjacent sections by substituting non-immunized rabbit serum (1:1000). In the case of type 5 17β-HSD antiserum (diluted 1:1000), immunoabsorption with an excess ($10^{-6}$ M) of the synthetic peptide used to raise the antibodies was also performed. The number of stained cells (type 5 17β-HSD) and nuclei (AR) were counted from colored photographs and their number presented in Table 1. The intensity of staining was compared and evaluated between the different stained cell types of the prostate on the same section. Similarly, the density of silver grains was compared between the labeled cells on the same section. The intensity of immunostaining and in situ hybridization reaction was presented in Table 2. Paraffin sections of cultured cells were inmuunostained using type 5 17β-HSD antiserum as mentioned above and the number of immunostained cells presented as a percentage of stained cells.

Antibody Preparation

Type 5 17β-HSD. The type 5 17β-HSD peptide sequence N-GLDRNLHYFNSDSFASHPNYPYS located at amino acid position 297 to 320 of the human type 5 17β-HSD was synthesized by "Le Service de Sequence de Peptides de l'Est du Québec" (SSPEQ) (CHUL Research Center, Quebec, Canada) and purified by HPLC. New Zealand rabbits (2.5 Kg) received a subcutaneous injection of 100 μg of the peptide solubilized in 1 ml phosphate saline buffer containing 50% of complete Freund's adjuvant. The animals received at one-month intervals two successive booster injections with 50 μg of the peptide in 1 ml of incomplete Freund's adjuvant. Two weeks after the last injection, the rabbits were killed and the blood collected. The antiserum was obtained by decantation and separation by centrifugation, then affinity purified and stored at −80° C.

Specificity of the antiserum was examined by immunoblot analysis. In brief, human embryonal kidney cells (293)

were transfected with CMV-neo vectors expressing human type 5 17β-HSD, types 1 and 3 3α-HSD and types 1 and 2 5α-reductase, respectively. Stable transfectants were selected by their resistance to $10^{-7}$M G418. Positive clones were confirmed by their ability to efficiently transform the appropriate substrate (Luu-The, et al. unpublished data). Forty micrograms of protein of the homogenate of each cell line were electrophoresed on a 5–15% sodium dodecyl sulfate (SDS)-polyacrylamide gel, before being transferred to the nitrocellulose filter using a Bio-Rad apparatus for 4 h at 60V. The blot was treated 3 times with 5% fat-free milk in PBS containing 0.1% Nonidet P-40 for 30 min. The antiserum developed against the type 5 17β-HSD peptide was diluted to 1/1000 and the blot was then incubated at 4° C. for 18 h in the diluted antiserum. The blot was then washed three times with PBS containing 5% fat-free milk and 0.1% Nonidet P-40. After incubation with horseradish peroxidase-conjugated anti-rabbit IgG in solution for 2 h, the membrane was washed and bound antibodies were detected with ECL detection reagents (Amersham) and finally the membrane was exposed to Hyperfilm.

3β-HSD. The antiserum used for immunocytochemical studies was raised by immunizing rabbits with purified human placental 3β-HSD. This antiserum has been widely used to localize the enzyme in tissues of several species including the human.

Androgen Receptor (AR). AR rabbit antiserum was generated against a synthetic peptide corresponding to the first 20 amino acid residues of the N-terminal domain of the human and rat AR. The antiserum was purified by immunoprecipitation and did not show any crossreactivity with estrogen or progesterone receptors. This antiserum was kindly provided by Dr. Théo H. van der Kwast, Dept. of Pathology, Erasmus University Rotterdam, The Netherlands.

RESULTS

Type 5 17β-HSD

Figure 1B:
Figure 1C:
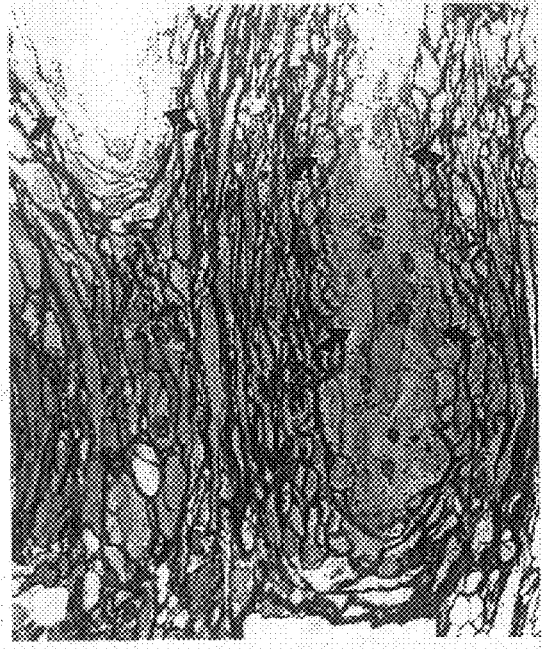
Figure 1D:

In situ hybridization. In the prostate specimens hybridized with the [$^3$H]-labeled type 5 17β-HSD probe, all basal cells are intensively labeled while the luminal secretory cells are poorly labeled (FIG. 1a). In the fibromuscular stroma, none or only few silver grains are located over smooth muscle cells, while the fibroblasts dispersed throughout the stroma or in association with the wall of blood vessels are well labeled (FIG. 1c). Interestingly, the endothelial cells lining blood vessels are strongly labeled. The smooth muscle cells and fibroblasts of the tunica media and adventitia show variable labeling intensity. When the hybridization was performed using $^3$H-labelled sense riboprobe as control, only a few scattered silver grains were detected over the epithelium (FIG. 1b) and blood vessels (FIG. 1d). The results obtained using [$^{35}$S]-UTP riboprobes (not shown) were found to be similar to the above mentioned results.

Immunostaining

Figure 2:
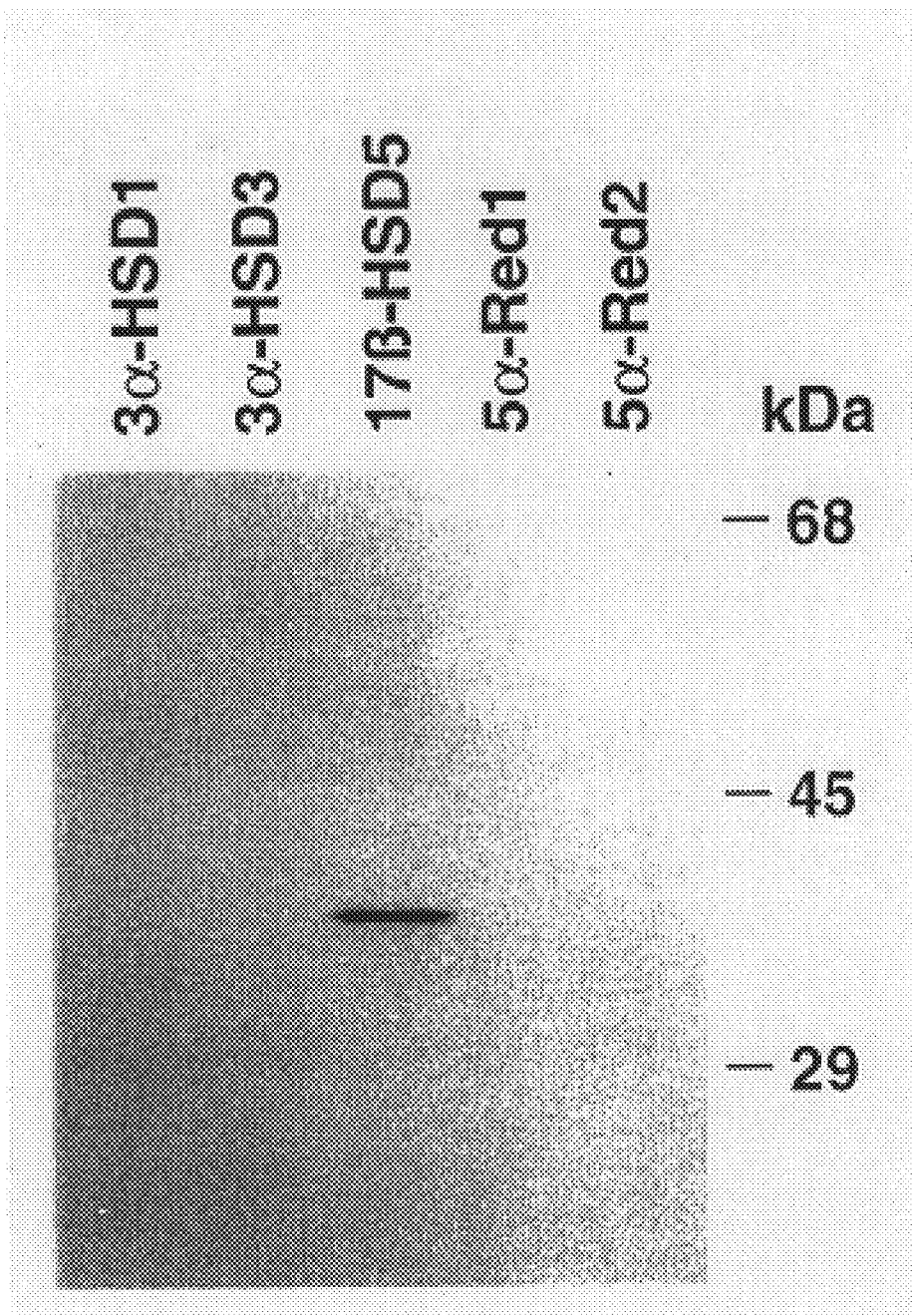
FIG. 2 shows the specificity of the antiserum used in the immunostaining of type 5 17β-HSD. Transfected human kidney cells (293) with human type 5 17β-HSD, types 1 and 3 3α-HSD and types 1 and 2 5α-reductase, were used for immunoblot analysis. The results indicate that the antiserum specifically reacts with type 5 17β-HSD. Types 1 and 3 3α-HSD which share 84 and 86% amino acid identity with type 5 17β-HSD, respectively, and types 1 and 2 5α-reductase, two other androgen-synthesizing enzymes present at high concentration in prostatic tissue were used as controls.
Figure 3A:
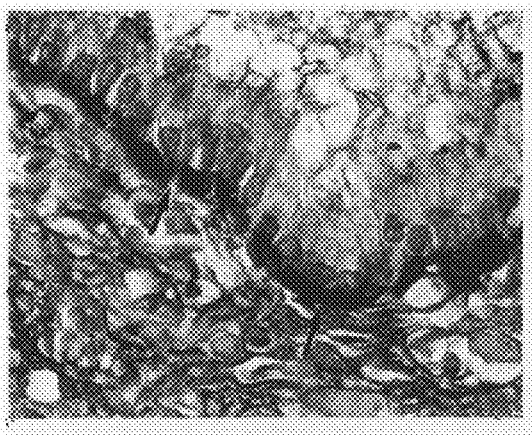
FIGS. 3a to 3e show paraffin sections of normal human prostate and cultured epithelial cells (PrEC 5500-1) immunostained with antibody to type 5 17β-HSD (×800).
Figure 3B:
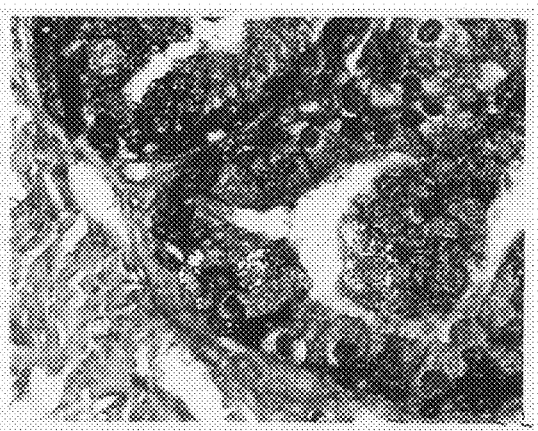
Figure 3C:
Figure 4A:
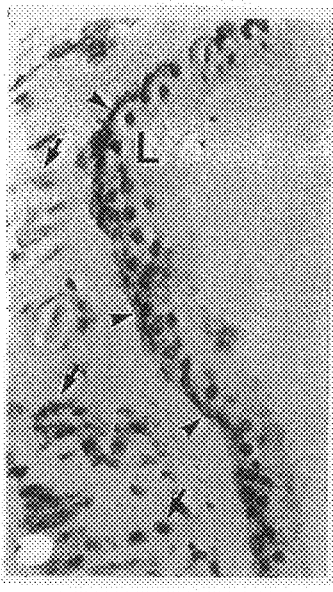
FIGS. 4a to g show paraffin sections of BPH tissue immunostained with antibody to type 5 17β-HSD.
Figure 4B:
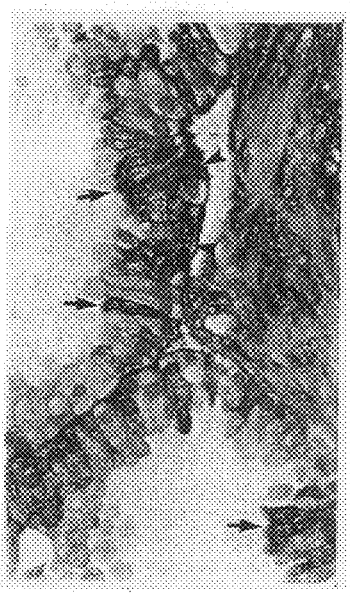
Figure 5A:
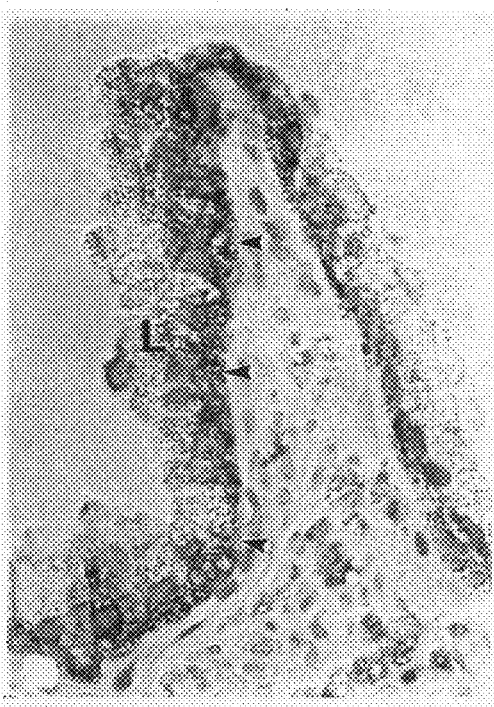
FIGS. 5a to e show paraffin sections of BPH tissue immunostained with antibodies for type 5 17β-HSD (a), 3β-HSD (b) and androgen receptor (c, d and e) (×800).
Figure 5B:
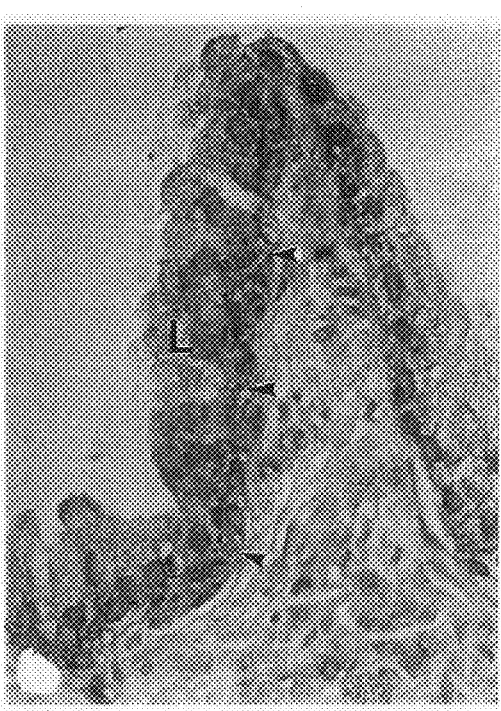

Type 5 17β-HSD Distribution. As illustrated in FIG. 2, immunoblot analysis indicates that the antiserum specifically reacts with type 5 17β-HSD. In fact, no crossreactivity was detected, either with types 1 or 3 3α-HSD which share 84% and 86% identity with type 5 17β-HSD, respectively, or with types 1 and 2 5α-reductase, two enzymes which are abundant in prostatic tissue When immunostained paraffin sections of BPH specimens and normal prostatic tissues were examined, similar results were found (FIGS. 3a–c, 4a,b). Some variation in the distribution and intensity of immunostaining was observed between the twelve BPH specimens examined. A similar degree of variation was found between the normal prostate specimens, and the overall pattern was similar between normal and BPH prostatic tissues. The variation in staining of the epithelium lining the tube-alveoli was observed not only between the different specimens but also between the tube-alveoli of the same specimens. A constant finding was the positive reaction detected in the stromal fibroblasts while the smooth muscle cells were not stained (FIGS. 3a–c, FIGS. 4a, b, d). Strong staining was consistently found in the basal cells of the epithelium (FIGS. 3a, 4a, 5a). In contrast, the luminal secretory cells exhibited highly variable and usually low immunoreactivity. In fact, in most alveoli (about 85%), no luminal cells were labelled (FIGS. 3a, 4a) while about 10% of alveoli contained a low detectable but positive reaction of all luminal cells (FIG. 3b), the basal cells being always strongly labelled. In some alveoli (about 5%), labeling of few luminal cells and all basal cells (Table 1) was found (FIGS. 3c, 4b).

Figure 4C:
Figure 4D:
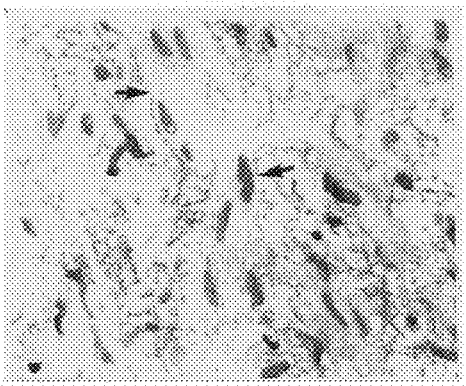
Figure 4E:
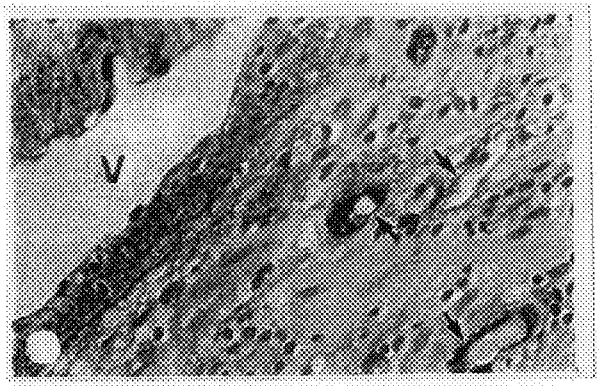
Figure 4F:
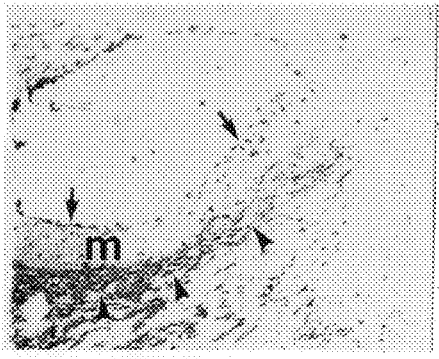
Figure 4G:
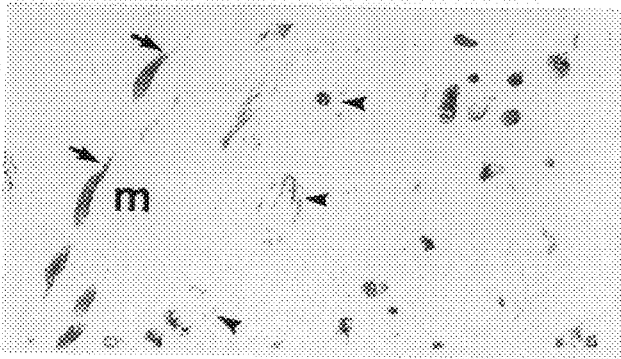

When the antiserum was immunoabsorbed with the antigen or when non-immunized rabbit serum was used, no staining could be detected (FIG. 4c). The endothelial cells of small (FIG. 4e) and large (FIGS. 4e–g) blood vessels were strongly immunoreactive. The staining reaction was variable in the smooth muscle cells of the tunica media, while fibroblasts of the tunica adventitia were intensively stained. Veins appeared strongly labelled because of the large number of fibroblasts in their walls (FIG. 4e). In arteries, the tunica media was lightly stained (FIGS. 4f, g), while the tunica adventitia was well stained (FIG. 4f).

Figure 3D:
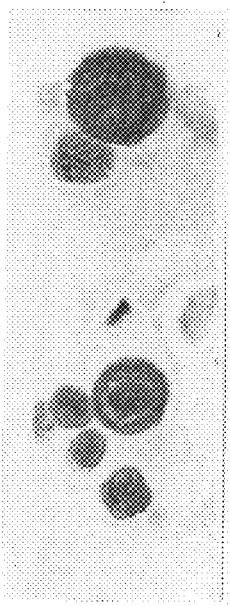
Figure 3E:
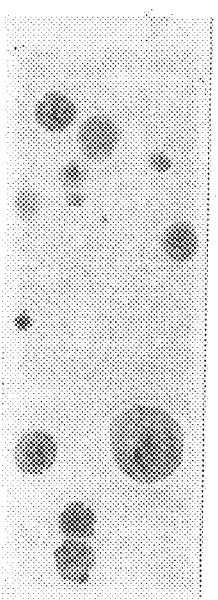

When the paraffin sections of cultured epithelial cells were examined after immunostaining using type 5 17β-HSD antibody, 58% of these cells were found to be positively stained (FIG. 3d).

3β-HSD Distribution. The results obtained following immunostaining with antibody to 3β-HSD were found to be very similar to those generated with the type 5 17β-HSD antiserum (FIGS. 5a, b). Although the staining reaction was generally weaker for 3β-HSD, the cellular distribution of the enzyme corresponds very well to that described above for type 5 17β-HSD. In the glandular epithelium of the prostate, all the basal cells were generally labelled while, in the luminal cells, the staining was variable, being intense in some cells and weak or absent in most others. In the stroma, the staining was restricted to the cytoplasm of fibroblasts. As observed for type 5 17β-HSD, specific immunolabelling was found in the endothelial cells and fibroblasts of blood vessel walls including arteries, veins and capillaries. In all the 3β-HSD-containing cells, the staining was restricted to the cytoplasm, no significant nuclear staining being detected.

Figure 5C:
Figure 5D:
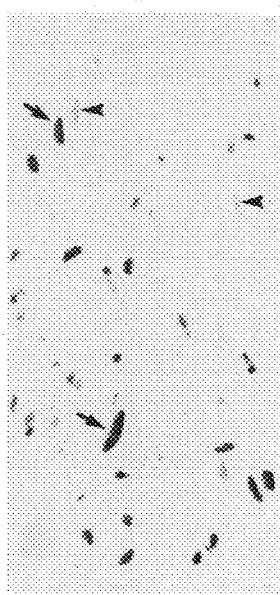
Figure 5E:
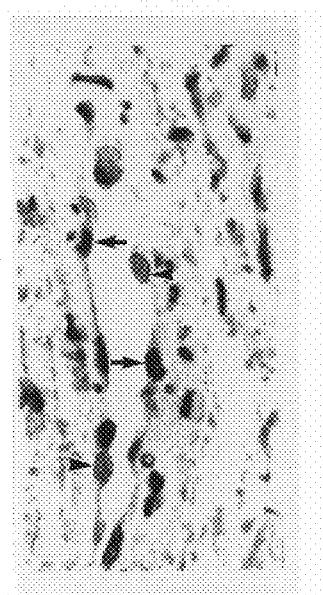
Figure 8:
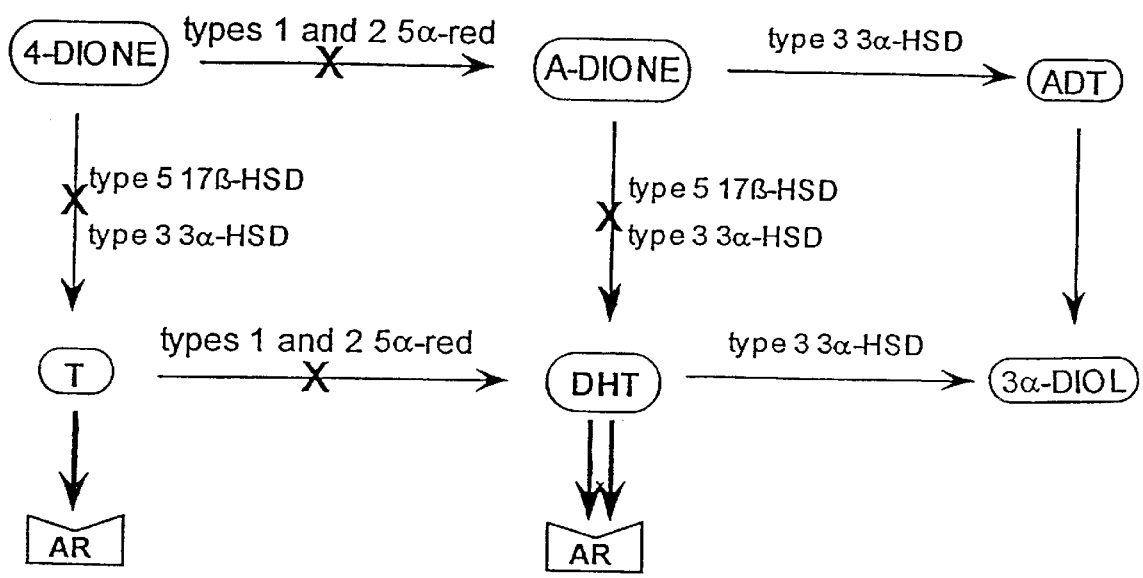
FIG. 8 is a schematic diagram showing the biosynthetic pathway of active androgens in human prostatic tissue.

Androgen receptor distribution. The AR appears exclusively localized in the nuclei of prostate cells in all the specimens examined. In the epithelium, immunostaining is detected in almost all the nuclei of the luminal cells, while most of the basal cell nuclei do not exhibit positive staining (FIG. 5c and Table 1). In the stroma, the majority of nuclei of the fibromuscular cells are labelled, but unstained nuclei of smooth muscle cells are also observed (FIG. 5d and Table 1). In the blood vessels, several nuclei of the endothelial cells lining the lumen are positive, but some display no reaction (FIG. 5e). In the tunica media of the arteries, most of the nuclei of the smooth muscle cells are stained while some remain negative (not shown). Comparable results were obtained for the nuclei of fibrocytes of the tunica adventitia.

DISCUSSION

In the present study, we have used two complementary approaches, namely in situ hybridization (using BPH specimens) and immunocytochemistry (using BPH, normal prostate tissues and cultured epithelial cells), to identify the cells which express type 5 17β-HSD in the human prostate. This enzyme was found mainly in the basal cells of the tube-alveoli, the fibroblasts of the stroma and blood vessels as well as in the endothelial cells of the blood vessels (Table 1, 2). This double approach permits to identify not only type 5 17β-HSD mRNA but also the enzyme itself. The present data are in agreement with results from this laboratory, which indicated the presence of androgenic 17β-HSD activity in human and rhesus monkey prostates.

The stratified epithelium lining the tube-alveoli is divided into two layers, namely the basal layer made of low cuboidal cells and a layer of columnar secretory cells (luminal cells). It is generally believed that prostatic stem cells are located in the basal cell layer. As revealed by both in situ hybridization and immunocytochemistry, the basal cells are expressing type 5 17β-HSD at a much higher level than the luminal cells. In fact, while many luminal cells exhibited some detectable hybridization signal, they have shown a high degree of variation and usually low level of immunostaining (FIGS. 3c, 4b). On the other hand, the majority of alveoli contained only strongly labeled basal cells (FIGS. 3a, 4a). However, in a few alveoli, staining was detectable either in some luminal cells (FIGS. 3c, 4b) or in all of them (FIG. 3b). This variable staining in luminal cells might be explained by variations in the biosynthetic activity among alveoli or among different luminal cells in the same alveolus. It is quite possible that the low level of the protein in an unknown proportion of luminal cells cannot be detected by immunocytochemistry. It is noteworthy to mention that very similar results were obtained with the antibody against 3β-HSD.

The cultured epithelial cells PrEC 5500-1 have shown approximately the same pattern of expression of type 5 17β-HSD as the epithelial cells of BPH and normal prostate tissues. We assumed that the cultured epithelial cells are a mixture of basal and luminal cells. Therefore, it is not surprising to find that only 58% of these cells expressed the enzyme.

It has been reported that types 1 and 2 5α-reductases are produced by both epithelial and stromal cells in the prostate. Using immunocytochemistry, it has been shown that staining for type 2 5α-reductase could be seen in both basal and luminal epithelial cells. On the basis of studies performed with human prostatic in vitro models, it has been suggested that the basal cells exert a stem cell role. On the other hand, in vivo studies performed in the rat prostate during maturation have established that both basal and secretory luminal cells are self-replicating cell types. The presence of type 5 17β-HSD, 3β-HSD and 5α-reductase isoenzymes in the basal cells suggests that this cell type is actively involved in androgen production and cannot be considered as being only a precursor of the luminal secretory cells.

Using cells transfected with the cDNAs of different types of 17β-HSD, Luu-The et al have shown that types 1 and 3 17β-HSD catalyze the reduction of estrone to estradiol and 4-androstenedione to testosterone, respectively. They have also shown that these enzymes are substrate and orientation selective. In fact, type 3 and 5 17β-HSDs have the same selective function, but type 3 was detected only in the testis and was not found in the human prostate. Therefore, in the prostate, the reduction of 4-Dione to testosterone is probably due to type 5 17β-HSD. Since type 5 17β-HSD and 3β-HSD are both highly expressed in basal cells while the androgen receptor is mainly present in luminal cells (FIG. 5c and Table 1), it is tempting to suggest that testosterone synthesized in the basal cells reaches the luminal cells in a paracrine fashion to be ultimately transformed into DHT in the luminal cells where the androgenic action is exerted and AR is highly expressed. DHT made in the luminal cells by the action of 5α-reductase would then exert its action in the luminal cells themselves, thus meeting the definition of intracrine activity. The involvement of two cell types in the biosynthesis of steroids has already been shown to occur in the ovary. In fact, in the ovary, C19 steroids (androstenedione and testosterone) synthesized by theca interna cells are transferred to granulosa cells where they are aromatized into estrogens. The present data suggest the possibility of a similar two-cell mechanism of androgen formation in the human prostate: testosterone is first synthesized in the basal cells before diffusing into the luminal cells where transformation into DHT occurs.

In the present study, the fibroblasts present in the stroma as well as those associated with blood vessels are shown to contain type 5 17β-HSD mRNA as well as the immunoreactive type 5 17β-HSD and 3β-HSD enzymes. The two types of 5α-reductase have also been detected in this cell type by various techniques. The role of the steroidogenic enzymes in fibroblasts remains to be established but since androgen receptors are present in the nuclei of most stromal cells (Table 1), it is likely that DHT could act in the fibroblasts themselves (intracrine action) to modulate the activity of these cells.

Previous study has shown that in normal prostate, basal cells contained the mRNA for AR but lacked an immunodetectable receptor while in the luminal cells both mRNA and immunodetectable receptor were present. These authors have also stated that AR localization in BPH was identical to that observed in normal prostate. Similarly, it has been found that the nuclei of the luminal and the majority of stromal cells were positive to androgen receptor antibody in hyperplastic as well as normal prostatic glands. It has also been found that primary, as well as metastatic, prostate carcinomas show nuclear staining for AR and that the proportion and the intensity of immunostained human prostate tumor cells decreased in the more aggressive tumors. The basal cells also express nuclear AR in normal and hyperplastic tissue. However, the receptor was most frequently expressed at lower levels in the basal cells when compared with the staining intensity detected in secretory luminal cells. It has been found that AR immunostaining was localized to the nuclei of luminal cells but was weak or absent in basal cells and of variable intensity in the stromal cells. In the present study, while 94% of luminal cells expressed nuclear AR, only 37% of basal cells were stained (Table 1) and their staining intensity was lower than that of luminal cells (Table 2). The majority (66%) of fibromuscular stromal cells also expressed AR. The findings of the present study are thus in agreement with previous studies performed in human, rat and mouse tissue. Since the stroma/epithelium cell ratio is higher in the hyperplastic prostate, it can be hypothesized that androgens synthesized intracellularly by fibroblasts can influence the production of collagen and elastic fibers in the stroma.

An unexpected finding was the localization of type 5 17β-HSD and 3β-HSD in blood vessel walls, including the endothelial cells. This observation, however, correlates well with recent findings from this laboratory indicating the presence of types 1 and 2 5α-reductase mRNA in blood vessel walls in human prostate and skin. Recently, we have also observed that immunoreactive type 5 17β-HSD is present in the blood vessel walls in other tissues such as skin, breast, uterus and ovary. The role of the steroidogenic intracrine enzymes in these vascular structures is unknown.

Previously, it has been shown that androgen receptors were present in vascular smooth muscle and endothelial cells of human skin. It has been found that nuclear androgen receptors were present in the muscular layer of almost all arteries within the rat testis. It has been suggested that testicular blood vessels could be a target organ for androgens and may mediate some of the effects of androgens on testicular microcirculation. Furthermore, in the developing human prostate, AR was positive in the nuclei of vascular smooth muscle and endothelial cells. Since androgen receptors are present in the endothelial cells, smooth muscle cells and fibroblasts of blood vessels (Table 1), it may be speculated that locally biosynthesized androgens are exerting a paracrine and/or intracrine action in blood vessels. It is also possible that these androgens are, up to an unknown extent, released into the blood circulation to reach some target tissues, although their global impact is likely to be minimal. Interestingly, it has been shown that in the rat prostate, testosterone could induce a rapid response of the vasculature which precedes growth of the glandular epithelium. It might well be that cells of the blood vessels are stimulated by locally made androgens to produce paracrine growth factors, which could promote the growth of the secretory epithelium. Further studies are required to elucidate the role of the steroids synthesized by cells of the blood vessel walls. The present data clearly indicate new mechanisms of androgen formation, which may play an important role, not only in normal human prostate physiology, but also in the pathogenesis of benign prostatic hyperplasia and possibly prostate cancer.

TABLE 1

Percentage of immunostained cells of BPH and normal human prostate tissues.

| | | Type 5 17β-HSD (%) | Androgen receptor (%) |
|---|---|---|---|
| Epithelium | Basal cells | 100 | 37 |
| | Luminal cells | 22 (*) | 94 |
| Fibro-muscular stromal cells | Fibrocytes | 100 | 66 (o) |
| | Smooth muscle cells | 0 | |
| Blood vessels | Endothelial cells of tunica intima | 100 | 75 |
| | Smooth muscle cells of tunica media | 35 (•) | 82 |
| | Fibrocytes of tunica adventitia | 100 | 56 |

(*) This percentage represents the number of stained luminal cells only in about 5% of the alveoli, as shown in FIGS. 3c and 4b. The vast majority of alveoli (about 85%) did not show stained luminal cells while all luminal cells were stained in about 10% of them (FIG. 3b).
(o) The number represents the percentage of stained nuclei of fibrocytes and smooth muscle cells together.
(•) The staining intensity is low in the stained smooth muscle cells of tunica media (as seen in FIG. 4f) as compared with other stained cells.

TABLE 2

Intensity of the in situ hybridization and immunostaining reactions in the different cell types of BPH and normal human prostatic tissue.

| | | In situ hybridization Type 5 17β-HSD | Immunostaining | | |
|---|---|---|---|---|---|
| | | | 3β-HSD | Type 5 17β-HSD | Androgen receptor |
| Epithelium | Basal cells | +++ | +++ | +++ | +/- |
| | Luminal cells | + | +/- | +/- | +++/- |
| Fibro- | Fibrocytes | +++ | +++ | +++ | +++/- |

TABLE 2-continued

Intensity of the in situ hybridization and immunostaining reactions in the different cell types of BPH and normal human prostatic tissue.

| | | In situ hybridization Type 5 17β-HSD | Immunostaining | | |
|---|---|---|---|---|---|
| | | | 3β-HSD | Type 5 17β-HSD | Androgen receptor |
| muscular stromal cells | Smooth muscle cells | - | - | - | +++/- |
| Blood vessels | Endothelial cells of tunica intima | +++ | +++ | +++ | +++/- |
| | Smooth muscle cells of tunica media | +/- | +/- | +/- | +++/- |
| | Fibrocytes of tunica adventitia | +/- | ++ | ++ | +++/- |

The presence of silver grains or positive immunostaining reaction is indicated by (+), graded from 1 to 3. The number of (+) thus corresponding to the intensity of the reaction and takes into account the percentage of labelled cells.
The absence of reaction is indicated by (-).
The possibility of being positively or negatively labeled is indicated by (+/-).

Human skin hybridized with type 5 17β-HSD cRNA probe. In a preliminary experiment of in situ hybridization, human skin has been hybridized with type 5 17β-HSD antisense and sense riboprobes the results show that the epidermis (except stratum corneum) (FIGS. 6a,b), the wall of blood vessels (FIGS. 6c,d), hair follicles as well as most of the fibrocytes of the dermis are labeled.

When paraffin sections immunostained with a specific antibody to type 5 17β-HSD were examined, the obtained results were in agreement with the in situ hybridization results. In the epidermis, few cells of the stratum granulosum were found to be heavily immunostained than all the other stained cells.

Localization of type 5 17β-HSD in human mammary gland. Immunostaining of tissue sections from several normal human mammary gland show that the epithelial cells lining the ducts and the alveoli are not stained while the connective tissue surrounding cells are stained. In the only one examined case of mammary gland tumor, the tumor cells themselves were not labeled but the epithelial cells lining the ducts were found to be heavily labeled (FIGS. 7a, b).

Localization of type 5 17β-HSD in monkey ovary. In a preliminary study of in situ hybridization, one of the growing follicles was examined. Theca cells, granulosa cells and the oocyte were found to be labeled.

PREFERRED INHIBITORS OF TYPE 5 17β-HYDROXYSTEROID DEHYDROGENASE

Set forth in the tables below are lists of compounds which we have found to be useful as inhibitors of type 5 17β-hydroxysteroid dehydrogenase. The tables also include in many instances further tests of a particular compound on other important parameters such as androgenic and antiandrogenic activity and the effect of a compound on androgen receptors, androgen-sensitive cells, and other effects more fully explained below. In each of tables 1–5 and 1'–5' below that do not include a "prime" (') in its table number, details of molecular structure of preferred inhibitors are set forth. The corresponding table with a "prime" (') in its table number shows certain information about the functional efficacy of each tested compound. The numbers in the column headings correspond to a description at the end of all of the tables regarding what information is reported in each column and how it is determined. Entries left blank are not yet determined.

TABLE 1

| Name | Example | A | $R^1 = CH_3$ | $R^6$ | $R_a$ | $R_b$ | Δ1 | Δ6 |
|---|---|---|---|---|---|---|---|---|
| EM-996 | 1 | $CH_3$ | NO | $CH_3$ | —$C_5H_{10}$ | Br | NO | YES |
| EM-1029 | 1 | $CH_3$ | " | $CH_3$ | —$C_4H_8$ | Cl | " | YES |
| EM-950 | 1 | $CH_3$ | " | $CH_3$ | cyclo$C_5H_8$ | H | " | YES |
| CS-245 | 2 | $CH_3$ | YES | $CH_3$ | —$C_3H_6$ | H | " | YES |
| EM-1003 | 1 | $CH_3$ | NO | $CH_3$ | —$C_3H_6$ | Br | " | YES |
| EM-1291 | 1 | $CH_3$ | " | $CH_3$ | —$CH_2$ | ΦOCH$_3$(p) | YES | YES |
| EM-1280 | 1 | $CH_3$ | " | $CH_3$ | —$C_2H_4$ | H | YES | YES |
| CS-251 | 1 | $CH_3$ | " | $CH_3$ | —$(CH_2)_3$ | COCH$_3$ | NO | YES |
| CS-243 | 2 | $CH_3$ | YES | $CH_3$ | —$C_2H_4$ | H | " | YES |
| EM-1195-CS | 1 | $CH_3$ | NO | $CH_3$ | —$C_4H_8$ | F | " | YES |
| EM-928 | 1 | $CH_3$ | " | $CH_3$ | —$C(CH_3)_2$ | H | " | YES |
| CS-241 | 1 | $CH_3$ | " | $CH_3$ | —$C_3H_6$ | Cl | " | YES |
| EM-1182-CS | 1 | $CH_3$ | " | $CH_3$ | —$C_5H_{10}$ | F | " | YES |
| EM-1173-CS | 1 | $CH_3$ | " | $CH_3$ | —$C_4H_8$ | Br | " | YES |
| EM-1171 | 1 | $CH_3$ | " | $CH_3$ | —$C_5H_{10}$ | Cl | " | YES |
| EM-949 | 1 | $CH_3$ | " | $CH_3$ | —$CH_2$ | Φ | " | YES |
| EM-978 | 1 | $CH_3$ | " | $CH_3$ | cyclo$C_6H_{10}$ | H | " | YES |
| EM-979 | 1 | $CH_3$ | " | $CH_3$ | tBu | H | " | YES |
| EM-1044 | 1 | $CH_3$ | " | $CH_3$ | $CH_2$ | ΦCl(p) | " | YES |
| CS-209 | 2 | $CH_3$ | YES | $CH_3$ | -iso$C_3H_6$ | H | " | YES |
| CS-256 | 1 | $CH_3$ | NO | $CH_3$ | —$CH_2$ | ΦF | " | YES |
| EM-1022 | 2 | $CH_3$ | YES | $CH_3$ | -cyclo$C_5H_8$ | H | " | YES |
| EM-1049 | 1 | $CH_3$ | NO | $CH_3$ | —$CH_2$ | ΦOCH$_3$(p) | " | YES |
| EM-1107 | 1 | $CH_3$ | NO | $CH_3$ | —$CH_2$ | ΦOCOter$C_4H_9$(p) | " | YES |
| EM-952 | 2 | $CH_3$ | YES | $CH_3$ | —$CH_2$ | H | " | YES |
| Megestrol Acetate | nil | $CH_3$ | NO | $CH_3$ | —$CH_2$ | H | " | YES |
| EM-995 | 2 | $CH_3$ | YES | $CH_3$ | —$C_5H_{10}$ | H | " | YES |
| EM-994 | 2 | $CH_3$ | YES | $CH_3$ | —$C_4H_8$ | H | " | YES |
| CS-220 | 2 | $CH_3$ | YES | $CH_3$ | -tBu | H | " | YES |
| CS-206 | 2 | $CH_3$ | NO | $CH_3$ | —$CH_2$ | H | " | YES |
| EM-1023 | 2 | $CH_3$ | NO | $CH_3$ | —$CH_2$ | H | " | YES |
| EM-1059 | 2 | $CH_3$ | YES | $CH_3$ | —$CH_2$ | Φ | " | YES |
| EM-1159 | 9 | N—$(CH_3)_2$ | NO | $CH_3$ | —$CH_2$ | H | " | YES |
| EM-1181-CS | 9 | —N(CH$_3$)C$_2$H$_5$ | NO | $CH_3$ | —$(CH_2)_3$ | Cl | " | YES |
| EM-1079 | 9 | —N(CH$_3$)C$_2$H$_5$ | NO | $CH_3$ | —$CH_2$ | H | " | YES |
| EM-1165 | 9 | —N(CH$_3$)C$_4$H$_9$ | NO | $CH_3$ | —$CH_2$ | H | " | YES |
| EM-1158 | 9 | —N(CH$_3$)Φ | NO | $CH_3$ | —$CH_2$ | H | " | YES |
| EM-1230-CS | 9 | —N(CH$_3$)C$_2$H$_5$ | NO | $CH_3$ | —$C(CH_3)_2$ | H | " | YES |
| EM-1264 | 9 | —N(CH$_3$)CH$_3$ | NO | $CH_3$ | —$C_2H_4$ | H | " | YES |
| EM-1268 | 9 | —N(CH$_3$)CH$_3$ | NO | $CH_3$ | —$C_3H_6$ | H | " | YES |
| EM-1315 | 9 | —N(CH$_3$)CH$_2$Φ | NO | $CH_3$ | —$C_3H_6$ | H | " | YES |
| EM-1316 | 9 | —N(CH$_3$)CH$_2$Φ | NO | $CH_3$ | —$C_2H_4$ | H | " | YES |
| EM-1326-CS | 9 | —N(CH$_3$)C$_3$H$_7$ | NO | $CH_3$ | —$C_2H_4$ | H | " | YES |
| EM-1327 | 9 | —N(CH$_3$)C$_3$H$_7$ | NO | $CH_3$ | —$C_3H_6$ | H | " | YES |
| EM-1317 | 9 | —N(CH$_3$)C$_3$H$_5$ | NO | $CH_3$ | —$C_2H_4$ | H | " | YES |
| EM-1318 | 9 | —N(CH$_3$)C$_3$H$_5$ | NO | $CH_3$ | —$C_3H_6$ | H | " | YES |
| EM-1321-CS | 9 | —N(CH$_3$)CH(CH$_3$)$_2$ | NO | $CH_3$ | —$C_2H_4$ | H | " | YES |
| EM-1322-CS | 9 | —N(CH$_3$)CH$_2$CH(CH$_3$)$_2$ | NO | $CH_3$ | —$C_2H_4$ | H | " | YES |
| EM-1323-CS | 9 | —N(CH$_3$CH$_2$CH(CH$_3$)$_2$ | NO | $CH_3$ | —$C_3H_6$ | H | " | YES |
| EM-1271-CS | 9 | —N(CH$_3$)CH$_3$ | NO | $CH_3$ | —$C(CH_3)_2$ | H | " | YES |
| EM-1010 | 11 | —OCH$_3$ | NO | $CH_3$ | —$CH_2$ | H | " | YES |
| EM-1106 | 10 | CH$_2$Φ | NO | $CH_3$ | —$CH_2$ | H | " | YES |
| EM-923 | 1 | $CH_3$ | NO | $CH_3$ | $C_4H_8$ | H | " | YES |
| EM-948 | 1 | $CH_3$ | NO | $CH_3$ | —$(CH_2)_2$cyclo $C_5H_8$ | H | " | YES |
| EM-1007 | 4 | $CH_3$ | NO | $CH_3$ | $C_3H_6CO_2CH_2$ | H | " | YES |
| EM-1081 | 10 | $C_3H_7$ | NO | $CH_3$ | —$CH_2$ | H | " | YES |

TABLE 1-continued

| Name | Example | A | $R^1 = CH_3$ | $R^6$ | $R_a$ | $R_b$ | Δ1 | Δ6 |
|---|---|---|---|---|---|---|---|---|
| EM-1007 | 1 | $CH_3$ | NO | $CH_3$ | —$C_5H_{10}$— | H | NO | YES |
| EM-918 | 1 | $CH_3$ | NO | $CH_3$ | —$C_2H_4$— | H | NO | YES |
| EM-920 | 1 | $CH_3$ | NO | $CH_3$ | $C_3H_6$ | H | NO | YES |
| EM-946 | 1 | $CH_3$ | NO | $CH_3$ | $C_2H_4$ | φ | NO | YES |
| EM-1018 | 2 | $CH_3$ | YES | $CH_3$ | $C_6H_{10}$ | H | NO | YES |
| EM-1048 | 1 | $CH_3$ | NO | $CH_3$ | $C_7H_{14}$ | Br | NO | YES |
| EM-1075 | Not reported | $CH_3$ | NO | $CH_3$ | $C_3H_6$ | COφ | NO | YES |
| EM-1081 | 10 | $C_3H_7$ | NO | YES | $CH_2$ | H | NO | YES |
| EM-1103 | Not reported | $CH_3$ | NO | NO | $CH_2$ | H | NO | YES |
| EM-1127 | 1 | $CH_3$ | NO | YES | $C_5H_{10}$ | H | NO | YES |
| EM-1188 | 2 | $CH_3$ | YES | YES | $CH_2$ | φF(p) | NO | YES |
| EM-1175 | 10 | —$C(CH_3)C_2H_5$ | NO | YES | $CH_2$ | H | NO | YES |
| EM-1141 | 10 | $C(CH_3)_3$ | NO | YES | $CH_2$ | H | NO | YES |
| EM-1209 | 10 | $C_4H_9$ | NO | YES | $CH_2$ | H | NO | YES |
| EM-1204 | 2 | $CH_3$ | YES | YES | $CH_2$ | φF(p) | NO | YES |
| EM-1213 | 2 | $CH_3$ | YES | YES | $CH_2$ | φ$OCH_3$(p) | NO | YES |
| EM-1216 | 2 | $CH_3$ | YES | YES | $CH_2$ | φBr(p) | NO | YES |
| EM-1217 | 2 | $CH_3$ | YES | YES | $CH_2$ | φCl(p) | NO | YES |
| EM-1224 | 2 | $CH_3$ | YES | YES | $CH_2$ | φ$OC_2H_5$(p) | NO | YES |
| EM-1231 | 1 | $CH_3$ | NO | YES | —$CH(CH_3)$— | φ | NO | YES |
| EM-1240 | 2 | $CH_3$ | YES | YES | $CH_2$ | φ$CH_3$(o) | NO | YES |
| EM-1241 | 2 | $CH_3$ | YES | YES | $CH_2$ | φ$CH_3$(p) | NO | YES |
| EM-1242 | 2 | $CH_3$ | YES | YES | $CH_2$ | φ$CH_3$(m) | NO | YES |
| EM-4243 | 2 | $CH_3$ | YES | YES | $CH_2$ | φ$CF_3$(p) | NO | YES |
| EM-4246 | 1 | $CH_3$ | NO | YES | $CH_2$ | φ$CH_3$(p) | NO | YES |
| EM-1253 | 1 | $CH_3$ | NO | YES | —$C(C_2H_2)$— | φ | NO | YES |
| EM-1263-CS | 2 | $CH_3$ | YES | YES | $CH_2$ | φ$NO_2$(p) | NO | YES |
| EM-1279-CS | 2 | $CH_3$ | YES | YES | —$C(C_2H_2)$— | φ | NO | YES |
| EM-1282-CS | 1 | $CH_3$ | NO | YES | —$C(CH_3)_2$— | φ | NO | YES |
| EM-1290 | 2 | $CH_3$ | YES | YES | $CH_2$ | φ-di-($OCH_3$)(m) | NO | YES |
| EM-1292-CS | 2 | $CH_3$ | YES | YES | $CH_2$ | φOH(p) | NO | YES |
| EM-1297 | 1 | $CH_3$ | NO | YES | $CH_2$ | φOH(p) | NO | YES |
| EM-1312 | 1 | $CH_3$ | NO | YES | $CH_2$ | φ$CH_3$(o) | NO | YES |
| EM-1339-CS | 1 | $CH_3$ | NO | YES | —$CH(CH_3)$— | φ$OCH_3$(p) | NO | YES |
| EM-1340 | 1 | $CH_3$ | NO | YES | $CH_2$ | φF(o) | NO | YES |
| EM-1343 | 1 | $CH_3$ | NO | YES | $CH_2$ | φ$OCH_3$(o) | NO | YES |
| EM-910 | 1 | $CH_3$ | NO | YES | $CH_2$ | H | YES | YES |
| EM-991 | 1 | $CH_3$ | YES | YES | $CH_2$ | H | YES | YES |
| EM-1294 | 1 | $CH_3$ | NO | YES | $CH_2$ | φ | YES | YES |
| EM-1308 | 1 | $CH_3$ | NO | YES | —$C(CH_3)_2$— | H | YES | YES |
| EM-1309 | 1 | $CH_3$ | NO | YES | $C_3H_6$ | H | YES | YES |
| EM-1319-CS | 1 | $CH_3$ | NO | YES | —$C(CH_3)_2CH_2$— | H | YES | YES |

TABLE 1'

| Name | 1 Oral Bio-availability AUC 0-7h (ng/mL.h) | 2 Inhibition Type V 17β-HSD IC$_{50}$ (nM) | (% Inh. At 3.10$^{-7}$) | 3 Reversibility (%) of 3.10$^{-6}$) control) | 4 Inhibition Type 1 17β-HSD Activity IC$_{50}$ (nM) [% Inh. at 3.10$^{-8}$M] | 5 Inhibition Type 2 17β-HSD Activity IC$_{50}$ (nM) [% Inh. at 3.10$^{-8}$M] | 6 Inhibition Type 3 17β-HSD Activity IC$_{50}$ (nM) [% Inh. at 3.10$^{-8}$M] | 7 Inhibition Type 1 3α-HSD Activity IC$_{50}$ (nM) [% Inh. at 3.10$^{-8}$M] | 8 Inhibition Type 3 3α-HSD Activity IC$_{50}$ (nM) [% Inh. at 3.10$^{-8}$M] | 9 Androgenic and Antiandrogenic Activity Shionogi Basal | E$^{-7}$ | 10 DHT E$^{-6}$ | [IC$_{50}$ (nM)] | 11 ZR-75-1 Activity Basal E$_2$ | E$^{-8}$ | 12 E$^{-6}$ | E$^{-3}$ | 13 % Inhibition Androgen Receptor *(E$^{-7}$ E$^{-5}$) | E$^{-8}$ | E$^{-6}$ | 14 % Inhibition Progesterone Receptor *(E$^{-7}$ E$^{-5}$) | E$^{-8}$ | E$^{-6}$ | 15 % Inhibition Glucocorticoid Receptor *(E$^{-7}$ E$^{-5}$) | E$^{-8}$ | E$^{-6}$ | 16 % Inhibition Estrogen Receptor *(E$^{-7}$ E$^{-5}$) | E$^{-8}$ | E$^{-6}$ |
|---|---|---|---|---|---|---|---|---|---|---|---|---|---|---|---|---|---|---|---|---|---|---|---|---|---|---|---|---|---|---|
| EM-996 | ND | 1.8 ± 0.1 | | | | | | | | −11 | −32 | −78 −126 [158 ± 59] | 0 | −8 | −35 | −53 | 0 | 0 | 1 | 9 | 88 | 0 | 67 | | 0 | 0 |
| EM-1029 | 10 ± 2.5 | 3 | | | [13] | | | | | −24 | −15 | −123 −146 [9.3] | 0 | −10 | −62 | −64 | 1 | 1 | 1 | 5 | 80 | 8 | 98 | | 0 | 0 |
| EM-950 | ND | 2.7 ± 0.3 9 | | | | | | | | −23 | −25 | −79 −110 [44 ± 5] | −17 | 0 | −39 | −46 | 13 | 4 | 1 | 2 | 58 | 18 | 95 | | 0 | 0 |
| CS-245 | 18 ± 5 | 3.2 ± 0.1 | | | | | | | | −28 | −34 | −106 −109 [12] | ND | ND | ND | ND | 5 | 71 | 0 | 0 | 26 | 0 | 43 | | 0 | 2 |
| EM-1003 | 16 ± 5 | 3.5 ± 0.3 | | | [67] | | | | | −17 | −15 | −83 −101 [35 ± 6] | −9 −13 | | −67 −73 | | 0 | 67 | 9 | 9 | 85 | 2 | 79 | | 0 | 0 |
| EM-1291 | 94 ± 23 | 7 ± 1 | 27 | | | | | | | −8 | −44 | −13 −48 | ND | | ND | | 0 | 0 | 0 | 0 | 33 | 1 | 69 | | 0 | 0 |
| EM-1280 | 18 ± 6.6 | 3 ± 0.5 | 31 | | [59] | | | | | 0 | 0 | −94 −111 [23] | ND | | ND | | 0 | 44 | 0 | 0 | 39 | 9 | 93 | | 1 | 0 |
| CS-251 | ND | 11 ± 1 | | | | | | | | 5 | −11 | −22 −109 −23 | −60 | | −47 | | 0 | 3 | 0 | 0 | 12 | 0 | 57 | | 1 | 1 |
| CS-243 | 11 ± 2.5 | 3.5 ± 0.1 | | | | | | | | −13 | −23 | −102 −129 0 | −60 | | −57 | | 0 | 33 | 0 | 0 | 27 | 0 | 29 | | 1 | 0 |
| EM-1195 CS | 31 ± 5.5 | 4 ± 0.5 | | | [40] | | | | | −27 | −34 | −105 −110 −11 [11] | 18 | | −38 | −40 | 1 | 62 | 0 | 0 | 70 | 3 | 90 | | 0 | 0 |
| EM-928 | ND | 3.7 ± 0.3 | | | [27] | | | | | 0 | −13 | −60 −107 0 [67 ± 6] | −11 | −50 | −84 | | 4* | 72* | 11* | 90* | | 21* | 99* | | 0* | 3 |
| CS-241 | ND | 4.1 ± 0.6 | | | [50] | | | | | 5 | 23 | −91 −93 [10] | ND | | ND | | 10 | 91 | 0 | 61 | | 9 | 96 | | 1 | 0 |
| EM-1182 | ND | 4.4 ± 0.4 | | | [28] | | | | | −14 | −16 | −94 −109 [18.5] | ND | | ND | | 0 | 51 | 18 | 78 | | 5 | 90 | | 0 | 0 |
| EM-1173-CS | 4.1 ± 1.4 | 4.6 ± 1.1 | | | [14] | | | | | −17 | −54 | −70 −121 197 [33] | 196 | 0 | 0 | | 0 | 28 | 6 | 76 | | 5 | 89 | | 0 | 0 |
| EM-1171 | 4 ± 1.3 | 5.3 ± 0.3 | | | [64] | | | | | −6 | −30 | −82 −111 98 [61] | 182 | 0 | −29 | | 1 | 36 | 5 | 76 | | 8 | 90 | | 0 | 0 |
| EM-949 | ND | 5.5 ± 1.1 | | | [39] | | | | | −19 | −13 | −45 −102 −8 [193 ± 41] | 0 | −23 | −17 | | 2* | 41* | 37* | 97* | | 11* | 94* | | 0* | 0 |
| EM-978 | ND | 6.8 ± 0.4 | | | [20] | | | | | −31 | −48 | −79 −132 −13 [93 ± 10] | −13 | −35 | −48 | | 7 | 17 | 0 | 48 | | 14 | 93 | | 0 | 0 |
| EM-979 EM-1044 | ND 53 ± 23 | 7.2 ± 0.7 5.1 | | | | | | | | −15 4 | −41 −27 | −39 −117 −12 −21 −87 0 | 0 19 | −26 0 | −40 −24 | | 6 0 | 7 0 | 1 74 | 41 74 | | 7 0 | 88 81 | | 0 0 | 0 0 |
| CS-209 | ND | 10.5 ± 2.7 | | | [62] | | | | | 13 | −30 | −67 −122 | 0 | 0 | −44 | −48 | 2 | 8 | 2 | 38 | | 2 | 29 | | 0 | 0 |

TABLE 1'-continued

| Name | 1 Oral Bio-availability AUC 0–7h (ng/mL.h) | 2 Inhibition Type V 17β-HSD IC₅₀ (nM) [% Inh. At 3.10⁻⁷] | 3 Reversibility (%) of control) | 4 Inhibition Type 1 17β-HSD Activity IC₅₀ (nM) [% Inh. at 3.10⁻⁸M] | 5 Inhibition Type 2 17β-HSD Activity IC₅₀ (nM) [% Inh. at 3.10⁻⁸M] | 6 Inhibition Type 3 17β-HSD Activity IC₅₀ (nM) [% Inh. at 3.10⁻⁸M] | 7 Inhibition Type 1 3α-HSD Activity IC₅₀ (nM) [% Inh. at 3.10⁻⁸M] | 8 Inhibition Type 3 3α-HSD Activity IC₅₀ (nM) [% Inh. at 3.10⁻⁸M] | 9 Androgenic and Antiandrogenic Activity Shionogi Basal / E⁻⁶ | 10 DHT E⁻⁷ / E⁻⁶ / [IC₅₀(nM)] / E⁻⁸ | 11 ZR-75-1 Basal / E⁻⁸ | 12 Activity E₂ E⁻⁶ / E⁻³ | 13 % Inhibition Androgen Receptor *(E⁻⁷ E⁻⁵) / E⁻⁸ / E⁻⁶ | 14 % Inhibition Progesterone Receptor *(E⁻⁷ E⁻⁵) / E⁻⁸ / E⁻⁶ | 15 % Inhibition Glucocorticoid Receptor *(E⁻⁷ E⁻⁵) / E⁻⁸ / E⁻⁶ | 16 % Inhibition Estrogen Receptor *(E⁻⁷ E⁻⁵) / E⁻⁸ / E⁻⁶ |
|---|---|---|---|---|---|---|---|---|---|---|---|---|---|---|---|---|
| CS-256 | 33 ± 7 | 5 ± 1 | | | | | | | −10 −24 / −12 −35 | −17 −89 / −68 −155  0 [82] | 20 | ND −40 | 4 5 / 0 9 | 2 75 / 0 25 | 2 51 / 0 44 | 0 0 |
| EM-1022 | ND | 5.4 ± 0.6 | | | | | | | | [128] | | | | | | |
| EM-1049 | 83 ± 16 | 9 ± 1 | | | [62] | | | | 10 −33 | −12 66  0 | 0 | −52 −71 | 0 1 | 0 63 | 0 62 | 0 0 |
| EM-1107 | ND | 17 ± 3 | | | [64] | | | | −9 −6 | 3 −34 | ND | | 4 3 | 0 48 | 1 64 | 0 0 |
| EM-952 | ND | 17.4 ± 5.1 | | | | | | | −19 −4 | −88 −104  0 [41 ± 4] | 0 | −17 −13 | 0 20 | 4 50 | 1 14 | 3 3 |
| Megestrol Acetate | 92 ± 17 | 17.4 ± 2.8 | | | | | | | ND | [10 ± 1.8] | ND | −70 −81 | 9* 92* / 5 39 | 36* 97* / 3 77 | 17* 98* / 0 82 | 01* 08* / 0 0 |
| EM-995 | ND | 21.3 ± 6.7 | | | [42] | | | | −4 −21 / −10 −27 | −51 −121 −29 / −82 −122  0 [75 ± 10] | −9 −8 | −12 −19 / −10 −35 | 0 10 / 0 19 | 5 72 / 6 64 | 0 27 / 0 33 | 0 0 / 0 3 |
| EM-994 | ND | 31 ± 5.1 | | | | | | | 0 −31 | 15 −106  0 [674] | 11 | −25 −11 | 0 0 | 0 20 | 0 23 | 2 0 |
| CS-220 | ND | 31 ± 33 | | | [32] | | | | −18 −40 / −11 −14 | −75 −118  0 / −108 −133 14 [40] | 0 0 / 61 66 | −12 −40 / 61 66 | 5 15 / 0 43 | 0 29 / 0 44 | 0 45 / 0 85 | 0 1 / 0 0 |
| CS-206 | ND | 40 ± 8.5 | | | [80] | | | | | | | | | | | |
| EM-1023 | ND | 50 ± 7 | | | [20] | | | | | | | | | | | |
| EM-1059 | ND | (70  92) | | | | | | | −7 −12 | −34 −18 | ND | ND | 0 3 | 0 41 | 0 23 | 0 0 |
| EM-923 | 10 ± 2 | (94  96) | | | [31] | | | | 10 5 / −26 −19 / 0 −31 | −73 −94  0 / −49 −105  0 / −14 −76 −8 | −12 0 0 | 60 −105 / −29 −36 / −41 −52 | 0 3 / 0 0 | 0 41 / ND 0 | 0 23 / ND 0 | 0 1 / ND 0 |
| EM-948 | ND | (91  93) | | | [49] | | | | | | | | | | | |
| EM-1007 | 16.4 | (81  86) | | | | | | | | | | | | | | |
| EM-1159 | 452 ± 170 | 14 ± 2 | | | [45] | | | | 15 −14 | 1 −71 | ND | ND | 1 1 | 2 4 | 8 59 | 0 1 |
| EM-1181-CS | 130 ± 35 | 5 ± 1 | | | | | | | −6 −12 | −89 −104 | ND | ND | 0 27 | ND 0 | 2 70 | 7 0 |
| EM-1079 | 252 ± 61 | 17 ± 1 | | | [28] | | | | −15 −23 | 7 −71 | ND | ND | 0 0 | 0 0 | 3 45 | 0 0 |
| EM-1165 | 24 ± 3.6 | 2.5 ± 5 | | | | | | | 5 −17 | −14 −102 [232] | ND | ND | 0 1 | 0 7 | 0 26 | 0 0 |
| EM-1158 | ND | 25 ± 5 | | | | | | | 0 0 | −16 −82 | ND | ND | 1 2 | 0 6 | 0 53 | 0 0 |
| EM-1230-CS | 82 ± 15 | 8 ± 1 | | | [65] | | | | −9 −30 | 1 −66 | ND | ND | 1 0 | 0 0 | 1 45 | 0 3 |

TABLE 1'-continued

| Name | 1 Oral Bioavailability AUC 0-7h (ng/mL.h) | 2 Inhibition Type V 17β-HSD IC₅₀ (nM) | 2 (% Inh. At 3.10⁻⁷) | 3 Reversibility (%) of control) | 4 Inhibition Type 1 17β-HSD Activity IC₅₀ (nM) [% Inh. at 3.10⁻⁸M] | 5 Inhibition Type 2 17β-HSD Activity IC₅₀ (nM) [% Inh. at 3.10⁻⁸M] | 6 Inhibition Type 3 17β-HSD Activity IC₅₀ (nM) [% Inh. at 3.10⁻⁸M] | 7 Inhibition Type 1 3α-HSD Activity IC₅₀ (nM) [% Inh. at 3.10⁻⁸M] | 8 Inhibition Type 3 3α-HSD Activity IC₅₀ (nM) [% Inh. at 3.10⁻⁸M] | 9 Androgenic and Antiandrogenic Activity Shionogi Basal | 9 E⁻⁷ | 9 E⁻⁶ | 10 DHT Basal | 10 E⁻⁷ | 10 E⁻⁶ [IC₅₀ (nM)] | 11 ZR-75-1 Activity Basal E₂ | 11 E⁻⁸ | 12 Basal E₂ E⁻³ | 13 % Inhibition Androgen Receptor *(E⁻⁷ E⁻⁵) | 13 E⁻⁸ | 13 E⁻⁶ | 14 % Inhibition Progesterone Receptor *(E⁻⁷ E⁻⁵) | 14 E⁻⁸ | 14 E⁻⁶ | 15 % Inhibition Glucocorticoid Receptor *(E⁻⁷ E⁻⁵) | 15 E⁻⁸ | 15 E⁻⁶ | 16 % Inhibition Estrogen Receptor *(E⁻⁷ E⁻⁵) | 16 E⁻⁸ | 16 E⁻⁶ |
|---|---|---|---|---|---|---|---|---|---|---|---|---|---|---|---|---|---|---|---|---|---|---|---|---|---|---|---|---|---|---|
| CS EM-1264 | 257 ± 81 | 6 ± 1 | | | | | | | | -25 | -56 | | -25 | -108 | | ND | | ND | 0 | 0 | | 0 | 5 | | 7 | 80 | | 3 | 0 | |
| EM-1268 | 58 ± 10 | 5.8 | | | | [51] | | | | -25 | -45 | | -86 [535] | -113 | | ND | | ND | 0 | 12 | | 1 | 7 | | 14 | 90 | | 1 | 6 | |
| EM-1315 | ND | 6.8 | | | | [80] | | | | -32 | -62 | | -66 [101] | -121 | | ND | | ND | 1 | 13 | | 0 | 14 | | 18 | 66 | | 0 | 0 | |
| EM-1316 | 23 ± 5 | 11.6 ± 3 | | | | [88] | | | | -23 | -64 | | -32 | -118 | | ND | | ND | 0 | 1 | | 0 | 13 | | 3 | 84 | | 0 | 0 | |
| EM-1326-CS | ND | 6 ± 1 | | | | [87] | | | | -28 | -56 | | -47 | 116 | | ND | | ND | 0 | 0 | | 0 | 4 | | 3 | 47 | | 0 | 0 | |
| EM-1327 | ND | 6 ± 1 | | | | [75] | | | | -41 | -59 | | -101 | -119 | | ND | | ND | 0 | 19 | | 0 | 7 | | 12 | 40 | | 0 | 0 | |
| EM-1317 | ND | 8 ± 1 | | | | [81] | | | | -20 | -56 | | -32 | -113 | | ND | | ND | 0 | 0 | | 0 | 0 | | 1 | 64 | | 0 | 0 | |
| EM-1318 | ND | 7 ± 1 | | | | [80] | | | | -30 | -53 | | -85 | -121 | | ND | | ND | 0 | 15 | | 0 | 11 | | 5 | 68 | | 0 | 0 | |
| EM-1321-CS | ND | 7 ± 2 | | | | [84] | | | | 0 | 0 | | -25 | -99 | | ND | | ND | 0 | 1 | | 0 | 5 | | 15 | 29 | | 0 | 0 | |
| EM-1322-CS | ND | 4 ± 1 | | | | [83] | | | | -38 | -40 | | -53 | -112 | | ND | | ND | 0 | 2 | | 0 | 3 | | 0 | 45 | | 0 | 0 | |
| EM-1323-CS | ND | 5 ± 1 | | | | [79] | | | | -33 | -44 | | -92 | -116 | | ND | | ND | 1 | 15 | | 0 | 11 | | 9 | 30 | | 1 | 0 | |
| EM-1271-CS | 181 ± 28 | 4.1 | | | | [73] | | | | -25 | -42 | | 0 | -68 | | ND | | ND | 0 | 0 | | 0 | 0 | | 9 | 82 | | 0 | 0 | |
| EM-1010 | ND | 31 ± 3.4 | (83 | 88) | | | | | | -26 | -25 | | -83 [58 ± 9] | -109 | 0 | 0 | | -50 -60 | 0 | 28 | | 0 | 47 | | 0 | 45 | | 0 | 0 | |
| EM-1106 | 29 ± 1.6 | | | | | [62] | | | | -19 | -33 | | -65 [55] | -108 | | ND | | ND | 1 | 23 | | 1 | 24 | | 1 | 50 | | 1 | 0 | |
| EM-917 | | | | | | | | | | -4 | -19 | | -69 | -109 | | | | | | | | | | | | | | | | |
| EM-918 | | | | | | | | | | 43 | 11 | | -50 | -97 | | | | | | | | | | | | | | | | |
| EM-920 | | | | | | | | | | 88 | 78 | | -26 | -50 | | | | | | | | | | | | | | | | |
| EM-946 | | (58 | 82) | | | | | | | -25 | -7 | | -39 | -82 | | | | | | | | | | | | | | | | |
| EM-1018 | | | | | | | | | | -9 | -36 | | -24 | -142 | | | | | | | | | | | | | | | | |

TABLE 1'-continued

| Name | 1 Oral Bioavailability AUC 0-7h (ng/mL.h) | 2 Inhibition Type V 17β-HSD IC$_{50}$ (nM) [% Inh. At 3.10$^{-7}$ | (% Inh. At 3.10$^{-6}$) | 3 Reversibility (%) of control) | 4 Inhibition Type 1 17β-HSD Activity IC$_{50}$ (nM) [% Inh. at 3.10$^{-8}$M] | 5 Inhibition Type 2 17β-HSD Activity IC$_{50}$ (nM) [% Inh. at 3.10$^{-8}$M] | 6 Inhibition Type 3 17β-HSD Activity IC$_{50}$ (nM) [% Inh. at 3.10$^{-8}$M] | 7 Inhibition Type 1 3α-HSD Activity IC$_{50}$ (nM) [% Inh. at 3.10$^{-8}$M] | 8 Inhibition Type 3 3α-HSD Activity IC$_{50}$ (nM) [% Inh. at 3.10$^{-8}$M] | 9 Androgenic and Antiandrogenic Activity Shionogi Basal | E$^{-7}$ | E$^{-6}$ | 10 DHT E$^{-7}$ | [IC$_{50}$ (nM)] E$^{-6}$ | 11 ZR-75-1 Activity E$^{-6}$ | 12 Basal E$_2$ E$^{-8}$ | E$^{-3}$ | 13 % Inhibition Androgen Receptor *(E$^{-7}$ E$^{-5}$) | E$^{-8}$ | E$^{-6}$ | 14 % Inhibition Progesterone Receptor *(E$^{-7}$ E$^{-5}$) | E$^{-8}$ | E$^{-6}$ | 15 % Inhibition Glucocorticoid Receptor *(E$^{-7}$ E$^{-5}$) | E$^{-8}$ | E$^{-6}$ | 16 % Inhibition Estrogen Receptor *(E$^{-7}$ E$^{-5}$) | E$^{-8}$ | E$^{-6}$ |
|---|---|---|---|---|---|---|---|---|---|---|---|---|---|---|---|---|---|---|---|---|---|---|---|---|---|---|---|---|---|---|
| EM-1048 | | (51 | 84) | | | | | | | -4 | -30 | -18 | -97 | | | | | | | | | | | | | | | | | |
| EM-1075 | | (40 | 90) | | | | | | | 10 | -26 | -10 | -82 | | | | | | | | | | | | | | | | | |
| EM-1081 | | (61 | 82) | | | | | | | -13 | -23 | -94 | -108 | | | | | | | | | | | | | | | | | |
| EM-1103 | | (59 | 86) | | | | | | | -5 | | -40 | -104 | | | | | | | | | | | | | | | | | |
| EM-1127 | | (71 | 91) | | | | | | | 85 | 92 | | | | | | | | | | | | | | | | | | | |
| EM-1188 | | (58 | 88) | | | | | | | -18 | -32 | -24 | -61 | | | | | | | | | | | | | | | | | |
| EM-1175 | | (32 | 86) | | | | | | | -30 | -47 | -35 | -106 | | | | | | | | | | | | | | | | | |
| EM-1141 | | (25 | 79) | | | | | | | 0 | -5 | -8 | -75 | | | | | | | | | | | | | | | | | |
| EM-1209 | | (95 | 94) | | | | | | | -35 | -40 | -53 | -105 | | | | | | | | | | | | | | | | | |
| EM-1204 | | (33 | 88) | | | | | | | 3 | -24 | -22 | -60 | | | | | | | | | | | | | | | | | |
| EM-1213 | | (35 | 83) | | | | | | | -9 | -32 | -22 | -51 | | | | | | | | | | | | | | | | | |
| EM-1216 | | (33 | 77) | | | | | | | -14 | -26 | -22 | -63 | | | | | | | | | | | | | | | | | |
| EM-1217 | | (36 | 81) | | | | | | | -5 | -36 | -21 | -59 | | | | | | | | | | | | | | | | | |
| EM-1224 | | (2 | 22) | | | | | | | -6 | -28 | -18 | -55 | | | | | | | | | | | | | | | | | |
| EM-1231 | | (91 | 96) | | | | | | | -28 | -36 | -58 | -112 | | | | | | | | | | | | | | | | | |
| EM-1240 | | (47 | 89) | | | | | | | -10 | -33 | -8 | -56 | | | | | | | | | | | | | | | | | |
| EM-1241 | | (4 | 53) | | | | | | | -6 | -41 | -3 | -56 | | | | | | | | | | | | | | | | | |
| EM-1242 | | (19 | 78) | | | | | | | -6 | -41 | -12 | -63 | | | | | | | | | | | | | | | | | |
| EM-1243 | | (2 | 16) | | | | | | | -14 | -52 | -28 | -89 | | | | | | | | | | | | | | | | | |
| EM-1246 | | (74 | 95) | | | | | | | -17 | -34 | -25 | -97 | | | | | | | | | | | | | | | | | |

TABLE 1'-continued

| Name | 1 Oral Bio-availability AUC 0-7h (ng/mL.h) | 2 Inhibition Type V 17β-HSD IC$_{50}$ (nM) | [% Inh. At $3.10^{-7}$] | 3 Reversibility (%) of $3.10^{-6}$ control) | 4 Inhibition Type 1 17β-HSD Activity IC$_{50}$ (nM) | 5 Inhibition Type 2 17β-HSD Activity IC$_{50}$ (nM) | 6 Inhibition Type 3 17β-HSD Activity IC$_{50}$ (nM) | 7 Inhibition Type 1 3α-HSD Activity IC$_{50}$ (nM) | 8 Inhibition Type 3 3α-HSD Activity IC$_{50}$ (nM) [% Inh. at $3.10^{-8}$M] | 9 Androgenic and Antiandrogenic Activity Shionogi Basal | $E^{-7}$ | 10 DHT [IC$_{50}$ (nM)] | $E^{-6}$ | 11 ZR-75-1 Activity Basal E$_2$ | 12 $E^{-8}$ | $E^{-3}$ | 13 % Inhibition Androgen Receptor *($E^{-7}$ $E^{-5}$) | $E^{-8}$ $E^{-6}$ | 14 % Inhibition Progesterone Receptor *($E^{-7}$ $E^{-5}$) | $E^{-8}$ $E^{-6}$ | 15 % Inhibition Gluco-corticoid Receptor *($E^{-7}$ $E^{-5}$) | $E^{-8}$ $E^{-6}$ | 16 % Inhibition Estrogen Receptor *($E^{-7}$ $E^{-5}$) | $E^{-8}$ $E^{-6}$ |
|---|---|---|---|---|---|---|---|---|---|---|---|---|---|---|---|---|---|---|---|---|---|---|---|---|
| EM-1253 | | (39 | 85) | | | | | | | −25 | −63 | −41 | −122 | | | | | | | | | | | |
| EM-1263-CS | | (7 | 22) | | | | | | | −13 | −60 | −32 | −115 | | | | | | | | | | | |
| EM-1279-CS | | (10 | 43) | | | | | | | −32 | −52 | −52 | — | | | | | | | | | | | |
| EM-1282-CS | | (91 | 94) | | | | | | | −32 | −59 | −39 | −114 | | | | | | | | | | | |
| EM-1290 | | (9 | 3) | | | | | | | −25 | −10 | −48 | −62 | | | | | | | | | | | |
| EM-1292-CS | | (45 | 87) | | | | | | | −14 | −31 | −19 | −53 | | | | | | | | | | | |
| EM-1297 | | (93 | 95) | | | | | | | −27 | −49 | −17 | −65 | | | | | | | | | | | |
| EM-1312 | | (93 | 96) | | | | | | | −7 | −37 | −28 | −100 | | | | | | | | | | | |
| EM-1339-CS | | (69 | 85) | | | | | | | 0 | −44 | −22 | −97 | | | | | | | | | | | |
| EM-1340 | | (81 | 82) | | | | | | | −5 | −21 | −25 | −102 | | | | | | | | | | | |
| EM-1343 | | (70 | 87) | | | | | | | 7 | −20 | −1 | −68 | | | | | | | | | | | |
| EM-910 | | (44 | 87) | | | | | | | | | | | | | | | | | | | | | |
| EM-991 | | (93 | 94) | | | | | | | | | | | | | | | | | | | | | |
| EM-1294 | | | | | | | | | | | | | | | | | | | | | | | | |
| EM-1308 | | (95 | 96) | | | | | | | 79 | 72 | −63 | 84 | | | | | | | | | | | |
| EM-1309 | | (94 | 95) | | | | | | | | | | | | | | | | | | | | | |
| EM-1319-CS | | | | | | | | | | | | | | | | | | | | | | | | |

TABLE 2

| Name | Example | $\Delta^1$ | $R^6$ | $R^{15\alpha}$ | $R^{16\alpha}$ | $R^{16\beta}$ | $R^{19}$ |
|---|---|---|---|---|---|---|---|
| EM-1183 | 8 | NO | H | H | $C_3H_7$ | F | $CH_3$ |
| EM-1134 | 8 | NO | H | H | $CH_2$-iso$C_3H_7$ | $CH_3$ | $CH_3$ |
| EM-1211 | 5 | NO | H | H | H | $CH_2$-iso$C_3H_7$ | $CH_3$ |
| EM-1061 | 6 | NO | H | H | 16-spiro $C_5H_8$ | | H |
| EM-1273-CS | 5 | NO | H | H | $CH_2$-iso$C_3H_7$ | H | $CH_3$ |
| EM-1097 | 5 | NO | H | H | $C_3H_7$ | H | $CH_3$ |
| EM-1082 | 6 | NO | H | H | 16-spiro $C_6H_{10}$ | | H |
| CS-195 | 6 | NO | H | H | 16-spiro $C_5H_8$ | | $CH_3$ |
| EM-1042 | 8 | NO | H | H | $C_3H_7$ | $CH_3$ | $CH_3$ |
| EM-1077 | 6 | NO | H | H | 16-spiro $C_5H_8$ | | $CH_3$ |
| EM-1151-CS | 8 | (1α-CH) NO | H | H | ⌐⌐ | ⌐⌐ | $CH_3$ |
| EM-922 | 6 | NO | H | H | 16-spiro $C_6H_{10}$ | | $CH_3$ |
| CS-204 | 6 | YES | H | H | 16-spiro $C_6H_{10}$ | | $CH_3$ |
| EM-1261 | 12 | NO | H | $CH_2CH=CH_2$ | H | H | $CH_3$ |
| EM-1277 | 13 | NO | H | H | =CH—$C_2H_5$ | | $CH_3$ |
| EM-1299 | 14 | NO | H | H | spiro bicyclo [3.1.0] hexane | | $CH_3$ |
| SA-208-59 | 15 | NO | H | —$C_3H_6$— | | H | $CH_3$ |
| CS-239 | Not reported | NO | H | H | $CH_3$ | $C_3H_7$ | $CH_3$ |
| EM-1039 | Not reported | YES | H | H | 16-spiro $C_5H_8$ | | $CH_3$ |
| EM-1057 | 6 | NO | $CH_3$ | H | 16-spiro $C_5H_8$ | | $CH_3$ |
| EM-1135 | 8 | NO | H | H | $C_3H_6Cl$ | $CH_3$ | $CH_3$ |
| EM-1155-CS | 8 | NO | H | H | $C_3H_6Br$ | $CH_3$ | $CH_3$ |
| EM-1192 | 8 | NO | H | H | $C_5H_{11}$ | $CH_3$ | $CH_3$ |
| EM-1245 | 12 | NO | H | $C_3H_7$ | H | H | $CH_3$ |
| EM-1257 | 8 | NO | H | H | $C_4H_9$ | F | $CH_3$ |
| EM-1260 | 12 | NO | H | $C_3H_7$ | H | H | $CH_3$ |
| EM-1262 | 8 | NO | H | H | $C_3H_5$ | F | $CH_3$ |
| EM-1272-CS | Not reported | NO | H | H | 16-spiro-$C_5H_8(CH_3)_2$ | | $CH_3$ |
| EM-1313 | 8 | NO | H | H | $C_4H_7$ | H | $CH_3$ |
| EM-1314 | 8 | NO | H | H | $C_3H_5$ | H | $CH_3$ |
| EM-1349-CS | 8 | NO | H | H | $C_3H_3F_2$ | $CH_3$ | $CH_3$ |
| EM-1353 | 13 | NO | H | H | =CHCH$(CH_3)_2$ | | $CH_3$ |
| EM-1359 | 8 | NO | H | H | $C_3H_5$ | Cl | $CH_3$ |
| EM-1361 | 12 | NO | H | $C_4H_7$ | H | H | $CH_3$ |

TABLE 2'

| Name | 1 Oral Bioavailability AUC (ng/mL.h) 0–7 h | 2 Inhibition Type V 17β-HSD IC$_{50}$ (nM) (% Inh. At 3·10$^{-7}$ 3·10$^{-7}$) | | 3 Reversibility (%) of control | 4 Inhibition Type 1 17β-HSD Activity IC$_{50}$ (nM) [% Inh.] at 3·10$^{-6}$ M | 5 Inhibition Type 2 17β-HSD Activity IC$_{50}$ (nM) [% Inh.] at 3·10$^{-6}$ M | 6 Inhibition Type 3 17β-HSD Activity IC$_{50}$ (nM) [% Inh.] at 3·10$^{-6}$ M | 7 Inhibition Type 1 3α-HSD Activity IC$_{50}$ (nM) [% Inh.] at 3·10$^{-6}$ M | 8 Inhibition Type 3 3α-HSD Activity IC$_{50}$ (nM) [% Inh.] at 3·10$^{-6}$ M | 9 Androgenic and Antiandrogenic Activity Shionogi Basal E$^{-7}$ E$^{-6}$ | 10 DHT E$^{-7}$ [IC$_{50}$ (nM)] E$^{-6}$ | 11 ZR-75-1 Activity E$^{-8}$ E$^{-6}$ | 12 Basal E$_2$ 3E$^{-8}$ E$^{-6}$ | 13 % Inhibition Androgen Receptor *(E$^{-7}$ E$^{-5}$) E$^{-8}$ E$^{-6}$ | 14 % Inhibition Progesterone Receptor *(E$^{-7}$ E$^{-5}$) E$^{-8}$ E$^{-6}$ | 15 % Inhibition Glucocorticoid Receptor *(E$^{-7}$ E$^{-5}$) E$^{-8}$ E$^{-6}$ | 16 % Inhibition Estrogen Receptor *(E$^{-7}$ E$^{-5}$) E$^{-8}$ E$^{-6}$ |
|---|---|---|---|---|---|---|---|---|---|---|---|---|---|---|---|---|---|
| EM-1183 | ND | 4.6 ± .4 | | | | | | | | 0 −17 | 0 −51 | ND ND | ND ND | 0 0 1 | *9 45 | 0 12 | 0 0 |
| EM-1134 | ND | 20 ± 4 | | | | | | | | 0 −13 | −36 −85 | ND ND | ND ND | 1 1 7 | 0 13 | 0 2 | 0 1 |
| EM-1211 | ND | (87 95) | | | [34] | [46] | | | | 0 −20 | [471] −7 −18 | −10 −10 | ND ND | 1 0 3 | 0 2 | 1 0 | 0 0 |
| EM-1061 | ND | (85 95) | | | | | | | | 14 −6 | 0 −10 | 0 −20 | 0 −20 | 0 0 0 | 0 0 | 0 0 | 0 1 |
| EM-1273-CS | 85 ± 26 | 9 | | 40 | | [31] | | | | 12 −36 | 9 −43 | 0 0 | 0 −30 | 0 0 0 | 0 0 | 0 1 | 0 0 |
| EM-1097 | 122 ± 5.7 | 10 | | 45 | | [64] | | [53] | [82] | 18 −12 | −3 −71 | −8 10 | 0 0 | 0 5 | 0 0 | 0 0 | 0 1 |
| EM-1082 | ND | 36 ± 11 | | | | [32] | | | | 4 −20 | 0 0 | ND ND | ND ND | 1 0 | 1 2 | 0 0 | 0 0 |
| CS-195 | ND | 19.4 ± 2 | | | | [09] | | | | 0 −18 | −4 −31 | −4 0 | 0 −15 | 0 0 | 0 2 | 0 2 | 0 0 |
| EM-1042 | ND | 35 ± 5 | | | | | | | | 0 −22 | −14 −85 | 0 10 | ND ND | −12 −11 | 0 0 | 0 0 | 3 0 |
| EM-1077 | ND | 35 ± 4 | | | | [32] | | | | 0 −24 | 0 −34 | 0 0 | ND ND | 0 1 | 0 0 | 4 3 | 0 3 |
| EM-1151 | ND | (76 95) | | | | [27] | | | | 0 −25 | −13 −48 | 0 0 | ND ND | 0 3 | 0 14 | 0 1 | 8 9 |
| EM-922 | ND | 66 ± 9 | | | | [23] | | | | 22 48 | 0 24 | 0 0 | 0 0 | ND ND | ND | ND | ND |
| CS-204 | ND | 94 | | | | [61] | | | | 0 −17 | −25 −13 | 0 0 | 0 −25 | 0 5 | 0 2 | 0 0 | 0 0 |
| EM-1261 | ND | (92 96) | | | | [49] | | | | 0 −31 | −11 −123 | ND ND | ND ND | 0 0 | 0 0 | 0 1 | 1 0 |
| EM-1277 | ND | (82 97) | | | | [49] | | | | 9 −16 | 11 −22 | ND ND | ND ND | 0 0 | 0 0 | 2 1 | 0 0 |
| EM-1299 | ND | (73 99) | | | | | | | | 5 10 | 0 −27 | ND ND | ND ND | 1 3 | 0 0 | 0 0 | 3 3 |
| SA-208-59 | ND | (72 88) | | | | | | | | ND | ND | ND | ND | ND | ND | ND | ND |

TABLE 2'-continued

| Name | 1 Oral Bioavailability AUC 0-7h (ng/mL.h) | | 2 Inhibition Type V 17B-HSD IC₅₀ (nM) (% Inh. At 3·10⁻⁷ | 3·10⁻⁷) | 3 Reversibility (%) of control | 4 Inhibition Type 1 17B-HSD Activity IC₅₀ (nM) [% Inh. at 3·10⁻⁶ M] | 5 Inhibition Type 2 17B-HSD Activity IC₅₀ (nM) [% Inh. at 3·10⁻⁶ M] | 6 Inhibition Type 3 17B-HSD Activity IC₅₀ (nM) [% Inh. at 3·10⁻⁶ M] | 7 Inhibition Type 1 3a-HSD Activity IC₅₀ (nM) [% Inh. at 3·10⁻⁶ M] | 8 Inhibition Type 3 3a-HSD Activity IC₅₀ (nM) [% Inh. at 3·10⁻⁶ M] | 9 Androgenic and Antiandrogenic Activity Shionogi Basal $E^{-7}$ $E^{-6}$ | | | 10 DHT $E^{-7}$ $E^{-6}$ [IC₅₀ (nM)] | | | 11 ZR-75-1 Activity $E^{-8}$ | 12 Basal $E_2$ $E^{-6}$ $3E^{-8}$ | | 13 % Inhibition Androgen Receptor *(E⁻⁷ E⁻⁵) $E^{-8}$ $E^{-6}$ | | 14 % Inhibition Progesterone Receptor *(E⁻⁷ E⁻⁵) $E^{-8}$ $E^{-6}$ | | 15 % Inhibition Glucocorticoid Receptor *(E⁻⁷ E⁻⁵) $E^{-8}$ $E^{-6}$ | | 16 % Inhibition Estrogen Receptor *(E⁻⁷ E⁻⁵) $E^{-8}$ $E^{-6}$ | |
|---|---|---|---|---|---|---|---|---|---|---|---|---|---|---|---|---|---|---|---|---|---|---|---|---|---|---|---|---|
| EM-925 | | | (46 | 81) | | [13] | | | | | 11 | −4 | 15 | −7 | | | | | | | | | | | | | | |
| EM-1057 | | | (57 | 90) | | | | | | | 16 | −2 | −20 | −64 | | | | | | | | | | | | | | |
| EM-1135 | | | (67 | 95) | | | | | | | 7 | −17 | −29 | −90 | | | | | | | | | | | | | | |
| EM-1155-CS | | | (49 | 90) | | | | | | | 0 | −12 | −7 | −93 | | | | | | | | | | | | | | |
| EM-1192 | | | (73 | 91) | | | | | | | −15 | −17 | −48 | −98 | | | | | | | | | | | | | | |
| CS-239 | | | (20 | 62) | | | | | | | 20 | 0 | 11 | −19 | | | | | | | | | | | | | | |
| EM-1257 | | | (96 | 97) | | | | | | | 0 | −37 | −8 | −49 | | | | | | | | | | | | | | |
| EM-1260 | | | (8 | 57) | | | | | | | −3 | −27 | −10 | −43 | | | | | | | | | | | | | | |
| EM-1262 | | | (93 | 97) | | | | | | | −1 | −29 | 4 | −47 | | | | | | | | | | | | | | |
| EM-1272-CS | | | (66 | 93) | | | | | | | −7 | −26 | −6 | −13 | | | | | | | | | | | | | | |
| EM-1313 | | | | | | | | | | | −7 | −40 | 2 | −51 | | | | | | | | | | | | | | |
| EM-1314 | | | | | | | | | | | −2 | −41 | 6 | −53 | | | | | | | | | | | | | | |

TABLE 2-continued

| | 1 Oral Bioavailability AUC 0–7 h (ng/mL·h) | 2 Inhibition Type V 17B-HSD IC$_{50}$ (nM) | | 3 Reversibility (%) of control | 4 Inhibition Type 1 17B-HSD Activity IC$_{50}$ (nM) [% Inh. at $3 \cdot 10^{-6}$ M] | 5 Inhibition Type 2 17B-HSD Activity IC$_{50}$ (nM) [% Inh. at $3 \cdot 10^{-6}$ M] | 6 Inhibition Type 3 17B-HSD Activity IC$_{50}$ (nM) [% Inh. at $3 \cdot 10^{-6}$ M] | 7 Inhibition Type 1 3a-HSD Activity IC$_{50}$ (nM) [% Inh. at $3 \cdot 10^{-6}$ M] | 8 Inhibition Type 3 3a-HSD Activity IC$_{50}$ (nM) [% Inh. at $3 \cdot 10^{-6}$ M] | 9 Androgenic and Antiandrogenic Activity Shionogi | | | | 10 | | 11 ZR-75-1 Activity | | 12 Basal E$_2$ | | 13 % Inhibition Androgen Receptor | | | 14 % Inhibition Progesterone Receptor | | | 15 % Inhibition Glucocorticoid Receptor | | | 16 % Inhibition Estrogen Receptor | | |
|---|---|---|---|---|---|---|---|---|---|---|---|---|---|---|---|---|---|---|---|---|---|---|---|---|---|---|---|---|---|---|---|---|---|
| | | ($3\cdot10^{-7}$) | ($3\cdot10^{-7}$) | | | | | | | Basal | | | DHT | | | | | | | *($E^{-7}$ | $E^{-5}$) | $E^{-8}$ | *($E^{-7}$ | $E^{-5}$) | $E^{-8}$ | *($E^{-7}$ | $E^{-5}$) | $E^{-8}$ | *($E^{-7}$ | $E^{-5}$) | $E^{-8}$ |
| Name | | (% Inh. At) | | | | | | | | $E^{-7}$ | $E^{-6}$ | $E^{-7}$ | $E^{-6}$ | [IC$_{50}$ (nM)] | $E^{-8}$ | $E^{-6}$ | $E^{-6}$ | $3E^{-8}$ | $E^{-6}$ | | | $E^{-6}$ | | | $E^{-6}$ | | | $E^{-6}$ | | | $E^{-6}$ |
| EM-1349-CS | | (61 | 93) | | | | | | | −6 | −35 | −21 | −71 | | | | | | | | | | | | | | | | | | | |
| EM-1353 | | (66 | 95) | | | | | | | 3 | −5 | −17 | −22 | | | | | | | | | | | | | | | | | | | |
| EM-1359 | | (86 | 93) | | | | | | | 2 | −19 | 7 | −52 | | | | | | | | | | | | | | | | | | | |
| EM-1361 | | (69 | 92) | | | | | | | 0 | −22 | −22 | −39 | | | | | | | | | | | | | | | | | | | |
| EM-1039 | | (64 | 82) | | [3] | | | | | 8 | −5 | 25 | 8 | | | | | | | | | | | | | | | | | | | |

TABLE 3

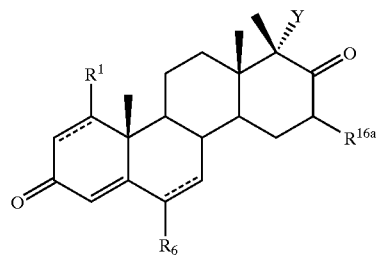

| Name | Example | Δ | R[1] | R[6] | R[16a] | Y |
|---|---|---|---|---|---|---|
| EM-1201-CS | 16 | $^6\Delta$ | H | $CH_3$ | H | $OCOC_4H_8Cl$ |
| EM-1202 | 16 | $^6\Delta$ | H | $CH_3$ | H | $OCOC_5H_{10}F$ |
| EM-1196-CS | 16 | $^6\Delta$ | H | $CH_3$ | H | $OCOC_4H_8F$ |
| EM-1078 | 16 | $^6\Delta$ | H | $CH_3$ | H | $OCO(CH_2)_2CH_3$ |
| EM-1172-CS | 16 | $^6\Delta$ | H | $CH_3$ | H | $OCOC_5H_{10}Cl$ |
| CS-237 | 16 | $^1\Delta, ^6\Delta$ | H | $CH_3$ | H | OAc |
| EM-1091 | 16 | $^6\Delta$ | H | $CH_3$ | H | $OCOC_2H_5$ |
| CS-259 | 16 | $^6\Delta$ | H | $CH_3$ | H | $OCO(CH_2)_5Br$ |
| CS-260 | 16 | $^6\Delta$ | H | $CH_3$ | H | $OCO(CH_2)_4CH_3$ |
| EM-1205-CS | 16 | $^6\Delta$ | H | $CH_3$ | Br | H |
| EM-1154-CS | 16 | $^6\Delta$ | α-$CH_3$ | $CH_3$ | H | $OCOcycloC_5H_9$ |
| EM-1143-CS | 16 | $^6\Delta$ | α-$CH_3$ | $CH_3$ | H | $OCOCH(CH_3)_2$ |
| EM-1098-CS | 16 | $^6\Delta$ | H | $CH_3$ | H | $OCOCH_2\Phi$ |
| EM-1108-CS | 16 | $^6\Delta$ | H | $CH_3$ | H | $OCO(CH_2)_3CH_3$ |
| EM-1146 | 16 | $^6\Delta$ | H | $CH_3$ | H | $OCOCH_2\Phi OCOC(CH_3)_3$ |
| CS-240 | 16 | $^6\Delta$ | α-$CH_3$ | $CH_3$ | H | OAc |
| EM-1142-CS | 16 | $^6\Delta$ | α-$CH_3$ | $CH_3$ | H | $OCOC_5H_{11}$ |
| CS-1Q98 | 16 | $^6\Delta$ | H | $CH_3$ | H | OAc |
| EM-1117-CS | Not reported | $^6\Delta$ | α-$CH_3$ | $CH_3$ | H | $OCOC_6H_{11}$ |
| EM-1121-CS | Not reported | $^6\Delta$ | α-$CH_3$ | $CH_3$ | H | $OCOC_4H_9$ |
| EM-1418-CS | Not reported | $^6\Delta$ | H | $CH_3$ | H | $OCOCH_2\phi OMe(o)$ |
| EM-1293 | Not reported | $^{1,6}\Delta$ | H | $CH_3$ | H | $OCO$-iso-$C_3H_7$ |
| EM-1144-CS | Not reported | $^6\Delta$ | α-$CH_3$ | $CH_3$ | H | $OCO$—$CH_2\phi$ |
| EM-1295-CS | Not reported | $^{1,6}\Delta$ | H | $CH_3$ | H | $OCOC_2H_5$ |
| EM-1296 | Not reported | $^{1,6}\Delta$ | H | $CH_3$ | H | $OCOC_3H_7$ |

TABLE 3'

| Name | 1 Oral Bioavailability AUC (ng/mL·h) 0–7 h | 2 Inhibition Type V 17β-HSD IC$_{50}$ (nM) (% Inh. At $3 \cdot 10^{-7}$) | 3 Reversibility (%) of control | 4 Inhibition Type 1 17β-HSD Activity IC$_{50}$ (nM) [% Inh.] at $3 \cdot 10^{-6}$ M | 5 Inhibition Type 2 17β-HSD Activity IC$_{50}$ (nM) [% Inh.] at $3 \cdot 10^{-6}$ M | 6 Inhibition Type 3 17β-HSD Activity IC$_{50}$ (nM) [% Inh.] at $3 \cdot 10^{-6}$ M | 7 Inhibition Type 1 3α-HSD Activity IC$_{50}$ (nM) [% Inh.] at $3 \cdot 10^{-6}$ M | 8 Inhibition Type 3 3α-HSD Activity IC$_{50}$ (nM) [% Inh.] at $3 \cdot 10^{-6}$ M | 9 Androgenic and Antiandrogenic Activity Shionogi Basal | | | 10 DHT | | [IC$_{50}$ (nM)] | 11 ZR-75-1 Activity Basal E$_2$ | | 12 | | 13 % Inhibition Androgen Receptor *($E^{-7}$) | $E^{-6}$ | 14 % Inhibition Progesterone Receptor *($E^{-7}$) | $E^{-6}$ | 15 % Inhibition Glucocorticoid Receptor *($E^{-7}$) | $E^{-6}$ | 16 % Inhibition Estrogen Receptor *($E^{-7}$) | $E^{-6}$ |
|---|---|---|---|---|---|---|---|---|---|---|---|---|---|---|---|---|---|---|---|---|---|---|---|---|---|---|---|
| | | | | | | | | | $E^{-7}$ | $E^{-6}$ | | $E^{-7}$ | $E^{-6}$ | | $E^{-8}$ | $E^{-6}$ | $3E^{-8}$ | $E^{-6}$ | *($E^{-8}$) | | *($E^{-8}$) | | *($E^{-8}$) | | *($E^{-8}$) | |
| EM-1201-CS | ND | 2.6 | | | | | | | –29 | –36 | | –99 | –110 | ND | ND | ND | ND | 7 | 45 | 8 | 73 | 2 | 90 | 0 | 0 |
| EM-1202 | ND | 3.4 | | | [24] | | | | –28 | –37 | | –88 | –109 | ND | ND | ND | ND | 4 | 30 | 7 | 64 | 10 | 86 | 0 | 0 |
| EM-1196-CS | ND | 6.5 ± 0.5 | 32 | | [21] | | | | –30 | –32 | | –98 | –109 | ND | ND | ND | ND | 0 | 37 | 1 | 44 | 7 | 79 | 0 | 0 |
| EM-1078 | ND | 3.8 ± 0.6 | | | [48] | | | | 5 | 45 | | –79 | –72 | ND | ND | ND | ND | 7 | 83 | 0 | 53 | 20 | 94 | 5 | 0 |
| EM-1172-CS | ND | 6.4 ± 1.1 | | | [15] | | | | –12 | –29 | | –84 | –114 | ND | ND | ND | ND | 0 | 22 | 5 | 73 | 10 | 87 | 0 | 0 |
| CS-237 | ND | 9 ± 1 | | | [13] | | | | –22 | –29 | | –51 [95] | –106 | ND | ND | ND | ND | 0 | 11 | 0 | 0 | 7 | 69 | 0 | 0 |
| EM-1091 | ND | 11 ± 1 | | | [38] | | | | –25 | –21 | | –88 [15] | –105 | ND | ND | ND | ND | 1 | 34 | 2 | 47 | 13 | 78 | 2 | 0 |
| CS-259 | ND | 4 ± 0.4 | | | [63] | | | | –25 | –25 | | –48 [40] | –108 | ND | ND | ND | ND | 2 | 12 | 3 | 68 | 0 | 17 | 2 | 0 |
| CS-260 | ND | 3 ± 0.3 | | | [66] | | | | –29 | –31 | | –80 [30] | –109 | ND | ND | ND | ND | 4 | 21 | 7 | 74 | 2 | 72 | 1 | 0 |
| EM-1205-CS | ND | 29.5 | | | [45] | | | | –15 | –38 | | –16 | –107 | ND | ND | ND | ND | 6 | 15 | 1 | 9 | 0 | 19 | 0 | 0 |
| EM-1154-CS | ND | 24.2 | | | | | | | 0 | –22 | | –23 [184] | –107 | ND | ND | 0 | 0 | 1 | 5 | 2 | 35 | 0 | 30 | 10 | 13 |
| EM-1143-CS | ND | 38.6 | | | | | | | –13 | –17 | | –19 [300] | –95 | ND | ND | ND | ND | 0 | 2 | 0 | 24 | 0 | 9 | 0 | 0 |
| EM-1098-CS | ND | 14.6 | | | [56] | | | | 0 | –17 | | –13 | –100 | ND | ND | ND | –34 | 1 | 3 | 0 | 66 | 0 | 24 | 0 | 0 |
| EM-1108-CS | ND | 8.9 | | | [70] | | | | –28 | –14 | | –92 [19] | –104 | ND | ND | ND | –4 | 4 | 42 | 0 | 55 | 4 | 73 | 0 | 0 |

TABLE 3'-continued

| Name | 1 Oral Bioavailability AUC 0-7 h (ng/mL·h) | 2 Inhibition Type V 17β-HSD IC$_{50}$ (nM) (% Inh. At 3·10$^{-7}$ 3·10$^{-7}$) | | 3 Reversibility (%) of control | 4 Inhibition Type 1 17β-HSD Activity IC$_{50}$ (nM) [% Inh.] at 3·10$^{-6}$ M | 5 Inhibition Type 2 17β-HSD Activity IC$_{50}$ (nM) [% Inh.] at 3·10$^{-6}$ M | 6 Inhibition Type 3 17β-HSD Activity IC$_{50}$ (nM) [% Inh.] at 3·10$^{-6}$ M | 7 Inhibition Type 1 3α-HSD Activity IC$_{50}$ (nM) [% Inh.] at 3·10$^{-6}$ M | 8 Inhibition Type 3 3α-HSD Activity IC$_{50}$ (nM) [% Inh.] at 3·10$^{-6}$ M | 9 Androgenic and Antiandrogenic Activity Shionogi Basal E$^{-7}$ E$^{-6}$ | | 10 DHT E$^{-7}$ E$^{-6}$ [IC$_{50}$ (nM)] | | 11 ZR-75-1 Activity Basal E$_2$ E$^{-8}$ E$^{-6}$ | | 12 Basal E$_2$ 3E$^{-8}$ E$^{-6}$ | | 13 % Inhibition Androgen Receptor *(E$^{-7}$ E$^{-5}$) E$^{-8}$ E$^{-6}$ | | | 14 % Inhibition Progesterone Receptor *(E$^{-7}$ E$^{-5}$) E$^{-8}$ E$^{-6}$ | | | 15 % Inhibition Glucocorticoid Receptor *(E$^{-7}$ E$^{-5}$) E$^{-8}$ E$^{-6}$ | | | 16 % Inhibition Estrogen Receptor *(E$^{-7}$ E$^{-5}$) E$^{-8}$ E$^{-6}$ | | |
|---|---|---|---|---|---|---|---|---|---|---|---|---|---|---|---|---|---|---|---|---|---|---|---|---|---|---|---|---|---|
| EM-1146 | ND | 29.7 | | | | | | | | 13 | -11 | 9 | -19 | ND | ND | ND | ND | 0 | 0 | 24 | 1 | 1 | 24 | 4 | 4 | 30 | 0 | 0 | 0 |
| CS-240 | ND | 28.5 ± 2.7 | | | | | | | | -12 | -32 | -41 | -106 [151] | | | | | 1 | 9 | | 0 | 0 | 9 | 0 | 0 | 13 | *(E$^{-7}$ E$^{-5}$) | 0 | 1 |
| EM-1142-CS | ND | (78 | 95) | | | [13] | | | | -15 | -32 | -40 | -102 | ND | ND | ND | ND | 0 | 6 | | 10 | 10 | 74 | 0 | 0 | 19 | 3 | 3 | 3 |
| CS-198 | ND | 38.5 ± 10.7 | | | | [13] | | | | -27 | -33 | -84 | -128 [82 ± 23] | -10 | -12 | -23 | -4 | 4 | 23 | | 0 | 0 | 44 | 1 | 1 | 73 | 0 | 0 | 0 |
| EM-1117-CS | ND | (72 | 95) | | | [75] | | | | | -39 | -3 | -93 | | | | | | | | | | | | | | | | |
| EM-1121-CS | ND | (82 | 94) | | | [83] | | | | -8 | -23 | -53 | -109 | | | | | | | | | | | | | | | | |
| EM-1144-CS | | (36 | 89) | | | | | | | 0 | 21 | -13 | -55 | | | | | | | | | | | | | | | | |
| EM-1418-CS | ND | | | | | [69] | | | | -7 | -34 | -18 | -71 | | | | | | | | | | | | | | | | |
| EM-1293-CS | ND | (94 | 94) | | | [67] | | | | -37 | -53 | -38 | -111 | | | | | | | | | | | | | | | | |
| EM-1295-CS | | (93 | 95) | | | [46] | | | | -48 | -50 | -81 | -112 | | | | | | | | | | | | | | | | |
| EM-1296 | | (94 | 95) | | | [27] | | | | -41 | -39 | -102 | -111 | | | | | | | | | | | | | | | | |

TABLE 4

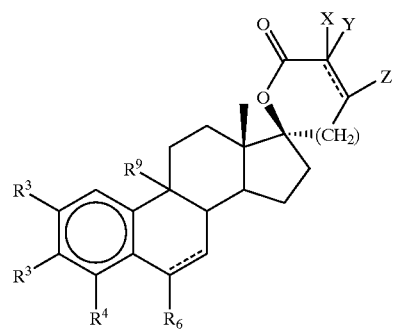

| Name | Example | R² | R³ | R⁴ | R⁶ | R⁹ | X | Y | Z |
|---|---|---|---|---|---|---|---|---|---|
| EM-1404 | 28 | H | —CONH₂ | H | H | H | CH₃ | CH₃ | H |
| EM-1403 | 28 | H | —CON(CH₃)₂ | H | H | H | CH₃ | CH₃ | H |
| EM-1401 | 28 | H | —COOH | H | H | H | CPh | CH₃ | H |
| EM-1394 | 31 | H | —OCH₃ | H | =O | H | CH₃ | CH₃ | H |
| EM-1424-CS | 29 | CONH₂ | —O(CH₂)₂OCH₃ | H | H | H | CH₃ | CH₃ | H |
| EM-1413-CS | 29 | CON(CH₃)₂ | —O(CH₂)₂OCH₃ | H | H | H | CH₃ | CH₃ | H |
| EM-1402-CS | 29 | COOCH₃ | —O(CH₂)₂OCH₃ | H | H | H | CH₃ | CH₃ | H |
| EM-1396 | 30 | CN | —O(CH₂)₂OCH₃ | H | H | H | CH₃ | CH₃ | H |
| EM-1393-CS | 24 | F | —O(CH₂)₂OCH₃ | H | H | H | CH₃ | CH₃ | H |
| EM-1131 | 19 | NO₂ | —OH | H | H | H | H | CH₃ | H |
| EM-1125-CS | 19 | NO₂ | —OH | H | H | H | CH₃ | CH₃ | H |
| EM-1408-CS | 31 | H | —O(CH₂)₂OCH₃ | H | =O | H | CH₃ | CH₃ | H |
| EM-1407-CS | 32 | | —CH=N—O— | H | H | H | CH₃ | CH₃ | H |
| EM-1126 | 19 | NO₂ | —OH | H | H | H | CH₃ | H | H |
| EM-1118 | 19 | NO₂ | —O(CH₂)₂OCH₃ | H | H | H | H | H | H |
| EM-1124 | 19 | NO₂ | —OH | H | H | H | H | H | H |
| CS-224 | 18 | H | —H | H | H | H | CH₃ | CH₃ | H |
| EM-1157-CS | 26 | H | —F | H | H | H | CH₃ | CH₃ | H |
| EM-1365-CS | 27 | H | —OSO₂CH₃ | H | H | H | CH₃ | CH₃ | H |
| EM-1364-CS | 27 | H | —OSO₂C₂H₅ | H | H | H | CH₃ | CH₃ | H |
| EM-1392-CS | 23 | Cl | —OSO₂CH₃ | Cl | H | H | CH₃ | CH₃ | H |
| EM-1391-CS | 23 | Cl | —OH | Cl | H | H | CH₃ | CH₃ | H |
| EM-1371-CS | 22 | Cl | —O(CH₂)₂OCH₃ | H | H | H | CH₃ | CH₃ | H |
| EM-1368-CS | 21 | H | —O(CH₂)₂OCH₃ | H | H | H | CH₃ | CH₃ | H |
| EM-1405 | 29 | COOH | —O(CH₂)₂OCH₃ | H | H | H | CH₃ | CH₃ | H |
| EM-1386 | 31 | H | —OCH₃ | H | =O | OH | CH₃ | CH₃ | H |
| EM-1388 | 28 | H | —COOCH₃ | H | H | H | CH₃ | CH₃ | H |
| EM-1370 | 21 | H | —OCH₃ | H | H | H | CH₃ | CH₃ | H |
| EM-1369 | 21 | H | —OC₂H₅ | H | H | H | CH₃ | CH₃ | H |
| EM-1389-CS | 21 | H | —O(CH₂)₂N(CH₃)₂ | H | H | H | CH₃ | CH₃ | H |
| EM-1412-CS | 33 | CH₃ | —OCH₃ | H | H | H | CH₃ | CH₃ | H |
| EM-1390-CS | 21 | H | —O(CH₂)₂cycloN—C₅H₁₀ | H | H | H | CH₃ | CH₃ | H |
| EM-1385-CS | 23 | Br | —OCH₃ | Br | H | H | CH₃ | CH₃ | H |
| EM-1366-CS | 27 | H | —OSO₂C₆H₅ | H | H | H | CH₃ | CH₃ | H |
| EM-1025 | 18 | H | —H | H | H | H | CH₃ | H | H |
| EM-1170-CS | 26 | H | —F | H | H | H | H | H | H |
| CS-242 | 25 | H | CH₃SC₂H₄O— | H | H | H | H | H | H |
| EM-919 | Not reported | H | HO— | H | H | H | H | H | H |
| EM-916 | 18 | H | —H | H | H | H | H | H | H |
| PB-132-140 | 35 | H | HO— | H | H | H | H | nil | nil |
| PB-132-146 | 35 | H | HO— | H | H | H | H | COOCH₃ | H |
| PB-132-152 | 35 | H | HO— | H | H | H | H | CH₂CHCH₂ | H |
| PB-132-142 | 35 | H | HO— | H | H | H | H | H | CH₃ |
| EM-1438 | 33 | CF₃ | —O(CH₂)₂OCH₃ | H | H | H | CH₃ | CH₃ | H |
| EM-1382-CS | 23 | Br | HO— | Br | H | H | CH₃ | CH₃ | H |
| EM-1372 | Not reported | H | —O(CH₂)₃CH₃ | H | H | H | CH₃ | CH₃ | H |
| EM-1373 | Not reported | H | —O(CH₂)₂OC₂H₅ | H | H | H | CH₃ | CH₃ | H |
| EM-1398 | Not reported | H | φCH₂OCO— | H | H | H | CH₃ | CH₃ | H |
| EM-1409 | Not reported | CF₃ | —OCH₃ | H | H | H | CH₃ | CH₃ | H |
| EM-1406-CS | Not reported | —CON(CH₃)₂ | —O(CH₂)₂OCH₃ | H | =O | H | CH₃ | CH₃ | H |
| EM-1413-CS | Not reported | —CON(CH₃)₂ | —O(CH₂)₂OCH₃ | H | H | H | CH₃ | CH₃ | H |
| EM-1416 | Not reported | H | —OH | H | H | H | C₂H₅ | C₂H₅ | H |

TABLE 4-continued

| Name | Example | R² | R³ | R⁴ | R⁶ | R⁹ | X | Y | Z |
|---|---|---|---|---|---|---|---|---|---|
| EM-1419 | Not reported | H | —OH | H | H | H | $C_2H_5$ | $C_2H_5$ | H |
| EM-01607-C | Not reported | H | —OH | H | H | H | $CH_3$ | $CH_3$ | H |
| EM-1608-D | Not reported | H | —OH | H | =O | H | $CH_3$ | $CH_3$ | H |
| EM-01645 | Not reported | —CN | —OH | H | H | H | $CH_3$ | $CH_3$ | H |
| EM-01646 | Not reported | H | —CN | H | H | H | $CH_3$ | $CH_3$ | H |
| EM-01660 | Not reported | —CONH₂ | —OH | H | H | H | $CH_3$ | $CH_3$ | H |
| EM-01661-B | Not reported | —CON(CH₃)₂ | —OH | H | H | H | $CH_3$ | $CH_3$ | H |
| EM-01662 | Not reported | —CO₂CH₃ | —OH | H | H | H | $CH_3$ | $CH_3$ | H |
| EM-01667C | Not reported | —Cl | —OH | H | H | H | $CH_3$ | $CH_3$ | H |
| EM-01668 | Not reported | —CO₂H | —OH | H | H | H | $CH_3$ | $CH_3$ | H |
| EM-1692 | Not reported | —I | —OH | H | H | H | $CH_3$ | $CH_3$ | H |
| EM-1695 | Not reported | H | —CN | H | H | H | H | H | H |
| EM-01807-B | Not reported | —CN | —OCH₃ | H | H | H | $CH_3$ | —CH₃ | H |
| EM-01905-B | Not reported | —CF₃ | —OH | H | H | H | $CH_3$ | $CH_3$ | H |
| EM-2016-D | Not reported | —CN | —OC₂H₅ | H | H | H | $CH_3$ | $CH_3$ | H |

TABLE 4'

| Name | 1 Oral Bioavailability AUC 0–7 h (ng · h/mL) | 2 Inhibition Type V 17β-HSD $IC_{50}$ (nM) (% Inh. At $3 \cdot 10^{-7}$   $3 \cdot 10^{-6}$) | 3 Reversibility ((%) of control) | 4 Inhibition Type 1 17β-HSD Activity $IC_{50}$ (nM) [% Inh. at $3 \cdot 10^8 M$] | 5 Inhibition Type 2 17β-HSD Activity $IC_{50}$ (nM) [% Inh. at $3 \cdot 10^{-8} M$] |
|---|---|---|---|---|---|
| EM-1404 | 3842 ± 197 | 3.2 ± 1.5 | | >>>$10^4$ | >>>$10^4$ |
| EM-1403 | | 7.2 ± 1.6 | | | |
| EM-1401 | 1629 ± 181 | 4 ± 1.5 | 31 | >>>$10^4$ | [76] |
| EM-1394 | 1764 ± 69 | 9 | 23 | >>>$10^4$ | >>>$10^4$ |
| EM-1424 | 368 ± 70 | 9.5 | 17 | >>>$10^4$ | >>>$10^4$ |
| EM-1413-CS | ND | 17 | 37 | | >>>$10^4$ |
| EM-1402-CS | 214 ± 36 + (EM-1405 576 ± 93) | 12 | 25 | >>>$10^4$ | >>>$10^4$ |
| EM-1396 | 196 ± 53 | 13 | 28 | >>>$10^4$ | >>>$10^4$ |
| EM-1393-CS | ND | 16 | 38 | | >>>$10^4$ |
| EM-1131 | 124 ± 27 | 3 | | | [70] |
| EM-1125-CS | 95 ± 6.5 | 2 | | | |
| EM-1408-CS | ND | 5.5 ± 1 | | | [66] |
| EM-1407-CS | ND | 12 ± 3 | | | [68] |
| EM-1126 | ND | 6 ± 1 | | | [59] |
| EM-1118 | 138 ± 10 | 4 | | | [97] |

TABLE 4'-continued

| | | | | | |
|---|---|---|---|---|---|
| EM-1124 | 5.1 ± 1 (8 h) | 3 ± 0.2 | | | |
| CS-224 | 18 ± 3.5 | 2.9 ± 0.4 10.7 | | | |
| EM-1157-CS | 40 ± 7 | 4 10 | 28 | >>>$10^4$ | >>>$10^4$ |
| EM-1365-CS | ND | 12 | 49 | >>>$10^4$ | >>>$10^4$ |
| EM-1364-CS | ND | 17 | | | [73] |
| EM-1392-CS | 305 ± 49 | 19 | 38 | | >>>$10^4$ |
| EM-1391-CS | 28 ± 3.4 | 19 | 49 | | >>>$10^4$ |
| EM-1371-CS | 64 ± 21 | 19 20 | 40 | | >>>$10^4$ |
| EM-1368-CS | ND | 21 | | | [73] |
| EM-1405 | ND | 23 | 53 | | >>>$10^4$ |
| EM-1386 | 5595 ± 789 | 25 | 54 | | >>>$10^4$ |
| EM-1388 | 136 ± 33 | 25 | 52 | | >>>$10^4$ |
| EM-1370 | ND | 43 | | | [33] |
| EM-1369 | ND | 46 | | | [62] |
| EM-1389-CS | 169 ± 2 | 25 | 40 | | >>>$10^4$ |
| EM-1412-CS | ND | 54 | 71 | | >>>$10^4$ |
| EM-1390-CS | 401 ± 5 | 48 | 50 | | >>>$10^4$ |
| EM-1385-CS | 301 ± 36 | 51 | 60 | | >>>$10^4$ |
| EM-1366-CS | ND | 54 | | | [62] |
| EM-1025 | ND | 6.1 ± 0.7 4.3 ± 0.7 | | | [64] |
| EM-1170-CS | ND | 7 ± 1 | | | [84] |
| CS-242 | 0 | 6.6 ± 0.9 | | | |
| EM-919 | 4.8 ± .8 | 10 ± 1.4 | | | [86] |
| EM-916 | ND | 10.3 ± 0.8 | | | [88] |
| PB-132-140 | ND | 49 ± 5 | | | |
| PB-132-146 | ND | 72 ± 3 | | | [75] |
| PB-132-152 | ND | 107 ± 9 | | | [50] |
| PB-132-142 | ND | 19 ± 1.5 | | | [69] |
| EM-1438 | ND | (90.6 95.2) | | | [72] |
| EM-1382-CS | ND | (74 86) | | | [70] |
| EM-1372 | 12 ± 7 | (39 81) | | | [65] |
| EM-1373 | 32 ± 7 | (77 88) | | | [69] |
| EM-1398 | ND | (70 89) | | | [64] |
| EM-1409 | 36 ± 13 | 170 ± 70 | | | [4] |
| EM-1406-CS | ND | (84 94) | | | [65] |
| EM-1413-CS | ND | | | | [69] |
| EM-1416 | ND | | | | [76] |
| EM-1419 | ND | | | | [74] |
| EM-01607-D | ND | | | | |
| EM-01608-D | ND | 3.6 ± 0.5 | | | [58] |
| EM-01645 | 52 ± 3 | 4.5 ± 0.3 | | | [38] |
| EM-01646 | ND | | | | [42] |
| EM-01660 | ND | 5.6 ± 0.4 | | | [59] |
| EM-01661-B | ND | 19.2 ± 1 | | | [55] |
| EM-01662 | ND | 35 ± 5 | | | [70] |
| EM-01667-C | 152 ± 18 | | | | [83] |
| EM-01668 | ND | (81 90) | | | [63] |
| EM-1692 | ND | (88 95) | | | [25] |
| EM-1695 | ND | (94 97) | | | [85] |
| EM-01807-B | 449 ± 115 | | | | [39] |
| EM-1808-B | 388 ± 71 | | | | [0] |
| EM-01905-B | ND | | | | [66] |
| EM-2016-D | ND | | | | |

| | 6 Inhibition Type 3 17β-HSD Activity | 7 Inhibition Type 1 3α-HSD-Activity | 8 Inhibition Type 3 3α-HSD Activity | 9 | 10 Androgenic and Antiandrogenic Activity Shionogi | | | |
|---|---|---|---|---|---|---|---|---|
| | IC$_{50}$ (nM) | IC$_{50}$ (nM) | IC$_{50}$ (nM) | | | | DHT | |
| Name | [% Inh. at 3 · $10^8$M] | [% Inh. at 3 · $10^8$M] | [% Inh. at 3 · $10^8$M] | Basal | | $E^{-7}$ | $E^{-6}$ | [IC$_{50}$ (nM)] |
| EM-1404 | >>>$10^4$ | >>>$10^4$ | >>>$10^4$ | 0 | 0 | | | [~1000] |
| EM-1403 | | | | 19 | 0 | 0 | -54 | |
| EM-1401 | >>>$10^4$ | [76] | >>>$10^4$ | 2 | 0 | | | [>1000] |
| EM-1394 | >>>$10^4$ | >>>$10^4$ | >>>$10^4$ | 4 | -12 | 0 | -23 | |
| EM-1424 | >>>$10^4$ | >>>$10^4$ | >>>$10^4$ | 0 | -17 | -22 | -58 | |
| EM-1413-CS | | | | 0 | 0 | -17 | -44 | |
| EM-1402-CS | >>>$10^4$ | >>>$10^4$ | >>>$10^4$ | 0 | -9 | -13 | -87 | |
| EM-1396 | >>>$10^4$ | >>>$10^4$ | >>>$10^4$ | 0 | -15 | -16 | -29 | |
| EM-1393-CS | | | | 88 | -10 | 27 | -104 | |
| EM-1131 | | | | 0 | 0 | -15 | -47 | |

TABLE 4'-continued

| Name | | | | | | | |
|---|---|---|---|---|---|---|---|
| EM-1125-CS | | | | | 3 | −10 | −30 | −43 |
| EM-1408-CS | | | | | 0 | −12 | −19 | −94 |
| EM-1407-CS | | | | | 0 | −23 | −16 | −96 |
| EM-1126 | | | | | 0 | −8 | 0 | −49 |
| EM-1118 | | | | | 15 | −20 | 0 | −25 |
| EM-1124 | | | | | 0 | −11 | 0 | −65 |
| CS-224 | | | | | 17 | 0 | 23 | −11 |
| EM-1157-CS | >>>$10^4$ | | >>>$10^4$ | >>>$10^4$ | 16 | −12 | 0 | −19 |
| EM-1365-CS | >>>$10^4$ | | >>>$10^4$ | >>>$10^4$ | 4 | −28 | −17 | −53 |
| EM-1364-CS | | | | | 0 | −16 | −11 | −59 |
| EM-1392-CS | | | | | 7 | −35 | 0 | −75 |
| EM-1391-CS | | | | | 0 | −13 | 0 | −19 |
| EM-1371-CS | | | | | 58 | 92 | 0 | −76 |
| EM-1368-CS | | | | | 8 | −22 | 0 | −44 |
| EM-1405 | | | | | 0 | 0 | 0 | 0 |
| EM-1386 | | | | | 5 | −17 | 0 | −27 |
| EM-1388 | | | | | −18 | −23 | 0 | −84 |
| EM-1370 | | | | | 12 | −11 | 0 | −28 |
| EM-1369 | | | | | 0 | 0 | 0 | −24 |
| EM-1389-CS | | | | | 0 | −41 | −94 | −103 |
| EM-1412-CS | | | | | 0 | −11 | 0 | −60 |
| EM-1390-CS | | | | | −18 | −43 | −36 | −119 |
| EM-1385-CS | | | | | −11 | −28 | 0 | −61 |
| EM-1366-CS | | | | | 0 | 0 | −13 | −67 |
| EM-1025 | | | | | 5 | 0 | −14 | −25 |
| EM-1170-CS | | | | | 12 | −27 | 15 | −38 |
| CS-242 | | | | | 0 | −32 | 9 | −66 |
| EM-919 | | | | | +73 | −17 | +38 | −95 |
| | | | | | | | | [609 ± 59] |
| EM-916 | | | | | +17 | −1 | +2 | −46 |
| | | | | | | | | [2100] |
| PB-132-140 | | | | | 30 | −18 | 16 | 0 |
| PB-132-146 | | | | | 29 | 0 | 14 | −40 |
| PB-132-152 | | | | | 39 | 0 | 14 | −19 |
| PB-132-142 | | | | | 25 | −17 | 0 | −13 |
| EM-1438 | | | | | 10 | −14 | 0 | −53 |
| EM-1382-CS | | | | | 0 | 0 | 0 | 0 |
| EM-1372 | | | | | −13 | −35 | −13 | −35 |
| EM-1373 | | | | | −5 | −31 | −4 | −42 |
| EM-1398 | | | | | 13 | −10 | 0 | −37 |
| EM-1409 | | | | | 5 | −23 | −5 | −105 |
| EM-1406-CS | | | | | −3 | 11 | −18 | −13 |
| EM-1413-CS | | | | | −1 | −24 | −18 | −44 |
| EM-1416 | | | | | 28 | −4 | 26 | −41 |
| EM-1419 | | | | | 16 | −29 | 2 | −64 |
| EM-01607-D | | | | | | | | |
| EM-01608-D | | | | | | | | |
| EM-01645 | | | | | −5 | 35 | −6 | −10 |
| EM-01646 | | | | | −4 | −42 | 8 | −74 |
| EM-01660 | | | | | −4 | −31 | −20 | −51 |
| EM-01661-B | | | | | 0 | −13 | 3 | −15 |
| EM-01662 | | | | | 0 | −27 | −11 | −51 |
| EM-01667-C | | | | | 6 | −3 | 9 | −42 |
| EM-01668 | | | | | −3 | 26 | 11 | 2 |
| EM-1692 | | | | | 8 | −12 | 3 | −78 |
| EM-1695 | | | | | 6 | −18 | −27 | −98 |
| EM-01807-B | | | | | 4 | −12 | −7 | −12 |
| EM-1808-B | | | | | 2 | −30 | −14 | −58 |
| EM-01905-B | | | | | 0 | −16 | −5 | −24 |
| EM-2016-D | | | | | | | | |

| | 11 | 12 | | | 13<br>% Inhibition<br>Androgen<br>Receptor<br>*($E^{-7}$  $E^{-5}$) | | 14<br>% Inhibition<br>Progesterone<br>Receptor<br>*($E^{-7}$  $E^{-5}$) | | 15<br>% Inhibition<br>Glucocorticold<br>Receptor<br>*($E^{-7}$  $E^{-5}$) | | 16<br>% Inhibition<br>Estrogen<br>Receptor<br>*($E^{-7}$  $E^{-5}$) | |
|---|---|---|---|---|---|---|---|---|---|---|---|---|
| | ZR-75-1 Activity<br>Basal $E_2$ | | | | | | | | | | | |
| Name | $E^{-8}$ | $E^{-6}$ | $3E^{-8}$ | $E^{-}$ | $E^{-8}$ | $E^{-6}$ | $E^{-8}$ | $E^{-6}$ | $E^{-8}$ | $E^{-6}$ | $E^{-8}$ | $E^{-6}$ |
| EM-1404 | 0 | 0 | 0 | 0 | 0 | 0 | 0 | 0 | 0 | 0 | 0 | 0 |
| EM-1403 | ND | | ND | | 0 | 0 | 0 | 0 | 0 | 0 | 0 | 0 |
| EM-1401 | ND | | ND | | 0 | 0 | 0 | 0 | 4 | 2 | 5 | 2 |
| EM-1394 | ND | | ND | | 0 | 0 | 2 | 4 | 3 | 2 | 4 | 8 |
| EM-1424 | 0 | 0 | −11 | −2 | 2 | 2 | 1 | 0 | 0 | 0 | 3 | 3 |
| EM-1413-CS | ND | | ND | | | | | | | | | |
| EM-1402-CS | 0 | −10 | 0 | −61 | 0 | 0 | 2 | 4 | 4 | 7 | 1 | 0 |
| EM-1396 | 0 | 0 | +12 | −1 | 0 | 2 | 0 | 0 | 0 | 1 | 3 | 2 |
| EM-1393-CS | ND | | ND | | | | | | | | | |
| EM-1131 | 7 | 15 | 0 | 0 | 2 | 1 | 2 | 10 | 0 | 0 | 5 | 3 |

TABLE 4'-continued

| | | | | | | | | | | | | |
|---|---|---|---|---|---|---|---|---|---|---|---|---|
| EM-1125-CS | 10 | 34 | 0 | 0 | 2 | 1 | 5 | 7 | 0 | 1 | 2 | 2 |
| EM-1408-CS | ND | | ND | | 0 | 0 | 0 | 0 | 0 | 0 | 0 | 6 |
| EM-1407-CS | ND | | ND | | 0 | 0 | 0 | 3 | 0 | 0 | 2 | 0 |
| EM-1126 | 0 | −89 | 0 | 0 | 2 | 10 | 5 | 14 | 0 | 0 | 1 | 0 |
| EM-1118 | 0 | 0 | 12 | 15 | 1 | 0 | 0 | 0 | 0 | 0 | 0 | 0 |
| EM-1124 | 0 | 12 | 0 | 0 | 1 | 7 | 1 | 20 | 1 | 1 | 0 | 0 |
| CS-224 | 16 | 128 | 13 | 19 | 0 | 0 | 2 | 5 | 1 | 5 | 0 | 2 |
| EM-1157-CS | ND | | ND | | 0 | 0 | 2 | 5 | 1 | 0 | 0 | 0 |
| EM-1365-CS | −17 | 0 | −17 | −48 | 0 | 0 | 2 | 2 | 0 | 5 | 2 | 4 |
| EM-1364-CS | 0 | +36 | −12 | −37 | 0 | 0 | 0 | 0 | 0 | 3 | 0 | 5 |
| EM-1392-CS | ND | | ND | | 0 | 0 | 2 | 2 | 0 | 8 | 0 | 0 |
| EM-1391-CS | ND | | ND | | 0 | 0 | 1 | 1 | 0 | 2 | 0 | 0 |
| EM-1371-CS | 0 | +137 | 0 | 0 | 0 | 1 | 0 | 3 | 1 | 0 | 2 | 1 |
| EM-1368-CS | 0 | +15 | 0 | −28 | 0 | 0 | 0 | 3 | 3 | 3 | 0 | 0 |
| EM-1405 | ND | | ND | | 0 | 0 | 0 | 0 | 0 | 0 | 0 | 0 |
| EM-1386 | 0 | −12 | 0 | −16 | 0 | 0 | 0 | 0 | 3 | 0 | 3 | 0 |
| EM-1388 | ND | | ND | | 0 | 0 | 2 | 3 | 2 | 0 | 0 | 0 |
| EM-1370 | 0 | +24 | 0 | 0 | 3 | 2 | 0 | 0 | 3 | 0 | 0 | 2 |
| EM-1369 | 0 | +84 | +18 | −1 | 0 | 1 | 1 | 3 | 1 | 2 | 2 | 0 |
| EM-1389-CS | ND | | ND | | 0 | 0 | 3 | 0 | 0 | 3 | 0 | 0 |
| EM-1412-CS | ND | | ND | | 0 | 0 | 0 | 0 | 0 | 2 | 0 | 0 |
| EM-1390-CS | ND | | ND | | 0 | 0 | 0 | 2 | 2 | 0 | 0 | 0 |
| EM-1385-CS | ND | | ND | | 0 | 0 | 2 | 2 | 0 | 5 | 2 | 4 |
| EM-1366-CS | 0 | 0 | +19 | −4 | 6 | 0 | 0 | 0 | 1 | 3 | 6 | 3 |
| EM-1025 | 20 | 201 | 0 | 0 | 0 | 0 | 0 | 4 | 0 | 0 | 1 | 4 |
| EM-1170-CS | ND | | ND | | 0 | 1 | 1 | 24 | 4 | 3 | 0 | 0 |
| CS-242 | ND | | ND | | 0 | 0 | 0 | 0 | 0 | 0 | 0 | 0 |
| EM-919 | 0 | −20 | −18 | −23 | 0* | 6* | 8* | 68* | 0* | 33* | 07* | 90* |
| EM-916 | 0 | 0 | 0 | −17 | 0* | 12* | 4* | 70* | 0* | 13* | 0* | 13* |
| PB-132-140 | 15 | 71 | 0 | −28 | ND | | ND | | ND | | ND | |
| PB-132-146 | 0 | 91 | 0 | −36 | ND | | ND | | ND | | ND | |
| PB-132-152 | 39 | 90 | −11 | −44 | ND | | ND | | ND | | ND | |
| PB-132-142 | 38 | 91 | 0 | −35 | ND | | ND | | ND | | ND | |
| EM-1438 | ND | | ND | | 0 | 10 | 0 | 0 | 1 | 0 | 4 | 0 |
| EM-1382-CS | ND | | ND | | 0 | 0 | 2 | 0 | 2 | 4 | 0 | 3 |
| EM-1372 | | | | | | | | | | | | |
| EM-1373 | | | | | | | | | | | | |
| EM-1398 | | | | | | | | | | | | |
| EM-1409 | | | | | | | | | | | | |
| EM-1406-CS | | | | | | | | | | | | |
| EM-1413-CS | | | | | | | | | | | | |
| EM-1416 | | | | | | | | | | | | |
| EM-1419 | | | | | | | | | | | | |
| EM-01607-D | | | | | | | | | | | | |
| EM-01608-D | | | | | | | | | | | | |
| EM-01645 | | | | | | | | | | | | |
| EM-01646 | | | | | | | | | | | | |
| EM-01660 | | | | | | | | | | | | |
| EM-01661-B | | | | | | | | | | | | |
| EM-01662 | | | | | | | | | | | | |
| EM-01667-C | | | | | | | | | | | | |
| EM-01668 | | | | | | | | | | | | |
| EM-1692 | | | | | | | | | | | | |
| EM-1695 | | | | | | | | | | | | |
| EM-01807-B | | | | | | | | | | | | |
| EM-1808-B | | | | | | | | | | | | |
| EM-01905-B | | | | | | | | | | | | |
| EM-2016-D | | | | | | | | | | | | |

TABLE 5

[Chemical structure of steroid compound with lactone ring, N-R group, X= substituent, and (CH₂)n side chain]

| Name | Example | X | R | Unsaturation | n | b | c |
|---|---|---|---|---|---|---|---|
| EM-1122-CS | 17 | O | CH₃ | 1Δ | 1 | H | H |
| CS-254 | 17 | O | H | nil | 2 | H | H |
| EM-980 | 17 | O | CH₃ | nil | 1 | H | H |
| CS-201 | 17 | O | H | nil | 1 | H | H |
| EM-1086 | 17 | S | H | nil | 1 | H | H |
| EM-1266-CS | Not reported | O | H | ¹Δ | 1 | CH₃ | CH₃ |
| EM-1267-CS | Not reported | O | H | nil | 1 | CH₃ | CH₃ |
| EM-1265 | Not reported | O | CH₃ | ¹Δ | 1 | CH₃ | CH₃ |
| EM-1269 | Not reported | O | CH₃ | nil | 1 | CH₃ | CH₃ |

| | 1 Oral Bioavailability ACU 0–7h (ng/mL.h) | 2 Inhibition Type V 17β-HSD IC$_{50}$ (nM) (% inh. At $3 \cdot 10^{-7}$  $3 \cdot 10^{-6}$) | 3 Reversibility (%) of control | 4 Inhibition Type 1 17β-HSD Activity IC$_{50}$ (nM) [% Inh. at $3 \cdot 10^{-4}$ M] | 5 Inhibition Type 2 17β-HSD Activity IC$_{50}$ (nM) [% Inh. at $3 \cdot 10^{-5}$ M] | 6 Inhibition Type 3 17β-HSD Activity IC$_{50}$ (nM) [% Inh. at $3 \cdot 10^{-6}$ M] | 7 Inhibition Type 1 3α-HSD Activity IC$_{50}$ (nM) [% Inh. at $3 \cdot 10^{-6}$ M] | 8 Inhibition Type 3 3α-HSD Activity IC$_{50}$ (nM) [% Inh. at $3 \cdot 10^{-6}$ M] |
|---|---|---|---|---|---|---|---|---|
| EM-1122-CS | ND | (80  95) | | | [90] | | | |
| CS-254 | ND | 20 ± 2 | | | | | | |
| EM-980 | ND | 27.8 ± 10 | | | [68] | | | |
| CS-201 | ND | 31.4 ± 5.4 | | | [70] | | | |
| CS-205 | ND | 83 ± 18 | | | [31] | | | |
| EM-1266-CS | ND | 26 | | | [81] | | | |
| EM-1267-CS | ND | 29 | | | [43] | | | |
| EM-1265 | ND | (83  95) | | | [77] | | | |
| EM-1269 | ND | (74  93) | | | [57] | | | |

| | 9 Androgenic and Antiandrogenic Activity Shionogl DHT | | 10 [IC$_{50}$ (nM)] | 11 ZR-75-1 Activity Basal E$_2$ | | 12 | 13 % Inhibition Androgen Receptor *($E^{-7}$  $E^{-5}$) | | 14 % Inhibition Progesterone Receptor *($E^{-7}$  $E^{-5}$) | | 15 % Inhibition Glucocorticoid Receptor *($E^{-7}$  $E^{-5}$) | | 16 % Inhibition Estrogen Receptor *($E^{-7}$  $E^{-5}$) | |
|---|---|---|---|---|---|---|---|---|---|---|---|---|---|---|
| Name | Basal $E^{-7}$ | $E^{-6}$ | | $E^{-8}$ $E^{-6}$ | 3$E^{-8}$ $E^-$ | | $E^{-8}$ | $E^{-6}$ | $E^{-8}$ | $E^{-6}$ | $E^{-8}$ | $E^{-6}$ | $E^{-8}$ | $E^{-6}$ |
| EM-1122-CS | 0  −11 | | −14  −74 [447] | ND | ND | | 1 | 8 | 0 | 3 | 0 | 0 | 2 | 0 |
| CS-254 | 0  7 | | −5  −7 | ND | ND | | 0 | 0 | 0 | 0 | 3 | 0 | 2 | 1 |
| EM-980 | 0  −34 | | 9  58 | 0  0 | 0 −19 | | 3 | 5 | 1 | 0 | 0 | 0 | 0 | 0 |
| CS-201 | −26  −37 | | −23  7 | 0  0 | 15  0 | | 0 | 0 | 0 | 0 | 0 | 0 | 0 | 0 |
| CS-205 | −26  −37 | | −74  −112 | 0  0 | 0  25 | | 1 | 15 | 0 | 7 | 0 | 0 | 2 | 2 |
| EM-1266-CS | 0  −22 | | −12  −10 | ND | ND | | 0 | 0 | 0 | 1 | 0 | 0 | 3 | 6 |
| EM-1267-CS | 0  −24 | | −12  −25 | ND | ND | | 0 | 0 | 0 | 3 | 3 | 1 | 3 | 4 |
| EM-1265 | 0  0 | | −11  −80 | | | | | | | | | | | |
| EM-1269 | 0  0 | | −10  −59 | | | | | | | | | | | |

LEGENDS TO TABLES

In column 1, the oral bioavailability of preferred type 5 inhibitors, expressed in ng/mL.h, was determined as described below in "Other Tests, A-In Vivo Assays of Bioavailability of Human Type 5 17β-HSD Inhibitors". Higher number are desirable. ND means that a determination was not done.

In column 2, the inhibition of human type 5 17β-hydroxysteroid dehydrogenase activity expressed by the concentration which produce 50% of inhibition ($IC_{50}$ in nM) is reported (centered numbers). The manner in which $IC_{50}$ was determined is described in "Efficacy of the Preferred Inhibitors". Lower numbers for $IC_{50}$ are desirable. When $IC_{50}$ was not determined, the percentage of inhibition is reported in parentheses at $3.10^{-7}$M (left number) and $3.10^{-6}$M (right number).

In column 3, the reversibility of the inhibition of type 5 17β-hydroxysteroid dehydrogenase activity expressed in percentage of control is reported. The manner in which the reversibility is determined is described in "Efficacy of Preferred Inhibitors: V. Reversibility of Human Type 5 17β-HSD Inhibitory Activity". Lower number is desirable. Blank means that a determination was not done.

In column 4, the inhibition of human type 1 17β-hydroxysteroid dehydrogenase activity expressed by the concentration which produce 50% of inhibition of enzymatic activity ($IC_{50}$ in nM) is reported. The manner in which $IC_{50}$ was determined is described in "Efficacy of Preferred Inhibitors: VI. Enzymatic assay for types 1, 2, and 3 17β-HSD and types 1 and 3 3α-HSD". Higher numbers of $IC_{50}$ are desirable. Blank means that a determination was not done. The % of inhibition at the concentration of $3.10^{-6}$M determined in preliminary screening test is reported in square braquets.

In column 5, the inhibition of human type 2 17β-hydroxysteroid dehydrogenase activity expressed by the concentration which produce 50% of inhibition of enzymatic activity ($IC_{50}$ in nM) is reported. The manner in which $IC_{50}$ was determined is described in "Efficacy of Preferred Inhibitors: VI. Enzymatic assay for types 1, 2, and 3 17β-HSD and types 1 and 3 3α-HSD". Higher numbers of $IC_{50}$ are desirable. Blank means that a determination was not done. The % of inhibition at the concentration of $3.10^{-6}$M determined in preliminary screening test is reported in square braquets.

In column 6, the inhibition of human type 3 17β-hydroxysteroid dehydrogenase activity expressed by the concentration which produce 50% of inhibition of enzymatic activity ($IC_{50}$ in nM) is reported. The manner in which $IC_{50}$ was determined is described in "Efficacy of Preferred Inhibitors: VI. Enzymatic assay for types 1, 2, and 3 17β-HSD and types 1 and 3 3α-HSD". Lower numbers of $IC_{50}$ are desirable. Blank means that a determination was not done. The % of inhibition at the concentration of $3.10^{-6}$M determined in preliminary screening test is reported in square braquets.

In column 7, the inhibition of human type 1 3α-hydroxysteroid dehydrogenase activity expressed by the concentration which produce 50% of inhibition of enzymatic activity ($IC_{50}$ in nM) is reported. The manner in which $IC_{50}$ was determined is described in "Efficacy of Preferred Inhibitors: VI. Enzymatic assay for types 1, 2, and 3 17β-HSD and types 1 and 3 3α-HSD". Higher numbers of $IC_{50}$ are desirable. Blank means that a determination was not done. The % of inhibition at the concentration of $3.10^{-6}$M determined in preliminary screening test is reported in square braquets.

In column 8, the inhibition of human type 3 3α-hydroxysteroid dehydrogenase activity expressed by the concentration which produce 50% of inhibition of enzymatic activity ($IC_{50}$ in nM) is reported. The manner in which $IC_{50}$ was determined is described in "Efficacy of Preferred Inhibitors: VI. Enzymatic assay for types 1, 2, and 3 17β-HSD and types 1 and 3 3α-HSD". Higher numbers of $IC_{50}$ are desirable. Blank means that a determination was not done. The % of inhibition at the concentration of $3.10^{-6}$M determined in preliminary screening test is reported in square braquets.

In column 9, the androgenic activity of preferred type 5 inhibitors expressed as the percentage of stimulation of proliferation of Shionogi cells at concentrations of $10^{-7}$ M (left number) and $10^{-6}$ M (right number) of inhibitor. The manner in which the stimulation is determined is described in "Other Tests; B-Androgenic/Antiandrogenic Activity". Lower numbers are desirable. ND means that a determination was not done.

In column 10, the antiandrogenic activity of preferred type 5 inhibitors expressed by the concentration which produce 50% of inhibition ($IC_{50}$ in nM) of DHT-induced proliferation of Shionogi cells is reported (bracketed centered numbers). The percentage of inhibition of DHT-induced proliferation of Shionogi cells at concentrations of $10^{-7}$M (left number) and $10^{-6}$M (right number) of inhibitor is also reported. For example, EM-1403 in Table 4', column 10, the number −54 means that at a concentration of $10^{-6}$ M, the stimulation of DHT-induced proliferation of Shionogi cells was 54% reduced. The manner in which the inhibition is determined is described in "Other Tests; B-Androgenic/Antiandrogenic Activity". Lower numbers are desirable. ND means that a determination was not done.

In column 11, the estrogenic activity of preferred type 5 inhibitors expressed as the percentage of stimulation of the proliferation of ZR-75-1 cells at concentrations of $10^{-7}$M (left number) and $10^{-6}$M (right number) of inhibitor. The manner in which the stimulation is determined is described in "Other Tests; C-Estrogenic/Antiestrogenic activity" Lower numbers are desirable. ND means that a determination was not done.

In column 12, the antiestrogenic activity of preferred type 5 inhibitors expressed as percentage of inhibition of $E_2$-induced proliferation of ZR-75-1 cells at a concentrations of $10^{-7}$M (left number) and $10^{-6}$ (right number) of inhibitor is reported. For example, EM-1402-CS in Table 4', column 12, the number −61 means that at a concentration of $10^{-6}$ M, the stimulation of $E_2$-induced proliferation of ZR-75-1 cells was 61% reduced. The manner in which the inhibition is determined is described in "Other Tests; C-Estrogenic/Antiestrogenic Activity". Lower numbers are desirable. ND means that a determination was not done.

In column 13, the binding on androgen receptor expressed as percentage of inhibition of the binding of [$^3$H]R1881 at the concentration of $10^{-8}$M (stared number at $10^{-7}$ M) (left number) and $10^{-6}$M (stared number at $10^{-5}$ M) (right number) of inhibitor is reported. The manner in which the percentage of inhibition is determined is described in "Other Tests; D-Androgen Receptor (AR) Assays". Lower numbers are desirable.

In column 14, the binding on progesterone receptor expressed as percentage of inhibition of the binding of [$^3$H]R5020 at the concentration of $10^{-8}$M (stared number at $10^{-7}$ M) (left number) and $10^{-6}$M (stared number at $10^{-5}$ M) (right number) of inhibitor is reported. The manner in which the percentage of inhibition is determined is described in "Other Tests; E-Progesterone Receptor Assay". Lower numbers are desirable.

In column 15, the binding on glucocorticoid receptor expressed as percentage of inhibition of the binding of

[6,7-$^3$H*(N)]-dexamethasone at the concentration of $10^{-8}$M (stared number at $10^{-7}$ M) (left number) and $10^{-6}$M (stared number at $10^{-5}$ M) (right number) of inhibitor is reported. The manner in which the percentage of inhibition is determined is described in "Other Tests; F-Glucocorticoid Receptor Assay".

In column 16, the binding on estrogen receptor expressed as percentage of inhibition of the binding of [$^3$H]E$_2$ at the concentration of $10^{-8}$M (stared number $10^{-7}$ (left number) and $10^6$M (stared number $10^{-5}$) (right number) of inhibition is reported. The manner in which the percentage of inhibition is determined is described in "Other Tests; G-Estrogen Receptor (ER) Assay".

EFFICACY OF THE PREFERRED INHIBITORS

A The Preferred Inhibitors of the Invention are Tested for their Type 5 17β-HSD Inhibitory Activity by the Following Method I) Cloning of Type 5 17β-HSD cDNA Using a oligoprimer pair (5'-GGA-AAT-CGT-GAC-AGG-GAA-TGG-ATT-CCA-AAC-AG-3', 5'-GGA-ATT-CTT-TAT-TGT-ATT-TCT-GGC-CTA-TGG-AGT-GAG-3') derived from human aldoketoreductase (Qin et al., J. Steroid Biochem. Molec. Biol. 46: 673–679, 1993) and polymerase chain reaction (PCR), we have amplified from a human placental λgt11 cDNA library (Clontech Laboratories Inc., Palo Alto, Calif.) a cDNA fragment that was used as probe to screen again a human placental λgt11 cDNA to get the full length cDNA clone. The amplified cDNA fragment was purified on agarose gel and labeled with [$\alpha^{32}$P]dCTP (Amersham Corp.) using the random primer labeling kit from Pharmacia Inc. PCR amplification reaction medium contained 50 mM KCl, 10 mM Tris-HCl, pH 8.3, 0.1% gelatin, 1 mM MgCl$_2$, 250 μM dNTP, 0.25 μM oligonucleotide primers, and 200 ng of DNA prepared from human placental λgt11 cDNA library. The aqueous phase was overlaid with 75 μL of mineral oil to avoid evaporation. The mixture was heated at 98° C. for 5 min, following the temperature reduction to 72° C., 1 unit of Taq DNA polymerase was added. Using a DNA Thermal Cycler (Perkin-Elmer Corp.), 30 cycles of amplification were carried out using a step program (94° C., 1 min; 60° C., 1 min; and 72° C., 1 min)/cycle.

Approximately 5×10$^5$ recombinant phage plaques were screened with 1.5×10$^6$ cpm/ml of the probe. Prehybridization was performed for 4 h at 42° C. in 50% formamide, 5× Denhardt's solution (1× Denhardt's being 0.02% polyvinyl pyrrolidone, 0.02 Ficoll, 0.02 bovine serum albumin), 5×SSPE (1×SSPE being 0.18M NaCl, 10 mM NaH$_2$PO$_4$, pH 7.4, 1 mM EDTA), 0.1% SDS, and 100 μg/ml yeast tRNA. The probe was denatured by heating at 100° C. for 5 min, before being added to the hybridization solution at 42° C. overnight. Filters were then washed twice at room temperature in 2×SSC (1×SSC being 0.015 M NaCl, 0.15M sodium citrate, pH 7.0), 0.1% SDS, and twice in 0.1×SSC, 0.1% SDS at 60° C. Positive recombinant plaques were purified by replating twice and grown in liquid culture. Phage DNA were isolated by centrifugation for 90 min at 105,000×g, and DNA was then isolated by phenol extraction and precipitation with isopropanol (Karen et al. 1987; In: Current Protocols in Molecular Biology (F. M. Ausubel, R. Brent, E. Kingston, D. D. Moore, T. G. Seidman, T. A. Smith and K. Struhl, eds), Wiley & Sons, New York, pp. 1.13.1–1.13.6).

II) Construction of Expression Vector, and Nucleotide Sequence Determination

The phage DNA were digested with EcoRI restriction enzymes and the resulting cDNA fragments were inserted into the EcoRI site downstream to the cytomegalovirus (CMV) promoter of the pCMV vector (kindly provided by Dr. Matthew, Cold Spring Harbor, N.Y., USA). Recombinant pCMV plasmids were amplified in *Escherichia Coli* DH5α competent cells, and were isolated by alkaline lysis procedure (Maniatis et al., In: Molecular cloning: a laboratory manual, Cold Spring Harbor Laboratory., 1982). Sequencing of double-stranded plasmid DNA was performed according to the dideoxy chain termination method (Sanger et al., PNAS 74: 5453–5467, 1977) using a T7 DNA polymerase sequencing kit (Pharmacia LKB Biotechnology). To avoid errors, all sequences were determined by sequencing both strands of the DNA. Oligonucleotide primers were synthesized in our laboratory with a 394 DNA/RNA synthesizer (Applied Biosystem).

The pCMV vector contain 576 nucleotides of the pCMV promoter (followed by 432 bp of small t intron (fragment 4713–4570) and poly adenylation signal (2825–2536)of SV40, followed by 1989 bp of the Pvu II(628)-AatII (2617) fragment from pUC 19 vector (New England Biolabs) that contains an *E. Coli* origin of replication and an ampicillin resistance gene for propagation in *E. Coli*.

III) Cells Overexpressing 17β-HSDs in Transformed Embryonal Kidney (293) Cells

A. Transient Transfection

Transfection was performed by the calcium phosphate procedure (Kingston et al., In: Current Protocols in Molecular Biology (Ausubel et al., eds), pp. 9.1.1–9.1.9, John Wiley & Sons, Inc., New York, 1987) using 1 to 10 μg of recombinant plasmid DNA per 10$^6$ cells. The total amount of DNA is keep at 10 μg of plasmid DNA per 10$^6$ by completing with pCMV plasmid without insert. The cells were initially plated at 10$^4$ cells/cm$^2$ in Falcon culture flasks and grown in Dulbecco's modified Eagle's medium containing 10% (vol/vol) fetal bovine serum (Hyclone, Logan, Utah) under a humidified atmosphere of air/CO$_2$ (95/5%) at 37° C. supplemented with 2 mM L-glutamine, 1 mM sodium pyruvate, 100 IU penicillin/ml, and 100 μg streptomycin sulfate/ml.

B. Stable Transfection

Cells were cultured in 6-wells falcon flasks to approximately 3 105 cells/well in DMEM. Five μg of pCMV-neo plasmid that expresses type 5 17β-HSD and Neomycin resistant gene, were transfected into 293 cells using lipofectin transfection kit (Life Technologies, Burlinton, ON). pCMV-neo vector were constructed by inserting 2685 bp of a BamH1—BamH1 DNA fragment that expresses a neomicin resistance gene isolated from the pMAMneo vector (Clontech Laboratories, Palo Alto, Calif.) at the BamH1 site of the pCMV vector. After 6 h incubation at 37° C., the transfection medium was removed and 2 ml of DMEM were added. Cells were further cultured for 48 h then transferred into a 10 cm petri dishes and cultured in DMEM containing 700 μg/ml of G-418 (Life Technologies, Burlinton, ON), in order to inhibit the growth of non-transfected cells. Medium containing G-418 was changed every two days until resistant colonies were observed. Resistant clones that incorporated Neomycin resistant gene were tested for 17β-HSD activity. The most actif clone was cultured and keep frozen at −70° C. for further inhibition study.

IV) Assay of Enzymatic Activity

Determination of activity was performed as described (Luu-The et al., Mol. Endocrionol. 4: 268–275, 1990, Lachance et al., J. Biol. Chem. 265: 20469–20475, 1990; Luu-The et al., DNA & Cell Biol. 14: 511–518, 1995).

Briefly, 0.1 µM of the indicated $^{14}$C-labeled substrate (Dupont Inc. (Canada), namely, DHEA, 4-androstene-3,17-dione (Δ4), in absence or presence of increasing concentration of preferred inhibitor of the invention, was added to freshly changed culture medium in a 6-well culture plate. After incubation for 1 h, the steroids were extracted twice with 2 ml of ether. The organic phase were pooled and evaporated to dryness. The steroids were solubilized in 50 µl of dichloromethane, applied to Silica gel 60 thin layer chromatography (TLC) plate (Merck, Darmstad, Germany) then separated by migration in the toluene-acetone (4:1) solvent system. Substrates and metabolites were identified by comparison with reference steroids and revealed by autoradiography and quantitated using the Phosphoimager System (Molecular Dynamics, Sunnyval, Calif.). Transfection could be also performed with HeLa, SW-13, 293, COS-1 cells, the preferred cell line is 293 cells.

V. Reversibility of Human Type 5 17β-HSD Inhibitory Activity

The reversibility assay was performed as described above for the standard type 5 17β-HSD enzymatic assay, except that before adding the $^{14}$C-labeled substrate, the cells were preincubated with 0.3 µM of the indicated inhibitor for 1 h, (or the indicated time interval), followed by two washes with phosphate saline buffer (PBS).

VI. Enzymatic Assay for Types 1, 2, and 3 17β-HSD and Types 1 and 3 3α-HSD

Enzyme sources. 293 cells transiently transfected with expression vectors encoding types 1, 2 and 3 17β-HSD (Luu-The et al., J. Steroid Biochem. Molec. Biol., 55: 581–587, 1995), types 1 and 2 5α-reductase (Luu-The et al., J. Invest. Dermatol., 102: 221–226, 1994) and types 1 and 3 3α-HSD (Dufort et al. Biochem. Biophys. Res. Commun. 228: 474–479, 1996), using the calcium phosphate procedure (Kingston et al., In: Current Protocols in Molecular Biology. Edited by E. M. Ausbel, R. Brent, R. E. Kingston, D. D. Moore, J. G. Seidman, J. A. Smith, K. Struhl. John Wiley & Sons, New York, pp. 9.1.1–9.1.9, 1991; Luu-The et al., J. Invest. Dermatol., 102: 221–226, 1994). For assays using cell subfractions, cells were sonicated in 50 mM sodium phosphate buffer (pH 7.4), containing 20% glycerol and 1 mM EDTA and centrifuged at 10 000×g for 30 min before centrifugation for 100 000×g for 1 h to separate the mitochondrial and microsomal fractions, respectively. The cytosol fractions (100 000×g supernatant) was used to determine type 1 activity while the microsomal fraction (pellet at 100 000×g) was used for measurement of types 2 and 3 17β-HSD activities.

Incubation. The enzymatic reaction was carried out at 37° C. in 1 ml of 50 mM sodium phosphate buffer, pH 7.4, containing 20% glycerol, 1 mM EDTA, and 2 mM cofactors (NADPH or AND$^+$) for 1 h in the presence of 0.1 µM $^{14}$C-labeled substrate: estrone and 4-dione for types 1 and 2 17β-HSD, respectively, testosterone for type 2 17β-HSD as well as types 1 and 2 5α-reductases, DHT for types 1 and 3 3α-HSD activities, and the indicated concentration of inhibitor.

Extraction of metabolites, migration on TLC and quantification were as described above for the assay of type 5 17β-HSD.

OTHER TESTS

A. In Vivo Assays of Bioavailability of Human Type 5 17β-HSD Inhibitors

1) Principle

The assays of the bioavailability of 17β-HSD Type 5 inhibitors were performed in male Sprague Dawley rats by measuring the plasma concentrations of the compounds after single oral administration of the compounds. The measurements at various time intervals were for values greater than or equal to 1.0 ng/mL and less than or equal to 50 ng/mL.

a) Animals and Treatment

Male Sprague-Dawley rats [Crl:CD(SD)Br] weighing 275–350 g were obtained from Charles-River Canada Inc. and housed 2 per cage during the acclimation period and individually during the study period. The animals were maintained under a regimen of 12 hours light: 12 hours dark (lights on at 08:00). Animals received certified Rodent feed (Lab Diet #5002, pellets) and tap water ad libitum. Rats were fasted (access to water only) starting on the evening prior to dosing.

Each compound to be tested was administered to three animals as a suspension in 0.4% methylcellulose by oral gavage at a dose of 0.5 mg/rat (1.0 ml/rat). Four to eight new compounds were tested each day and one group of animals received megestrol acetate (MGA) under the same conditions on each dosing day as a reference. One blood sample of ~0.7 ml was collected from the jugular vein of rats under Isoflurane-induced anesthesia at 1, 2, 3, 4, and 7 hours post-gavage. Blood samples were immediately transferred into a refrigerated 0.75 ml Microtainer containing EDTA and kept in an ice-water bath until centrifugation at 3000 rpm for 10 minutes. Plasma separation was performed rapidly (less than 50 minutes) after blood collection. One aliquot of 0.25 ml of plasma was then transferred into a borosilicate tube (13×100) and was rapidly frozen on dry-ice. Plasma samples were kept at −80° C. until measurement of plasma concentration of the inhibitor(s) by LCMS/MS.

2) LCMS Measurements a) Apparatus

1. Vacuum manifold
2. Turbo Vap LV evaporator
3. Mass spectrometer API III or API-300 (PE/Sciex) with associated peripherals
4. Automatic Injector
5. HPLC pump
6. Infusion pump
7. Calibrated pipets b) Reagents and Solutions 1. Methanol, HPLC grade
2. Water, Ultrapure (Super Q)
3. Ethanol, reagent grade
4. N-butyl chloride, HPLC grade
5. Acetone, HPLC grade
6. Male rat plasma (EDTA)
7. 17β-HSD type 5 inhibitors in reference standard ethanol solution approximately 100 µg/mL
8. EM 248 Internal Standard reference standard (solution of 50 ng/mL)
9. Mass calibrator solution Polypropylene Glycol (PE/Sciex)

c) Mass Spectrometer Conditions

Detector: Mass spectrometer API-300 (PE/Sciex)

Interface: Turbo Ion spray inlet (split 1/5)

Auxiliary flow: 4.5 L/minute (nitrogen)

Nebulizer Flow: 11

Curtain Gas Flow: 11

Probe Temperature: 460° C.

Pressure: Approximately $3 \times 10^{-5}$ Torr

CAD gas thickness: 3

Count Control: 1

Mobile Phase: Gradient of Methanol with 1 mm Ammonium formate and Water with 1 mm Ammonium formate Flow Rate: 1 mL/minute d) Mass Spectrometer Analysis Parameters for EM-1118

Dwell time: 150 msec

Pause time: 30 msec

Duration: 4 minute

MRM mode for

EM-1118 analysis: 444.2 and 398.3

Injection: 10 µL

Data handling: "API Standard Software" update version.

e) Preparation of Standard Solutions

Stock solutions for each type 5 inhibitor were prepared in methanol and, when not in use, the methanol solutions were stored at −20° C. Calibration curve standard solutions for each compound were prepared in male rat plasma as illustrated in Table 1.

A solution of internal standard in methanol containing EM-248 at 50 ng/mL, was prepared from stock standard solutions of EM-248 stored at −20° C.

| Concentration of inhibitor 17β-HSD | Volume of solution | Volume of plasma |
|---|---|---|
| Std 50 ng/mL | 90 µl of 1 µg/mL | 1.71 mL |
| Std 20 ng/mL | 0.8 mL of 50 ng/mL | 1.2 mL |
| Std 10 ng/mL | 0.9 mL of 20 ng/mL | 0.9 mL |
| Std 5 ng/mL | 0.8 mL of 10 ng/mL | 0.8 mL |
| Std 2 ng/mL | 0.6 mL of 5 ng/mL | 0.9 mL |
| Std 1 ng/mL | 0.5 mL of 2 ng/mL | 0.5 mL |
| Std 0 | N/A | 0.5 mL |
| Blank | N/A | 0.5 mL | f) Extraction Procedure for Type 5 Inhibitors From Rat Plasma

Aliquots of rat plasma (0.250 mL) were transferred to 13×100 mm borosilicate tubes. Water (1.0 mL) and internal standard solution (0.1 mL) were added to each sample and vortexed for 2 min. A mixture of N-butyl chloride and acetone (v:v, 7:3) (3 mL) was added to each sample and vortexed for 2 min. This step was repeated and the combined organic phases were evaporated to dryness under nitrogen in a Turbo Vap evaporator at 35° C. The residue was reconstituted with 1 mL of methanol and evaporated in a Turbo Vap evaporator at 35° C. The final extract was reconstituted into 0.1 mL of methanol/water (v:v, 75:25) and then transferred into a conical vial for injection into the mass spectrometer.

g) Assay

The assay procedure was performed by analyzing, in duplicate, rat plasma samples spiked at six different Type 5 inhibitor concentrations (1, 2, 5, 10, 20 and 50 ng/mL). As example, the results of EM-1118 are presented in FIG. 1. The lower limit of quantitation (LOQ) was established at 1.0 ng/mL. Values lower than 1.0 ng/mL were expressed as below limit of quantification (BLQ).

h) Linearity

The assay procedures for EM-1118 were found to be linear over the 1.0 to 50 ng/mL range. Weighted (1/X) linear regression analysis gave a correlation ($r^2$) of 0.991.

i) Calculation of AUC Values

For all compounds studied, the area under the plasma concentration versus time curve (AUC) from time 0 to 7 hours post-dosing was determined. $AUC_{0-7}$ values were calculated by the linear trapezoidal method (model-independent) for each rat and data were expressed as mean $AUC_{0-7} \pm SEM$ (n=3).

B. Androgenic/Antiandrogenic Activity

Androgenic/antiandrogenic activity of some preferred compounds has been measured using the Shionogi mouse mammary carcinoma cells.

Materials

Minimal essential culture medium (MEM), non-essential amino acids, and fetal calf serum were purchased from Flow Laboratories. In order to remove endogenous steroids, serum was incubated overnight at 4° C. with 1% activated charcoal (Norit A, Fisher) and 0.1% Dextran T-70 (Pharmacia). A 2-h supplementary adsorption was performed at 25° C. in order to further remove protein-bound steroids. Serum was also inactivated by a 20-min incubation at 56° C.

5α-dihydrotestosterone (DHT) was obtained from Steraloids. The antiandrogen hydroxyflutamide (OH-FLU) was kindly supplied by Drs. T. L. Nagabuschan and R. Neri (Schering Corporation, Kenilworth, U.S.A.).

Cell Dispersion, Culture and Cloning

Shionogi male mice bearing androgen-sensitive mammary tumors were obtained from Drs. Keishi Matsumoto, Osaka, Japan, and Yvonne Lefebvre, Ottawa, Canada. For primary culture, tumors were excised and washed in ice-cold sterile 25 mM Hepes buffer (137 mM NaCl; 5 mM KCl; 0.7 mM $Na_2HPO_4$; 10 mM glucose, pH 7.2). After mincing with scissors, the tumor minces were digested for 2 h at 37° C. in Hepes buffer containing 3.8 mg/ml collagenase (Clostridium, Boehringer), 1.5 mg/ml hyaluronidase II (Sigma), and 3% bovine serum albumin fraction V (Schwartz-Mann). Dispersed cells were collected by centrifugation (500×g for 10 min), washed twice by suspension in minimal essential medium (MEM) containing 5% dextran-coated charcoal-treated fetal calf serum (DCC-FCS), 1% non-essential amino acids, 10 IU/ml penicillin, 50 µg/ml streptomycin, and 100 nM dihydrotestosterone (DHT) (Steraloids).

Cells were plated in the same medium at a density of 75 000 cells/ml in 75 $cm^2$ flasks under an atmosphere of 5% carbon dioxide in air at 37° C. The medium was changed weekly. The steroids and antisteroids were dissolved in ethanol and kept in stock solutions chosen to yield final ethanol concentrations less than 0.01% in the culture medium. Such a concentration of ethanol does not affect cell growth.

Cells were subcultured at near-confidence by gentle digestion in a solution of 0.1% pancreatin (Flow Laboratories) in Hepes buffer containing 3 mM ethylenediaminetetraacetic acid (EDTA) (pH 7.2). Cells were pelleted by centrifugation, resuspended in culture medium, counted in a Coulter counter, and replated as described above. Soft agar cloning was performed as described (Stanley et al., Cell 10: 35–44, 1977) in the presence of 100 nM DHT.

Measurement of Cell Growth and Sensitivity to Steroids and Antisteroids

Cells were plated in 24-well plates at a density of 20 000 cells/well. The indicated increasing concentrations of agents were added to triplicate dishes, and cells were grown for 10–12 days with changes of medium every 3–4 days. Cell number was measured by direct counting in a Coulter counter.

Calculations and Statistical Analysis $ED_{50}$ values of action of DHT and glucocorticoids were calculated according to a least-square regression as described (Rodbard, Endocrinology 94: 1427–1431, 1974). Statistical significance was calculated according to a multiple-range test (Kramer, Biometrics 12: 307–310,1956).

C. Estrogenic/Antiestrogenic Activity

Estrogenic/antiestrogenic activity of some preferred compounds has been measured using the ZR-71-1 human breast cancer cell line as described in more detail below.

Maintenance of Stock Cultures

ZR-75-1 cells (83$^{rd}$ passage) were obtained from the American Type Culture Collection (Rockville, Md.) and routinely cultured in phenol red free RPMI 1640 supplemented with 1 nM estradiol ($E_2$), 2 mM L glutamine, 1 mM sodium pyruvate, 15 mM N-2-hydroxyethyl piperazine-N'-2-ethanesulfonic acid, 100 IU penicillin/ml, 100 µg streptomycin/ml, and 10% (v/v) fetal bovine serum (Hyclone, Logan, Utah) under a humidified atmosphere of 95% air, 5% $CO_2$, at 37° C. All media and medium supplments were purchased from Sigma. Cells were subcultured weekly by treatment with a pancreatic solution containing EDTA (0.2 g/L). The cell cultures used for the experiments herein describied were between passages 89 and 94.

Measurements of Cell Proliferation

Cells in their logarithmic growth phase were harvested, briefly centrifuged, and resuspended in RPMI 1640. Cells were then plated in triplicate in LIMBRO 24-well plastic culture plates (2 cm$^2$/well). Since plating density influences the effect of hormones on ZR-75-1 cell growth, cells were plated at a density of 1×10$^4$ cells/well. After 72 h, medium was replaced with fresh medium containing the inhibitor at the concentration of 3.10$^{-7}$ and 10$^{-6}$ M in absence or presence of 0.1 M estradiol ($E_2$). Control cultures received the ethanol vehicle only. Cells were then allowed to grow at 37° C. for 10 days with medium changes (of identical composition) every 2 days. In absence of inhibitors, in 0.1M estradiol ($E_2$)-containing medium, ZR-75-1 cells have doubling time of about 48 h.

After $E_2$ and/or antiestrogen treatment, cells were harvested by addition of 0.5 ml of a pancreatin solution (Sigma) for 5–10 min at 37° C. before addition of 0.5 mnl of RPMI 1640 containing 5% dextran coated charcoal-free bovine serum in order to block enzymatic action. Cell number (0.10 ml aliquot) was determined by measurement of DNA content as previously described (Simard et al., Endocrinology 126: 3223–3231,1990).

D. Androgen Receptor (AR) Assays

Tissue Preparation

Male Sprague-Dawley rats (Crl: CD(SD)Br) weighing 200–300 g were obtained from Charles-River Inc. (St-Constant, Québec, Canada). The rats were gonadectomized under general anesthesia (Isoflurane) and killed by cervical dislocation 24 hours later. The ventral prostates were rapidly removed, dissected free from adhering tissue and frozen on dry-ice. Prostates were kept at −80° C. until assay.

All subsequent steps were performed at 0–4° C. Prostates were homogenized in 5 vol (wt/vol) of buffer A (25 mM Tris-HCl, 1.5 mM EDTA disodium salt, 10 mM α-monothioglycerol, 10% glycerol, and 10 mM sodium molybdate, pH 7.4), using a Polytron PT-10 homogenizer (Brinkman Instruments, Canada) at a setting of 5 for three periods of 10 sec, with intervals of 10 sec for cooling. The homogenate was then centrifuged at 105,000×g for 60 min in a Beckman L5-65 ultracentrifuge (Fullerton, Calif.). The protein concentration of the cytosol fraction was measured according to the method of Bradford (Anal. Biochem. 72: 248–254, 1976), using bovine serum albumin as standard.

Androgen Receptor Assay

Androgen binding was measured using the hydroxylapatite assay (HAP). In brief, the radioactive steroid [$^3$H]R1881 solubilized in ethanol was diluted into buffer A. Aliquots of prostate cytosol preparation (0.1 ml) were then incubated with 8 nM [$^3$H]R1881 (0.1 ml, ~200,000 cpm) in the presence or absence of the indicated concentrations of unlabeled compounds (0.1 ml, prepared in buffer A containing 10% ethanol) for 16–18 h at 0–4° C. Triamcinolone acetonide (150 nM) was added in order to mask progesterone receptors. Unbound steroids were separated by incubation for 40 min at 0–4° C. with 0.3 ml HAP prepared in buffer P (50 mM, Tris-HCl, 10 mM $KH_2PO_4$, pH 7.4) as follows: 10 g HAP were washed with buffer P until the supernatant reached a pH of 7.4 and then following centrifugation and decantation of the supernatant, 37.5 ml of buffer P were added. After incubation with HAP and 10 minutes of centrifugation at 1,000×g, the pellet was washed 3 times with 1 ml buffer P. Thereafter, the radioactivity was extracted from the pellet by incubation at room temperature for 60 minutes with 1 ml EtOH. After centrifugation, the supernatant was decanted into a scintillation vial and the pellet was extracted again with ethanol. Thereafter, 10 ml Formula-989 scintillation liquid was added to pooled supernatant and the radioactivity was measured in a Beckman counter.

Calculations

The results were reported as the percentage of inhibition of the binding of [$^3$H]R1881 at the concentrations of 10$^{-8}$ and 10$^{-6}$ M of the inhibitor.

E. Progesterone Receptor Assay

Chemicals

[17α-methyl-$^3$H]-promegestone (R5020) (84 Ci/mmol) and the corresponding unlabeled compound were purchased from New England Nuclear (Lachine, Québec, Canada). All other chemicals were of analytical grade.

Stock solutions of the unlabeled steroids were kept at 4° C. in ethanol. The desired steroid solutions were then prepared by appropriate dilution in buffer B (10 mM Tris-HCl, 1.5 mM EDTA, 10 mM α-monothioglycerol, pH 7.4) containing 30% ethanol.

Tissue Preparation

Female Sprague-Dawley rats weighing 200–300 g were obtained from Charles-River Inc. (St-Constant, Québec, Canada). The rats were gonadectomized under general anesthesia (Isoflurane) and killed by cervical dislocation 24 hours later. The uteri are rapidly removed, dissected free from adhering tissue and frozen on dry-ice. Tissues were kept at −80° C. until use.

Cytosol Preparation

All procedures were performed at 4° C. Tissues were pulverized frozen in dry ice with a Thermovac pulverizer. The samples were then homogenized in 10 vol (w/v) of buffer A (25 mM Tris-HCl, 1.5 mM EDTA, 10 mM α-monothioglycerol, 10% glycerol, 10 mM sodium molybdate, pH 7.4) using a Polytron PT-10 homogenizer (Brinkmann Instruments, Canada) at a setting of 5 for two periods of 10 sec, with intervals of 10 sec for cooling. The homogenate was then centrifuged at 105,000×g for 90 min. The supernatant was used immediately for assay.

Binding Assays

Progesterone binding was measured using the dextran-coated charcoal adsorption technique. Incubations were performed at 0–4° C. for 16–18 h using 100 µl of cytosol, 100 µl of [$^3$H]-R5020 (5 nM final, which contained 1,000 nM of dexamethasone in order to mask the glucocorticoid receptors) and 100 μl of unlabeled compounds at the indicated concentrations. Each concentration was done in triplicate. Assay was ended with 300 μl of DCC (1% Norit A and 0.1% Dextran T-70 in Buffer B). After 10 min of incubation, tubes were centrifuged at 2,000×g for 10 min. and decanted in vials with 6 ml of BCS liquid scintillation (New England Nuclear, Dupont). The radioactivity was measured in a Beckman counter at a counting efficiency of 35%.

Calculations

The results were reported as the percentage of the inhibition of the binding of [$^3$H]R5020 at the concentrations of $10^{-8}$ and $10^{-6}$M of the inhibitors.

F. Glucocorticoid Receptor Assay

Chemicals

[6,7-$^3$H(N)]-Dexamethasone (39 Ci/mmol) was purchased from New England Nuclear (Lachine, Québec, Canada) while unlabeled dexametasone was obtained from Steraloids (Wilton, N.H.). All other chemicals were of analytical grade.

Stock solutions of the unlabeled steroids were kept at 4° C. in ethanol. The desired steroid solutions were then prepared by appropriate dilution in buffer B (10 mM Tris-HCl, 1.5 mM EDTA, 10 mM α-monothioglycerol, pH 7.4) containing 30% ethanol.

Tissue Preparation

Male Sprague-Dawley rats weighing 200–300 g were obtained from Charles-River Inc. (St-Constant, Québec, Canada). The rats were killed by cervical dislocation and the liver were rapidly removed, dissected free from adhering tissue and frozen on dry-ice. Tissues were kept at −80° C. until use.

Cytosol Preparation

All procedures were performed at 4° C. Tissues were eminced and homogenized in 10 vol (w/v) of buffer A (25 mM Tris-HCl, 1.5 mM EDTA, 10 mM α-monothioglycerol, 10% glycerol, 10 mM sodium molybdate, pH 7.4) using a Polytron PT-10 homogenizer (Brinkmann Instruments, Canada) at a setting of 5 for two periods of 10 sec, with intervals of 10 sec for cooling. The homogenate was then centrifuged at 105,000×g for 90 min. The supernatant was used immediately for assay.

Binding Assays

Glucocorticoid binding was measured using the dextran-coated charcoal adsorption technique. Incubations were performed at 0–4° C. for 16–18 h using 100 μl of cytosol, 100 μl of [$^3$H]-Dexamethasone (5 nM final) and 100 μl of unlabeled compounds at the indicated concentrations. Each concentration was done in triplicate. Assay was ended with 300 μl of DCC (2.5% Norit A and 0.25% Dextran T-70 in Buffer B). After 10 min of incubation, tubes were centrifuged at 2,000×g for 10 min. and decanted in vials with 6 ml of BCS liquid scintillation (New England Nuclear, Dupont). The radioactivity was measured in a Beckman counter at a counting efficiency of 35%.

Calculations

The results were reported as the percentage of the inhibition of the binding of [$^3$H]-dexamethasone at the concentrations of $10^{-8}$ and $10^{-6}$M of the inhibitor.

G. Estrogen Receptor (ER) Assay

Tissue Preparation

Female Sprague-Dawley rats (Crl: CD(SD)Br) weighing 200–300 g were obtained from Charles-River Inc. (St-Constant, Québec, Canada). The rats were gonadectomized under general anesthesia (Isoflurane) and killed by cervical dislocation 24 hours later. The uteri were rapidly removed, dissected free from adhering tissue and frozen on dry-ice. Uteri were kept at −80° C. until assay. All subsequent steps were performed at 0–4° C. Uteri were homogenized in 10 vol (wt/vol) of buffer A (25 mM Tris-HCl, 1.5 mM EDTA disodium salt, 10 mM α-monothioglycerol, 10% glycerol, and 10 mM sodium molybdate, pH 7.4), using a Polytron PT-10 homogenizer (Brinkman Instruments, Canada) at a setting of 5 for three periods of 10 sec, with intervals of 10 sec for cooling. The homogenate was then centrifuged at 105,000×g for 60 min in a Beckman L5-65 ultracentrifuge (Fullerton, Calif.). The protein concentration of the cytosol fraction was measured according to the method of Bradford (Anal. Biochem. 72: 248–254, 1976), using bovine serum albumin as standard.

Estrogen binding was measured using the dextran-coated charcoal adsorption technique as described previously (Asselin et al., Endocrinology, 101: 666–671, 1977; Asselin and Labrie, J. Steroid Biochem., 9: 1079–1082, 1978). Briefly, [$^3$H]E$_2$ solubilized in ethanol were diluted into buffer A. Aliquots of uterine cytosol preparation (0.1 ml) were incubated with 5 nM [$^3$H]E$_2$ (~200,000 cpm, 0.1 ml) in the presence or absence of the indicated concentrations of unlabeled compounds (0.1 ml, prepared in buffer A containing 10% ethanol) for 3 h at room temperature. Unbound steroids were then separated by incubation for 15 min at 0–4° C. with 0.3 ml 0.5% Norit-A and 0.05% Dextran T-70 in buffer B (1.5 mM EDTA disodium salt, 10 mM monothioglycerol, and 10 mM Tris-HCl, pH 7.4) and centrifuged at 3,000×g for 15 min. Aliquots of the supernatant (0.3 ml) were removed for radioactivity measurement. After the addition of 10 ml Formula-989 scintillation liquid (New England Nuclear-DuPont), the radioactivity was measured in a Beckman counter at a counting efficiency of 62%.

Calculations

The results were reported as the percentage of inhibition of the binding of E$_2$ at the concentrations of $10^{-8}$ and $10^{-6}$M of the inhibitor.

Primary criteria in selecting preferred inhibitors include bioavailability desirable inhibition of type 5 17β-hydroxysteroid dehydrogenase, extent of undesirable inhibition on type 2 17β-hydroxysteroid dehydrogenase and androgenicity. It is believed that the methyl groups in 5' position in EM 1394 and analogous compounds promote selectivity of type 5 inhibition (versus undesirable type 2 inhibition). Of the compounds in the foregoing tables, the most preferred and their molecular structures are set forth below:

EM-1291

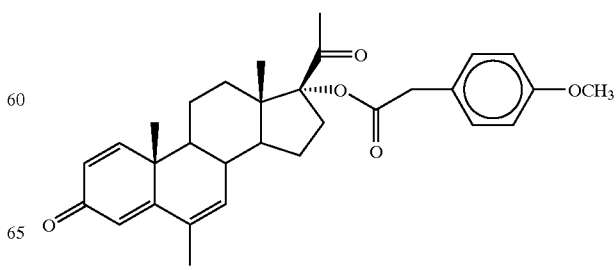

EM-1195-CS
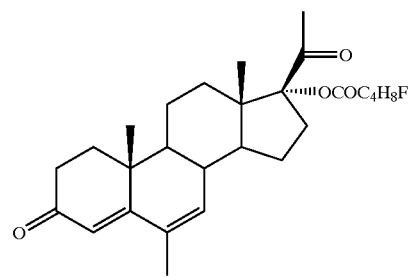
CS-243
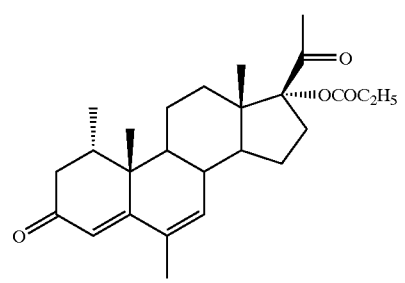
CS-245
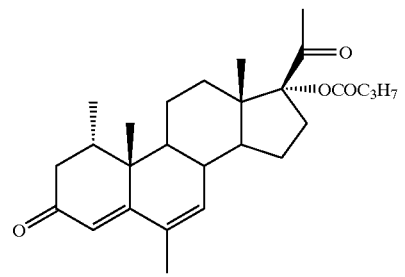
EM-1183
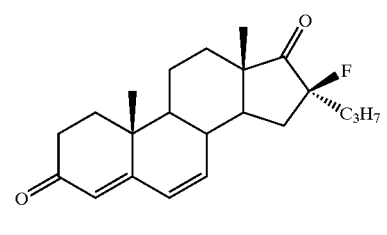
EM-1097
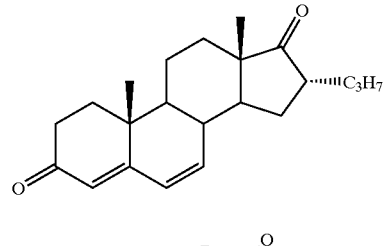
EM-1273-CS
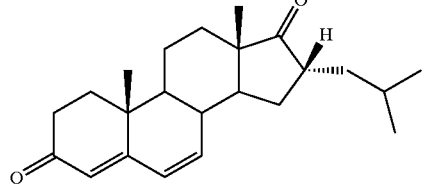
EM-1401
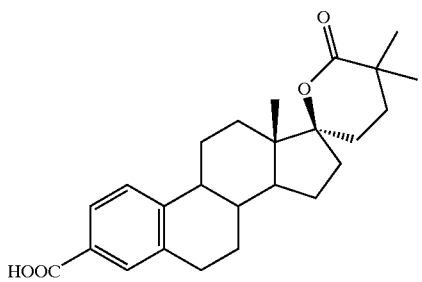
EM-1404
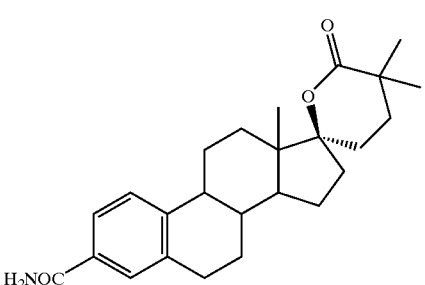
CS-237
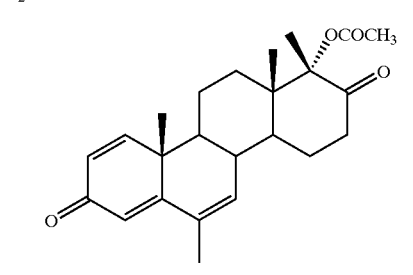
EM-1078
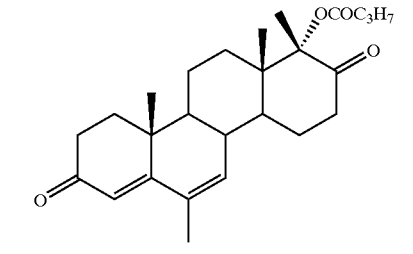
EM-1196-CS
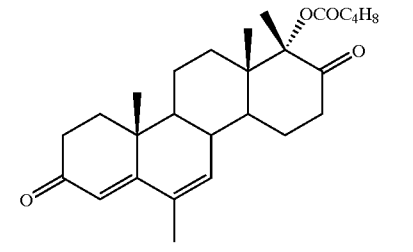
EM-1394
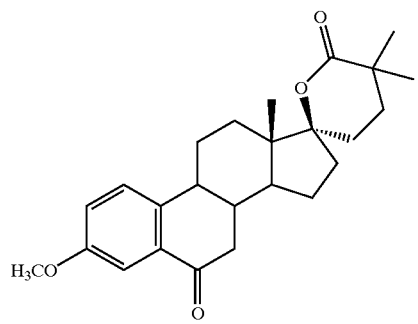

EM-1424
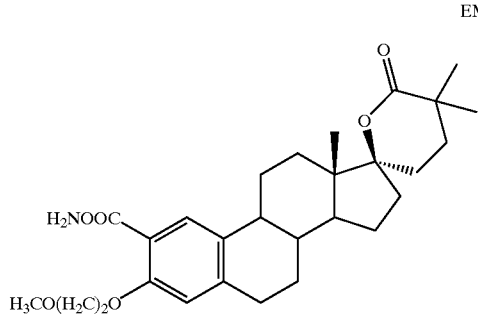
EM-1157-CS
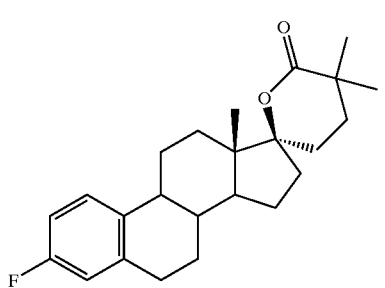
EM-1125
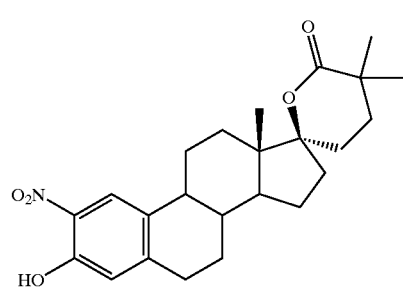
EM-1402-CS
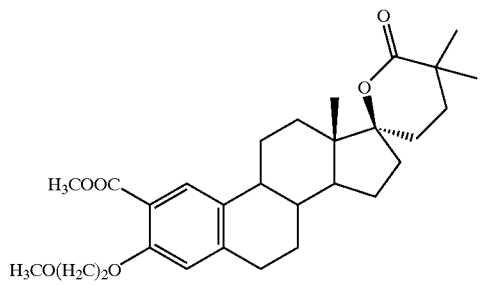
EM-1396
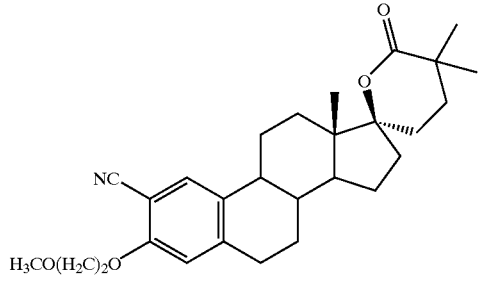
EM-1181
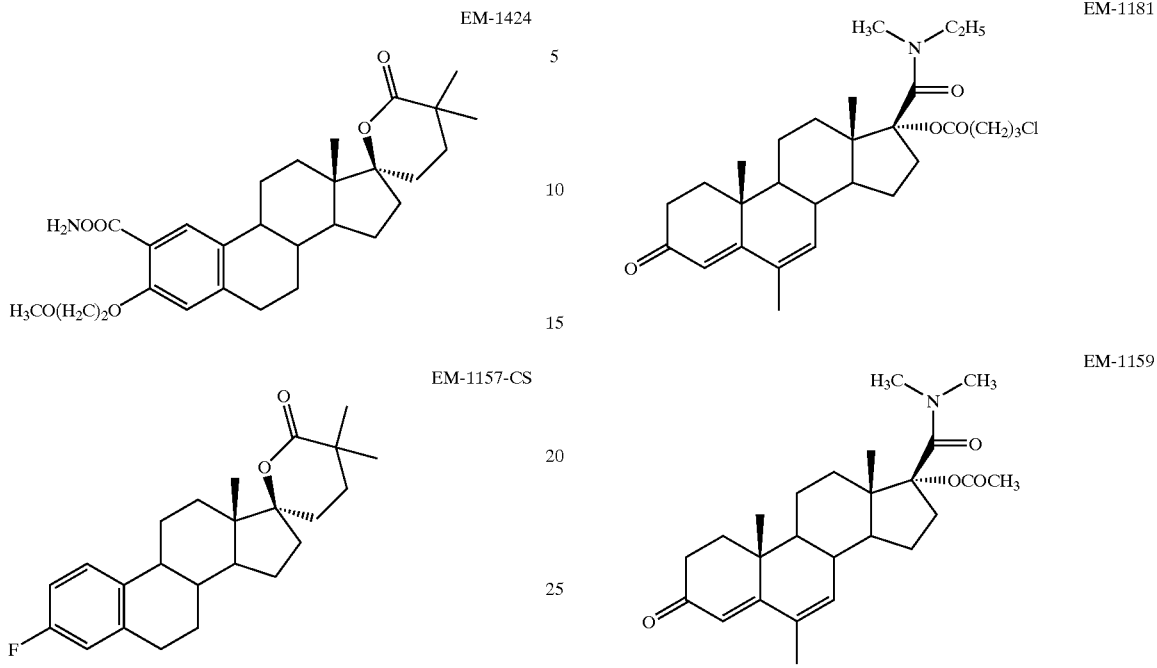
EM-1159
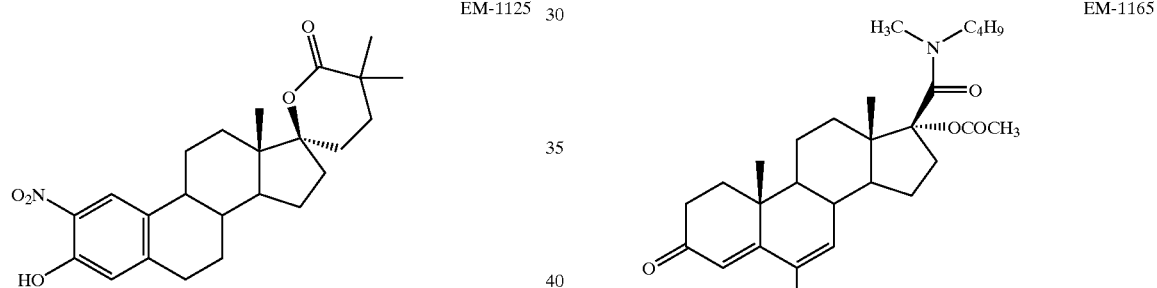
EM-1165
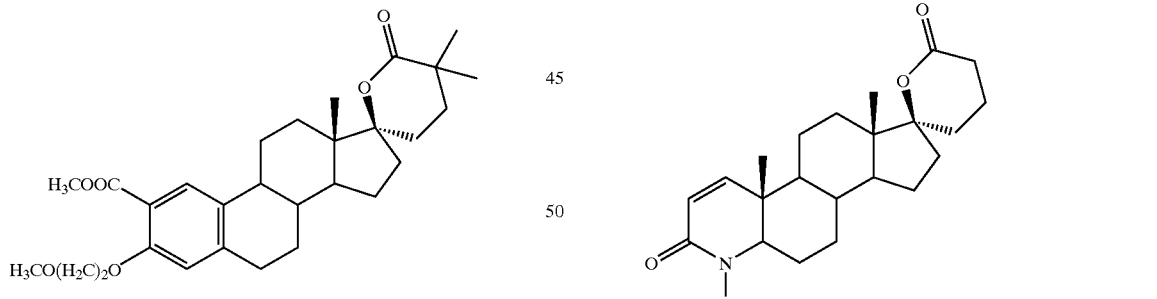
EM-1122-CS
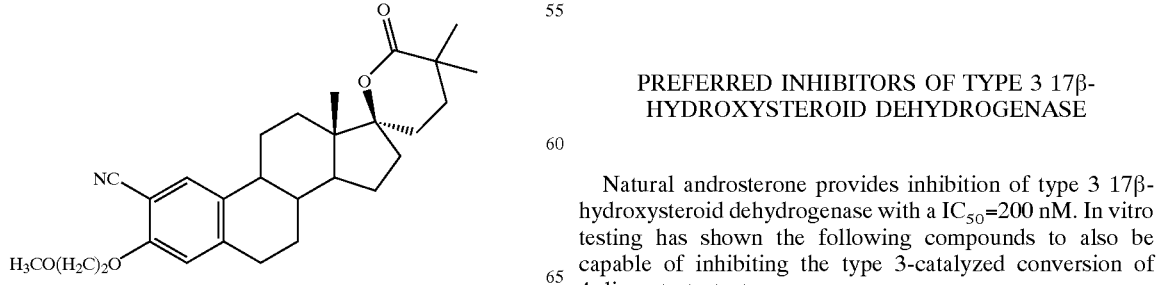
PREFERRED INHIBITORS OF TYPE 3 17β-HYDROXYSTEROID DEHYDROGENASE
Natural androsterone provides inhibition of type 3 17β-hydroxysteroid dehydrogenase with a $IC_{50}=200$ nM. In vitro testing has shown the following compounds to also be capable of inhibiting the type 3-catalyzed conversion of 4-dione to testosterone:

TABLE 6

% of Inhibition of the Type 3 17β-HSD Activity*

| Name | R | 3.10⁻⁷ M | 3.10⁻⁶ M |
|---|---|---|---|
| EM-1071 | —O(CH₂)₂OC₂H₅ | 73 | 91 |
| EM-1065 | —S(CH₂)₂SCH₃ | 63 | 94 |
| EM-1066 | —OCH₂SCH₃ | 63 | 93 |
| EM-1064 | —SCH₂OCH₃ | 62 | 92 |
| EM-1074 | —O(CH₂)₃CH₃ | 62 | 92 |
| EM-1073 | —O(CH₂)₂OCH₃ | 51 | 87 |
| EM-1070 | —OCH₂OCH₃ | 57 | 90 |

*The inhibition of human type 3 17β-hydroxysteroid dehydrogenase activity, expressed as the percentage of inhibition of enzymatic activity at 3.10⁻⁷ M (left column) and 3.10⁻⁶ M (right column), is reported. The manner in which the percentage of inhibition was obtained is described in "Efficacy of types 1, 2, and 3 17β-HSD and types 1 and 3 3α-HSD supra". Higher numbers are desirable.

TABLE 7

Inhibition of the Type 3 17β-HSD Activity* IC₅₀ (nM)

| Name | n | IC₅₀ (nM) |
|---|---|---|
| CS-213 | 1 | 31 ± 4 |
| EM-1324-CS | 2 | 31 ± 4 |

*The inhibition of human type 3 17β-hydroxysteroid dehydrogenase activity, expressed by the concentration which produce 50% of inhibition of enzymatic activity (IC₅₀ is nM), is reported. The manner in which IC₅₀ was determined is described in "Efficacy of types 1, 2, and 3 17β-HSD and types 1 and 3 3α-HSD". Lower numbers of IC₅₀ are desirable.

EXAMPLES OF SYNTHESIS OF PREFERRED INHIBITORS

The IR spectra herein were taken on a Perkin-Elmer 1600 Series FT-IR spectrophotometer. Proton NMR spectra were recorded on a Brucker AC-F 300 instrument. The following abbreviations have been used: s, singlet; d, doublet; dd, doublet of doublet; t, triplet; q, quadruplet; and m, multiplet. The chemical shifts (δ) were referenced to chloroform (7.26 ppm for $^1$H and 77.00 ppm for $^{13}$C) and were expressed in ppm. Optical rotations were measured at room temperature on a Jasco DIP 360 polarimeter. Mass spectra (MS) were obtained on a V.G. Micromass 16F machine. Thin-layer chromatography (TLC) was performed on 0.25 mm Kieselgel 60F254 plates (E. Merck, Darmstadt, FRG). For flash chromatography, Merck-Kieselgel 60 (230–400 mesh A.S.T.M.) was used. Unless otherwise noted, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Starting materials and reagents were available from Aldrich Chemical Company, Inc. (Milwaukee, Wis.)

LIST OF ABBREVIATIONS

| | |
|---|---|
| DHP | 3,4-dihydro-2H-pyran |
| EDTA | Ethylenediaminetetraacetic acid |
| HPLC | High pressure liquid chromatography |
| PTSA | p-toluenesulfonic acid |
| THF | Tetrahydrofuran |
| THP | Tetrahydropyranyl |
| TMS | Tetramethylsilyl |

Example 1

Synthesis of 6-Methyl 4,6-Pregnadien/1,4,6-pregnatrien-17-ol-3,20-dione Alkanoates/Benzoates These syntheses are described in Schemes 1 and 2.

Scheme 1

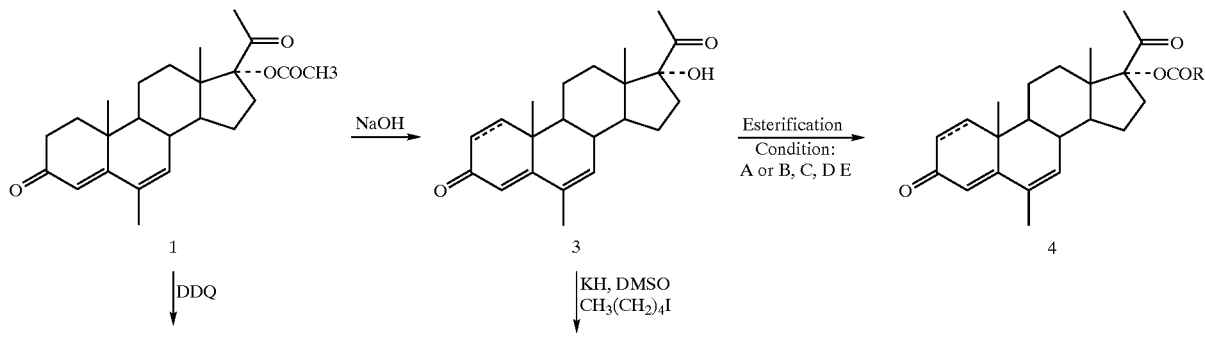

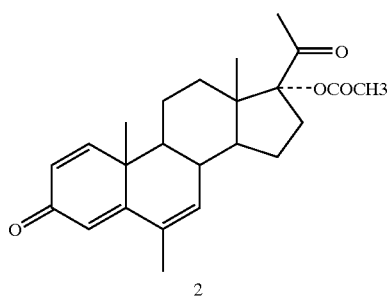

2

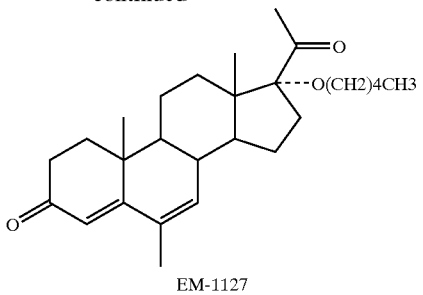

EM-1127

Scheme 2

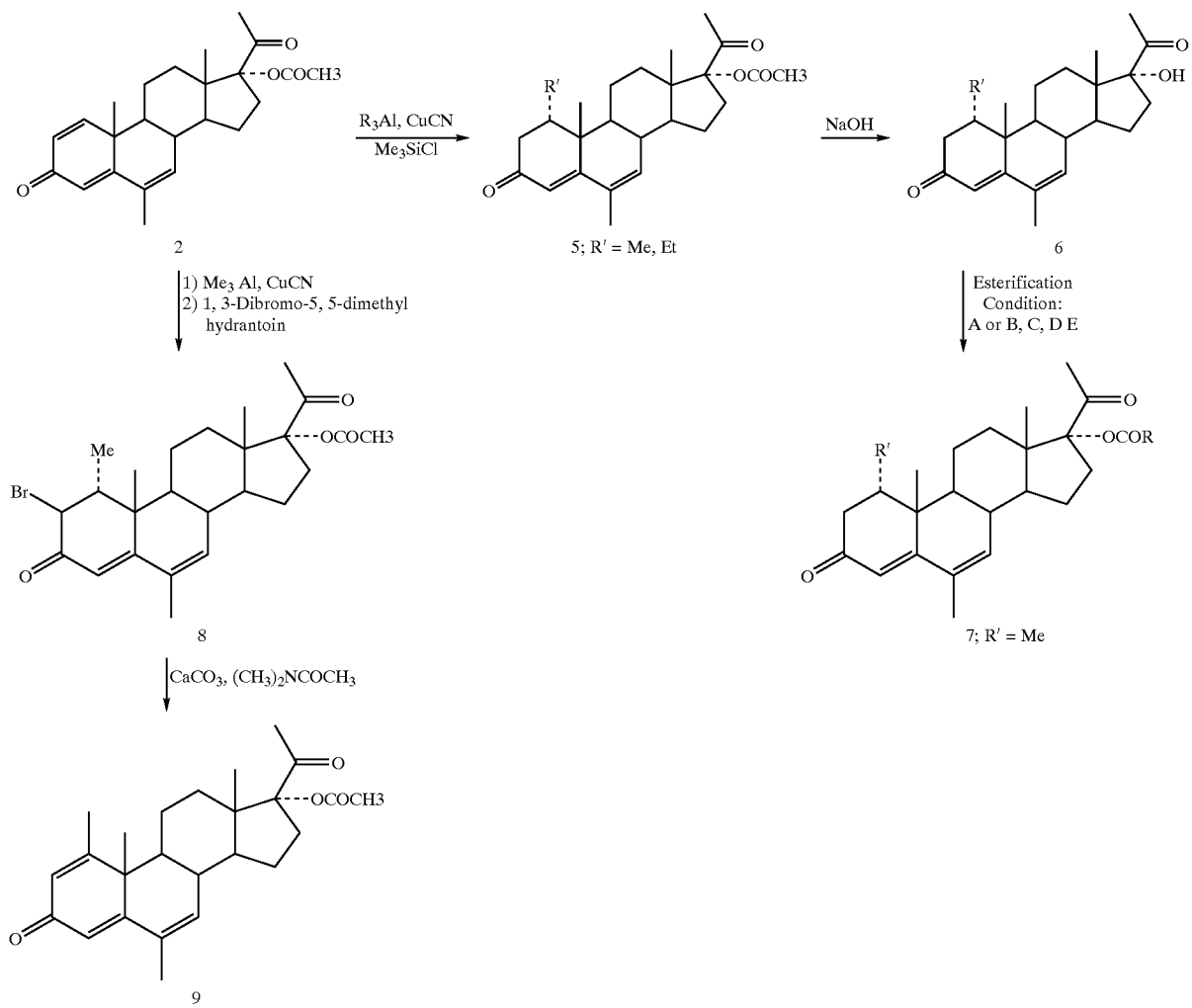

Example 1A

6-Methyl-1,4,6-pregnatrien-17α-ol-3,20-dione Acetate (2; EM-910)

Megestrol acetate (2.5 g; 6.7 mmol) and DDQ (5.07 g; 22 mmol) in dioxane (30 mL) were refluxed for 2 h. Solvent was removed and the mixture in EtOAc was washed with saturated $NaHCO_3$ solution (3 times). Solvent was dried ($MgSO_4$) and evaporated to give the product. Purification on silica gel column (hexanes/acetone) gave the trienone (2.1 g) in 90% yield; IR (KBr, $cm^{-1}$) 2953, 2895, 1729, 1709, 1658, 1646, 1610, 1365, 1264, 1247, 887. $^1$H NMR ($CDCl_3$) δ 0.69 (s, 3H, H-C18), 1.13 (s, 3H, H-C19), 1.87(s, 3H, 6-CH3), 2.0(s, 3H) 2.02(s, 3H), 2.89–2.98 (m, 1H), 5.79 (s, 1H), 6.22 (s, 1H), 6.20–6.24 (m, 1H, 2-H), 7.04 (d, 1H, 1-H, J=10 Hz); $^{13}$C NMR ($CDCl_3$) δ 203.7, 186.4, 170.6, 163.2, 153.4, 134.5, 131.8, 127.7, 121.6, 96.2, 49.1, 47.9, 47.1, 41.1, 37.7, 31.1 30.3, 26.4, 23.2, 21.5, 20.5 19.2, 14.4.

Example 1B

6-Methyl-4,6-pregnadien-17α-ol-3,20-dione (3)

Megestrol acetate (11.2 g) was dissolved in 200 mL of boiling MeOH and to this, was added 2N NaOH (20 mL). The mixture was refluxed for 5 h. Approx. 100 mL of MeOH was removed, and water (50 mL) was added and the suspension was cooled to 0° C. to give a solid, which was filtered and washed with water (9.6 g, 96%); IR (KBr, cm$^{-1}$) 3493, 2942, 2767, 1702, 1658, 1646, 1623, 1575. $^1$H NMR (CDCl$_3$) δ 0.75 (s, 3H, H-C18), 1.06 (s, 3H, H-C19), 1.81(s, 3H, 6-CH3), 2.25(s, 3H), 2.96 (s, 1H), 5.83 (s, 1H), 5.95 (s, 1H); $^{13}$C NMR (CDCl$_3$) δ 211.3, 200.0, 164.4, 138.5, 131.1, 121.0, 89.5, 50.3, 48.7, 47.9, 36.9, 36.1, 34.0 33.5, 30.2, 27.7, 23.3, 20.1, 19.8 16.3, 15.2.

Example 1C

6-Methyl-4,6-pregnadien-17α-ol-3,20-dione Aklanoates/Benzoates (4)

Esterification was conducted by following the method A or B, C, D, E. Condition A; Using Trifluoromethanesulfonic Anhydride: To a concentrated solution of the organic acid (1.1 eq.) in CH$_2$Cl$_2$ (1 mol/L), was added trifluoromethanesulfonic anhydride (1.2 eq.) at room temperature. After 15 min, the mixed anhydride was added to a solution of megestrol 3 in CH$_2$Cl$_2$ (1 mol/L) at 0° C. The mixture was stirred for 1 h at 0° C. followed by 1 h at room temperature. Saturated solution of NaHCO$_3$ was added and the aq. layer was extracted with CH$_2$Cl$_2$ (3 times). The combined organic layer was dried and evaporated to give the dark brown oil, which was purified on a silica gel column using hexanes/acetone as an eluent to give pure product (yields range from 40 to 80%)

Condition B; Using Trifluoroacetic Anhydride: Acid (5.61 mmol) was added to trifluoroacetic anhydride (5.33 mmol) in CH$_2$Cl$_2$ (5 mL) at room temperature and the solution was stirred for 3 h. The resulting solution was transferred to compound 3 (0.56 mmol) in CH$_2$Cl$_2$ (5 mL) at room temperature and the reaction was followed by TLC. The reaction mixture was diluted with CH$_2$Cl$_2$ (50 mL) and the organic solution was washed with saturated NaHCO$_3$ solution and then with saturated NaCl solution, dried (MgSO$_4$). Evaporation of solvents gave the crude product which was purified by column chromatography using hexanes/acetone as an eluent to give the pure product.

Condition C; Using Acid chloride or Acid anhydride and p-Toluenesulfonic acid: To a solution of megestrol 3 in CH$_2$Cl$_2$, was added p-toluenesulfonic acid (1 eq.) followed by acid chloride/acid anhydride (2 to 3 eq.). The reaction mixture was stirred for 8 to 10 h depending upon the alkyl chains. The mixture was poured in ice water and extracted with CH$_2$Cl$_2$. The organic layer was washed with saturated NaHCO$_3$, dried, and solvents removed to give the product which was purified by column chromatography using hexanes/acetone as an eluent.

Condition D; Using Acid chloride or Acid anhydride and phosphoric acid: To a solution of megestrol 3 in CH$_2$Cl$_2$ was added 85% aq phosphoric acid (1 eq.) followed by acid chloride/acid anhydride (2 to 3 eq.). The reaction mixture was stirred for 8 to 10 h depending upon the alkyl chains. The mixture was poured in ice water and extracted with CH$_2$Cl$_2$. The organic layer was washed with saturated NaHCO$_3$, dried, and solvents removed to give the product which was purified by column chromatography using hexanes/acetone as an eluent.

Condition E; Using Acid Anhydride and Scandium Trifluoromethanesulfonate: To compound 3 (1.12 mmol), was added propionic acid (47 mmol) and scandium trifluoromethanesulfonate (1 mol %; 5 mg) under argon and left for 3 h while stirring. The mixture was diluted with EtOAc and washed twice with saturated NaHCO$_3$ solution. Organic solvents were evaporated to give the product which was purified by column chromatography using hexanes/EtOAc as a solvent system to give pure product.

Example 1D

The followings are non-limiting examples of physicochemical characteristics of inhibitors of Example 1.

EM-917 (4; R=n-C$_5$H$_{11}$); Yield, 74%; IR (NaCl, cm$^{-1}$) 2950, 2870, 1731, 1661, 1626, 1580, 1458, 1352, 1249, 1159, 1110; $^1$H NMR (CDCl$_3$) δ 0.69 (s, 3H, H-C18), 0.86 (t, 3H, H-C6', J=7 Hz), 1.07 (s, 3H, H-C19), 1.82 (s, 3H, 6-C$_3$) 2.02 (s, 3H, H-C21), 2.31 (t, 2H, H-C2', J=7 Hz), 2.44–2.56 (m, 2H), 2.92–3.01(m, 1H), 5.85 (s, 1H), 5.94 (s, 1H); $^{13}$C NMR (CDCl$_3$) δ 203.9, 199.8, 173.3, 164.0, 137.9, 131.4, 121.3, 96.2, 50.3, 49.1, 47.6, 37.1, 36.1, 34.4, 34.1, 33.6, 31.3, 31.2, 30.4, 26.4, 24.5, 23.3, 22.3, 20.3, 19.9, 16.4, 14.3, 13.9.

EM-923 (4; R=n-C$_4$H$_9$); Yield, 82%; IR (NaCl, cm$^{-1}$) 2951, 2872, 1731, 1660, 1626, 1580, 1458, 1387, 1351, 1263, 1160, 1110; $^1$H NMR (CDCl$_3$) δ 0.71 (s, 3H, H-C18), 0.90 (t, 3H, H-C5', J=7 Hz), 1.08 (s, 3H, H-C19), 1.84 (s, 3H, 6-CH$_3$), 2.03 (s, 3H, H-C21), 2.20–2.27(m, 1H), 2.38 (t, 2H, H-C2', J=7 Hz), 2.40–2.59 (m, 2H), 2.94–3.03 (m, 1H), 5.86 (s, 1H), 5.95 (s, 1H); $^{13}$C NMR (CDCl$_3$) δ 203.9, 199.8, 173.3, 164.0, 137.9, 131.4, 121.2, 96.1, 50.3, 49.1, 47.5, 37.1, 36.1, 34.2, 34.1, 33.6, 31.1, 30.4, 26.8, 26.4, 23.3, 22.2, 20.3, 16.4, 14.3, 13.6.

EM-928 (4; R=CH(CH$_3$)$_2$); Yield, 58%; IR (NaCl, cm$^{-1}$) 2947, 2874, 1731, 1660, 1626, 1580, 1469, 1387, 1351, 1272, 1215, 1197, 1154, 1111, 1084, 1060; $^1$H NMR (CDCl$_3$) δ 0.71 (s, 3H, H-C18), 1.08 (s, 3H, H-C19), 1.18 (t, 6H, 2'-CH$_3$, J=7 Hz), 1.83 (s, 3H, 6-CH3), 2.01(s, 3H, H-C21), 2.45–2.60(m, 3H), 2.93–3.02 (m, 1H), 5.86 (s, 1H), 5.94 (s, 1H); $^{13}$C NMR (CDCl$_3$) δ 203.8, 199.8, 176.2, 164.0, 137.9, 131.4, 121.3, 96.0, 50.3, 49.2, 47.7, 37.1, 36.1, 34.2, 34.1, 33.6, 31.2, 30.4, 26.3, 23.3, 20.3, 19.9, 18.8, 18.6, 16.4, 14.4.

EM-948 (4; R=CH$_2$Cypent); Yield, 68%; IR (NaCl, cm$^{-1}$) 2947, 2867, 1731, 1681, 1626, 1579, 1455, 1352, 1262, 1160; $^1$H NMR (CDCl$_3$) δ 0.66 (s, 3H, H-C18), 1.00 (s, 3H, H-C19), 1.79 (s, 3H, 6-CH$_3$), 1.98 (s, 3H, H-C21), 2.29 (t, 2H, H-C2', J=8 Hz), 2.38–2.54 (m, 2H), 2.89–2.97 (m, 1H), 5.84 (s, 1H), 5.92 (s, 1H); $^{13}$C NMR (CDCl$_3$) δ 203.9, 199.8, 173.4, 164.0, 137.9, 131.4, 121.3, 96.1, 50.3, 49.1, 47.5, 39.6, 37.1, 36.1, 34.1, 33.7, 33.6, 32.4, 32.3, 31.1, 30.8, 30.4, 26.4, 25.1, 23.3, 20.3, 19.9, 15.3, 14.3.

EM-949 (4; R=CH$_2$Ph); Yield, 47%; IR (NaCl, cm$^{-1}$) 2946, 2870, 1730, 1658, 1625, 1579, 1454, 1351, 1264, 1141; $^1$H NMR (CDCl$_3$) δ 0.67 (s, 3H, H-C18), 1.07 (s, 3H, H-C19), 1.86 (s, 3H, 6-CH$_3$), 1.90 (s, 3H, H-C21), 2.00–2.04 (m, 1H), 2.17–2.19 (m, 1H), 2.43–2.64 (m, 2H), 2.90–2.98 (m, 1H), 3.65 (s, 2H, H-C2'), 5.90 (s, 2H), 7.22–7.33 (m, 5H, Ar); $^{13}$C NMR (CDCl$_3$) δ 203.6, 199.9, 170.8, 164.0, 137.9, 133.4, 131.4, 129.3, 128.7, 127.3, 121.3, 96.8, 50.4, 48.9, 47.7, 41.9, 37.1, 36.1, 34.2, 33.5, 31.0, 30.2, 26.2, 23.2, 20.3, 19.9, 16.4, 14.3.

EM-950 (4; R=Cypent); Yield, 49%; IR (NaCl, cm$^{-1}$); 2948, 2869, 1726, 1660, 1625, 1578, 1475, 1351, 1271, 1193, 1155, 1110; $^1$H NMR (CDCl$_3$) δ 0.72 (s, 3H, H-C18), 1.09 (s, 3H, H-C19), 1.85 (s, 3H, 6-CH$_3$), 2.03 (s, 3H, H-C21), 2.21–2.24(m, 1H), 2.41–2.63 (m, 2H), 2.72–2.79 (m, 1H, H-C2'), 2.94–3.03 (m, 1H), 5.88 (s, 1H), 5.95 (s, 1H); $^{13}$C NMR (CDCl$_3$) δ 203.9, 199.8, 175.9, 164.0, 138.0, 131.4, 121.3, 96.0, 50.3, 49.2, 47.6, 44.0, 37.1, 36.1, 34.1, 33.6, 31.2, 30.5, 29.7, 29.6, 26.3, 25.7, 25.6, 23.4, 20.3, 19.9, 16.4, 14.3.

EM-978 (4; R=Cyhex); Yield, 48%; IR (NaCl, cm$^{-1}$) 2935, 2857, 1726, 1660, 1625, 1579, 1449, 1351, 1316, 1247, 1159; $^1$H NMR (CDCl$_3$) δ 0.71 (s, 3H, H-C18), 1.09 (s, 3H, H-C19), 1.85 (s, 3H, 6-CH$_3$), 2.01 (s, 3H, H-C21), 2.24–2.37(m, 2H), 2.42–2.64 (m, 2H), 2.94–3.03 (m, 1H), 5.88 (s, 1H), 5.95 (s, 1H); $^{13}$C NMR (CDCl$_3$) δ 203.8, 199.8, 175.3, 164.0, 138.0, 131.4, 121.3, 95.9, 50.3, 49.2, 47.6, 43.2, 37.1, 36.1, 34.0, 33.6, 31.3, 30.5, 28.8, 28.7, 26.3, 25.6, 25.3, 23.4, 20.3, 19.9, 16.4, 14.4.

EM-979 (4; R=t-Bu); Yield, 82%; IR (NaCl, cm$^{-1}$) 2949, 2872, 1724, 1660, 1626, 1580, 1152; $^1$H NMR (CDCl$_3$) δ 0.71 (s, 3H, H-C18), 1.09 (s, 3H, H-C19), 1.22 (s, 9H, 2'-CH$_3$), 1.84 (s, 3H, 6-CH$_3$), 2.01 (s, 3H, H-C21), 2.21–2.25(m, 1H), 2.42–2.62 (m, 2H), 2.95–3.04 (m, 1H), 5.87 (s, 1H), 5.94 (s, 1H); $^{13}$C NMR (CDCl$_3$) δ 203.7, 199.8, 177.5, 164.0, 137.9, 131.4, 121.3, 95.9, 50.4, 49.4, 47.8, 39.0, 37.1, 36.1, 34.0, 33.6, 31.4, 30.4, 26.9, 26.2, 23.3, 20.3, 19.9, 16.4, 14.3.

EM-996 (4; R=(CH$_2$)$_5$Br); Yield, 43%; IR (NaCl, cm$^{-1}$) 2946, 2868, 1731, 1660, 1626, 1579, 1457, 1387, 1352, 1260, 1194, 1123, 1110; $^1$H NMR (CDCl$_3$) δ 0.70 (s, 3H, H-C18), 1.07 (s, 3H, H-C19), 1.83 (s, 3H, 6-CH$_3$), 2.03 (s, 3H, H-C21), 2.35 (t, 2H, H-C2', J=7 Hz), 2.93–3.02(m, 1H), 3.37 (t, 2H, H-C6', J=7 Hz), 5.85 (s, 1H), 5.94 (s, 1H); $^{13}$C NMR (CDCl$_3$) δ 203.8, 199.8, 172.9, 164.0, 137.8, 131.4, 121.2, 96.2, 50.2, 49.0, 47.5, 37.0, 36.0, 34.1, 34.0, 33.5, 33.3, 32.2, 31.1, 30.4, 27.6, 26.5, 23.9, 23.2, 20.2, 19.8, 16.3, 14.3.

EM-1003 (4; R=(CH$_2$)$_3$Br); Yield, 13%; IR (NaCl, cm$^{-1}$) 2947, 1731, 1659, 1625, 1579, 1444, 1124; $^1$H NMR (CDCl$_3$) δ 0.74 (s, 3H, H-C18), 1.01 (s, 3H, H-C19), 1.85 (s, 3H, 6-CH$_3$), 2.07 (s, 3H, H-C21), 2.55 (t, 2H, H-C2', J=5 Hz), 2.96–3.05(m, 1H), 3.47 (t, 2H, H-C6', J=7 Hz), 5.89 (s, 1H), 5.96 (s, 1H); $^{13}$C NMR (CDCl$_3$) δ 203.6, 199.7, 172.0, 163.9, 137.7, 131.3, 121.2, 96.4, 50.1, 48.9, 47.5, 37.0, 36.0, 33.9, 33.5, 32.5, 32.4, 31.0, 30.4, 27.2, 26.5, 23.2, 20.2, 19.8, 16.3, 14.2.

EM-1029 (4; R=(CH$_2$)$_4$Cl); Yield, 30%; IR (NaCl, cm$^{-1}$) 2947, 2871, 1730, 1659, 1625, 1579, 1458, 1445, 1353, 1271, 1059; $^1$H NMR (CDCl$_3$) δ 0.67 (s, 3H, H-C18), 1.04 (s, 3H, H-C19), 1.79 (s, 3H, 6-CH3), 2.00 (s, 3H, H-C21), 2.16–2.23 (m, 1H), 2.34 (t, 2H, H-C2', J=7 Hz), 2.89–2.98 (m, 1H), 3.49 (t, 2H, H-C5', J=7 Hz), 5.81 (s, 1H), 5.91 (s, 1H); $^{13}$C NMR (CDCl$_3$) δ 203.6, 199.6, 172.5, 163.9, 137.8, 131.2, 121.0, 96.2, 50.1, 48.9, 47.4, 44.2, 36.9, 35.9, 33.9, 33.4, 31.6, 30.9, 30.3, 26.4, 23.1, 21.9, 20.1, 19.7, 16.2, 14.1.

EM-1044 (4; R=CH$_2$PhCl(p)); Yield, 38%; IR (KBr, cm$^{-1}$) 2948, 1734, 1656, 1625, 1578, 1492, 1459, 1352, 1262, 1154, 1089, 1017; $^1$H NMR (CDCl$_3$) δ 0.67 (s, 3H, H-C18), 1.07 (s, 3H, H-C19), 1.86 (s, 3H, 6-CH$_3$), 1.92 (s, 3H, H-C21), 2.15–2.22(m, 1H), 2.41–2.67 (m, 2H), 2.88–2.96 (m, 1H), 3.61 (s, 2H, H-C2'), 5.89 (s, 2H), 7.18 (d, 2H, J=8.3 Hz), 7.27 (d, 2H, J=8.3 Hz); $^{13}$C NMR (CDCl$_3$) δ 203.6, 199.9, 170.3, 164.0, 137.7, 133.4, 131.8, 131.5, 130.7, 128.8, 121.3, 96.9, 50.4, 48.9, 47.8, 41.1, 37.1, 36.1, 34.1, 33.6, 31.0, 30.3, 26.4, 23.1, 20.3, 19.9, 16.4, 14.3.

EM-1049 (4; R=CH$_2$PhOMe(p)); Yield, 40%; IR (KBr, cm$^{-1}$) 2947, 2871, 1729, 1657, 1625, 1578, 1513, 1459, 1352, 1302, 1249, 1151, 1035; $^1$H NMR (CDCl$_3$) δ 0.64 (s, 3H, H-C18), 1.05 (s, 3H, H-C19), 1.83 (s, 3H, 6-CH$_3$), 1.87 (s, 3H, H-C21), 1.96–2.08 (m, 1H), 2.13–2.20(m, 1H), 2.39–2.62 (m, 2H), 2.85–2.93 (m, 1H), 3.56 (s, 2H, H-C2'), 3.72 (s, 3H, p-OCH$_3$), 5.86 (s, 1H), 5.89 (s, 1H), 6.83 (d, 2H, J=8.5 Hz), 7.18 (d, 2H, J=8.5 Hz); $^{13}$C NMR (CDCl$_3$) δ 203.8, 199.9, 171.1, 164.1, 158.9, 137.9, 131.4, 130.3, 125.4, 121.3, 114.0, 96.7, 55.3, 50.3, 48.9, 47.7, 40.9, 37.1, 36.1, 34.1, 33.6, 31.0, 30.2, 26.2, 23.2, 20.3, 19.9, 16.4, 14.3.

EM-1107 (4; R=CH$_2$PhOCO-t-Bu(p)); Yield, 38%; IR (NaCl, cm$^{-1}$) 2972, 2872, 1731, 1659, 1625, 1579, 1508, 1263, 1202, 1118; $^1$H NMR (CDCl$_3$) δ 0.67 (s, 3H, H-C18), 1.07 (s, 3H, H-C19), 1.33 (s, 9H, tert-Butyl), 1.85 (s, 3H, 6-CH$_3$), 1.91 (s, 3H, H-C21), 3.64 (s, 2H, H-C2'), 5.88 (s, 1H), 5.93 (s, 1H), 6.97–7.0 (m, 2H), 7.25–7.28 (m, 2H); $^{13}$C NMR (CDCl$_3$) δ 203.7, 200.0, 177.0, 170.6, 164.1, 150.4, 138.0, 131.4, 130.6, 130.2, 121.8, 121.3, 96.9, 50.3, 49.0, 47.7, 41.2, 39.1, 37.1, 36.1, 34.0, 33.6, 30.9, 30.2, 27.1, 26.3, 23.2, 20.2, 19.9, 16.4, 14.3.

CS-251 (4; R=(CH$_2$)$_3$COCH$_3$); Yield, 26%; IR (NaCl, cm$^{-1}$) 2949, 2873, 1732, 1660, 1626, 1580, 1463, 1356, 1258, 1060; $^1$H NMR (CDCl$_3$) δ 0.63 (s, 3H, H-C18), 1.00 (s, 3H, H-C19), 1.77 (s, 3H, 6-CH$_3$), 1.96 (s, 3H, H-C6'), 2.05 (s, 3H, H-C21), 2.29 (t, 2H, J=7 Hz), 2.43 (t, 2H, J=7 Hz), 5.77 (s, 1H), 5.87 (s, 1H); $^{13}$C NMR (CDCl$_3$) δ 207.5, 203.6, 199.6, 172.5, 163.8, 137.7, 131.1, 120.9, 96.0, 50.0, 48.8, 47.4, 42.0, 36.8, 35.8, 33.8, 33.4, 33.1, 30.8, 30.2, 29.7, 26.3, 23.1, 20.0, 19.6, 18.4, 16.1, 14.1.

CS-256 (4; R=CH$_2$PhF(p)); Yield, 32%; IR (KBr, cm$^{-1}$) 2948, 2872, 1734, 1657, 1625, 1578, 1510, 1458, 1352, 1264, 1224, 1152; $^1$H NMR (CDCl$_3$) δ 0.65 (s, 3H, H-C18), 1.05 (s, 3H, H-C19), 1.84 (s, 3H, 6-CH$_3$), 1.88 (s, 3H, H-C21), 1.96–2.02 (m, 1H), 2.13–2.21(m, 1H), 2.38–2.49 (m, 2H), 2.87–2.95 (m, 1H), 3.59 (s, 2H, H-C2'), 5.86 (s, 1H), 5.89 (s, 1H), 6.93–6.99 (m, 2H), 7.18–7.82 (m, 2H); $^{13}$C NMR (CDCl$_3$) δ 203.6, 199.9, 170.6, 164.0, 163.7, 160.5, 137.8, 131.4, 130.9, 130.8, 129.12, 129.07, 121.3, 115.7, 115.4, 96.9, 50.4, 48.9, 47.7, 40.9, 37.0, 36.1, 34.1, 33.6, 31.0, 30.2, 26.3, 23.1, 20.3, 19.9, 16.4, 14.3.

Example 2

Synthesis of 1α-Alkyl-6-methyl-4,6-pregnadien-17α-ol-3,20-dione Alkanoates/Benzoates These syntheses are described in Scheme 2.

Example 2A

1α-Alkyl-6-methyl-4,6-pregnadien-17α-ol-3,20-dione Acetate (5)

The following example is a representative: To trienone 2 (500 mg; 1.33 mmol) in THF (30 mL), were added CuBr (12 mg; 0.08 mmol), timethylaluminum (2.6 mL; 5.2 mmol) and chlorotrimethylsilane (0.659 mL; 5.2 mmol) under argon. The reaction mixture was stirred for 1 h. Exess of reagents was destroyed by the slow addition of MeOH at 0° C. The mixture was extracted with CH$_2$Cl$_2$, dried and solvents removed. Purication on silica gel column using hexanes/EtOAc as an eluent gave the la-methyl compound, EM-952 (466 mg) in 90% yield; IR (KBr, cm$^{-1}$) 2972, 2892, 1734, 1715, 1661, 1625, 1368, 1259; $^1$H NMR (CDCl$_3$) δ 0.66 (s, 3 H, 18-CH$_3$), 0.93 (d, 3H, 1-CH$_3$, J=7 Hz), 1.12 (s, 3H, 19-CH$_3$), 1.88(s, 3H, 6-CH3), 1.99(s, 3H), 2.05(s, 3H), 2.78–2.97 (m, 2H), 5.81 (s, 1H), 5.89 (s, 1H); $^{13}$C NMR (CDCl$_3$) δ 203.6, 199.2, 170.5, 160.3, 137.8, 131.8, 120.5, 96.3, 49.0, 47.3, 44.6, 41.1, 39.2, 36.8, 35.6, 30.99, 30.2, 26.2, 23.2, 21.5, 19.7, 19.6, 18.9, 14.8, 14.2.

Example 2B

1α-Alkyl-6-methyl-4,6-pregnadien-17α-ol-3,20-dione (6)

The following example is a representative: To 1α-Methyldienone 5 (517 mg; 1.3 mmol) in MeOH (30 mL), was added aq NaOH (52 mg in 1 mL of water and the mixture was refluxed for 1 h. The mixture was diluted with brine and extracted with $CH_2Cl_2$ (3×50 mL), dried, and solvents were removed under reduced pressure to the 17α-hydroxy compound 6 (430 mg) in 93% yield; IR (KBr, $cm^{-1}$) 3445, 2972, 2892, 1703, 1647, 1622, 1576, 1259; $^1H$ NMR ($CDCl_3$) δ 0.75 (s, 3H, H-C18), 0.91 (d, 3H, 1-$CH_3$, J=7 Hz), 1.14 (s, 3H, H-C19), 1.81(s, 3H, 6-CH3), 2.25(s, 3H $COCH_3$), 2.69–2.88 (m, 2H), 3.0 (s, 1H), 5.83 (s, 1H), 5.93 (s, 1H); $^{13}C$ NMR ($CDCl_3$) δ 211.3, 199.6, 160.9, 138.5, 131.8, 120.5, 89.6, 48.9, 48.2, 44.8, 42.1, 39.2, 36.8 35.7, 33.5, 30.2, 27.7, 23.3, 19.8, 19.6, 18.9, 15.3, 14.8.

Example 2C

1α-Alkyl-6-methyl-4,6-pregnadien-17α-ol-3,20-dione Aklanoates/Benzoates (7)

Esterification was conducted by following the method A or B, C, D, E of Example 1.

Example 2D

The following is a non-limiting example of physico-chemical characteristics of inhibitors of Example 2.

EM-1022 (7; R=Cypent); Yield 54%; IR ($CDCl_3$) 1733, 1717, 1652, 1623, 1576 $cm^{-1}$; $^1H$ NMR ($CDCl_3$) δ 0.69 (s, 3H), 0.95 (d, 3H, J=7 Hz), 1.15 (s, 3H), 1.82 (s, 3H), 2.00 (s, 3H), 2.71–3.00 (m, 3H), 5.84 (s, 1H), 5.91 (s, 1H); 2 (s, 3H), $^{13}C$ NMR ($CDCl_3$) δ 203.8, 199.3, 175.9, 160.4, 137.9, 131.9, 120.6, 95.9, 49.3, 47.6, 44.7, 43.7, 42, 39.2, 36.9, 35.7, 31.2, 30.4, 29.7, 29.5, 26.2, 25.7, 25.6, 23.3, 19.9, 19.7, 19, 14.8, 14.3.

EM-1059 (7; R=$CH_2Ph$); Yield 74%; IR ($CDCl_3$) 1731, 1651, 1576 $cm^{-1}$; $^1H$ NMR ($CDCl_3$) δ 0.59 (s, 3H), 0.92 (d, 3H, J=7 Hz), 1.08 (s, 3H), 1.79 (s, 3H), 1.84 (s, 3H), 2.85 (m, 2H), 3.59 (s, 2H), 5.81 (s, 2H) 7.19 (m, 5H); $^{13}C$ NMR ($CDCl_3$) δ 203.6, 199.3, 170.7, 160.5, 137.9, 133.4, 131.9, 129.3, 128.6, 127.2, 120.6, 96.7, 49.1, 47.8, 44.7, 42.1, 41.8, 39.2, 39.9, 35.9, 35.8, 30.8, 30.1, 26.1, 23.1, 19.9, 19.7, 19, 14.9, 14.2.

CS-209 (7; R=$CH(CH_3)_2$); Yield 33%; IR ($CDCl_3$) 1731, 1659, 1624, 1577 $cm^{-1}$; $^1H$ NMR ($CDCl_3$) δ 0.72 (s, 3H), 0.98 (d, 3H, J=7 Hz), 1.18 (s, 3H), 1.18 (d, 3H, J=7 Hz), 1.20 (d, 3H, J=7 Hz), 1.85 (s, 3H), 2.03 (s, 3H), 2.56–2.66 (m, 1H), 2.85–3.05 (m, 2H), 5.88 (s, 1H), 5.94 (s, 1H); $^{13}C$ NMR ($CDCl_3$) δ 203.7, 199.4, 176.3, 160.4, 137.9, 132, 120.6, 95.9, 49.3, 47.7, 44.8, 42, 39.2, 36.7, 35.7, 34, 31.2, 30.4, 26.2, 23.3, 19.9, 19.7, 19, 18.7, 18.6, 14.9, 14.3.

CS-243 (7; R=$CH_2CH_3$); Yield 67%; IR ($CDCl_3$) 1732, 1716, 1659, 1625, 1577 $cm^{-1}$; $^1H$ NMR ($CDCl_3$) δ 0.68 (s, 3H), 0.94 (d, 3H, J=7 Hz), 1.12 (t, 3H, J=5.8 Hz), 1.14 (s, 3H), 1.81 (s, 3H), 2 (s, 3H), 2.80–2.90 (m, 2H), 5.83 (s, 1H), 5.91 (s, 1H); $^{13}C$ NMR ($CDCl_3$) δ 203.8, 199.4, 173.9, 160.5, 137.9, 132, 120.7, 96, 49.1, 47.5, 44.6, 41.9, 39.1, 36.9, 35.6, 31, 30.2, 27.7, 26.2, 23.2, 19.8, 19.6, 18.9, 14.8, 14.2, 8.9.

CS-245 (7; R=$(CH_2)_2CH_3$); Yield 70%; IR ($CDCl_3$) 1731, 1715, 1660, 1625, 1577 $cm^{-1}$; $^1H$ NMR ($CDCl_3$) δ 0.67 (s, 3H), 0.91 (t, 3H, J=7 Hz), 0.94 (d, 3H, J=7 Hz), 1.14 (s, 3H), 1.81 (s, 3H), 1.99 (s, 3H), 2.29 (t, 2H, J=7 Hz), 2.80–2.90 (m, 2H), 5.82 (s, 1H), 5.9 (s, 1H); $^{13}C$ NMR ($CDCl_3$) δ 203.7, 199.3, 173.1, 160.4, 137.9, 131.9, 120.6, 96, 49.1, 47.5, 44.6, 42, 39.2, 36.9, 36.2, 35.7, 31, 30.3, 26.2, 23.2, 19.8, 19.6, 18.9, 18.2, 14.8, 14.2, 13.6.

Example 3

6-Methyl-4,6-pregnadien-17α-ol-3,20-dione 4'-Carbomethoxybutyrate (EM-1007)

To a solution of megestrol 3 (400 mg; 1.17 mmol) in $CH_2Cl_2$, was added p-toluenesulfonic acid (90 mg; 0.47 mmol).) followed by glutaryl chloride (2.1 g; 12.5 mmol) at 20° C. After addition, the reaction mixture was stirred for 7.5 h. The mixture was cooled to 0° C. and quenched with exess of MeOH. After 10 min, the mixture was poured in brine and extraced with $CH_2Cl_2$. The organic layer was washed with saturated $NaHCO_3$, dried, and solvents removed to give the product which was purified by column chromatography using hexanes/acetone: 80/20 as an eluent to give EM-1007 (161 mg) in 30% yield; IR (NaCl, $cm^{-1}$) 2949, 2873, 1732, 1860, 1626, 1580, 1443, 1363, 1260, 1198, 1144; $^1H$ NMR ($CDCl_3$) δ 0.72 (s, 3H, H-C18), 1.09 (s, 3H, H-C19), 1.85 (s, 3H, 6-$CH_3$), 1.96 (t, 2H, H-C4', J=7 Hz), 2.06 (s, 3H, H-C21), 2.21–2.27 (m, 1H), 2.39 (t, 2H, H-C2', J=7 Hz), 2.95–3.04(m, 1H), 3.67 (s, 3H, 5'-$OCH_3$), 5.88 (s, 1H), 5.95 (s, 1H); $^{13}C$ NMR ($CDCl_3$) δ 203.6, 199.6, 173.0, 172.3, 163.9, 137.8, 131.2, 121.0, 96.2, 51.4, 50.0, 48.8, 47.4, 36.9, 35.9, 33.8, 33.4, 33.2, 32.7, 30.9, 30.2, 26.3, 23.1, 20.1, 19.7, 16.2, 14.1.

Example 4

6-Methyl-17α-pentyloxy-4,6-pregnadien-3,20-dione (EM-1127)

Powered potassium hydroxide (263 mg; 4.7 mmol) was added to DMSO (4 mL) under argon. After 5 min, megestrol (3) (400 mg; 1.17 mmol) was added followed by 1-iodopentane (305 μl; 2.3 mmol). The reactiom mixture was stirred for 1 h and water (20 mL) was added, and extracted with $CH_2Cl_2$ (3×20 ml). The organic layer was washed with brine (20 mL), dried, and solvents removed to give the crude product which was purified on silica gel column using hexanes/EtOAc as eluent to give pure product (33 mg) in 7% yield: IR (NaCl, $cm^{-1}$) 2932, 2868, 1706, 1662, 1625, 1579; $^1H$ NMR ($CDCl_3$) δ 0.63 (s, 3H, H-C18), 0.88 (t, 3H, J=6.9 Hz), 1.06 (s, 3H, H-C19), 1.82(s, 3H, 6-CH3), 2.11(s, 3H, $COCH_3$), 2.42–2.56 (m, 3H), 2.91 (app. q, 1H), 3.34 (app. q, 1H), 5.85 (s, 1H), 5.95 (s, 1H); $^{13}C$ NMR ($CDCl_3$) δ 211.2, 200.1, 164.5, 138.7, 131.0, 121.0, 95.9, 64.4, 50.1, 48.5, 48.1, 37.2, 36.1, 33.9, 33.6, 30.7, 29.9, 28.3, 26.5, 23.5, 23.1, 22.5, 20.4, 19.8, 16.3, 14.7, 14.0.

Example 5

16α-Substituted 4,6-Androstadien-3,17-dione Derivatives

These syntheses are described in Scheme 3.

Scheme 3

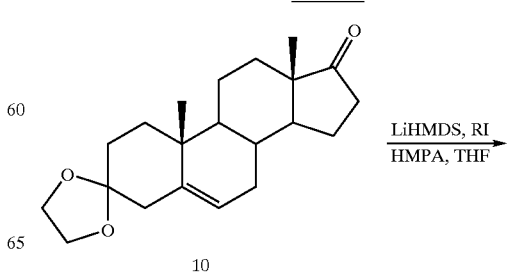

10

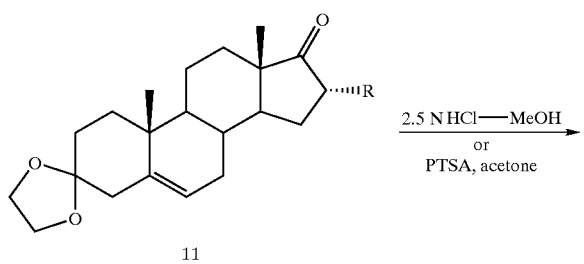

11

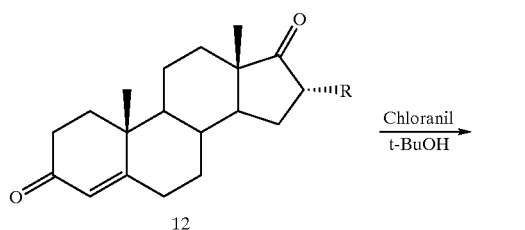

12

13

Example 5A

General Method for 16α-Substituted 4,6-Androstadien-3,17-dione (13) 16α-Substituted 5-Androsten-3,17-dione 3-Ethyleneketal (11)

Under argon atmosphere, a solution of 5-androsten-3,17-dione 3-ethyleneketal 10 in anhydrous THF (3.3% W/V) was cooled at 0° C. and treated with a 1.0 M solution of lithium bis(trimethylsilyl)amide in THF (1.0 equiv) and HMPA (2.0 equiv). The solution was stirred 20 min at room temperature, cooled at −78° C., and treated with 1.2 equiv of alkyl iodide. The reaction mixture was allowed to reach room temperature and stirred overnight (for R=isobutyl). For smaller R group (e.g.: R=Pr), the reaction was allowed to reach −40° C. and stirred 3 h. The reaction was quenched with saturated ammonium chloride and diluted with ethyl acetate. The organic phase was washed with brine, dried over magnesium sulfate, filtered, and evaporated. The crude mixture was purified by flash chromatography (hexanes to hexanes-acetone 19-1) to provide compound 11 (e.g., R=isobutyl, 8%): $^1$H NMR (300 MHz, CDCl$_3$) δ 0.88 (d, J=6.3 Hz, 3H), 0.92 (s, 3H), 0.92 (d, J=6.1 Hz, 3H), 1.05 (s, 3H), 1.08–1.84 (m, 17H), 2.11 (m, 2H), 2.46 (m, 1H), 2.58 (m, 1H), 3.95 (m, 4H), 5.37 (m, 1H).

16α-Substituted 4-Androsten-3,17-dione (12)

Under argon atmosphere, a solution of compound 11 and p-toluenesulfonic acid (0.11 equiv) in acetone (1.0% W/V) was refluxed for 2.5 h. The crude mixture was warmed to room temperature, diluted with distilled water, and evaporated (acetone). The aqueous phase was extracted with dichloromethane. The organic phase was washed two times with saturated sodium bicarbonate and brine, dried over magnesium sulfate, filtered, and evaporated. The crude mixture was purified by flash chromatography (hexanes-acetone 49-1 to hexanes-acetone 19-1) to provide compound 12 (e.g., R=isobutyl, 81%): $^1$H NMR (300 MHz, CDCl$_3$) δ 0.88 (d, J=6.5 Hz, 3H), 0.92 (d, J=6.5 Hz, 3H), 0.96 (s, 3H), 1.21 (s, 3H), 0.98–2.02 (m, 16H), 2.38 (m, 5H), 5.75 (s, 1H).

16α-Substituted 4,6-Androstadien-3,17-dione (13)

Under argon atmosphere, a solution of compound 12 and chloranil (4.8 equiv) in anhydrous tert-butanol (2.6% W/V) was refluxed for 3 h. The reaction mixture was cooled at room temperature and the suspension was filtered to remove excess of chloranil and then evaporated. The crude mixture was diluted with dichloromethane and the obtained solution was washed 3 times with distilled water, 4 times with 5% sodium hydroxide, and 4 times with distilled water. The organic phase was dried over magnesium sulfate, filtered, and evaporated. The crude mixture was purified by 2 flash chromatographies (hexanes to hexanes-acetone 9-1; and hexanes-ethyl acetate 97-3 to hexanes-ethyl acetate 17-3) to provide compound 13 (e.g., EM-1273-CS, R=isobutyl, 29%): IR (CHCl$_3$) 3010, 2957, 2871, 1733, 1656, 1619, 1467 cm$^{-1}$; $^1$H NMR (300 MHz, CDCl$_3$) δ 0.89 (d, J=6.5 Hz, 3H), 0.93 (d, J=6.4 Hz, 3H), 1.01 (s, 3H), 1.14 (s, 3H), 1.05–2.05 (m, 13H), 2.34–2.58 (m, 4H), 5.70 (s, 1H), 6.18 (m, 2H); $^{13}$C NMR (75 MHz, CDCl$_3$) δ 14.45, 16.32, 19.92, 21.35, 23.44, 26.57, 27.45, 31.52, 33.87, 36.13, 36.97, 40.02, 43.06, 46.56, 48.88, 50.86, 124.16, 128.76, 138.37, 162.91, 199.30, 221.43.

Example 6

16-Symmetrical-disubstituted 4,6-Androstadien-3,17-dione and 4,6-Estradien-3,17-dione Derivatives Scheme 4

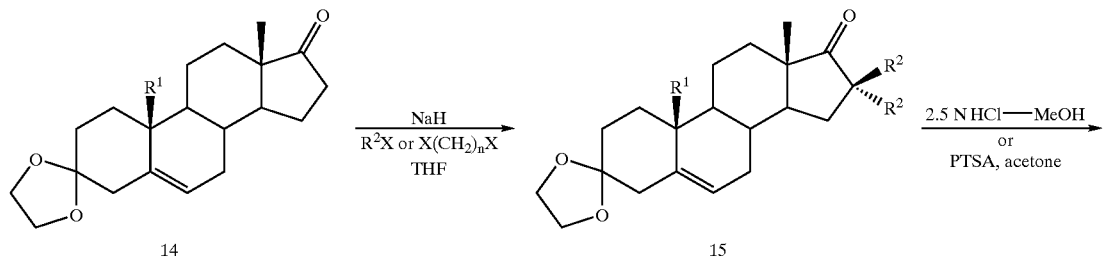

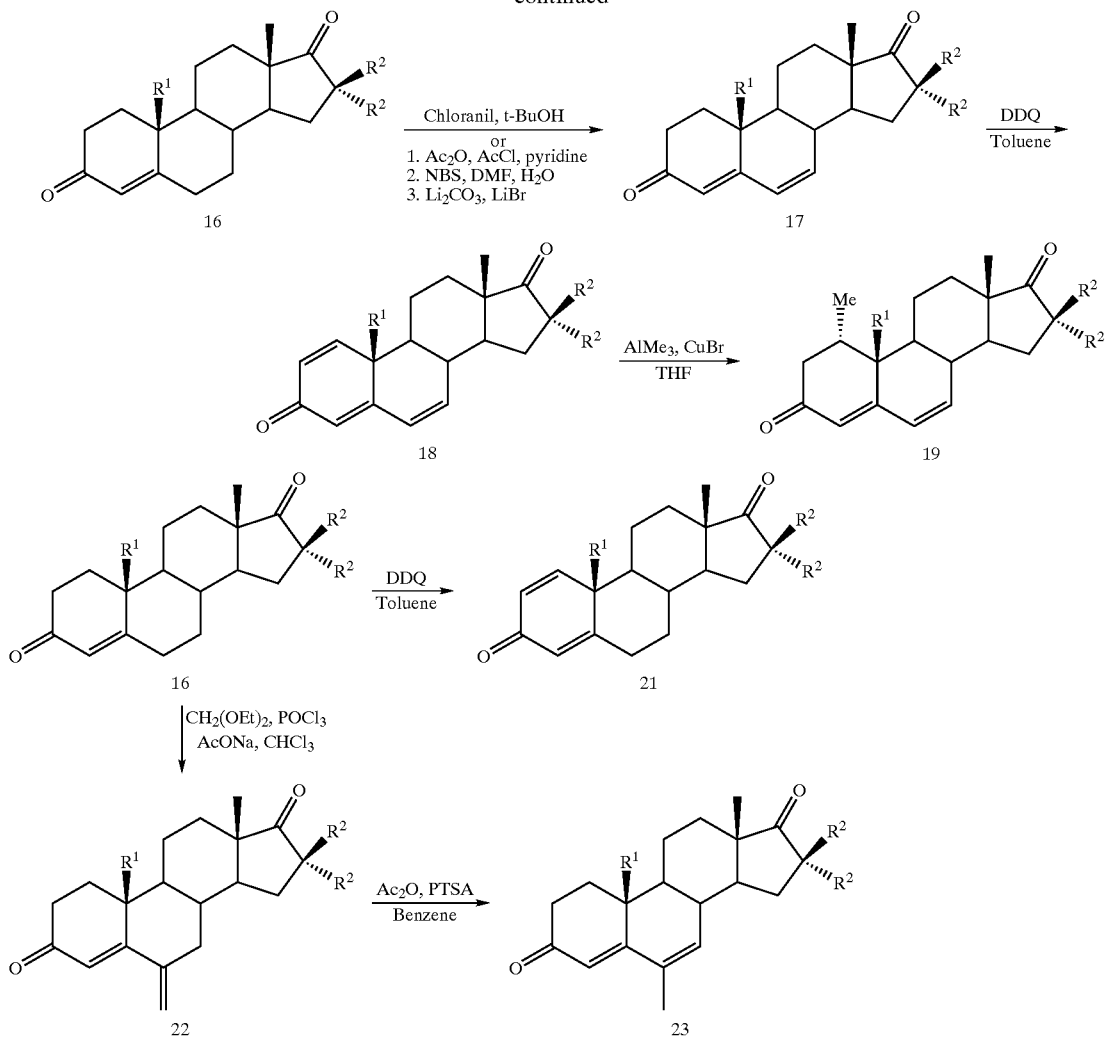

Example 6A

General Method for 16-Symmetrical-disubstituted 4,6-Androstadien-3,17-dione and 4,6-Estradien-3,17-dione (17)

16-Symmetrical-disubstituted 5-Androsten-3,17-dione 3-Ethyleneketal (15)

Under argon atmosphere, a solution of 5-androsten-3,17-dione 3-ethyleneketal (14) in anhydrous THF (2.4% W/V) was treated with sodium hydride in 60% dispersion in mineral oil (10 equiv) and alkyl dihalide (1.5 equiv) or alkyl halide (10 equiv) and refluxed for 20 h. The reaction mixture was cooled at room temperature and quenched with ethanol, and then the solvents were evaporated. The crude mixture was diluted with dichloromethane and washed with saturated ammonium chloride and brine. The organic phase was dried over magnesium sulfate, filtered, and evaporated. The crude compound 16 (e.g. $R^1$=$CH_3$, $R^2$=—$(CH_2)_4$—) was directly used for the next step: $^1$H NMR (300 MHz, $CDCl_3$) δ 0.88 (s, m, 3H), 1.05 (s, 3H), 1.0–2.2 (m, 24H), 2.58 (m, 1H), 3.95 (m, 4H), 5.37 (m, 1H). When alkyl halide was used, compounds 15 were purified by flash chromatography.

16-Symmetrical-disubstituted 4-Androsten-3,17-dione (16)

The same procedure for compound 12 was used, starting from compound 15. The crude mixture was purified by flash chromatography (hexanes-acetone 19-1 to hexanes-acetone 4-1) to provide compound 16 (e.g. EM-844, $R^1$=$CH_3$, $R^2$=—$(CH_2)_4$—, 74%). A sample was recrystallized from hexanes-acetone 4-1: IR (KBr) 2950, 2925, 2858, 1730, 1674, 1617, 1448 cm$^{-1}$; $^1$H NMR (300 MHz, $CDCl_3$) δ 8 0.89 (s, 3H), 1.18 (s, 3H), 0.93–2.04 (m, 19H), 2.26–2.44 (m, 4H), 5.70 (s, 1H); $^{13}$C NMR (75 MHz, $CDCl_3$) δ 14.03, 17.36, 20.31, 25.37, 25.93, 30.93, 31.89, 32.58, 33.89, 34.71, 35.65, 38.18, 38.66, 39.21, 39.93, 48.00, 48.54, 53.94, 56.15, 124.06, 170.39, 199.22, 225.41.

16-Symmetrical-disubstituted 4,6-Androstadien-3,17-dione (17)

A solution of compound 16 in acetic anhydride (12.4 equiv) and pyridine (1.1 equiv) was treated with acetyl chloride (13.0 equiv), refluxed for 3 h, cooled at room temperature, and stirred overnight. The reaction mixture was evaporated and coevaporated 2 times with ethanol and 1 time with toluene. The crude dienol acetate was dissolved in wet DMF (97%). The solution was treated with N-bromosuccinimide (1.03 equiv), stirred for 45 min, treated with lithium carbonate (2.4 equiv) and lithium bromide (1.02 equiv), and heated at 100° C. for 3 h. The reaction mixture was cooled at room temperature, treated with saturated ammonium chloride, and extracted 3 times with ethyl acetate. The combined organic phase was dried over magnesium sulfate, filtered, and evaporated. The crude mixture was purified by flash chromatogaphy (hexanes to hexanes-acetone 19-1) and recrystallization (hexanes-acetone 49-1) to provide compound 17 (e.g. CS-195, $R^1$=$CH_3$, $R^2$=—$(CH_2)_4$—, 61%): IR ($CHCl_3$) 2947, 2872, 1731, 1657, 1619 $cm^{-1}$; $^1$H RMN (300 MHz, $CDCl_3$) δ 0.98 (s, 3H), 1.14 (s, 3H), 1.2–2.05 (m, 18H), 2.35–2.65 (m, 3H), 5.70 (s, 1H), 6.17 (m, 2H); $^{13}$C RMN (75 MHz, $CDCl_3$) δ 14.04, 16.33, 20.00, 25.38, 25.93, 31.86, 33.87, 36.17, 36.65, 37.73, 39.20, 39.98, 46.57, 48.84, 50.91, 56.24, 124.12, 128.70, 138.68, 163.00, 199.32, 224.69.

Example 6B

16-Symmetrical-disubstituted 1,4,6-Androstatrien-3, 17-dione (18)

Under argon atmosphere, a solution of compound 17 and 2,3-dichloro-5,6-dicyano-1,4-benzoquinone (1.7 equiv) in toluene (4.3% W/V) was refluxed for 5 h. The reaction mixture was cooled at room temperature, diluted with ethyl acetate, and washed with saturated sodium carbonate and brine. The organic phase was dried over magnesium sulfate, filtered, and evaporated. The crude mixture was purified by flash chromatography (hexanes to hexanes-acetone 19-1) and triturated in hexanes to provide compound 18 (e.g. EM-1039, $R^1$=$CH_3$, $R^2$=—$(CH_2)_4$—, 52%): IR ($CHCl_3$) 2946, 1732, 1652, 1603 $cm^{-1}$; $^1$H NMR (300 MHz, $CDCl_3$) δ 1.01 (s, 3H), 1.23 (s, 3H), 1.29–2.04 (m, 16H), 2.45 (m, 1H), 6.03 (m, 2H), 6.29 (m, 2H), 7.06 (d, J=10.1 Hz, 1H); $^{13}$C NMR (75 MHz, $CDCl_3$) δ 14.14, 20.76, 21.22, 25.37, 25.93, 31.84, 37.20, 37.70, 39.18, 39.99, 41.18, 46.75, 48.40, 48.58, 56.22, 124.28, 128.34, 128,49, 135.99, 152.41, 161.78, 186.13, 224.32.

Example 6C

1α-Methyl-16-symmetrical-disubstituted 4,6-Androstadien-3,17-dione (19)

Under argon atmosphere, a solution of compound 18 and cuprous bromide (0.01 equiv) in anhydrous THF (15% W/V) was treated with a 2.0 M solution of trimethylaluminum in toluene (1.1 equiv) and stirred 1 h at room temperature. The reaction mixture was hydrolyzed with water and the solid filtered off and washed. The crude mixture was purified by flash chromatography (hexanes-acetone 19-1) to provide compound 19 (e.g. EM-1077, $R^1$=$CH_3$, $R^2$=—$(CH_2)_4$—, 55%): IR ($CHCl_3$) 3014, 2948, 2873, 1731, 1651, 1618, 1253 $cm^{-1}$; $^1$H NMR (300 MHz, $CDCl_3$) δ 0.95 (d, J=6.8 Hz, 3H), 0.99 (s, 3H), 1.23 (s, 3H), 1.25–2.05 (m, 16H), 2.19–2.38 (m, 3H), 2.85 and 2.91 (dd, J=5.4 and 17.8 Hz, 1H), 5.71 (s, 1H), 6.17 (m, 2H); $^{13}$C NMR (75 MHz, $CDCl_3$) 814.10, 14.85, 19.02, 19.47, 25.40, 25.96, 31.84, 35.82, 36.63, 37.77, 39.23, 39.32, 40.02, 42.38, 45.47, 46.79, 49.00, 56.22, 123.70, 129.54, 138.41, 159.77, 198.95, 224.71.

Example 6D

16-Symmetrical-disubstituted 4-Androsten-3,17-dione-6-methylene (22)

A solution of 16-symmetrical-disubstituted 4-androsten-3,17-dione (16), sodium acetate (4.4 equiv), diethoxymethane (89 equiv), and phosphorus oxychloride (15 equiv) in chloroform (3.3% W/V) was refluxed for 1 h. The reaction mixture was cooled at rt, quenched slowly with saturated sodium carbonate, and diluted in chloroform. The organic phase was washed with distilled water and brine. The crude mixture was purified by flash chromatography (hexanes-ethyl acetate 9-1 to hexanes-ethyl acetate 4-1) and recrystallization (acetone-hexanes 1-19) to provide compound XI (e.g. EM-921, $R^1$=$CH_3$, $R^2$=—$(CH_2)_5$—, 59%): IR (KBr) 2931, 2857, 1726, 1673, 1596, 1444, 1267, 1227 $cm^{-1}$; $^1$H NMR (300 MHz, $CDCl_3$) δ 0.91 (s, 3H), 1.11 (s, 3H), 1.14–2.08 (m, 22H), 2.35–2.50 (m, 2H), 2.58 and 2.26 (dd, J=3.3 and 12.9 Hz, 1H), 4.98 (d, J=1.9 Hz, 1H), 5.09 (d, J=2.0 Hz, 1H), 5.92 (s, 1H); $^{13}$C NMR (75 MHz, $CDCl_3$) δ 14.29, 17.10, 20.24, 22.40, 22.55, 25.42, 31.87, 31.92, 33.00, 33.79, 34.77, 35.10, 36.65, 39.02, 39.18, 48.25, 48.56, 50.47, 52.80, 114.44, 121.91, 145.54, 168.43, 199.61, 223.84.

Example 6E

16-Symmetrical-disubstituted 4,6-Androstadien-3, 17-dione-6-methyl (23)

A solution of 16-symmetrical-disubstituted 4-androsten-3,17-dione-6-methylene (22) in benzene (0.67% W/V) was treated with acetic anhydride (15 equiv) and a solution of p-toluenesulfonic acid (5 equiv) in benzene (8.4% W/V), and refluxed for 3.5 h. The reaction mixture was cooled at rt, quenched with distilled water, and diluted with benzene. The organic phase was washed 1 time with distilled water, 2 times with 5% sodium bicarbonate, and 4 times with brine. The organic phase was dried over magnesium sulfate, filtered, and evaporated. The crude mixture was purified by flash chromatography (hexanes-ethyl acetate 9-1 to hexanes-ethyl acetate 4-1) and recrystallization (acetone-hexanes 1-19) to provide compound 23 (e.g. EM-925, $R^1$=$CH_3$, $R^2$=—$(CH_2)_5$—, 60%); IR (KBr) 2926, 2858, 1726, 1662, 1629, 1582, 1444, 1268 $cm^{-1}$; $^1$H NMR (300 MHz, $CDCl_3$) δ 0.97 (s, 3H), 1.11 (s, 3H), 1.20–2.62 (m, 26H), 5.89 (s, 1H), 6.06 (s, 1H); $^{13}$C NMR (75 MHz, $CDCl_3$) δ 14.31, 16.39, 19.89, 19.98, 22.46, 22.58, 25.40, 31.81, 32.01, 32.53, 33.61, 34.02, 36.22, 36.63, 46.13, 49.27, 50.59, 51.13, 121.45, 131.85, 136.56, 163.88, 199.82, 223.45.

Example 7

16-Symmetrical-disubstituted 1,4-Androstadien-3, 17-dione (21)

The same procedure for compound 18 was used, starting from compound 16. The reflux period was 20 h instead of 5 h. The crude mixture was purified by 2 flash chromatographies (hexanes to hexanes-acetone 9-1) to provide compound 21 (e.g. EM 1123, $R^1$=$CH_3$, $R^2$=—$(CH_2)_4$—, 74%). A sample was recrystallized in acetone-hexanes (1-49): IR ($CHCl_3$) 3014, 2946, 2871, 1730, 1661,1622, 1603 $cm^{-1}$; $^1$H NMR (300 MHz, $CDCl_3$) δ 0.96 (s, 3H), 1.26 (s, 3H), 1.14–2.05 (m, 19H), 2.35–2.60 (m, 2H), 6.09 (s, 1H), 6.23 and 6.26 (dd, J=2.0 and 10.2 Hz), 7.05 (d, J=10.2 Hz, 1H); $^{13}$C NMR (75 MHz, $CDCl_3$) δ 14.16, 18.72, 22.14, 25.38, 25.94, 31.81, 32.50, 32.59, 34.71, 38.37, 39.23, 39.98, 43.49, 48.16, 52.45, 56.13, 124.13, 127.72, 155.34, 168.37, 186.22, 225.19.

Example 8

16-Asymmetrical-disubstituted 6-Methyl-4,6-androstadien-3,17-dione (27)

These syntheses are described in Scheme 5.

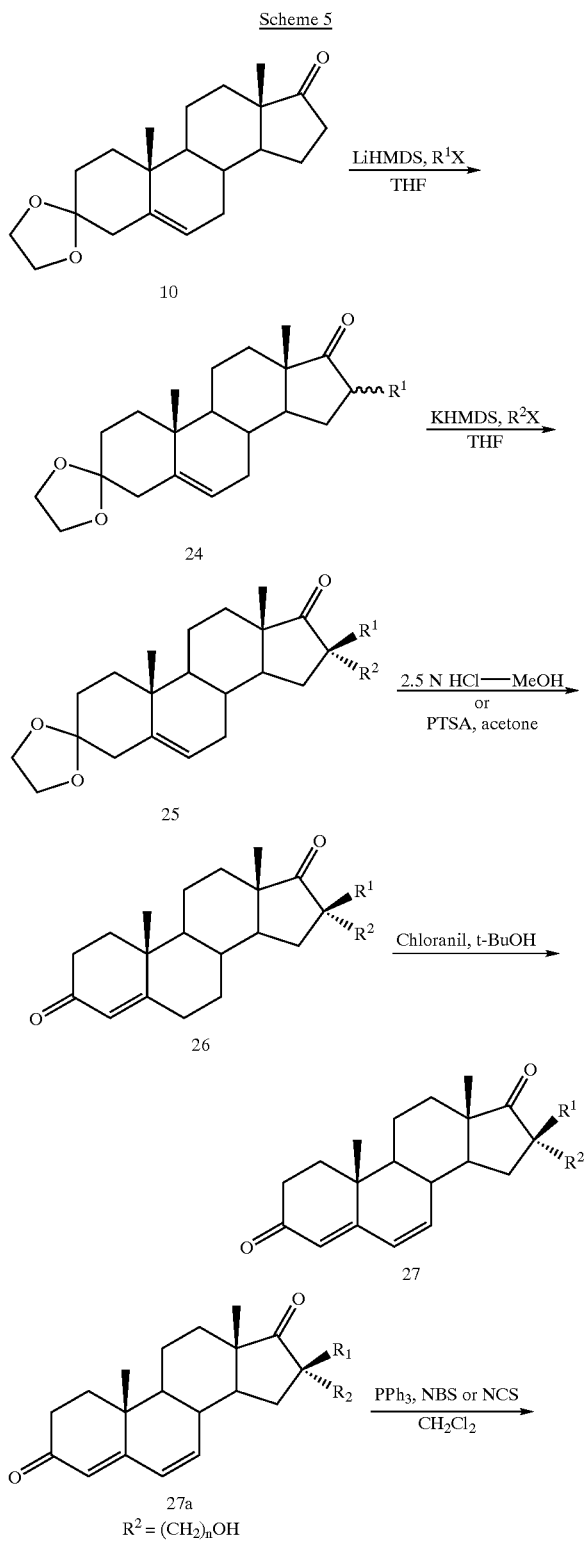

Scheme 5

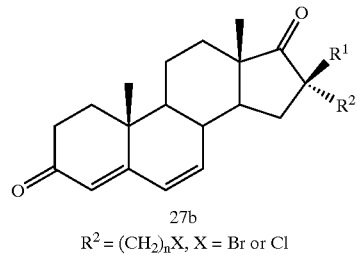

27b
$R^2 = (CH_2)_nX$, X = Br or Cl

Example 8A

General Method for 16-Asymmetrical-disubstituted 4,6-Androstadien-3,17-dione (27)

16-Monosubstituted 5-Androsten-3,17-dione 3-Ethyleneketal (24)

Under argon atmosphere, a solution of 5-androsten-3,17-dione 3-ethyleneketal (10) in anhydrous THF (4.6% W/V) was cooled at −20° C., treated with a 1.0 M solution of lithium bis(trimethylsilyl)amide in THF (1.0 equiv), warmed to room temperature for 15 min, cooled at −78° C., and treated with alkyl iodide (1.05 equiv). The reaction mixture was warmed to room temperature, stirred for 2 h, quenched with saturated ammonium chloride, and evaporated (THF). The aqueous phase was extracted with dichloromethane. The combined organic phase was washed with brine, dried over magnesium sulfate, filtered, and evaporated. The crude mixture was purified by flash chromatography (hexanes-acetone 99-1 to hexanes-acetone 19-1) to provide compound 24 (e.g. $R^1=CH_3$, 7:3 16α/β ratio, 69%): $^1$H NMR (300 MHz, $CDCl_3$) δ 0.84 (s, 0.9H), 0.91 (s, 2.1H), 1.04 (s, 3H), 1.09 (d, J=6.5 Hz, 2.1H), 1.20 (d, J=7.0 Hz, 0.9H), 1.25–1.86 (m, 13H), 2.05–2.16 (m, 3H), 2.56 (m, 2H), 3.95(m, 4H), 5.36 (m, 1H).

16-Asymmetrical-disubstituted 5-Androsten-3,17-dione 3-Ethyleneketal (25)

Under argon atmosphere, a solution of compound 24 in anhydrous THF (4.0% W/V) was cooled at −40° C., treated with 0.5 M solution of potassium bis(trimethylsilyl)amide in toluene (1.2 equiv), warmed to room temperature for 15 min, cooled at −78° C., and treated with 1.5 equiv of alkyl iodide. The reaction mixture was allowed to reach room temperature, refluxed for 2 h, and cooled at room temperature. The reaction mixture was quenched with saturated ammonium chloride, evaporated (THF), and extracted with dichloromethane. The combined organic phase was washed with brine, dried over magnesium sulfate, filtered, and evaporated. The crude mixture was purified by flash chromatography (hexanes-acetone 99-1 to hexanes-acetone 19-1) to provide compound 25 (e.g. $R^1=CH_3$, $R^2$=isobutyl, 56%): $^1$H NMR (300 MHz, $CDCl_3$) δ 0.85 (d, J=6.6 Hz, 3H), 0,90 (d, J=6.6 Hz, 3H), 0.93 (s, 3H), 1.05 (s, 3H), 1.15 (s, 3H), 1.27–2.16 (m, 19H), 2.56 (m, 1H), 3.95 (m, 4H), 5.37 (m, 1H).

16-Asymmetrical-disubstituted 4-Androsten-3,17-dione (26)

The same procedure for compound 12 was used, starting from compound 25. The crude mixture was purified by flash chromatography (hexanes-acetone 49-1 to hexanes-acetone 19-1) to provide compound 26 (e.g. EM-1133, $R^1$=CH$_3$, $R^2$=isobutyl, 96%): IR (KBr) 2951, 2869, 1734, 1676, 1616, 1454 cm$^{-1}$; $^1$H NMR (300 MHz, CDCl$_3$) δ 0.86 (d, J=6.6 Hz, 3H), 0.90 (d, J=6.6 Hz, 3H), 0.96 (s, 3H), 1.17 (s, 3H), 1.21 (s, 3H), 1.02–2.07 (m, 16H), 2.31–2.49 (m, 4H), 5.75 (s, 1H); $^{13}$C NMR (75 MHz, CDCl$_3$) δ 15.06, 17.30, 20.13, 24.64, 24.88, 25.15, 25.96, 30.85, 32.05, 32.55, 33.89, 34.65, 35.12, 35.61, 38.66, 46.27, 47.74, 48.21, 48.90, 54.02, 124.06, 170.40, 199.31, 224.70.

16-Asymmetrical-disubstituted 4,6-Androstadien-3, 17-dione (27)

The same procedure for compound 13 was used, starting from compound 26. The crude mixture was purified by flash chromatography (hexanes-acetone 49-1 to hexanes-acetone 19-1) to provide compound 27 (e.g. EM-1134, $R^1$=CH$_3$, $R^2$=isobutyl, 57%): IR (KBr) 2954, 2870, 1735, 1665, 1618, 1584, 1466 cm$^{-1}$; $^1$H NMR (300 MHz, CDCl$_3$) δ 0.88 (d, J=6.7 Hz, 3H), 0.91 (d, J=6.6 Hz, 3H), 1.01 (s, 3H), 1.14 (s, 3H), 1.20 (s, 3H), 1.22–2.65 (m, 16H), 5.71 (s, 1H), 6.18 (m, 2H); $^{13}$C NMR (75 MHz, CDCl$_3$) δ 15.10, 16.29, 19.82, 24.56, 24.89, 25.15, 25.97, 31.99, 33.78, 33.87, 34.80, 36.15, 36.59, 45.77, 46.27, 48.98, 50.92, 124.07, 128.77, 138.70, 163.05, 199.34, 224.32.

Example 8B

16α-Alkylhalide-16β-alkyl 4,6-Androstadien-3,17-dione (27b)

Under argon atmosphere, a solution of 16α-hydroxyalkyl-16β-alkyl 4,6-androstadien-3,17-dione (27a) and triphenylphosphine (1.2 equiv) in dichloromethane (10% W/V) was cooled at 0° C. and treated with N-chlorosuccinimide (or N-bromosuccinimide) (1.2 equiv). The reaction mixture was warmed to room temperature for 30 min and diluted with dichloromethane. The organic phase was washed with brine, dried over magnesium sulfate, filtered, and evaporated. The crude mixture was purified by 2 flash chromatographies (hexanes-ethyl acetate 9-1 to hexanes-ethyl acetate 7-3; and dichloromethane to dichloromethane-ethyl acetate 9-1) to provide compound 27b (e.g. EM-1135, $R^1$=CH$_3$, $R^2$=(CH$_2$)$_3$Cl, 51%): IR (CHCl$_3$) 3010, 2946, 2873, 1733, 1657, 1619 cm$^{-1}$; $^1$H NMR (300 MHz, CDCl$_3$) δ 1.02 (s, 3H), 1.14 (s, 3H), 1.21 (s, 3H), 1.26–2.11 (m, 14H), 2.35–2.65 (m, 3H), 3.49 (m, 2H), 5.71 (s, 1H), 6.17 (m, 2H); $^{13}$C NMR (75 MHz, CDCl$_3$) δ 14.91, 16.32, 19.80, 25.16, 27.97, 31.78, 33.80, 33.89, 34.83, 35.25, 36.16, 36.60, 45.19, 46.01, 48.10, 49.36, 50.89, 124.21, 128.89, 138.43, 162.92, 199.40, 223.36.

Example 9

17α-Acyloxy-6-methyl-4,6-androstadien-3-one-17β-carboxamide (34)

These syntheses are described in Scheme 6.

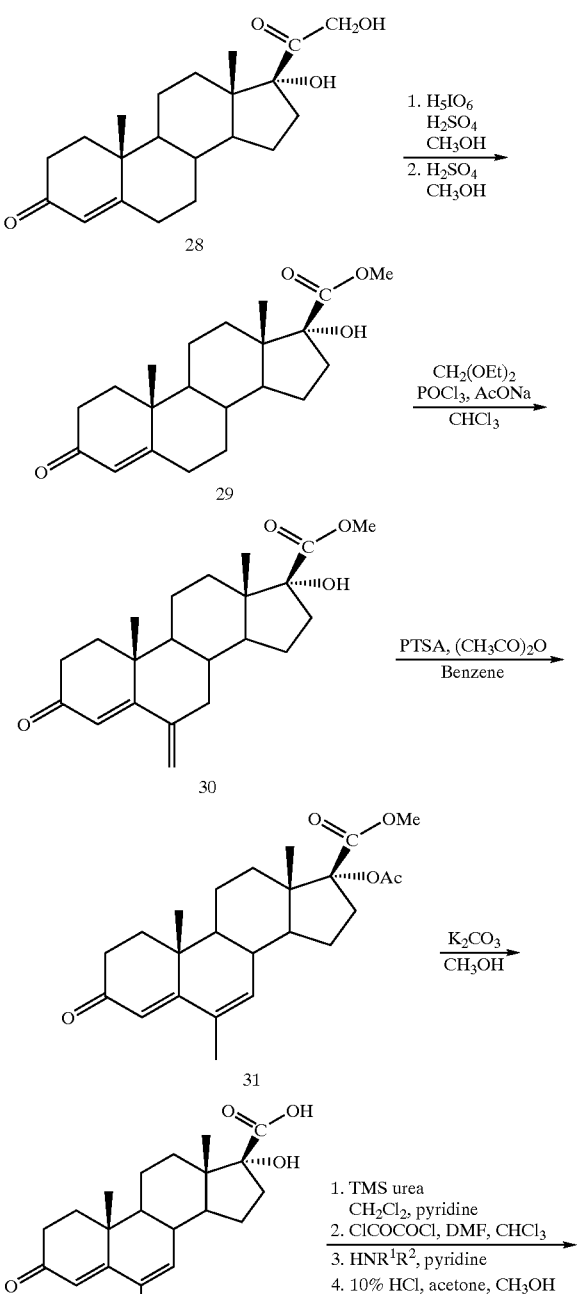

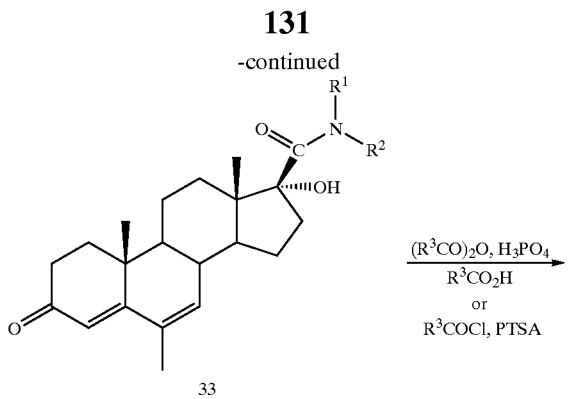

Example 9A

General Method for 17α-Acyloxy-6-methyl-4,6-androstadien-3-one-17β-carboxamide (34)

4-Androsten-17α-ol-3-one-17β-carboxylic Acid Methyl Ester (29)

A solution of 4-pregnen-17,21-diol-3,20-dione (28) (6.93 g, 0.0200 mol) in methanol (500 mL) was treated with a 0.075 M periodic acid (300 mL, 0.0225 mol) and 2.5 M sulfuric acid (70 mL, 0.175 mol) and stirred 3 h. The reaction mixture was evaporated (methanol) and filtered. The crude mixture was dried to afford 4-androsten-17α-ol-3-one-17β-carboxylic acid (6.50 g). A solution of the carboxylic acid (4.56 g, 0.0137 mol) and 6 drops of concentrated sulfuric acid in methanol (250 mL) was refluxed for 30 h. The reaction mixture was cooled to room temperature, evaporated, diluted with ethyl acetate, dichloromethane, and water, and treated with sodium bicarbonate. The mixture was extracted 3 times with ethyl acetate. The combined organic phase was washed with brine, dried over magnesium sulfate, filtered, and evaporated. The crude mixture was purified by flash chromatography (hexanes to hexanes-ethyl acetate 3-2) to provide the methyl ester 29 (4.12 g, 87%): $^1$H NMR (300 MHz, CDCl$_3$) δ 0.72 (s, 3H), 1.18 (s, 3H), 0.94–1.89 (m, 13H), 2.01 (m, 1H), 2.36 (m, 4H), 2.65 (m, 1H), 2.85 (s, 1H), 3.75 (s, 3H), 5.72 (s, 1H).

Example 9B

6-Methylene-4-androsten-17α-ol-3-one-17β-carboxylic Acid Methyl Ester (30)

A suspension of sodium acetate (6.65 g, 0.081 mol), diethoxymethane (201 mL, 1.62 mol) and phosphorus oxychloride (25 mL, 0.27 mol) in chloroform (250 mL) was refluxed for 1 h, treated with a solution of compound 29 (6.02 g, 0.018 mol) in chloroform (50 mL), and refluxed for 2 h. The reaction mixture was cooled at room temperature, diluted with water, and extracted with dichloromethane. The combined organic phase was stirred in the presence of sodium carbonate for 1 h, decanted, washed with water and brine, dried over magnesium sulfate, filtered, and evaporated. The crude mixture was purified by flash chromatography (hexanes to hexanes-ethyl acetate 1-1) to provide the methyl ester 30 (3.60 g, 56%): $^1$H NMR (300 MHz, CDCl$_3$) δ 0.71 (s, 3H), 1.08 (s, 3H), 1.13–2.08 (m, 13H), 2.45 (m, 3H), 2.67 (m, 1H), 2.85 (m, 1H), 3.76 and 3.77 (2s, 2.2 and 0.8H), 4.93 (d, J=1.9 Hz, 1H), 5.05 (d, J=1.6 Hz, 1H), 5.90 (s, 1H).

Example 9C

17α-Acetoxymethyl-4,6-androstadien-3-one-17β-carboxylic Acid Methyl Ester (31)

The same procedure for compound 23 was used, starting from compound 30. The crude mixture was purified by flash chromatography (hexanes to hexanes-ethyl acetate 7-3) to provide compound 31 (EM-1010, 75%): IR (KBr) 2967, 2871, 1742, 1668, 1628, 1584, 1458, 1366, 1260, 1245 cm$^{-1}$; $^1$H NMR (300 MHz, CDCl$_3$) δ 0.77 (s, 3H), 1.09 (s, 3H), 1.23–2.02 (m, 11H), 1.84 (broad s, 3H), 2.04 (s, 3H), 2.24 (m, 1H), 2.42–2.65 (m, 2H), 2.98 (m, 1H), 3.71 (s, 3H), 5.87 (s, 1H), 5.96 (s, 1H); $^{13}$C NMR (75 MHz, CDCl$_3$) 14.43, 16.38, 19.86, 20.15, 21.05, 23.36, 30.35, 31.90, 33.61, 34.08, 36.12, 37.23, 48.01, 48.40, 50.36, 52.08, 90.58, 121.22, 131.37, 138.02, 164.12, 170.25, 170.41, 199.88.

Example 9D

6-Methyl-4,6-androstadien-17α-ol-3-one-17β-carboxylic Acid (32)

A solution of compound 31 (3.00 g, 7.50 mmol) in methanol (225 mL) and 10% potassium carbonate (62 mL, 0.045 mol) was refluxed for 21 h. The crude mixture was cooled at room temperature, evaporated (methanol), acidified with 10% hydrochloric acid, and diluted with water. The precipitate was filtered, washed with water, and dried. The filtrate was extracted with dichloromethane. The organic phase was washed 3 times with brine, dried over magnesium sulfate, filtered, and evaporated. A solution of the combined solids in methanol-dichloromethane 1-1 (300 mL) was treated with 10% hydrochloric acid (60 mL), stirred for 3 h, and evaporated (methanol and dichloromethane). The aqueous phase was extracted 3 times with dichloromethane. The combined organic phase was washed 4 times with brine, dried over magnesium sulfate, filtered, and evaporated to provide carboxylic acid 32 (2.05 g, 80%): $^1$H NMR (CDCl$_3$, CD$_3$OD) δ 0.68 (s, 3H), 0.95 (s, 3H), 1.05–1.88 (m, 13H), 1.68 (s, 3H), 2.09 (m, 1H), 2.55 (m, 1H), 5.69 (s, 1H), 5.89 (s, 1H).

Example 9E

6-Methyl-4,6-androstadien-17α-ol-3-one-17β-carboxamide (33)

A solution of compound 32 and 1,3-bis(trimethylsilyl)urea (1.5 equiv) in dichloromethane-pyridine 8-1 (5.7% W/V) was refluxed for 21 h. The reaction mixture was cooled at room temperature, filtered, evaporated (dichloromethane), dissolved in dichloromethane, filtered, and evaporated. A solution of the silylated α-hydroxycarboxylic acid in chloroform-dimethylformamide 99-1 (5.1% W/V) was cooled at 0° C., treated with oxalyl chloride (1.2 equiv), stirred for 1 h, and warmed to room temperature for 30 min. The reaction mixture was cooled at 0° C., treated with pyridine (4 equiv), and amine (3 equiv), stirred for 1 h, and warmed to room temperature for 3 h. The reaction mixture was diluted with water and extracted with ethyl acetate. The combined organic phase was washed with 10% hydrochloric acid and brine, dried over magnesium sulfate, filtered, and evaporated. A solution of the crude mixture in methanol-acetone 1-1 (10 mL) was treated with 10% hydrochloric acid (2 mL) and stirred for 3 h. The reaction mixture was evaporated and extracted 3 times with ethyl acetate. The combined organic phase was washed 2 times with brine, dried over magnesium sulfate, filtered, and evaporated. The crude mixture was purified by flash chromatography (hexanes to hexanes-ethyl acetate 2-1) to provide compound 33 (e.g. $R^1$=Me, $R^2$=Et, 41%): $^1$H NMR (300 MHz, CDCl$_3$) δ 0.83 (broad s, 3H), 1.09 (s, 3H), 1.13 (t, J=7.0 Hz, 3H), 1.22–2.23 (m, 12H), 1.84 (s, 3H), 2.45–2.63 (m, 3H), 3.08 (m, 5H), 3.80 (m, 1H), 5.86 (s, 1H), 5.98 (s, 1H).

Example 9F

17α-Acyloxy-6-methyl-4,6-androstadien-3-one-17β-carboxamide (34)

A solution of compound 33 and p-toluenesulfonic acid (0.14 equiv) in acid chloride (4.7% W/V) was stirred 10 h at room temperature. The reaction mixture was quenched with methanol and water, stirred for 30 min, and extracted with ethyl acetate. The combined organic phase was washed with saturated sodium bicarbonate and brine, dried over magnesium sulfate, filtered, and evaporated. The crude mixture was purified by 2 flash chromatographies (hexanes to hexanes-ethyl acetate 3-2 and dichloromethane to dichloromethane-acetone 49-1) to provide compound 34 (e.g. EM-1181-CS, $R^1$=Me, $R^2$=Et, $R^3$=(CH$_2$)$_3$Cl, 50%): IR (KBr) 2944, 2871, 1738, 1659, 1640, 1631, 1580 cm$^{-1}$; $^1$H NMR (300 MHz, CDCl$_3$) δ 0.84 (s, 3H), 1.10 (m, 6H), 1.25–2.25 (m, 14H), 1.85 (s, 3H), 2.40–2.63 (m, 4H), 2.89 and 2.99 (2s, 0.7 and 2.3H), 3.43 (m, 3H), 3.62 (t, J=6.1 Hz, 2H), 5.88 (s, 1H), 5.98 (s, 1H); $^{13}$C NMR (75 MHz, CDCl$_3$) δ 11.49, 14.70, 16.32, 19.85, 20.54, 22.91, 27.12, 30.99, 32.93, 33.57, 33.99, 34.10, 35.44, 36.02, 37.28, 43.87, 45.18, 48.51, 48.91, 50.04, 94.76, 121.15, 131.28, 138.10, 164.07, 167.31, 170.78, 199.87.

Example 10

17β-Acyl-17α-acyloxy-6-methyl-4,6-androstadien-3-one

These syntheses are described in Scheme 7.

Scheme 7

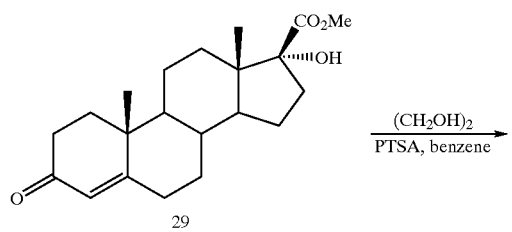

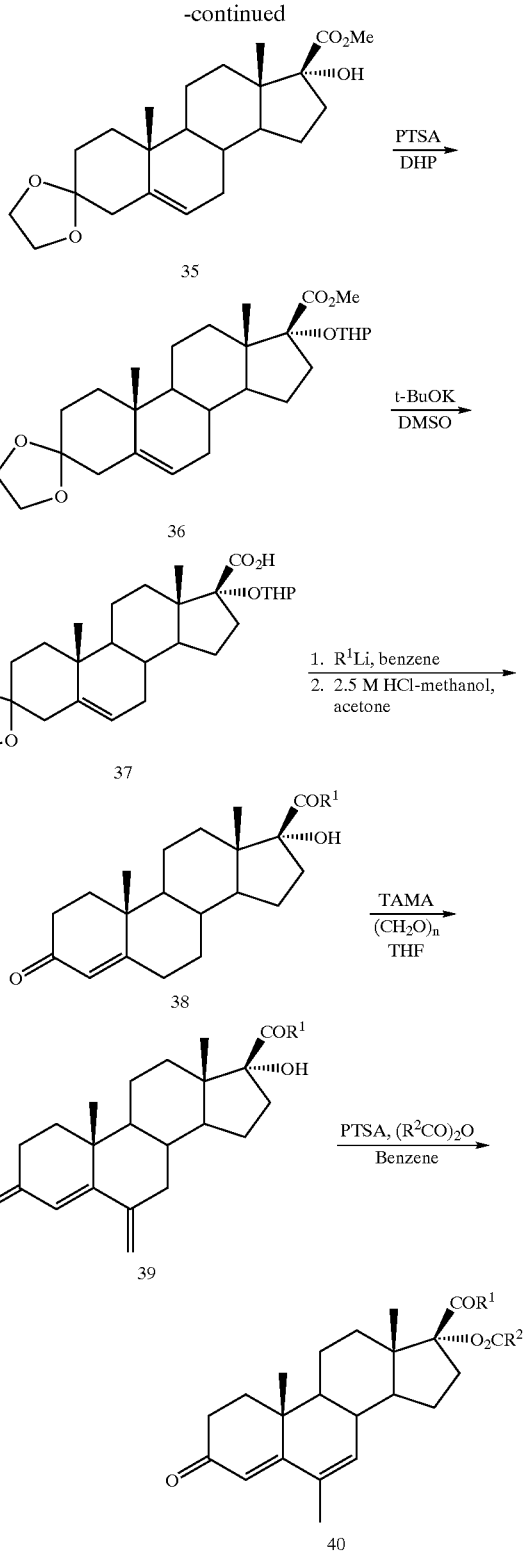

General Method for 17β-Acyl-17α-acyloxy-6-methyl 4,6-Androstadien-3-one (40)

Example 10A

5-Androsten-17α-ol-3-one-17β-carboxylic Acid 3-Ethyleneketal Methyl Ester (35)

A solution of 4-androsten-17α-ol-3-one-17β-carboxylic acid methyl ester (29) (5.16 g, 0.0154 mol) and ethylene glycol (2.87 g, 0.0463 mol) in benzene (500 mL) was refluxed with a Dean-Stark apparatus for 1 h, treated with p-toluenesulfonic acid (100 mg, 0.53 mmol), and refluxed for 6.5 h. The reaction mixture was cooled to room temperature, diluted with ethyl acetate, washed with saturated sodium bicarbonate, and 2 times with water, dried over magnesium sulfate, filtered, and evaporated. The crude mixture was purified by flash chromatography (hexanes to hexanes-ethyl acetate 7-3) to provide the ketal 35 (5.12 g, 85%): $^1$H NMR (300 MHz, CDCl$_3$) δ 0.70 (s, 3H), 1.03 (s, 3H), 1.08–1.82 (m, 15H), 2.01 (m, 1H), 2.10 and 2.15 (dd, J=2.6 and 14.2 Hz, 1H), 2.61 (m, 2H), 2.78 (s, 1H), 3.75 (s, 3H), 3.94 (m, 4H), 5.35 (m, 1H).

Example 10B

17α-(2'-Tetrahydro-2'H-pyranyloxy)-5-androsten-3-one-17β-carboxylic Acid 3-Ethyleneketal Methyl Ester (36)

A solution of compound 35 (4.94 g, 0.0126 mol) in 3,4-dihydro-2H-pyran (100 mL) was cooled at 0° C., treated with p-toluenesulfonic acid (300 mg, 1.6 mmol), and stirred for 5 h. The reaction mixture was diluted with ethyl acetate, washed with saturated sodium bicarbonate and 2 times with water, dried over magnesium sulfate, filtered, and evaporated. The crude mixture was purified by flash chromatography (hexanes to hexanes-ethyl acetate 21-4) to quantitatively provide the diketal 36 (6.10 g): $^1$H NMR (300 MHz, CDCl$_3$) δ 0.66 (s, 1.1H), 0.67 (s, 1.9H), 1.01 (s 3H), 1.09–2.15 (m, 22H), 2.47 (m, 3H), 3.37 (m, 0.7H), 3.51 (m, 1.3H), 3.65 (s, 1.7H), 3.69 (s, 1.3H), 3.93 (m, 4H), 4.56 (m, 0.6H), 4.77 (m, 0.4H), 5.34 (m, 1H).

Example 10C

17α-(2'-Tetrahydro-2'H-pyranyloxy)-5-androsten-3-one-17β-carboxylic Acid 3-Ethyleneketal (37)

Compound 36 (3.73 g, 0.00786 mol) was treated with 1 N potassium tert-butoxide in dimethyl sulfoxide (118 mL). The reaction mixture was stirred 4 h at room temperature, diluted with water, aciditied to pH 2, and extracted 3 times with ethyl acetate. The combined organic phase was washed with brine and water, dried over magnesium sulfate, filtered, and evaporated. The crude mixture was purified by flash chromatography (hexanes to ethyl acetate) to provide the carboxylic acid 37 (2.50 g, 69%): $^1$H NMR (300 MHz, CDCl$_3$) δ 0.76 (s, 2.0H), 0.80 (s, 1.0H), 0.82–2.15 (m, 22H), 1.03 (s, 3H), 2.38–2.58 (m, 3H), 3.4–3.6 (2m, 2H), 4H), 4.68 (m, 1H), 5.35 (m, 1H).

Example 10D

17β-Acyl-4-androsten-17α-ol-3-one (38)

Under argon atmosphere, a solution of compound 37 in dry benzene (3.0% W/V) was cooled at 0° C., treated with an organolithium solution (7.0 equiv), and stirred 20 h at room temperature. The reaction mixture was cooled to 0° C., quenched with saturated ammonium chloride, diluted with water, and extracted 3 times with ethyl acetate. The combined organic phase was washed with brine, dried over magnesium sulfate, filtered, and evaporated. The crude mixture was dissolved in methanol-acetone 1-1 (2% W/V), treated with 2.5 M hydrochloric acid, and refluxed for 1 h. The reaction mixture was cooled at room temperature, evaporated (solvents), diluted in water, and extracted 3 times with ethyl acetate. The combined organic phase was washed with brine and water, dried over magnesium sulfate, filtered, and evaporated. The crude mixture was purified by flash chromatography (hexanes to hexanes-ethyl acetate 3-1) to provide compound 38 (e.g. R$^1$=Bn, 42%): $^1$H NMR (300 MHz, CDCl$_3$) δ 0.74 (s, 3H), 0.96–1.88 (m, 13H), 1.17 (s, 3H), 2.02 (m, 1H), 2.35 (m, 4H), 2.76 (m, 2H), 3.77 (d, J=16.5 Hz, 1H), 4.07 (d, J=16.4 Hz, 1H), 5.72 (s, 1H), 7.16–7.33 (m, 5H).

Example 10E

17β-Acyl-6-methylene-4-androsten-17α-ol-3-one (39)

A solution of compound 38, paraformaldehyde (5.4 equiv), and N-methylanilinium trifluoacetate (4.8 equiv) in THF (2.9% W/V) was refluxed for 2.5 h. The reaction mixture was cooled at room temperature, treated with 2.5 M hydrochloric acid, stirred for 15 min, and extracted 3 times with ethyl acetate. The combined organic phase was washed with water, saturated sodium bicarbonate, and brine, dried over magnesium sulfate, filtered, and evaporated. The crude mixture was purified by flash chromatography (hexanes to hexanes-ethyl acetate 4-1) to provide compound 39 (e.g. R$^1$=Bn, 33%): $^1$H NMR (300 MHz, CDCl$_3$) δ 0.75 (s, 3H), 1.09 (s, 3H), 1.15–2.08 (m, 13H), 2.45 (m, 3H), 2.78 (m, 2H), 3.78 (d, J=16.3 Hz, 1H), 4.07 (d, J=16.3 Hz, 1H), 4.94 (s, 1H), 5.06 (s, 1H), 5.91 (s, 1H), 7.17–7.34 (m, 5H).

Example 10F

17β-Acyl-17α-acyloxy-6-methyl-4,6-androstadien-3-one (40)

The same procedure for compound 23 was used, starting from compound 39. The crude mixture was purified by 2 flash chromatographies (dichloromethane to dichloromethane-acetone 99-1 and hexanes to hexanes-ethyl acetate 17-3) to provide compound 40 (e.g. EM-1106, R$^1$=Bn, R$^2$=CH$_3$, 45%): IR (KBr) 2943, 2857, 1736, 1718, 1656, 1628, 1579, 1266, 1236; $^1$H NMR (300 MHz, CDCl$_3$) δ 0.72 (s, 3H), 1.09 (s, 3H), 1.26–2.25 (m, 12H), 1.86 (s, 3H), 2.14 (s, 3H), 2.43–2.64 (m, 2H), 3.06 (m, 1H), 3.68 (m, 2H), 5.89 (s, 1H), 5.97 (s, 1H), 7.16–7.33 (m, 5H); $^{13}$C NMR (75 MHz, CDCl$_3$) δ 14.52, 16.39, 19.94, 20.35, 21.35, 23.30, 30.76, 31.21, 33.64, 34.07, 36.12, 37.11, 45.02, 47.91, 49.06, 50.23, 96.42, 121.29, 126.85, 128.32, 129.94, 131.49, 133.88, 137.93, 164.08, 170.76, 199.97, 203.41.

Example 11

17α-Acyloxy-6-methyl-4,6-androstadien-3-one-17β-carboxyester

These syntheses are described in Scheme 8.

Scheme 8

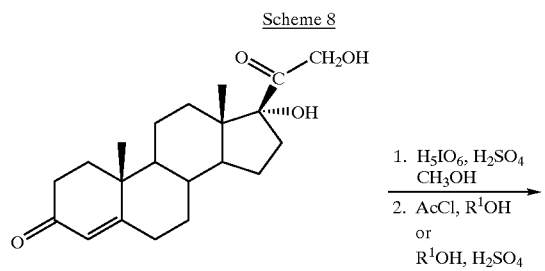

28

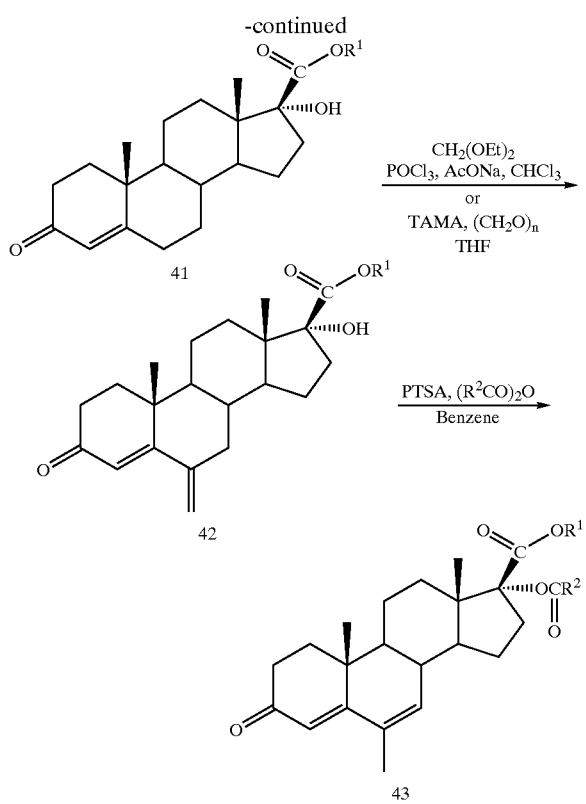

Example 11A

4-Androsten-17α-ol-3-one-17β-carboxyester (41)

The same procedure for compound 29 was used and provide compound 41 (e.g., compound 41, $R^1=CH_3$).

Example 11B

6-Methylene-4-androsten-17α-ol-3-one-17β-carboxester (42)

The same procedure for compound 30 was used and provide compound 42 (e.g. compound 42, $R^1=CH_3$).

Example 11C

17α-Acyl-6-methyl-4,6-androstadien-17α-ol-3-one-17β-carboxester (43)

The same procedure for compound 31 was used and provide compound 43 (e.g. compound 43, $R^1, R^2=CH_3$).

Example 12

15α-Substituted 4,6-Androstadien-3,17-dione Derivatives

These Synthesis are described in Scheme 9.

Scheme 9

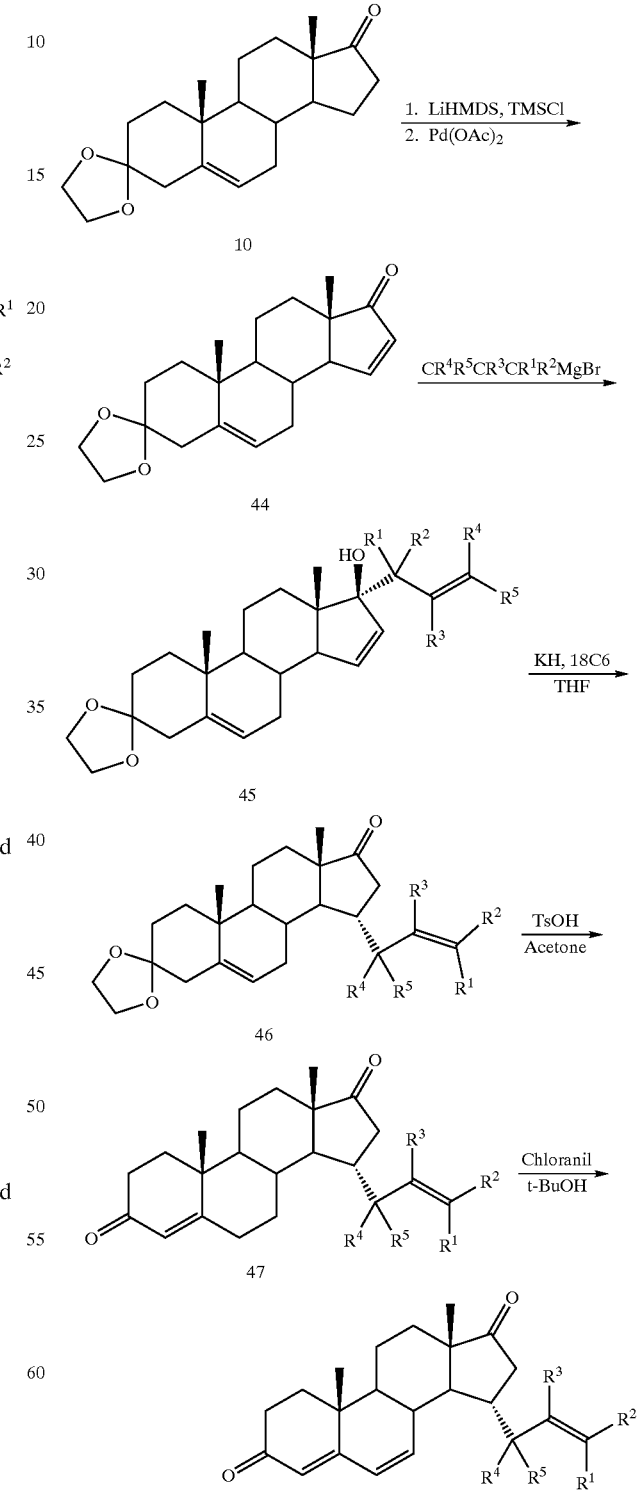

Example 12A 5,15-Androstadien-3,17-dione 3-Ethyleneketal (44)

Under argon atmosphere, a solution of 5-androsten-3,17-dione 3-ethyleneketal 10 (4.95 g, 0.0150 mol) in anhydrous THF (150 mL) was cooled at 0° C. and treated with 1.0 M solution of lithium bis(trimethylsilyl)amide in THF (18 mL, 0.018 mol). The solution was stirred 20 min at room temperature, cooled at −78° C., and treated with chlorotrimethylsilane (2.24 mL, 0.0176 mol). The reaction was allowed to warm to room temperature, then evaporated. The residue was diluted with dichloromethane, washed two times with water and brine, dried over magnesium sulfate, filtered, and evaporated. A solution of the crude silylenol ether in a dichloromethane-acetonitrile 2-5 (140 mL) was treated with palladium acetate (4.04 g 0.0180 mol) and refluxed for 30 min. The reaction mixture was cooled to room temperature and evaporated. The black residue was purified by flash chromatography (hexanes-ethyl acetate 4-1) to provide the enone 44 (3.49 g, 71%): $^1$H NMR (300 MHz, CDCl$_3$) δ 1.085 (s, 3H), 1.09 (s, 3H), 1.21–1.93 (m, 11H), 2.15 (dd, J=2.7 and J=14.1 Hz, 1H), 2.26–2.34 (m, 2H), 2.58 (d, J=14.1 Hz, 1H), 3.95 (m, 4H), 5.40 (d, J=5.1 Hz, 1H), 6.04 (dd, J=3.2 and J=6 Hz, 1H), 7.50 (d, J=5.8 Hz, 1H).

Example 12B

17α-Substituted Allyl 5,15-Androstadien-17β-ol-3-one 3-Ethyleneketal (45)

Under argon atmosphere, a solution of compound 44 in anhydrous THF (10% W/V) was cooled at 0° C., treated with a solution of substituted allylmagnesium bromide or chloride in THF or ether (3 equiv) and stirred 3 h. The reaction mixture was quenched with saturated ammonium chloride and diluted with ethyl acetate. The organic phase was washed with brine, dried over magnesium sulfate, filtered, and evaporated. The crude residue was purified by flash chromatography (hexanes-ethyl acetate 9-1 to hexanes-ethyl acetate 4-1) to provide compound 45 (e.g., $R^1$, $R^2$, $R^3$, $R^4$, $R^5$=H, 70%): $^1$H NMR (300 MHz, CDCl$_3$) δ 0.92 (s, 3H), 1.06 (s, 3H), 1.11–1.81 (m, 11H), 1.95 (d, J=9.3 Hz, 1H), 2.10–2.21 (m, 3H), 2.30–2.36 (m, 1H), 2.57 (d, J=5 Hz, 1H), 3.95 (m, 4H), 5.10–5.16 (m, 2H), 5.36 (broad d, J=5 Hz, 1H), 5.61 (dd, J=3.1 and 5.7 Hz, 1H), 5.83 (d, J=5.8 Hz, 1H), 5.84–5.94 (m, 1H).

Example 12C

15α-Substituted Allyl-5-androsten-3,17-dione 3-Ethyleneketal (46)

Under argon atmosphere, a solution of compound 45 in dry THF (10% W/V) was cooled at 0° C., treated with potassium hydride in 35% dispersion in mineral oil (2 equiv), and stirred 30 min. Then, the resulting suspension was treated with 18-crown-6 ether (1.5 equiv), allowed to reach room temperature, and stirred 2 h. The black mixture was quenched with saturated ammonium chloride then diluted with ethyl acetate. The organic phase was washed with brine, dried over magnesium sulfate, filtered, and concentrated. The oily residue was purified by flash chromatography (hexanes-ethyl acetate 4-1) to provide compound 46 (e.g., $R^1$, $R^2$, $R^3$, $R^4$, $R^5$=H, 71%): $^1$H NMR (300 MHz, CDCl$_3$) δ 0.94 (s, 3H), 1.06 (s, 3H), 1.1–1.5 (m, 5H), 1.5–2.0 (m, 11H), 2.14 (d, J=14.1 Hz, 1H), 2.19–2.29 (m, 2H), 2.62 (dd, J=8.3 and 19.3 Hz, 2H), 3.95 (m, 4H), 4.66 (d, J=16 Hz, 2H), 5.35 (s, 2H).

Example 12D

15α-Substituted Allyl 4-Androsten-3,17-dione (47)

The same procedure for compound 12 was used, starting from compound 46. The crude mixture was purified by flash chromatography (hexanes-ethyl acetate 9-1 to hexanes-ethyl acetate 41) to provide compound 47 (e.g., EM-1284, $R^1$, $R^2$, $R^3$, $R^4$, $R^5$=H, 85%): IR (CHCl$_3$) 3020, 2954, 1733, 1664, 1617, 1275, 1230 cm$^{-1}$; $^1$H NMR (300 MHz, CDCl$_3$) δ 0.97 (s, 3H), 1.21 (s, 3H), 0.99–1.60 (m, 4H), 1.60–2.05 (m, 10H), 2.05–2.50 (m, 4H), 2.65 (dd, J=8.7 and 16.2 Hz, 2H), 5.03 (m, 2H), 5.67–5.73 (m, 2H); $^{13}$C NMR (75 MHz, CDCl$_3$) δ 15.30, 17.62, 20.26, 31.09, 32.40, 32.57, 33.91, 35.79, 35.88, 36.59, 38.73, 40.17, 42.42, 49.94, 53.91, 54.36, 116.78, 123.72, 135.93, 169.93, 199.15, 219.08.

Example 13E

15α-Substituted Allyl 4,6-Androstadien-3,17-dione (48)

The same procedure for compound 13 was used, starting from compound 47. The crude residue was purified by 2 flash chromatographies (hexanes-acetone 9-1 and hexanes-ethyl acetate 17-3) to provide compound 48 (e.g., EM-1261, $R^1$, $R^2$, $R^3$, $R^4$, $R^5$=H, 61%): IR (CHCl$_3$) 3013, 2943, 2865, 1734, 1655, 1619, 1229 cm$^{-1}$; $^1$H NMR (CDCl$_3$, 300 MHz) δ 1.02 (s, 3H), 1.12 (s, 3H), 1.30–1.55 (m, 4H), 1.64–2.20 (m, 6H), 2.30–2.80 (m, 6H), 5.03–5.08 (m, 2H), 5.65–5.85 (m, 2H), 6.17 (dd, J=2.7 and 10.0 Hz, 1H), 6.42 (dd, J=1.8 and 10.0 Hz, 1H); $^{13}$C NMR (75 MHz, CDCl$_3$) δ 15.41, 16.31, 19.79, 31.12, 33.85, 33.95, 35.29, 36.03, 38.40, 39.96, 42.25, 50.57, 52.61, 117.31, 123.97, 128.29, 135.19, 139.01, 162.35, 199.12, 218.20.

Example 13

(E)-16-Monosubstituted Methylene 4,6-Androstadien-3,17-dione

These syntheses are described in Scheme 10.

Scheme 10

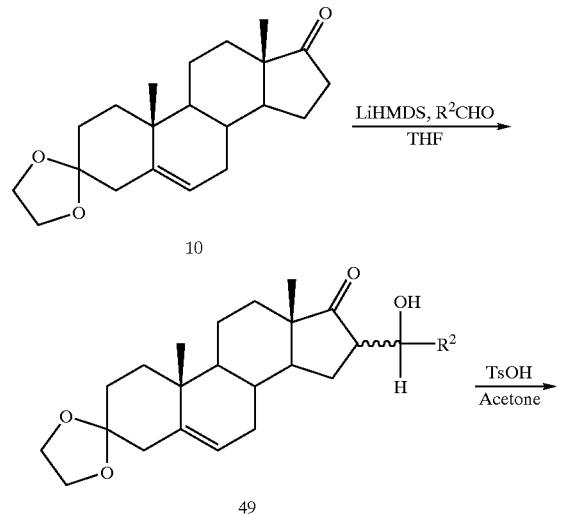

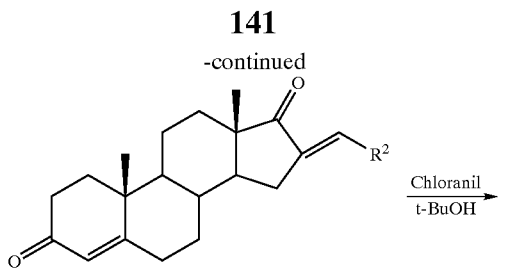

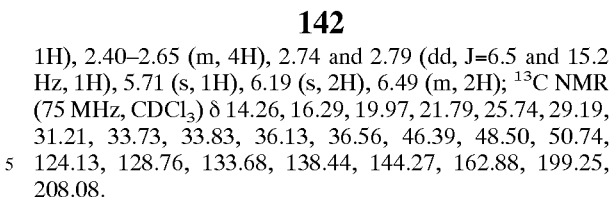

Example 13A

16-Monosubstituted Hydroxymethyl 5-Androsten-3, 17-dione 3-Ethyleneketal (49)

Under argon atmosphere, a solution of 5-androsten-3,17-dione 3-ethyleneketal (10) in anhydrous THF (3.3% W/V) was cooled at 0° C. and treated with a 1.0 M solution of lithium bis(trimethylsilyl)amide in THF (1.0 equiv) and HMPA (2.0 equiv). The solution was stirred 20 min at room temperature, cooled at −78° C., and treated with 1.2 equiv of aldehyde. The reaction mixture was allowed to reach room temperature and stirred over 3 h. The reaction was quenched with saturated ammonium chloride and diluted with ethyl acetate. The organic phase was washed with brine, dried over magnesium sulfate, filtered, and evaporated. The crude mixture was used to carry out the next step without further purification (e.g., $R^2$=isopropyl, quantitative yield): $^1$H NMR (300 MHz, CDCl$_3$) δ 0.89–0.99 (m, 9H), 1.01–2.00 (m, 14H), 2.2–2.6 (m, 6H), 3.5–4.0 (m, 5H), 5.72 (m, 2H).

Example 13B

(E)-16-Monosubstituted Methylene 4-Androsten-3, 17-dione (50)

The same procedure for compound 12 was used, starting from compound 49. The crude mixture was purified by flash chromatography (hexanes-ethyl acetate 97-3 to hexanes-ethyl acetate 17-3) to provide compound 50 (e.g., $R^2$=isopropyl, 19%): $^1$H NMR (300 MHz, CDCl$_3$) δ 0.88 (s, 3H), 0.99 (d, J=6.6 Hz, 3H), 1.00 (d, J=6.6 Hz, 3H), 1.18 (s, 3H), 1.1–1.5 (m, 5H), 1.6–1.8 (m, 3H), 1.8–2.1 (m, 4H), 2.2–2.6 (m, 6H), 5.70 (s, 1H), 6.38 (m, 1H).

Example 13C

(E)-16-Monosubstituted Methylene 4,6-Androstadien-3,17-dione (51)

The same procedure for compound 13 was used, starting from compound 50. The crude mixture was purified by 2 flash chromatographies (hexanes-ethyl acetate 19-1 to hexanes-ethyl acetate 7-3) to provide compound 51 (e.g., EM-1353, $R^2$=isopropyl, 60%): IR (CHCl$_3$) 2961, 2868, 1722, 1656, 1619, 1465, 1374, 1269, 1209, 914, 733 cm$^{-1}$; $^1$H NMR (300 MHz, CDCl$_3$) δ 0.98 (s, 3H), 1.05 (d, J=6.4 Hz, 3H), 1.07 (d, J=5.9 Hz, 3H), 1.16 (s, 3H), 1.25–1.55 (m, 4H), 1.71–1.80 (m, 2H), 1.94–2.05 (m, 2H), 2.18–2.28 (m, 1H), 2.40–2.65 (m, 4H), 2.74 and 2.79 (dd, J=6.5 and 15.2 Hz, 1H), 5.71 (s, 1H), 6.19 (s, 2H), 6.49 (m, 2H); $^{13}$C NMR (75 MHz, CDCl$_3$) δ 14.26, 16.29, 19.97, 21.79, 25.74, 29.19, 31.21, 33.73, 33.83, 36.13, 36.56, 46.39, 48.50, 50.74, 124.13, 128.76, 133.68, 138.44, 144.27, 162.88, 199.25, 208.08.

Example 14

4,6-Androstadien-3,17-dione-16-spirobicyclo [3'.1'.0']hexane

These syntheses are described in Scheme 11.

Scheme 11

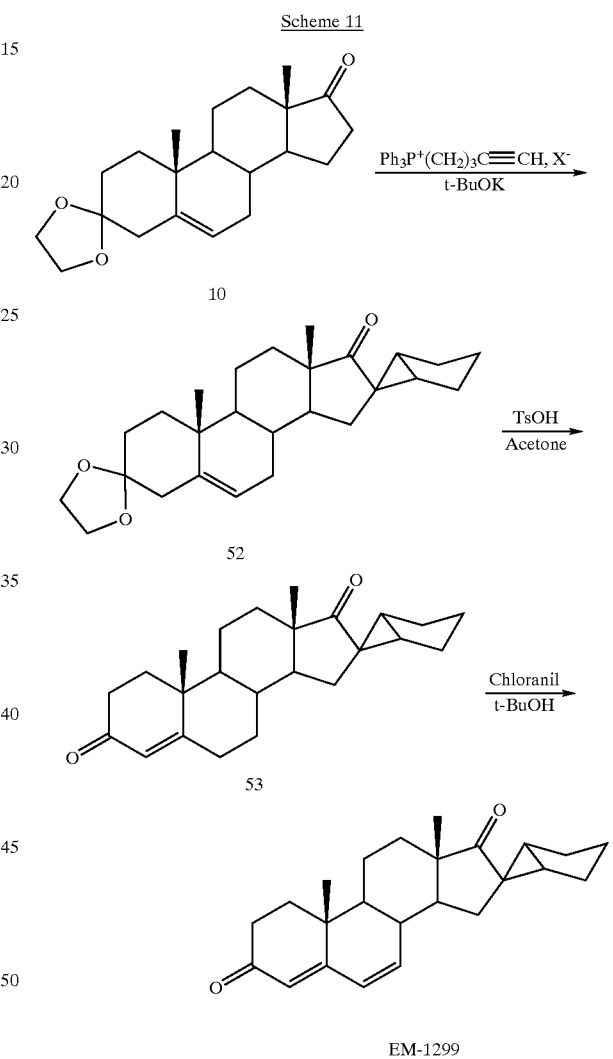

Example 14A

5-Androsten-3,17-dione-16-spirobicyclo[3'.1'.0']-hexane 3-ethyleneketal (52)

Under argon atmosphere, a solution of 5-androsten-3,17-dione 3-ethyleneketal (10) (3.96 g, 0.0120 mol), potassium tertbutylate (0.70 g, 0.059 mol) and 4-pentynyltriphenylphosphonium iodide (2,90 g, 0.0635 mol) in dry toluene (3% W/V) was heated at 100° C. for 1 h. The reaction mixture was cooled at room temperature, poured into ice-water and extracted several times with ethyl acetate. The combined organic phase was washed with water and brine, dried over magnesium sulfate, filtered, and evaporated. The obtained solid was purified by flash chromatography (hexanes-ethyl acetate 9-1to hexanes-ethyl acetate 4-1) to provide spirobicycloketal 52 (0.95 g, 20%): $^1$H NMR (300 MHz, CDCl$_3$) δ 0.94 (s, 3H), 1.06 (s, 3H), 1.15–2.04 (m, 22H), 2.16 (dd, J=2.7 and J=14.1 Hz, 1H), 2.57 (m, 2H), 3.96 (m, 4H), 5.38 (s, 1H).

Example 14B

4-Androsten-3,17-dione-16-spirobicyclo[3'.1'.0']-hexane (53)

The same procedure for compound 12 was used, starting from compound 52. The crude mixture was purified by flash chromatography (hexanes-ethyl acetate 9-1) to provide spirobicycloenone 53 (50%): $^1$H NMR (300 MHz, CDCl$_3$) δ 0.95 (s, 3H), 1.18 (s, 3H), 1.02–2.10 (m, 22H), 2.25–2.45 (m, 3H), 5.8 (s, 1H).

Example 14C 4,6-Androstadien-3,17-dione-16-spirobicyclo[3'.1'.0']-hexane (EM-1299)

The same procedure for compound 13 was used, starting from compound 53. The crude mixture was purified by flash chromatography (hexanes-ethyl acetate 9-1 to hexanes-ethyl acetate 4-1) to provide spirobicyclodienone EM-1299 (51%): IR (CHCl$_3$) 3008, 2943, 2878, 1730, 1643, 1611 cm$^{-1}$; $^1$H NMR (300 MHz, CDCl$_3$) δ 1.01 (s, 3H), 1.14 (s, 3H), 1.15–1.80 (m, 13H), 1.84–2.15 (m, 5H), 2.38–2.54 (m, 3H), 5.70 (s, 1H), 6.14–6.24 (m, 2H); $^{13}$C NMR (75 MHz, CDCl$_3$) δ 14.51, 16.32, 19.92, 23.12, 23.24, 25.77, 31.21, 33.83, 35.35, 36.16, 36.28, 47.54, 48.58, 50.87, 124.12, 128.70, 138.65, 163.01, 199.31, 218.66.

Example 15

15α, 16α, (E-Ring)-4,6-androstadien-3,7-dione Derivatives

These syntheses are described in Scheme 12.

Scheme 12

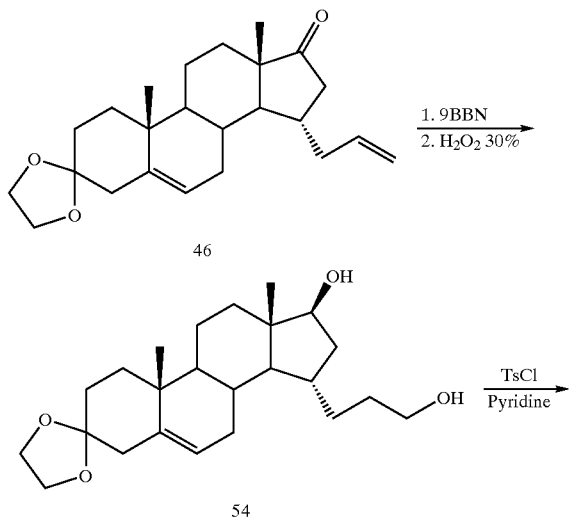

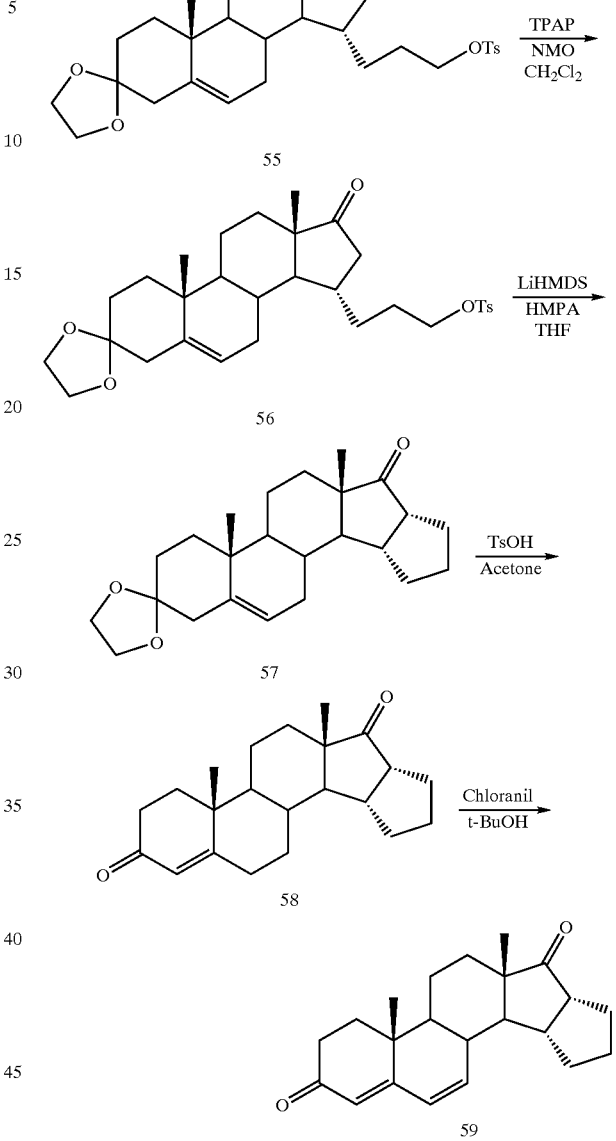

Example 15A

15α-[1-(3-Hydroxypropyl)]-5-androsten-17β-ol-3one 3-ethyleneketal (54)

Under argon atmosphere, a solution of compound 46 (1.20 g, 3.24 mmol) in dry THF (6 mL) was cooled at 0° C. and treated with a 0.5 M solution of 9-BBN in THF (20 mL, 10 mmol). The reaction mixture was allowed to warm to room temperature and stirred overnight. The reaction mixture was cooled at 0° C. and treated with few drops of methanol, 3 N sodium hydroxide (5 mL) and 30% hydrogen peroxide (5 mL). The reaction mixture was vigorously stirred 2 h and neutralized with 10% hydrochloric acid. After evaporating of the solvent, the aqueous phase was extracted with dichloromethane. The organic phase was washed with brine, dried over magnesium sulfate, filtered, and evaporated. The crude mixture was purified by flash chromatography (dichloromethane-ethyl acetate 9-1 to dichloromethane-ethyl acetate 4-1) to provide the diol 54 (0.97 g, 77%): $^1$H NMR (300 MHz, CDCl$_3$) δ 0.78 (s, 3H), 1.04 (s, 3H), 1.07–1.89 (m, 19H), 2.11 (dd, J=2.6 and 14 Hz, 2H), 2.55 (d, J=14.1 Hz, 1H), 3.60 (m, 3H), 3.92 (m, 4H), 5.32 (s, 1H).

Example 15B

15α-[1-(3-Tosyloxypropyl)]-5-androsten-17β-ol-3-one 3-ethyleneketal (55)

Under argon atmosphere, a solution of compound 54 (558 mg, 1.43 mmol) in dry pyridine (5 mL) was cooled at 0° C., treated with p-toluenesulfonyl chloride (328 mg, 1.72 mmol), and stirred 5 h. The reaction mixture was diluted with ethyl acetate and washed with 10% hydrochloric acid and brine. The organic phase was dried over magnesium sulfate, filtered, and evaporated. The crude mixture was purified by flash chromatography (hexanes-ethyl acetate 9-1) to give the hydroxytosylate 55 (389 mg, 50%): $^1$H NMR (300 MHz, CDCl$_3$) 0.74 (s, 3H), 1.04 (s, 3H), 1.06–1.76 (m, 19H), 2.12 (dd, J≈2 and 15 Hz, 2H), 2.45 (s, 3H), 2.55 (d, J=15 Hz, 1H), 3.58 (t, J≈8 Hz, 1H), 3.92–4.12 (m, 4H), 5.29 (s, 1H), 7.34 (d, J=8.4 Hz, 2H), 7.75 (d, J=8.2 Hz, 2H).

Example 15C

15α-[1-(3-Tosyloxypropyl)]-5-androsten-3,17-dione 3-ethyleneketal (56)

Under argon atmosphere, a solution of compound 55 (258 mg, 0.474 mmol) in dry dichloromethane (10 mL) was treated with 4-methylmorpholine N-oxide (82 mg, 0.70 mmol) and molecular sieves 4 Å, stirred 30 min, treated with a catalytic amount of tetrapropylammonium perruthenate (5 mg) and stirred 2 h. Filtrating and evaporating of the reaction mixture afforded a black residue which was purified by flash chromatography (hexanes-ethyl acetate 7-3) to provide the ketotosylate 56 (129 mg, 50%): $^1$H NMR (300 MHz, CDCl$_3$) δ 0.74 (s, 3H), 1.05 (s 3H), 1.08–2.16 (m, 20H), 2.45 (s, 3H), 2.54–2.66 (m, 2H), 3.90–4.00 (m, 4H), 4.03 (t, J=6.4 Hz, 2H), 5.30 (s, 1H), 7.35 (d, J=8.4 Hz, 2H), 7.79 (d, J=8.2 Hz, 2H).

Example 15D

15α,16α-1,3-Propylene)-5-androsten-3,17-dione 3-ethyleneketal (57)

Under argon atmosphere, a solution of compound 56 in dry THF (10 mL) was cooled at 0° C. and treated with 1 M solution of lithium bis(trimethylsilyl)amide in THF (0.50 mL, 0.50 mmol) and HMPA (57.5 μL, 0.330 mmol). The reaction mixture was stirred 10 min, quenched with saturated ammonium chloride, evaporated (THF) and extracted with dichloromethane. The organic phase was washed with brine, dried over magnesium sulfate, filtered, and evaporated. The crude mixture was purified by flash chromatography (hexanes-ethyl acetate 4-1 to hexanes-ethyl acetate 7-3) to provide the pentacyclic ketone 57 (96 mg, 78%): $^1$H NMR (300 MHz, CDCl$_3$) δ 0.95 (t, J=10.4 Hz, 1H), 1.02 (s, 3H), 1.07 (s, 3H), 1.13–1.88 (m, 17H), 2.12 (dd, J=2.6 and 14.2 Hz, 2H), 2.55 (m, 2H), 2.99 (m, 1H), 3.95 (m, 4H), 5.3 (s, 1H).

Example 15E

15α,16α-1,3-Propylene)-4-androsten-3,17-dione (58)

The same procedure for compound 12 was used, starting from compound 57. The crude mixture was purified by flash chromatography (hexanes-ethyl acetate 4-1) to provide pentacyclic enone 58 (~100%): $^1$H NMR (300 MHz, CDCl$_3$) δ 0.85 (t, J=10.6 Hz, 1H), 0.94–1.02 (m, 1H), 1.05 (s, 3H), 1.22 (s, 3H), 1.24–1.87 (m, 14H), 2.06 (m, 2H), 2.31–2.48 (m, 3H), 2.58 (m, 1H), 3.01 (m, 1H), 5.30 (s, 1H).

Example 19F

15α,16α-1,3-Propylene)-4,6-androstadien-3,17-dione (59)

The same procedure for compound 13 was used, starting from compound 58. The crude mixture was purified by 2 flash chromatographies (hexanes-acetone 9-1 and hexanes-ethyl acetate 97-3 to hexanes-ethyl acetate 17-3) to provide the pentacyclic dienone 59 (60%). The $^1$H NMR spectrum shows the presence of pentacyclic enone 58 in 10%. $^1$H NMR (300 MHz, CDCl$_3$) δ 1.04 (t, J=≈10 Hz, 1H), 1.09 (s, 3H), 1.13 (s, 3H), 1.22–1.86 (m, 12H), 1.99 (m, 1H), 2.16–2.60 (m, 3H), 2.72 (q, J=8.2 Hz, 1H), 3.05 (m, 1H), 5.70 (s, 1H), 6.18 (dd, J=9.8 and 2.5 Hz, 1H), 6.32 (d, J=10 Hz, 1H).

Example 16

6,17α,β-Dimethyl/1α,6,17αβ-trimethyl-D-Homo-4, 6-androstadien/1,4,6-androstatrien-17aα-ol-3, 17-dione Alkanoate These syntheses are described in Scheme 13.

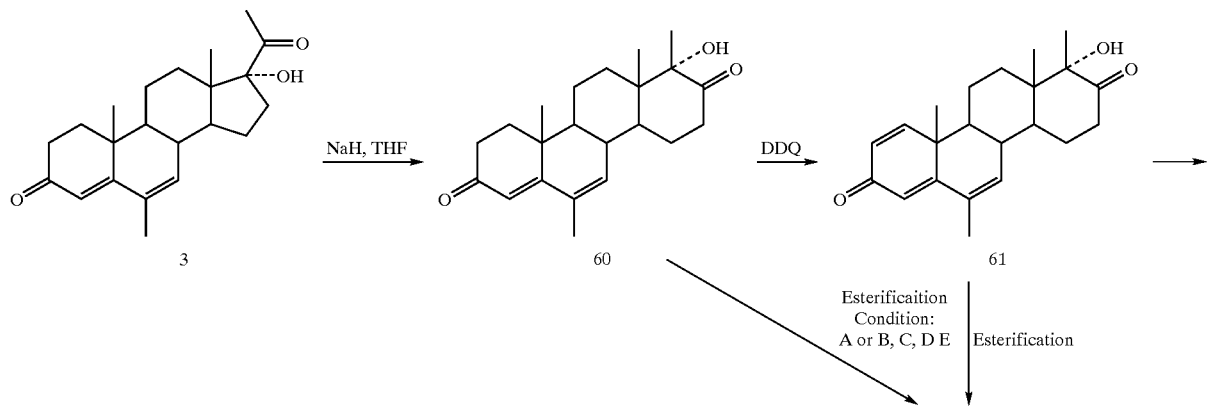

Scheme 13

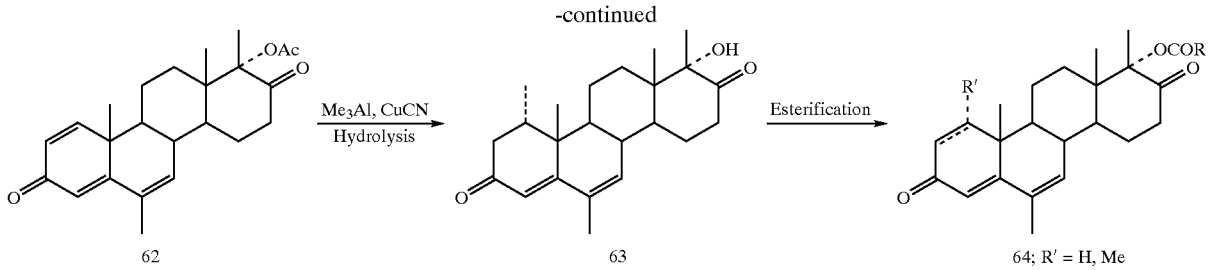

Example 16A

6,17aβ-Dimethyl-D-Homo-4,6-androstadien-17aα-ol-3,17-dione (60)

The following example is a representative: Megestrol (44.1 g; 129 mmol) was dissolved in THF (550 mL). Sodium hydride (10.2 g; 3.2 eq.) was added portion-wise at 0° C. After addition, the mixture was stirred for 9 h at room temperature and cooled to 0° C., and water (300 mL) was added slowely. Approximately THF (300 mL) was evaporated under vacuum and another 300 mL of water was added. The suspension was cooled to 0° C. Solid was filtered and washed with water. Solid, thus obtained was triturated with boiling MeOH (150 mL) and cooled to room temperature. This gave pure product which was filtered and washed with MeOH, and dried (36.4 g; 82% yield).

Example 16B

6,17aβ-Dimethyl-D-Homo-1,4,6-androstatrien-17aα-ol-3,17-dione (61)

Compound 60 (5 g; 14.7 mmol) and DDQ (10 g; 3 eq) in dioxane (60 mL) were refluxed for 3 h. Solvent was removed and the mixture in EtOAc was washed with saturated NaHCO$_3$ solution (3 times). Solvent was dried (MgSO$_4$) and evaporated to give the product. Purification on silica gel column (hexanes/acetone) gave the trienone 61 (3.7 g) in 76% yield.

Example 16C

1α,6,17aβ-Trimethyl-D-Homo-4,6-androstadien-17aα-ol-3,17-dione (63)

This compound was prepared by following the methods, described above.

Example 16D

6,17aβ-Dimethyl/1α,6,17aβ-trimethyl-D-Homo-4,6-androstadien-17aα-ol-3,17-dione Alkanoate (64)

The alcohols were esterified by using the conditions A, B, C, D or E.

Example 16E

The followings are non-limiting examples of physico-chemical characteristics of inhibitors of Example 16.

EM-1078 (64, R'=H, R=(CH$_2$)$_2$CH$_3$); Yield, 66%; IR (KBr, cm$^{-1}$) 2948, 2871, 1735, 1660, 1624, 1577, 1458, 1375, 1317, 1269, 1188, 1099; $^1$H NMR (CDCl$_3$) δ 0.80 (s, 3H, H-C18), 0.96 (t, 3H, H-C4', J=7 Hz), 1.06 (s, 3H, H-C19),1.34 (s, 3H, 17a-CH$_3$), 1.87 (s, 3H, 6-CH$_3$), 2.01–2.06 (m, 2H), 2.32 (t, 2H, H-C2', J=7 Hz), 5.89 (s, 1H), 6.13 (s, 1H); $^{13}$C NMR (CDCl$_3$) δ 208.0, 200.0, 172.5, 163.7, 136.5, 131.8, 121.0, 87.6, 49.5, 45.4, 40.4, 37.3, 36.3, 36.1, 33.7, 33.4, 31.8, 26.1, 20.2, 19.8, 18.3, 16.2, 13.6, 13.0.

EM-1091 (64, R'=H, R=CH$_2$CH$_3$); Yield, 53%; IR (KBr, cm$^{-1}$) 2944, 1734, 1664, 1625, 1581, 1444, 1352, 1273, 1194, 1098; $^1$H NMR (CDCl$_3$) δ 0.77 (s, 3H, H-C18), 1.01 (s, 3H, H-C19), 1.12 (t, 3H, H-C3', J=7 Hz), 1.30 (s, 3H, 17a-CH$_3$), 1.83 (s, 3H, 6-CH$_3$), 2.34 (q, 2H, H-C2', J=7 Hz), 5.84 (s, 1H),6.10 (s, 1H); $^{13}$C NMR (CDCl$_3$) δ 207.8, 199.8, 173.2, 163.5, 136.4, 131.9, 121.4, 121.2, 87.7, 49.7, 45.5, 40.6, 37.4, 36.2, 33.9, 33.6, 31.9, 27.9, 26.1, 20.2, 19.9, 16.3, 13.7, 13.1, 9.0.

EM-1098 (64, R'=H, R=CH$_2$Ph); Yield, 37%; IR (KBr, cm$^{-1}$) 2946, 2869, 1735, 1657, 1624, 1578, 1456, 1268, 1127, 1098; $^1$H NMR (CDCl$_3$) δ 0.72 (s, 3H, H-C18), 1.01 (s, 3H, H-C19), 1.30 (s, 3H, 17a-CH$_3$), 1.90 (s, 3H, 6-CH$_3$), 3.65 (s, 2H, H-C2'), 5.93 (s, 1H), 6.00 (s, 1H), 7.26 (s, 5H, Aromatics); $^{13}$C NMR (CDCl$_3$) δ 207.5, 199.9, 169.7, 165.6, 136.5, 131.6, 129.3, 128.6, 127.2, 121.0, 88.2, 49.6, 45.5, 42.0, 39.9, 37.2, 37.1, 36.1, 33.9, 33.5, 31.8, 25.8, 20.1, 20.2, 19.9, 19.2, 13.6, 14.0.

EM-1146 (64, R'=H, R=CH$_2$PhOCO-t-Bu(p)); Yield, 14%; IR (KBr, cm$^{-1}$) 2955, 2871, 1736, 1660, 1624, 1582, 1508, 1458, 1393, 1270, 1202, 1166, 1117; $^1$H NMR (CDCl$_3$) δ 0.69 (s, 3H, H-C18), 1.05 (s, 3H, H-C19), 1.31 (s, 3H, 17a-CH$_3$), 1.34 (s, 9H, t-Butyl), 1.88 (s, 3H, 6-CH$_3$), 3.64 (s, 2H, H-C2'), 5.90 (s, 1H), 6.10 (s, 1H), 6.97 (d, 2H, J=8.3 Hz), 7.28 (d, 2H, J=8.3 Hz); $^{13}$C NMR (CDCl$_3$) δ 207.7, 199.9, 177.0, 169.7, 163.6, 150.5, 136.7, 131.7, 130.5, 130.4, 121.9, 121.2, 88.4, 49.8, 45.6, 41.4, 40.2, 39.1, 37.4, 37.2, 36.2, 33.8, 33.6, 31.8, 27.1, 25.9, 20.2, 19.9, 16.3, 13.7, 13.1.

CS-259 (64, R'=H, R=(CH$_2$)-$_5$Br); Yield, 32%; IR (KBr, cm$^{-1}$) 2943, 2869, 1734, 1660, 1624, 1579, 1458, 1375, 1270, 1194, 1099; $^1$H NMR (CDCl$_3$) δ 0.81 (s, 3H, H-C18), 1.06 (s, 3H, H-C19), 1.34 (s, 3H, 17a-CH$_3$), 1.87 (s, 3H), 6-CH$_3$), 1.89–2.07 (m, 1H), 2.38 (t, 2H, H-C2', J=7 Hz), 3.40 (t, 2H, H-C6', J=7 Hz), 5.89 (s, 1H), 6.13 (s, 1H); $^{13}$C NMR (CDCl$_3$) δ 207.8, 199.8, 172.2, 163.5, 136.4, 131.8, 121.0, 87.8, 49.5, 45.3, 40.4, 37.3, 36.1, 34.1, 33.7, 33.4, 32.1, 31.8, 27.5, 26.0, 23.8, 20.2, 19.8, 16.1, 13.6, 13.0.

CS-260 (64, R'=H, R=(CH$_2$)$_4$CH$_3$); Yield, 41%; IR (KBr, cm$^{-1}$) 2953, 2870, 1735, 1660, 1624, 1579, 1458, 1375, 1317, 1270, 1098; $^1$H NMR (CDCl$_3$) δ 0.79 (s, 3H, H-C18), 0.87 (t, 3H, H-C6'), 1.06 (s, 3H, H-C19), 1.32 (s, 3H, 17a-CH$_3$), 1.86 (s, 3H, 6-CH$_3$), 2.00–2.06 (m, 2H), 2.33 (t, 2H, H-C2', J=7 Hz), 5.88 (s, 1H), 6.12 (s, 1H); $^{13}$C NMR (CDCl$_3$) δ 208.0, 199.9, 172.7, 163.6, 136.5, 131.9, 121.2, 87.7, 49.7, 45.5, 40.5, 37.4, 36.2, 34.4, 33.8, 33.5, 31.9, 31.3, 26.1, 24.5, 22.3, 20.2, 19.9, 16.2, 13.9, 13.7, 13.1.

CS-237 (64, R'=H, □1, R=CH$_3$); Yield 67%; IR (CDCl$_3$) 1735, 1652, 1609, 1582 cm$^{-1}$; $^1$H NMR (CDCl$_3$) δ 0.79 (s, 3H), 1.1 (s, 3H), 1.29 (s, 3H), 1.89 (s, 3H), 2.02 (s, 3H), 2.41–2.50 (m, 1H), 5.96 (s, 1H) 6.17 (s, 1H), 6.24 (d, 1 H, J=10 Hz), 7.06 (d, 1H, J=10 Hz); $^{13}$C NMR (CDCl$_3$) δ 207.6, 186.3, 169.9, 162.7, 153.1, 132.7, 132.3, 127.8, 121.5, 87.7, 77.4, 77, 76.6, 47.2, 45, 41.1, 40.7, 38, 37.2, 31.7, 26.1, 21.3, 21.1, 20.2, 19.5, 13.6, 13.

CS-240 (64, R=CH$_3$); Yield 70%; IR (CDCl$_3$) 1737, 1651, 1622, 1578 cm$^{-1}$; $^1$H NMR (CDCl$_3$) δ 0.78 (s, 3H), 0.96 (d, 3H, J=7 Hz), 1.12 (s, 3H), 1.31 (s, 3 H), 1.84 (s, 3H), 2.01 (s, 3H), 2.80–2.90 (dd, 1H, J=5.1, 17.5 Hz), 5.85 (s, 1 H), 6.1 (s, 1H); $^{13}$C NMR (CDCl$_3$) δ 207.8, 199.4, 169.9, 159.9, 136.5, 132.5, 120.6, 87.9, 45.5, 44, 42, 40.6, 39.3, 37.4, 37.3, 35.5, 31.8, 26, 21.2, 20.2, 19.3, 18.8, 14.8, 13.7, 13.

EM-1117 (64, R=Cyhex); Yield 38%; IR (CDCl$_3$) 1731, 1703, 1658, 1619, 1578 cm$^{-1}$; $^1$H NMR (CDCl$_3$) δ 0.80 (s, 3H), 0.99 (d, 3H, J=7 Hz), 1.14 (s, 3H), 1.31 (s, 3H), 1.87 (s, 3H), 5.89 (s, 1H,) 6.1 (s, 1H); $^{13}$C NMR (CDCl$_3$) δ 208.1, 199.7, 174.7, 160.2, 136.7, 132.5, 120.6, 87.4, 45.7, 44.2, 43, 42.8, 42.1, 40.9, 39.4, 37.4, 35.6, 32, 29.7, 28.9, 28.8, 28.7, 26.2, 25.6, 25.3, 25.2, 20.3, 19.4, 18.9, 14.9, 13.8, 13.2.

EM-1121 (64, R=(CH$_2$)$_3$CH$_3$); Yield 70%; IR (CDCl$_3$) 1735, 1657, 1622, 1578 cm$^{-1}$; $^1$H NMR (CDCl$_3$) δ 0.77 (s, 3H), 0.85 (t, 3H, J=7 Hz), 0.94 (d, 3H, J=7 Hz), 0.87 (s, 3H), 1.11 (s, 3H), 1.83 (s, 3H), 2.33 (t, 2H, J=7.4 Hz), 2.47 (m, 1H), 2.80–2.88 (dd, 1H, 5.3, 17.8 Hz), 5.84 (s, 1H,) 6.09 (s, 1H); $^{13}$C NMR (CDCl$_3$) δ 207.9, 199.4, 172.7, 160, 136.5, 132.4, 120.5, 87.6, 45.5, 44, 42, 40.7, 39.2, 37.4, 37.3, 35.5, 34, 31.9, 26.7, 26, 22.1, 20.2, 19.3, 18.8, 14.8, 13.7, 13.6, 13.

EM-1142 (64, R=(CH$_2$)-$_4$CH$_3$); Yield 39%; IR (CDCl$_3$) 1735, 1657, 1621, 1578 cm$^{-1}$; $^1$H NMR (CDCl$_3$) δ 0.80 (s, 3H), 0.87 (t, 3H, J=7 Hz), 0.98 (d, 3H, J=7 Hz), 1.15 (s, 3H), 1.33 (s, 3H), 1.87 (s, 3H), 2.84–2.91 (dd, 1H, J=5.1, 17.6 Hz), 5.89 (s, 1H), 6.11 (s, 1H); $^{13}$C NMR (CDCl$_3$) δ 208.10, 199.6, 172.8, 160.1, 136.6, 132.5, 120.6, 87.7, 45.6, 44.2, 42.1, 40.8, 39.4, 37.5, 37.6, 34.4, 33.8, 32, 31.2, 26.1, 24.4, 22.3, 20.3, 19.4, 18.9, 14.9, 13.9, 13.2.

EM-1143 (64, R=CH(CH$_3$)$_2$); Yield 34%; IR (CDCl$_3$) 1733, 1657, 1622, 1578 cm$^{-1}$; $^1$H NMR (CDCl$_3$) δ 0.80 (s, 3H), 0.96 (d, 3H, J=7 Hz), 1.14 (s, 3H), 1.17 (d, 3H, J=7 Hz), 1.18 (d, 3H, J=7 Hz), 1.31 (s, 3H), 1.86 (s, 3H), 284–2.92 (dd, 1H, J=5.1, 17.6 Hz), 5.87 (s, 1H,) 6.1 (s, 1H); $^{13}$C NMR (CDCl$_3$) δ 207.8, 199.5, 175.8, 160, 136.5, 132.6, 120.7, 87.5, 61.9, 45.8, 44.2, 42.1, 40.9, 39.4, 37.4, 35.6, 34.1, 32, 26.2, 20.3, 19.4, 18.9, 18.7, 14.9, 14.1, 13.8, 13.1.

EM-1144 (64, R=CH$_2$Ph); Yield 34%; IR (CDCl$_3$) 1734, 1654, 1623, 1578 cm$^{-1}$; $^1$H NMR (CDCl$_3$) δ 0.72 (s, 3H), 0.99 (d, 3H, J=7 Hz), 1.06 (s, 3H), 1.29 (s, 3H), 1.89 (s, 3H), 2.83–2.90 (dd, 1H, J=5, 17.4 Hz), 3.66 (s, 2H), 5.91 (s, 1H,) 5.96 (s, 1H); $^{13}$C NMR (CDCl$_3$) δ 207.6, 199.5, 169.7, 160, 136.6, 133.6, 132.2, 129.4, 128.7, 127.2, 120.5, 88.1, 45.7, 44, 42, 40.1, 39.2, 37.2, 37.1, 35.6, 31.8, 25.8, 20.2, 19.3, 18.8, 14.9, 13.7, 13.

EM-1154 (64, R=Cypent); Yield 30%; IR (CDCl$_3$) 1731, 1657, 1622, 1578 cm$^{-1}$; $^1$H NMR (CDCl$_3$) δ 0.79 (s, 3H), 0.97 (d, 3H, J=7 Hz), 1.14 (s, 3H), 1.31 (s, 3H), 1.86 (s, 3H), 2.79–2.84 (m, 2H), 5.87 (s, 1H,) 6.1 (s, 1H); $^{13}$C NMR (CDCl$_3$) δ 208.1, 199.5, 175.5, 160, 136.6, 132.6, 120.7, 87.5, 45.7, 44.2, 43.8, 42.1, 40.9, 39.4, 37.4, 37.3, 35.6, 32, 29.9, 29.6, 26.2, 25.8, 25.7, 20.3, 19.4, 18.9, 14.9, 13.8, 13.1.

Example 17

Synthesis of 4-Aza-androstan-3-one-spiro γ/δ-lactone Derivatives

These syntheses are described in Scheme 14.

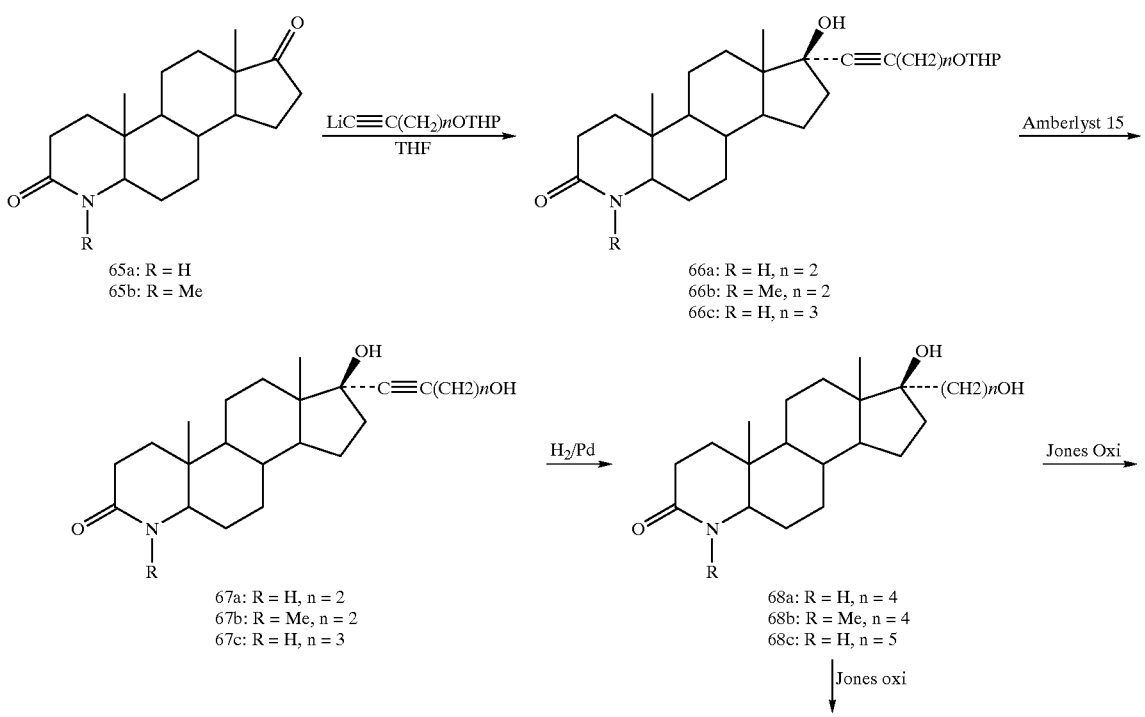

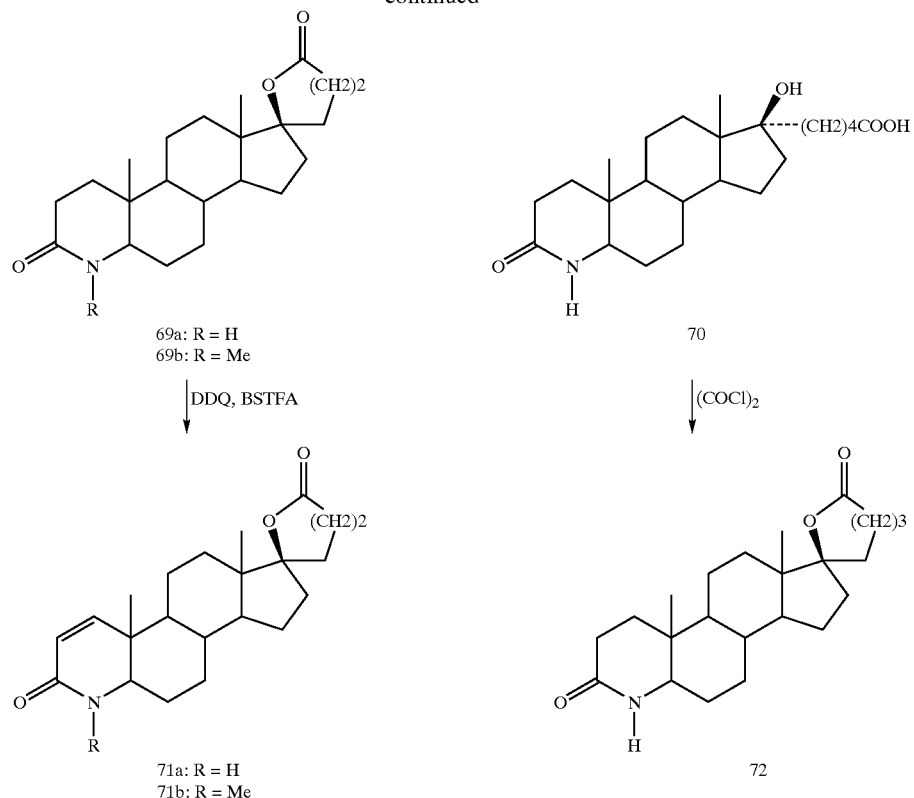

69a: R = H
69b: R = Me

|DDQ, BSTFA

71a: R = H
71b: R = Me

70

|(COCl)₂

72

Example 17A

General Procedure for 66a and 66c

A flask was charged with HC≡C(CH₂)ₙOTHP (n=2 or 3) (41.5 mmol) and dry THF (300 mL) under argon, and cooled to −50° C. in a cold bath. To this solution, was added n-BuLi (1.6 M, 41.4 mmol) via a syringe slowly, and the solution was allowed to warm up to 0° C. over a course of 2 h. Then, the solution was cooled to −78° C., and the ketone 65a (10.4 mmol) was added as a solid. The reaction mixture was stirred and allowed to warm up to room temperature over a course of 3 h, and stirred for additional 2 h at room temperature. Saturated aqueous NH₄Cl solution (50 mL) was added. The resulting two phase was seperated, and water phase was extracted with CH₂Cl₂ (2×100 mL). The combined solvents were removed and the residue was extracted with CH₂Cl₂ (2×150 mL). Solution was washed with brine and dried over MgSO₄. Solvent was removed on a rotary evaporator. The purification of the residue by flash column gave the product as a white solid.

17β-Hydroxy-17α-{4'-(2"-tetrahydro-2"H-pyranyloxy)butyn-1'-yl}-4-aza-5α-androstan-3-one (66a)

Yield, 73%; IR (KBr, cm⁻¹) 3520–3210 (br), 2906, 2838, 1642; ¹H NMR (CDCl₃) δ 0.81 (s, 3H, 18-CH₃), 0.88 (s, 3H, 19-CH₃), 2.52 (dd, 2H, J=4.8, 11.2 Hz), 2.61 (t, 2H, J=7.7 Hz), 3.01 (dd, 1 h, J=3.2, 12.2 Hz), 3.48–3.56 (m, 2H), 3.78–3.86 (m, 2H), 4.64 (t, 1H, J=3.1 Hz), 6.14 (br, s, 1H); ¹³C NMR (CDCl₃) 172.4, 98.6, 84.6, 83.1, 79.6, 65.8, 62.0, 60.7, 50.9, 49.9, 35.7, 35.6, 33.31 32.6, 30.5, 29.6, 29.2, 29.0, 28.5, 27.2, 25.4, 22.9, 20.8, 20.3, 19.3, 12.8, 11.3.

17β-Hydroxy-17α-{5'-(2"-tetrahydro-2"H-pyranyloxy)pentyn-1'-yl}-4-aza-5α-androstan-3-one (66c)

Yield, 70%; IR (KBr, cm⁻¹) 3242, 3136, 2906, 2842, 1642; ¹H NMR (CDCl₃) δ 0.78 (s, 3H, 18-CH₃), 0.86 (s, 3H, 19-CH₃), 2.28–2.58 (m, 3H), 3.0 (dd, 1H, J=3.4, 12.3 Hz), 3.39–3.47 (m, 2H), 3.74–3.84 (m, 2H), 4.55 (br s, 1H), 6.44 (s, 1H); ¹³C NMR (CDCl₃, ppm) δ 172.3, 98.7, 85.3, 84.0, 79.5, 65.8, 62.1, 60.7, 50.9, 49.8, 46.9, 38.9, 35.6, 33.3, 32.5, 30.5, 29.3, 29.0, 28.9, 28.5, 27.1, 25.3, 22.9, 20.8, 19.4, 15.6, 12.8, 11.3.

Example 17B

17β-Hydroxy-17α-{4'-(2"-tetrahydro-2"H-pyranyloxy)butyn-1'-yl}-4-methyl-4-aza-5α-androstan-3-one (66b)

A flask was charged with HC≡C(CH₂)₂THP (3.05 g, 19.8 mmol) and anhydrous THF (200 mL) under argon, and cooled to −50° C. in a cold bath. To this solution was added n-BuLi (1.6 M, 19.8 mmol) and the solution was allowed to warm up to 0° C. over a course of 2 h. Then, the solution was cooled to −78° C., and ketone 65b in dry THF (100 mL) was added via a cannula. The reaction mixture was stirred under argon and allowed to warm up to room temperature over a course of 3 h, and stirred for additional 2 h at room temperature. Saturated aqueous NH₄Cl solution (50 mL) was added. The resulting two phase was seperated, and water phase was extracted with CH₂Cl₂ (2×100 mL). The combined solvents were removed and the residue was extracted with CH₂Cl₂ (2×150 mL). Solution was washed with brine and dried over MgSO₄. Solvent was removed on a rotary evaporator. The purification of the residue by a flash column gave the product as a white solid (3.18 g, 7.12 mmol, 72%); IR (KBr, cm$^{-1}$) 3530–3130 (br), 2920, 2850,1620; $^1$H NMR (CDCl$_3$) δ 0.84 (s, 3H, 18-CH$_3$), 0.90 (s, 19-CH$_3$), 2.54 (t, 2H, J=7.1 Hz), 2.93 (s, 3H), 3.54 (dd, 1 h, J=3.3, 12.9 Hz), 3.51–3.59 (m, 2H), 3.78–3.89 (m, 2H), 4.11–4.64 (m, 1H); $^{13}$C NMR (CDCl$_3$, ppm) δ 172.1, 98.2, 84.1, 83.1, 79.4, 65.9, 65.2, 62.1, 60.9, 60.7, 53.8, 50.7, 49.8, 46.5, 38.3, 35.6, 35.4, 33.1, 31.3, 29.4, 28.3, 27.5, 26.8, 25.7, 21.4, 20.9, 20.6, 12.7, 11.4.

Example 17C

General procedure for 67a–67c

Compound 66 (5 mmol) was dissolved in methanol (100 mL) and amberlyst-15 (0.4 g) was added. The raction mixture was stirred for 2 to 3 h (monitored by TLC) at room temperature and filtered. Solvent was removed on a rotary evaporator, and purification of the residue by flash column gave product as a white solid.

17β-Hydroxy-17α-{4'-hydroxybutyn-1-yl}-4aza-5α-androstan-3-one (67a)

Yield, 87%; IR (KBr, cm$^{-1}$) 3490–3108 (br), 2910, 2832, 1636; $^1$H NMR (CDCl$_3$) δ 0.80 (s, 3H, 18-CH), 0.86 (s, 3H, 19-CH$_3$), 2.45 (t, 2H, J=6.9 Hz), 3.02 (dd, 1H, J=3.4, 12.1 Hz), 3.67 (t, 2H, J=6.8 Hz), 6.23 (br, s, 1H); $^{13}$C NMR (CDCl$_3$, ppm) δ 172.6, 85.6, 82.7, 79.3, 60.8, 60.6, 50.8, 49.7, 49.2, 46.8, 38.8, 35.6, 33.1, 32.6, 29.0, 28.4, 27.0, 23.1, 22.9, 20.7, 12.8, 11.2.

17β-Hydroxy-17α-{4'-hydroxybutyn-1'-yl}-4-methyl-4-aza-5α-androstan-3-one (67b)

Yield, 91%; IR (KBr, cm$^{-1}$) 3540–3120, 2904, 2836, 1624; $^1$H NMR (CDCl$_3$) δ 0.83 (s, 3H, 18-CH$_3$), 0.89 (s, 3H, 19-CH$_3$), 2.43–2.51 (m, 4H), 2.92 (s, 3H), 3.35 (dd, 1H, J=3.4, 12.5 Hz), 3.69 (t, 2H, J=6.2 Hz); $^{13}$C NMR (CDCl$_3$, ppm) δ 171.1, 85.6, 82.8, 79.4, 65.7, 60.9, 60.7, 51.6, 49.9, 46.9, 38.9, 36.4, 34.9, 32.8, 29.7, 29.2, 29.0, 25.2, 23.2, 22.9, 20.8, 12.9, 12.4

17β-Hydroxy-17α-{5'-hydroxypentyn-1'-yl}-4-aza-5α-androstan-3-one (67c)

Yield, 84%; IR (KBr, cm$^{-1}$) 3530–3082, 2902, 2842, 1618; $^1$H NMR (CDCl$_3$) δ 0.83 (s, 3H, 18-CH$_3$), 0.89 (s, 3H, 19-CH$_3$), 2.24(t, 2H, J=6.9 Hz), 2.29 (dd, 2H, J=4.7, 5.5 Hz), 2.95 (dd, 1H, J=3.8, 12.6 Hz), 3.59 (t, 2H, J=6.3 Hz), 6.26 (br, s 1H); $^{13}$C NMR (CDCl$_3$, ppm) δ 173.0, 84.9, 83.9, 79.2, 60.7, 60.4, 50.7, 49.7, 46.7, 38.7, 35.4, 32.9, 31.1, 28.9, 28.8, 28.1, 26.7, 22.8, 20.6, 15.1, 12.7, 11.1.

Example 17D

General Procedure for 68a –68c

A flask was charged with compound 67 (5 mmol), 10 mmol % of Pd/C, CH$_3$OH (30 mL), ethyl acetate (120 mL) and stir bar, and then the compound was hydrogenated using a balloon. The reaction mixture was stirred at room temperature for 3 h and filtered. Solvent was removed on a rotary evaporator, and purification of the residue by flash column gave product as a white solid.

17β-Hydroxy-17α-{4'-hydroxybutan-1'-yl}-4-aza-5α-androstan-3-one (68a)

Yield, 65%; $^1$H NMR (CDCl$_3$) δ 0.87 (s, 3H, 18-CH$_3$), 0.91 (s, 3H, 19-CH$_3$), 2.39–2.44(m, 2H), 3.04 (dd, 1H, J=4.2, 11.9 Hz), 3.67 (t, 2H, J=5.8 Hz), 5.93 (br, s 1H).

17β-Hydroxy-17α-{4'-hydroxybutan-1'-yl}-4-methyl-4-aza-5α-androstan-3-one (68b)

Yield, 81%; $^1$H NMR (CDCl$_3$) δ 0.87 (s, 3H, 18-CH$_3$), 0.89 (s, 3H, 19-CH$_3$), 2.41–2.46(m, 2H), 2.92 (s, 3H), 3.02 (dd, 1H, J=3.5, 12.5 Hz) 3.68–7.26 (br, s, 2H).

17β-Hydroxy-17α-{5'-hydroxypentan-1'-yl}-4-aza-5α-androstan-3-one (68c)

Yield, 76%; IR (thin film, cm$^{-1}$) 1663 (s); $^1$H NMR (CDCl$_3$) δ 0.87 (s, 3H, 18-CH$_3$), 0.92 (s, 3H, 19-CH$_3$), 2.41–2.46 (m, 2H), 3.08 (dd, 1H, J=4.8, 11.5 Hz), 3.62 (br, s, 2H), 5.48 (br, s, 1H); $^{13}$C NMR (CDCl$_3$) δ 172.3, 83.2, 62.8, 60.8, 51.2, 50.1, 46.6, 36.6, 35.9, 35.8, 34.3, 33.4, 32.7, 31.4, 29.4, 28.6, 27.3, 26.6, 23.6, 23.3, 20.9, 14.5, 11.4.

Example 17E

General Procedure for 69a and 69b

Alcohol 68 (5 mmol) was dissolved in 150 mL of acetone and the solution was cooled to 0° C. in an ice bath. Jones' reagent (0.5 M, 12.5 mmol) was added dropwise. After addition, the mixture was stirred for 30 min at 0° C. Then 100 mL of water was added and producted was extracted with CH$_2$Cl$_2$ (3×150 mL). The combined organic layer was washed with saturated aqueous NaHCO$_3$ solution, water and brine, and then dried over MgSO$_4$. Solvents were removed on a rotary evaporator and the purification of the residue by flash column gave product as a white solid.

4-Aza-5α-androstan-3-one-17(R)-spiro-2'-(6'-oxo) tetrahydropyran) (69a)

Yield, 58%; IR (thin film, cm$^{-1}$) 1725 (s), 1663 (s). $^1$H NMR (CDCl$_3$) δ 0.92 (s, 3H, 18-CH$_3$), 0.98 (s, 3H, 19-CH$_3$), 5.53 (s, 1H, br, NH); $^{13}$C NMR (CDCl$_3$) δ 172.2, 171.9, 93.0, 59.5, 51.0, 49.3, 47.1, 35.7, 35.4, 33.8, 33.4, 31.7, 29.3, 29.2, 28.5, 27.8, 27.1, 23.6, 20.6, 15.8, 14.4, 11.3. Anal. Calcd for C$_{22}$H$_{33}$NO$_3$: C 73.50; H 9.25, N 3.90. Found: C 73.23; H 9.29, N 3.78.

4-Methyl-4aza-5α-androstan-3-one-17(R)-spiro-2'-(6'-oxo)tetrahydropyran) (69b)

Yield, 64%; IR (thin film, cm$^{-1}$) 1727 (s), 1641 (s); $^1$H NMR (CDCl$_3$) δ 0.89 (s, 3H, 18-CH$_3$), 0.97 (s, 3H, 19-CH$_3$), 2.91 (s, 3H, NMe); $^{13}$C NMR (CDCl$_3$, ppm) δ 171.9, 170.6, 93.0, 65.6, 51.7, 49.3, 47.0, 36.4, 34.7, 33.9, 32.9, 31.8, 29.9, 29.4, 29.0, 27.8, 25.2, 23.6, 20.6, 15.8, 14.4, 12.3. Anal. Calcd for C$_{23}$H$_{35}$NO$_3$: C 73.96; H 9.44, N 3.75. Found: C 73.85; H 9.59, N 3.50.

Example 17F

General Procedure for 71a and 71b

A flask was charged with 69 (1.11 mmol), DDQ (1.11 mmol) and anhydrous dioxane (8 mL). Bis(trimethylsilyl) trifluoroacetamide (BSTFA) (4.56 mmol) was added via a syringe. The reaction mixture was stirred at room temperature under argon for 18 h, and then refluxed for 8 h. The mixture was poured into CH$_2$Cl$_2$ (80 mL), and the solution was washed with saturated NaHCO$_3$ (2×50 mL) and Brine. The organic layer was dried over MgSO$_4$. Solvents were removed on a rotary evaporator and the residue purified by a flash column to give product as a white solid.

4-Aza-5α-1-androst-1-en-3-one-17(R)-spiro-2'-(6'-oxo)tetrahydropyran (71a)

Yield, 52%; IR (thin film, cm$^{-1}$) 1715 (s), 1674 (s), 1599 (m). 1H NMRS (CDCl$_3$) δ 0.95 (s, 3H, 18-CH$_3$), 0.96 (s, 3H, 19-CH$_3$), 5.76 (d, 1H, J=10.0 Hz, CH═CH), 6.67 (br, s, 1H, NH), 6.76 (d, 1H, J=10.0 Hz, CH═CH); $^{13}$C NMR (CDCl$_3$) δ 172.0, 166.9, 151.0, 123.0, 92.9, 59.6, 49.3, 47.4, 47.2, 39.3, 35.6, 33.8, 31.7, 29.4, 29.1, 27.8, 25.6, 23.7, 20.7, 15.7, 14.5, 11.9.

4-Methyl-4-aza-5α-androst-1-en-3-one-17(R)-spiro-2'-(6'-oxo)tetrahydropyran (71b)

Yield, 25%; IR (thin film, cm$^{-1}$) 1725 (s), 1661 (s), 1604 (m); $^1$H NMR (CDCl$_3$) δ 0.92 (s, 3H, 18-CH$_3$), 0.98 (s, 3H, 19-CH$_3$), 2.93 (s, 3H, NMe), 5.83 (d, 1H, J=9.9 Hz, CH═CH), 6.67 (d, 1H, J=9.9 Hz, CH═CH); $^{13}$C NMR (CDCl$_3$) δ 171.9, 165.5, 148.5, 123.2, 92.9, 63.7, 49.2, 47.6, 47.1, 39.5, 35.0, 33.9, 31.7, 29.6, 29.4, 27.8, 27.6, 24.3, 23.6, 20.7, 15.7, 14.5, 12.1.

Example 17G

17β-Hydroxy-17α-{4'-carboxybutan-1'yl}-4-methyl-4-aza-5α-androstan-3-one (70)

Alcohol 68c (1.82 g, 5.00 mmol) was dissolved in 100 mL of acetone and the solution was cooled to 0° C. in an ice bath. Jones' reagent (0.5 M, 25.0 mL, 12.5 mmol) was added dropwise. Then saturated aqueous NaHCO$_3$ (150 mL) and ethyl acetate (100 mL) were added and the mixture was stirred vigorously for overnight. Two phases were separated and the water phase was acidified using 1 M HCl. The acidic solution was extracted with CH$_2$Cl$_2$ (3×120 mL). The combined organic layer were washed with water and brine, and then dried over MgSO$_4$. Removal of solvents gave the product as a white solid (1.25 g, 3.20 mmol, 64%); IR (thin film, cm$^{-1}$) 1704 (s), 1632 (s); $^1$H NMR (pyridine-d$_5$) δ 1.22 (s, 3H, 18-CH$_3$), 1.45 (s, 3H, 19-CH$_3$), 8.41 (s, 1H, NH); $^{13}$C NMR (pyridine-d$_5$) δ 176.1, 171.4, 82.6, 60.9, 51.5, 50.5, 47.2, 37.5, 36.2, 35.9, 35.2, 34.5, 34.0, 32.1, 29.9, 29.4, 27.5, 26.8, 24.2, 21.3, 15.4, 11.4.

Example 17H

Preparation of the Lactone 72

To acid 70 (100 mg, 0.258 mol) in 20 mL of CH$_2$Cl$_2$ was added oxalyl chloride (1.2 eq, 42 mL) at 0° C. under argon, and the reaction mixture was stirred for 1 h. After 1 h, no more acid was detected on the TLC. Then, pyridine (4 eq, 50 mL) was added and the mixture was stirred for 48 h at room temperature. The product was extracted with ethyl acetate, dried over MgSO$_2$ and purified by a flash column using CH$_2$Cl$_2$/MeOH (gradient, 2 to 8%) as an eluent to give the lactone 72 as a white solid (43 mg, 45%); IR (thin film, cm$^{-1}$) 1714 (s), 1660 (s); $^1$H NMR (CDCl$_3$, ppm) δ 0.88 (s, 3H, 18-CH$_3$), 0.96 (s, 3H, 19-CH$_3$), 6.57 (s, 1H, NH); $^{13}$C NMR (CDCl$_3$, ppm) δ 175.6, 172.8, 60.7, 51.2, 48.8, 36.1, 35.6, 33.6, 33.3, 30.9, 30.6, 29.7, 28.5, 27.1, 24.2, 24.1, 23.1, 22.6, 20.6, 15.3, 14.1, 11.4.

Example 18

Syntheses of Unsubstituted-A-ring-1,3,5(10)-estratrien-17-spiro-δ-lactone Derivatives These syntheses are described in Scheme 15.

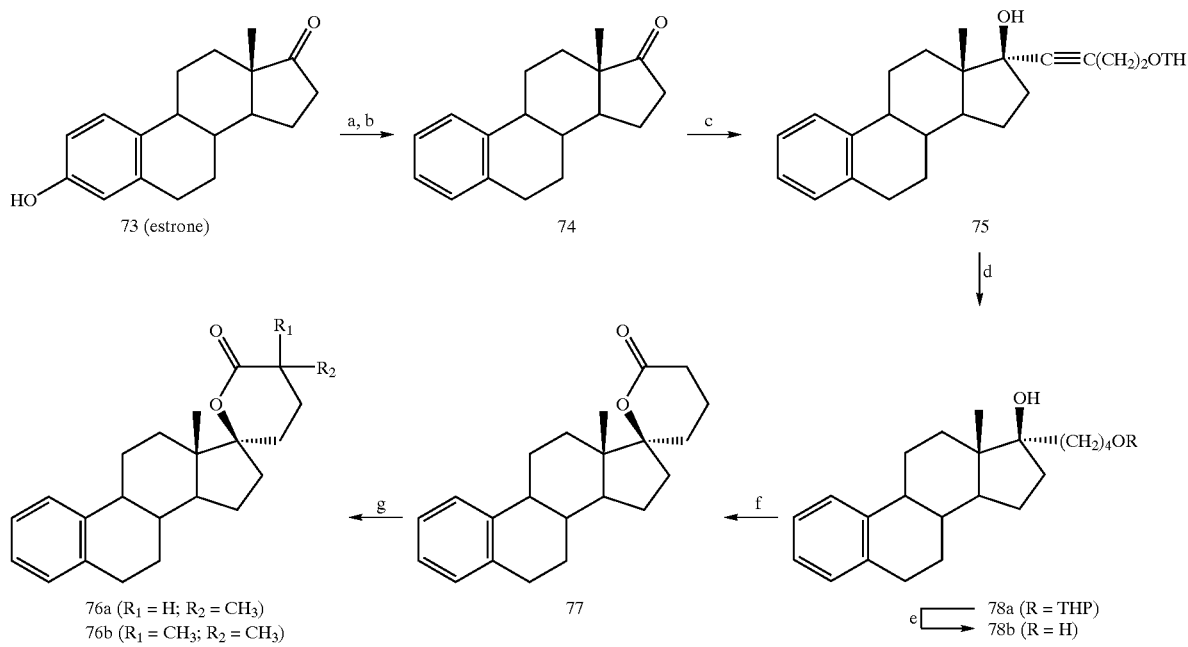

Scheme 15 a: Tf$_2$O pyridine
b: HCOOH, PPh$_3$, Pd(OAc)$_2$, Et$_3$N
c: tetrahydro-2-(butynyloxy)-2-H-pyran, THF, n-BuLi, 0° C.
d: H$_2$, 10% Pd on charcoal
e: p-TSA, methanol, room temperature
f: 1) Jones' reagent, acetone; 2) isopropyl alcohol
g: n-BuLi, diisopropylamine, THF, CH$_3$I, room temperature

Example 18A

Synthesis of 3-Deoxygenated-estrone (74)

At 0° C., 1.0 g (3.7 mmol) of estrone (73) was dissolved in 50 mL of dry pyridine and 1.24 mL (7.4 mmol) of trifluoroacetic anhydride ($Tf_2O$) was added slowly to the solution. After 1 h, the crude solution was poured into a cold aqueous solution of $CuSO_4$ (1M) and the organic phase washed with the same solution until the blue color disappear. Next, the solution was extracted with EtOAc and the organic phase washed with water, and dried over $MgSO_4$. After evaporation of the solvent, the crude estrone-triflate was dissolved in 50 mL of dry DMF. To the resulting mixture, we added 1.54 mL (11 mmol) of $Et_3N$, 0.41 mL (11 mmol) of HCOOH, 0.143 mg (0.55 mmol) of $PPh_3$, and 30.8 mg (0.14 mmol) of $Pd(OAc)_2$. After 3 h at room temperature, the solution was quenched with aqueous HCl (5%) and extracted with $CH_2Cl_2$. The organic phase was washed with water, dried over $MgSO_4$, and solvents evaporated to dryness. The crude compound was purified by flash chromatography with hexanes/EtOAc (9:1) as eluent to give 615 mg (65% two steps) of 1,3,5(10)-estratrien-17-one (74). White solid; IR ν (film): 1738 (C=O); $^1$H NMR ($CDCl_3$) δ 0.94 (s, 3H, 18-$CH_3$), 2.94 (m, 2H, 6-$CH_2$), 7.16 (m, 3H, 1-CH, 2-CH, 3-CH), 7.32 (d, J=5.9 Hz, 1H, 4-CH); $^{13}$C NMR ($CDCl_3$) δ 13.76 (C-18), 21.51 (C-15), 25.61 (C-11), 26.42 (C-7), 29.29 (C-6), 31.56 (C-12), 35.77 (C-16), 38.04 (C-8), 44.40 (C-9), 47.88 (C-13), 50.49 (C-14), 125.22 (C-3), 125.73 (C-2 and C-1), 128.98 (C-4), 136.37 (C-5), 139.62 (C-10), 220.63 (C-17).

Example 18B

Synthesis of Alcohol 75

To a solution of tetrahydro-2-(butynyloxy)-2-H-pyran (0.94 mL, 5.9 mmol) in 30 mL of dry THF was added at 0° C., 3.53 mL of n-BuLi 1.6 M (5.7 mmol), and the mixture was stirred for 40 min. A solution of 3-deoxygenated-estrone (74) (500 mg, 1.96 mmol) in 10 mL of THF was then added dropwise at −78° C. and the mixture stirred for 11 h. After this time, a solution of aqueous $NaHCO_3$ (5%) was added and aqueous phase was extracted with EtOAc. Organic layer was washed with brine, and dried over $MgSO_4$. After evaporation of solvent, the crude compound was purified by flash chromatography with hexane/EtOAc (9:1) as eluent to give 566 mg (68%) of 17β-hydroxy-17α-[4'-[(tetrahydro-2"H-pyranyl)oxy]butynyl]-1,3,5(10)-estratrien (75). Colorless oil; IR ν (film): 3438 (OH, alcohol), 2233 very weak (C≡C); $^1$H NMR ($CDCl_3$) δ 0.88 (s, 3H, 18-$CH_3$), 2.57 (t, J=7.0 Hz, 2H, C≡$CCH_2$), 2.87 (m, 2H, 6-$CH_2$), 3.55 and 3.86 (2m, 4H, $CH_2O$ of side chain and $CH_2O$ of THP), 4.68 ($s_{app}$, 1H, CH of THP), 7.13 (m, 3H, 1-CH, 2-CH, 3-CH), 7.31 (d, J=6.7 Hz, 1H, 4-CH); $^{13}$C NMR ($CDCl_3$) δ 12.72 (C-18), 19.21 (C-4" of THP), 20.30 (C-3'), 22.76 (C-15), 25.37 (C-5" of THP), 26.18 (C-11), 27.13 (C-7), 29.49 (C-6), 30.48 (C-3" of THP), 32.87 (C-12), 38.98 (C-16), 39.14 (C-8), 43.07 (C-9), 47.07 (C-13), 49.53 (C-14), 61.95 (C-2" of THP), 65.78 (C-4'), 79.81 (C-17), 83.07 (C-2'), 84.68 (C-1'), 98.58 (C-1" of THP), 125.25 (C-3), 125.47 (C-2), 125.51 (C-1), 128.91 (C-4), 136.62 (C-5), 140.22 (C-10).

Example 18C

Synthesis of Lactone 77 a) Reduction of triple bond (75→78a). To a solution of compound 75 (650 mg, 1.6 mmol) in EtOAc was added 40 mg of palladium on activated charcoal (10%), and the mixture was stirred at room temperature overnight under an hydrogen atmosphere. After this time, it was filtered through celite, washed with EtOAc, and evaporated to dryness to give the compound 78a as a white foam.

b) Hydrolysis of THP group (78a→78b). The crude alcohol 78a was dissolved in 60 mL of methanol and 20 mg of p-TSA was added. After 2 h at room temperature, water was added to the mixture, the methanol was evaporated, and the resulting mixture extracted with EtOAc. The organic phase was washed with water and dried over $MgSO_4$. Then the solvent was evaporated to dryness to give 455 mg of crude diol 78b.

c) Jones' oxidation with lactonization (78b→77) The crude diol 78b (450 mg) was dissolved in 30 mL of acetone and 0.9 mL of Jones' reagent (2.7M) was added dropwise at 0° C. After the addition was completed, the mixture was stirred at room temperature for 2 h. Then 2 mL of isopropyl alcohol was added and the resulting green solution was evaporated to dryness. The solid was dissolved in water and EtOAc, and the mixture extracted with EtOAc. Organic layer was washed with brine and dried over $MgSO_4$. After evaporation of solvent, the crude compound was purified by flash chromatography with hexanes/EtOAc (8:2) as eluent to give 392 mg (65%, three steps) of 1,3,5(10)-estratrien-17 (R)-spiro-2'-(6'-oxo)tetrahydropyran (77). White solid; IR ν (KBr): 1732 (C=O, lactone); $^1$H NMR ($CDCl_3$) δ 1.03 (s, 3H, 18-$CH_3$), 2.88 (m, 2H, 6-$CH_2$), 7.12 (m, 3H, 1-CH, 2-CH, 3-CH), 7.29 (d, J=5.8 Hz, 1H, 4-CH); $^{13}$C NMR ($CDCl_3$) δ 14.03 (C-18), 15.59 (C-2'), 23.22 (C-15), 25.54 (C-11), 27.13 (C-1'), 27.63 (C-7), 29.17 (C-6 and C-3'), 31.69 (C-12), 33.67 (C-16), 38.56 (C-8), 43.83 (C-9), 46.92 (C-13), 48.64 (C-14), 92.93 (C-17), 124.92 (C-3), 125.39 (C-1 and C-2), 128.70 (C-1), 136.18 (C-10), 139.56 (C-5), 171.70 (C-4'); EI-HRMS: calcd for $C_{22}H_{28}O_2$ 324.20892, found 324.20702.

Example 18D

Synthesis of Lactones 76a and 76b

A mixture of 127 μL (1.0 mmol) of diisopropylamine, 0.5 mL (0.80 mmol) of n-BuLi (1.6M) and 5 mL of dry THF was stirred at 0° C. for 30 min. The solution was cooled at −78° C., and 75 mg (0.233 mmol) of lactone 77 in 10 mL of dry THF was added dropwise. After 1 h, 90 μL of $CH_3I$ was added and the mixture stirred overnight and let warm to room temperature. Then, the solution was quenched with water and extracted with EtOAc. The organic phase was washed with water and dried over $MgSO_4$. After evaporation of the solvent, the crude compound was purified by flash chromatography with hexanes/EtOAc (95:5) as eluent to give 28 mg (36%, two steps) of mono-methylated lactone 76a and 33 mg (40%, two steps) of dimethylated lactone 76b.

1,3,5(10)-Estratrien-17(R)-spiro-2'-(5'-methyl-6'-oxo)tetrahydropyran (76a)

[Major Isomer Only]. White solid; IR ν (film): 1734 (C=O, lactone); $^1$H NMR ($CDCH_3$) δ 1.02 (s, 3H, 18-$CH_3$), 1.25 (d, J=6.8 Hz, 3H, $CHCH_3$), 2.56 (m, 1H, C$\underline{H}CH_3$), 2.87 (m, 2H, 6-$CH_2$), 7.12 (m, 3H, 1-CH, 2-CH, 3-CH), 7.29 (d, J=6.1 Hz, 1H, 4-CH); $^{13}$C NMR ($CDCl_3$) δ 14.34 (C-18), 17.26 (CH$\underline{C}H_3$), 23.52 (C-15), 24.44 (C-2'), 26.78 (C-11), 27.28 (C-1'), 27.40 (C-7), 29.41 (C-6), 32.01 (C-12), 33.51 (C-3'), 34.00 (C-16), 38.84 (C-8), 44.14 (C-9), 47.21 (C-13), 48.76 (C-14), 92.75 (C-17), 125.22 (C-3), 125.56 (C-1 and C-2), 128.97 (C4), 135.51 (C-10), 139.87 (C-5), 175.84 (C-4').

1,3,5(10)-Estratrien-17(R)-spiro-2'-(5',5'-dimethyl-6'-oxo)tetrahydropyran (76b)

White solid; IR ν (film): 1724 (C=O, lactone); $^1$H NMR ($CDCl_3$) δ 1.02 (s, 3H, 18-$CH_3$), 1.28 (s, 6H, 2×$CH_3$), 2.88

(m, 2H, 6-CH$_2$), 7.13 (m, 3H, 1-CH, 2-CH, 3CH), 7.30 (d, J=6.2 Hz, 1H, 4-CH); $^{13}$C NMR (CDCl$_3$) δ 14.41 (C-18), 23.29 (C-15), 25.59 (C-1'), 25.84 (C-11), 27.39 (C-7), 27.54 and 27.76 (2×CH$_3$), 29.42 (C-6), 31.51 (C-12), 32.02 (C-16), 34.82 (C-2'), 37.79 (C-3'), 38.87 (C-8), 44.15 (C-9), 47.25 (C-13), 48.84 (C-14), 93.55 (C-17), 125.21 (C-3), 125.52 (C-2), 125.56 (C-1), 128.99 (C-4), 135.52 (C-10), 139.87 (C-5), 177.82 (C-4').
Example 19
Synthesis of 2-Nitro-1,3,5(10)-estratrien-17-spiro-δ-lactone Derivatives
These syntheses are described in Scheme 16.
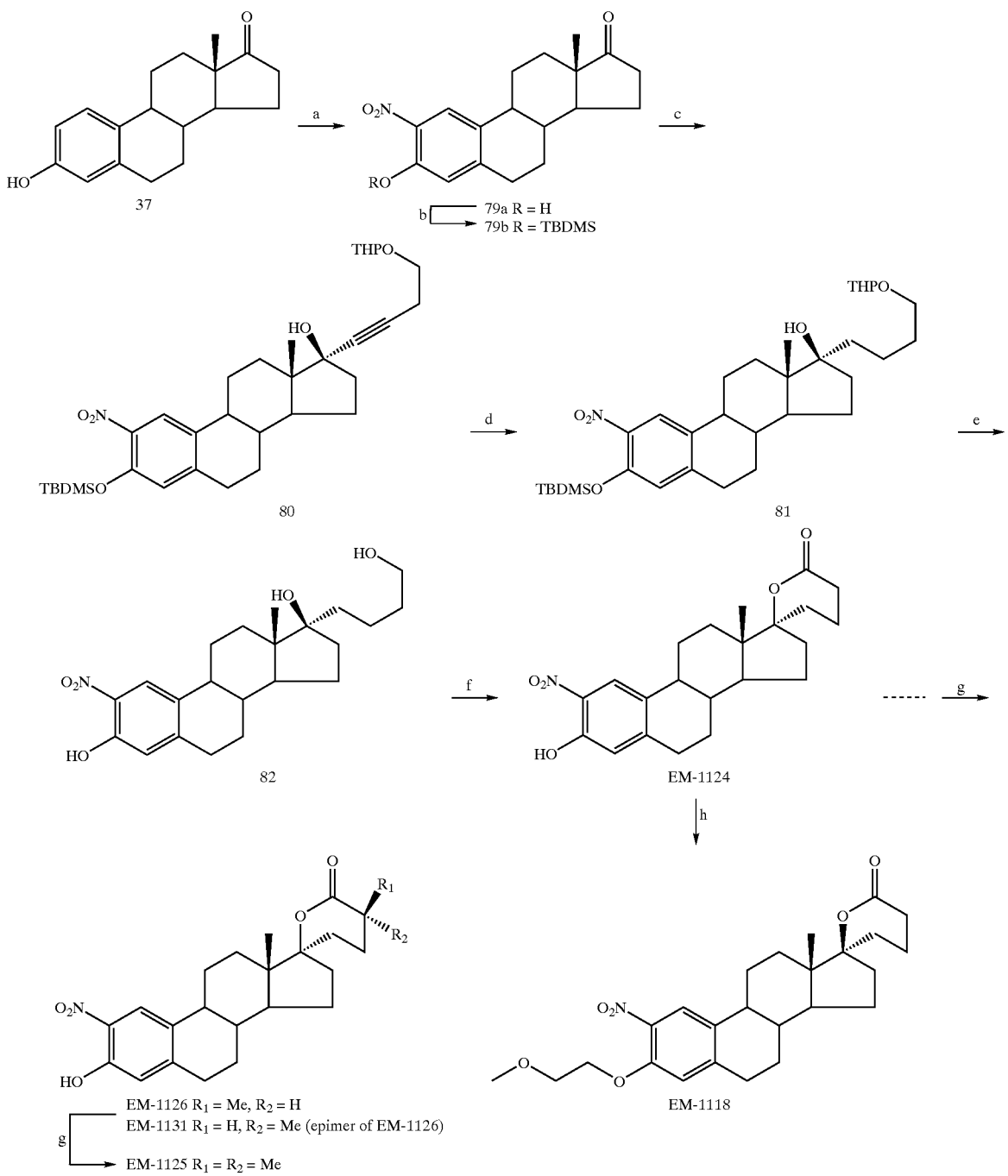
a. NaNO$_2$, HNO$_3$, AcOH b. TBDMSCl, imidazole c. HCC(CH$_2$)$_2$OTHP, MeLi d. H$_2$, Pd/CaCO$_3$ e. 5% HCl, MeOH
f. Jones reagent g. LDA, MeI h. K$_2$CO$_3$, CH$_3$OCH$_2$CH$_2$Cl, CH$_3$CN, Δ

Example 19A

3-Hydroxy-2-nitro-1,3,5(10)-estratrien-17-one (79a)

The titled compound was prepared as described by Stubenrauch and Knuppen[2]. The procedure is described below.

Estrone (37,18.004 g, 66.6 mmol) was dissolved in boiling acetic acid (540 mL) and allowed to cool down to 50° C. The nitrating mixture was prepared from 70% nitric acid (4.5 mL, 70 mmol), water (10 mL) and a few crystal of sodium nitrite, warmed up to 50° C. and added dropwise to the solution of estrone with stirring. After stirring overnight at room temperature, the yellow precipitate was filtered by suction and recrystallized from 92% aqueous acetic acid. 4-nitro derivative (6.800 g, 32%) was thus obtained as a pale yellow solid. IR (v) 3227 (OH), 2931, 2864, 1723 (C=O), 1626, 1584, 1523, 1458, 1404, 1374, 1295, 1264, 1245, 1211, 1169, 1085, 1062, 1027, 954, 930, 908, 881, 823, 796, 719, 654, 588, 556, 530, 494 cm$^{-1}$; $^1$H NMR (Pyridine-d$_5$) δ 0.85 (3H, s, 18'-CH$_3$), 2.85 (2H, d, 6'-CH$_2$), 5.00 (1H, s, OH), 7.11 (1H, d, J=8.7 Hz, 2'-CH), 7.26 (1H, d, J=8.7 Hz, 1'-CH); $^{13}$C NMR (Pyridine-d$_5$) δ 13.8 (C-18), 21.6 (C-15), 24.4 (C-11), 25.7 (C-7), 26.2 (C-12), 32.0 (C-6), 35.9 (C-16), 37.7 (C-8), 44.0 (C-14), 47.9 (C-13), 50.1 (C-9), 115.4 (C-2), 128.4 (C-1), 129.0 (C-10), 131.8 (C-5), 148.4 (C-3), 219.2 (C-17).

The reaction filtrate from above was evaporated under reduced pressure and the residue was recrystallized from EtOH/H$_2$O 8.5:1.5. A brown solid (7.854 g) was obtained which was further purified by flash chromatography on SiO$_2$ column (EtOAc/hexanes, gradient 8–20%) to give pure compound 79a (6.284 g, 30%) as a yellow solid. IR (n): 3300 (OH), 2933, 2864, 1737 (C=O), 1630, 1562, 1522, 1480, 1431, 1372, 1311, 1252, 1216, 1146, 1084, 1054, 1035, 1008, 905, 832, 762, 722, 662, 600, 520 cm$^{-1}$. $^1$H NMR (Pyridine-d$_5$) δ 0.85 (3H, s, 18'-CH$_3$), 2.76 (2H, d, 6'-CH$_2$), 4.99 (1H, s, OH), 6.98 (1H, s, 4'-CH), 7.96 (1H, s, 1'-CH). $^{13}$C NMR (Pyridine-d$_5$) δ 13.8 (C-18), 21.7 (C-15), 25.8 (C-11), 26.1 (C-7), 29.6 (C-12), 31.9 (C-6), 35.9 (C-16), 37.8 (C-8), 43.5 (C-14), 47.9 (C-13), 50.3 (C-9), 119.8 (C-4), 122.2 (C-1), 132.8 (C-10), 147.8 (C-2), 152.6 (C-3), 219.1 (C-17).

Example 19B

3-(Tert-butyldimethylsilyloxy)-2-nitro-1,3,5(10)-estratrien-17-one (79b)

A solution of 2-nitro-estrone (79a, 1.118 g, 3.55 mmole), imidazole (0.670 g, 9.84 mmole) and TBDMSCI (0.781 g, 5.18 mmole) in dry DMF (50 mL) was stirred under Ar(g) overnight. The mixture was then poured onto ice/water (80) mL. The white precipitate was filtered, washed with water and then dried in vacuo to give (79b) as a yellowish powder (1.447 g, 95%). [a]$^{25}_D$ +123.9° (c 1.03, CHCl$_3$); IR (NaCl) 2933, 2860, 1736 (s, C=O), 1617, 1561, 1518, 1492, 1408, 1351, 1291, 1256, 1054, 909, 832, 790, 697 cm$^{-1}$; $^1$H NMR δ 0.24 (6H, s, Si(CH$_3$)$_2$), 0.92 (3H, s, 18-CH$_3$), 1.01 (9H, s, SiC(CH$_3$)$_3$), 1.40–1.78 (6H, m), 1.90–2.35 (5H, m). 2.37–2.60 (2H, m), 2.90 (2H, m, 6-CH$_2$), 6.67 (1H, s, 4-CH), 7.76 (1H, s, 1-CH); $^{13}$C NMR δ 220.2, 147.2, 143.8, 139.6, 133.3, 122.6, 122.1, 50.3, 47.9, 43.6, 37.8, 35.8, 31.3, 29.4, 26.1, 25.7, 25.6, 21.5, 18.2, 13.8, 4.4.

Example 19C

3-(Tert-butyldimethylsilyloxy)-17β-hydroxy-2-nitro-17α-(4'-(2"-tetrahydro-2"H-pyranyloxy)-butynyl)-1,3,5(10)-estratriene (80)

To a stirred solution of tetrahydro-2-(butynyloxy)-$_2$H-pyran (1.71 mL, 10.91 mmole) in dry THF (75 mL) under Ar (g) at −35° C. was dropwise added (MeLi 1.4M in ether 7.80 mL, 10.92 mmole). The solution was stirred for 45 min. after which was added at −35° C. a solution of ketone 79b (1.294 g, 3.01 mmole) in dry THF (20 mL). After 75 min. ice (20 g) and saturated aqueous NaHCO$_3$ (70 mL) were added to the reaction mixture and the aqueous phase was extracted with EtOAc. The combined organic layers were washed with brine, dried with magnesium sulfate, filtered and then concentrated in vacuo. The crude yellow oil was purified on SiO$_2$ (40 g, 2:8 EtOAc/hexanes) to give compound 80 as a yellow foam (1.617 g, 92%). [α]$_D^{25}$ −57.5° (c 0.72, CHCl$_3$); IR (NaCl) 3423 (broad, OH), 2936, 2870, 2366, 1654, 1630, 1578, 1560,1527, 1481, 1458, 1438, 1313, 1268, 1121, 1080, 1032, 899, 869, 761, 669 cm$^{-1}$; $^1$H NMR δ 0.23 (6H, s, Si(CH$_3$)$_2$), 0.87 (3H, s, 18-CH$_3$), 1.00 (9H, s, SiC(CH$_3$)$_3$), 1.20–2.35 (20H, m), 2.55 (2H, t, J=6.9 Hz, CCCH$_2$), 2.84 (2H, m, 6-CH$_2$), 3.55 (2H, m, CH$_2$O of chain), 3.85 (2H, m, CH$_2$O of THP), 4.65 (1H, m, CH of THP), 6.65 (1H, s, 4-CH), 7.76 (1H, s, 1-CH); $^{13}$C NMR δ 147.0, 144.2, 139.5, 133.9, 122.6, 122.0, 98.8, 84.5, 83.4, 79.8, 65.8, 62.2, 49.4, 47.1, 43.2, 38.9, 32.6, 30.6, 29.6, 26.7, 26.2, 25.6, 25.4, 22.8, 20.4, 19.4, 18.2, 12.7, −4.4.

Example 19D

3-(Tert-butyldimethylsilyloxy)-17β-hydroxy-2-nitro-17α-(4'-(2"-tetrahydro-2"H-pyranyloxy)-butyl)-1,3,5(10)-estratriene (81)

A solution of compound 80 (2.00 g, 3.42 mmol) and 5% Pd/CaCO$_3$ (400 mg) in dry MeOH (400 mL) was stirred under H$_2$(g) atmosphere (balloon) for 1 h. The mixture was then filtered through celite and the filtrate rotary evaporated. The residue was purified on silica gel (2:8 EtOAc/hexanes) to give compound 81 as a white foamy solid (1.483 g, 74%). [α]$_D^{25}$ +31.30° (c 0.90, CHCl$_3$); IR (NaCl) 3458 (broad, OH), 2935, 2860, 1616, 1563, 1518 (NO$_2$), 1491, 1408, 1348 (NO$_2$), 1291, 1256, 1119, 1070, 1023, 925, 893, 832, 784, 672 cm$^{-1}$; $^1$H NMR δ 0.23 (6H, s, Si(CH$_3$)$_2$), 0.91 (3H, s, 18-CH$_3$), 1.00 (9H, s, SiC(CH$_3$)$_3$), 1.20–2.38 (26H, m), (2.85 (2H, m, 6-CH$_2$), 3.48 (2H, m, CH$_2$O of chain), 3.83 (2H, m, CH$_2$O of THP), 4.59 (1H, m, CH of THP), 6.65 (1H, s, 4-CH), 7.75 (1H, s, 1-CH); $^{13}$C NMR δ 146.9, 144.1, 139.4, 134.0, 122.4, 121.9, 98.9, 83.2, 67.6, 67.6, 62.4, 62.4, 49.3, 46.6, 36.3, 34.1, 31.3, 30.7, 30.3, 29.5, 26.9, 26.0, 25.5, 25.4, 23.3, 20.4, 19.6, 18.1, 14.3, −4.4.

Example 19E

17α-(4'-Hydroxybutyl)-3,17β-dihydroxy-2-nitro-1,3,5(10)-estratriene (82)

A solution of compound 81 (300 mg, 0.510 mmol) in 5% HCl in MeOH (10 mL) was stirred at room temperature and under argon atmosphere for 12 h. The reaction mixture was then poured into NaHCO$_3$/ice and MeOH was evaporated under reduced pressure. The aqueous phase was extracted with EtOAc and the combined organic layers were washed with brine, dried over MgSO$_4$, filtered and evaporated to dryness. This gave a crude yellow foam (198 mg, 100%). Purification by flash chromatography (column loaded with CH$_2$Cl$_2$ and then eluted with EtOAc/CH$_2$Cl$_2$ 2:8, 4:6, 1:1, 6:4, 9:1) gave compound 82 as a yellow solid (127.0 mg, 64%). Rf 0.21 (8:2 EtOAc/Hexanes); M.p. 184–6° C.; [α]$^{26}_D$ +58.8° (c. 1.00, CHCl); IR (v) 3335, 2934, 2865, 1735, 1719, 1654, 1630, 1576, 1522, 1479, 1434, 1373, 1305, 1266, 1169, 1112, 1067, 1033, 1000, 896, 874, 762, 659 cm$^{-1}$; $^1$H NMR δ 0.90 (3H, s), 3.69 (2H, d, J=5.7 Hz), 6.84 (1H, s), 7.98 (1H, s), 10.42 (1H, s); $^{13}$C NMR δ 14.3, 19.8, 23.3, 26.1, 26.8, 29.8, 31.2, 33.3, 34.3, 36.1, 39.0, 43.2, 46.5, 49.4, 61.7, 62.8, 83.4, 118.8, 121.4, 131.6, 133.7, 149.2, 152.8.

Example 19F

2-Nitro-1,3,5(10)-estraetriene-3-ol-17(R)-spiro-2'-(6'-oxo)tetrahydropyran (EM-1124)

To a stirred solution of compound 82 (128 mg, 0.33 mmole) in dry acetone (25 mL) at 0° C. was slowly added a first 1.1 equivalent of Jones' reagent (1.25 M, 0.29 mL, 0.80 mmol). The orange solution was then stirred for 0.5 h then a second equivalent was added. The dark solution was stirred for a further 0.5 h then quenched with isopropanol (green precipitate formed). the mixture was stirred for 10 min. then filtered through celite and the filtrate rotary evaporated. The residue was taken in EtOAc then washed with aq. sat. $NaHCO_3$, $H_2O$, brine, dried ($MgSO_4$), filtered, rotovaped. The crude solid was purified by flash chromatography on $SiO_2$ (3:7 EtOAc/Hexanes) to give EM-1124 (108 mg, 85%) as a yellow solid. M.p. 213° C.; $[\alpha]^{25}_D$ +90.0° (c 0.70, $CHCl_3$); IR (NaCl) 3198, 2934, 2876, 2245, 1720 (s, C=O, lactone), 1630, 1577, 1522, 1480, 1434, 1378, 1314, 1267, 1234, 1199, 1169, 1151, 1120, 1070, 1036, 1024, 992, 914, 851, 759, 732, 662, 585 $cm^{-1}$; $^1H$ NMR δ 1.02 (3H, s, 18-$CH_3$), 1.20–2.23 (16H, m), 2.25–2.65 (3H, m), 2.90 (2H, m, 6-$CH_2$), 6.85 (1H, s, 4-CH), 7.97 (1H, s, 1-CH), 10.41 (1H, s, OH phenol); $^{13}C$ NMR δ 171.9, 152.8, 148.9, 133.3, 131.7, 121.5, 118.9, 93.0, 48.8, 47.1, 43.1, 38.4, 33.9, 31.6, 29.7, 29.4, 27.9, 26.8, 25.8, 23.4, 15.8, 14.2.

Example 19G

2-Nitro-1,3,5(10)-estratrien-3-ol-17(R)-spiro-2'-(5'-methyl-6'-oxo)tetrahydropyran (EM-1126, EM-1131)

LDA was prepared as follows: To a stirred solution of diisopropylamine (92 μL, 71 mg, 0.70 mmol) in dry THF (5 mL) at −78° C. under Ar(g) was added n-BuLi (1.2 M/Hexane, 580 μL, 0.68 mmol) and the solution was then stirred at 0° C. for 25 min. then cooled down to −78° C. A solution of EM-1124 (66 mg, 0.17 mmol) in dry THF (5 mL) was added and the resulting dark orange solution was then stirred for 30 min. Dry HMPA (2 mL) was added and after 15 min., MeI (107 μL, 243 mg, 1.71 mmol). The solution was then stirred for a further 4 h. The reaction was quenched with aqueous saturated $NH_4Cl$ and extracted with EtOAc. The organic phase was washed with 1 M aqueous $CuSO_4$ (4×), $H_2O$, aqueous 1M $Na_2SO_3$, brine, dried ($MgSO_4$), filtered then rotary evaporated to give a crude solid (103 mg). Purification by flash chromatography on SiO2 (1:9→2:8 EtOAc/Hexanes) provided first EM-1126 (11 mg, 16%) closely followed by EM-1131 (34 mg, 34%) both as yellow solids. EM-1126: M.p. 204–6° C.; $[\alpha]^{25}_D$ +73.4° (c 1.67, $CDCl_3$); IR ν 3422 (br, OH), 2937, 2874, 1725 (vs, CO), 1630, 1577, 1525, 1479, 1458, 1432, 1378, 1311, 1269, 1249, 1205, 1188, 1150, 1118, 1088, 1071, 1007, 990, 934, 896, 760, 731, 668, 585, 495 $cm^{-1}$; $^1H$ NMR δ 1.03 (3H, s), 1.30 (3H, d, J=7.1 Hz), 1.31–1.77 (10H, m), 1.89–2.03 (5H, m,), 2.15 (1H, td, J=7.1 Hz, J'=5.0 Hz), 2.30–2.50 (2H, m), 2.90 (2H, dd, J=8.3 Hz, J'=4.9 Hz), 6.85, (1H, s), 7.98 (1H, s), 10.43 (1H, s, OH); $^{13}C$ NMR δ 174.8, 152.9, 149.0, 133.4, 131.7, 121.5, 118.9, 93.4, 48.7, 47.1, 43.1, 38.5, 36.2, 34.6, 31.6, 29.7, 28.6, 26.9, 25.9, 25.2, 23.4, 17.4, 14.4.

EM-1131 (5'-epimer of EM-1126, real configuration not determined): M.p. 206–8° C.; $[\alpha]^{25}_D$ +62.6° (c 0.68, $CDCl_3$); IR ν 3422 (br, OH), 3192, 2934, 2876, 2858, 2824, 1721 (vs, CO), 1631, 1578, 1522, 1482, 1458, 1436, 1377, 1314, 1271, 1237, 1204, 1173, 1120, 1103, 1082, 1051, 1019, 1002, 933, 901, 877, 860, 759, 663, 638, 600, 495 $cm^{-1}$; $^1H$ NMR δ 1.01 (3H, s), 1.24 (3H, d, J=7.0 Hz), 1.31–1.80 (10H, m), 1.89–2.20 (6H, m), 2.35 (1H, br s), 2.55 (1H, sextuplet, J=7.5 Hz), 2.89 (2H, t, J=5.2 Hz), 6.84 (1H, s), 7.96 (1H, s), 10.41 (H, s, OH); $^{13}C$ NMR δ 175.8, 152.8, 148.9, 133.3, 131.6, 121.4, 118.8, 92.5, 77.4, 77.0, 76.6, 48.5, 47.0, 43.0, 38.4, 33.8, 33.4, 31.6, 29.7, 27.16, 26.7, 25.8, 24.3, 23.6, 17.2, 14.3.

Example 19H

2-Nitro-1,3,5(10)-estratrien-3-ol-17(R)-spiro-2'-(5',5'-dimethyl-6'-oxo)tetrahydropyran (EM-1125)

LDA was prepared as follows: To a stirred solution of diisopropylamine (206 μL, 159 mg, 1.57 mmol) in dry THF (12 mL) at −78° C. under Ar(g) was added n-BuLi (1.2 M/Hexane, 1,28 mL, 1.53 mmol) and the solution was then stirred at 0° C. for 20 min. then cooled down to −78° C. A solution of a mixture of EM-1126 and EM-1131 (153 mg, 0.38 mmol) in dry THF (10 mL) was added and the resulting dark orange solution was then stirred for 20 min. Dry HMPA (4.7 mL) was added and after 15 min., MeI (238 μL, 544 mg, 3.83 mmol). The solution was then stirred for 5 min. then was warmed up to −30° C. and stirred for a further 1 h. The reaction was quenched with aqueous saturated $NH_4Cl$ and extracted with EtOAc. The organic phase was washed with brine (6×), aqueous 1M $Na_2SO_3$, brine, dried ($MgSO_4$), filtered then rotary evaporated to give a crude liquid. Purification by flash chromatography on $SiO_2$ (1:9→2:8 EtOAc/Hexanes) provided EM-1125 (82 mg, 52%) as a yellow solid. M.p. 195–7° C.; $[\alpha]^{25}_D$ +72.8° (c 1.61, $CDCl_3$); IR ν 3421 (br, OH), 3194, 2954, 2927, 2873, 1718 (vs, CO), 1631, 1578, 1523, 1476, 1458, 1438, 1386, 1312, 1298, 1271, 1204, 1151, 1118, 1059, 1032, 1016, 931, 898, 872, 855, 758, 663, 595 $cm^{-1}$; $^1H$ NMR δ 1.02 (3H, s), 1.28 (6H, s), 1.32–1.77 (10H, m), 1.85–2.15 (6H, m), 2.36 (1H, br s), 2.89 (2H, dd, J=8.2 Hz, J'=4.9 Hz), 6.85 (1H, s), 7.97 (1H, s), 10.42 (H, s, OH); $^{13}C$ NMR δ 177.7, 152.8, 149.0, 133.3, 131.7, 121.5, 118.9, 93.4, 48.6, 47.1, 43.1, 38.5, 37.8, 34.7, 31.6, 31.5, 29.7, 27.7(4), 27.6(8), 26.7, 25.9, 25.5, 23.3, 14.4.

Example 19I

2-Nitro-3-methylthioethyloxy-1,3,5(10)-estratrien-17(R)-spiro-2'-(6'-oxo)tetrahydropyran (EM-1118)

To a solution of EM-1124 (40 mg, 0.117 mmol) in anhydrous acetonitrile (20 mL) at room temperature under Ar(g) was added $K_2CO_3$ (16 mg, 0.117 mmol) and chloroethylmethyl sulfide (39 mg, 35 mL, 0.350 mmol). The solution was refluxing for 44 h. The acetonitrile solution was evaporated to dryness and ethyl acetate (40 mL) was then added. The organic phase was washed with water, brine and dried with $MgSO_4$ to gave crude product (49 mg). Purification by flash chromatography on silica gel ($SiO_2$, 3 g) using ethyl acetate/hexanes (2:8) as eluent gave EM-1118 (35 mg, 70%). IR (ν) 2921, 1727, 1608, 1576, 1499, 1466, 1438, 1382, 1348, 1330, 1310, 1280, 1236, 1187, 1159, 1100, 1067, 1036, 992, 931, 914, 860, 818, 731 $cm^{-1}$; $^1H$ NMR ($CDCl_3$) δ 1.01 (3H, s), 1.25–2.57 (19H, m), 2.20 (3H, s) 2.85 (4H, t, J=6.88 Hz), 4.12 (2H, t, J=6.74 Hz), 6.62 (1H, d, J=2.49 Hz), 6.71 (1H, dd, J1=2.58 Hz J2=5.89 Hz), 7.19 (1H, d, J=8.54 Hz); $^{13}C$ NMR($CDCl_3$) δ 14.8, 15.9, 16.2, 23.5, 26.1, 27.5, 28.0, 29.5, 29.7, 32.0, 33.1, 34.0, 39.1, 43.7, 47.3, 48.9, 67.4, 93.3, 112.1, 114.6, 126.3, 132.6, 137.9, 156.5, 172.1.

Example 20

Synthesis of 3-Hydroxy-1,3,5(10)-estratrien-17(R)-spiro-2'-(5',5'-dimethyl-6'-oxo)tetrahydropyran (89)

This synthesis is described in Scheme 17.

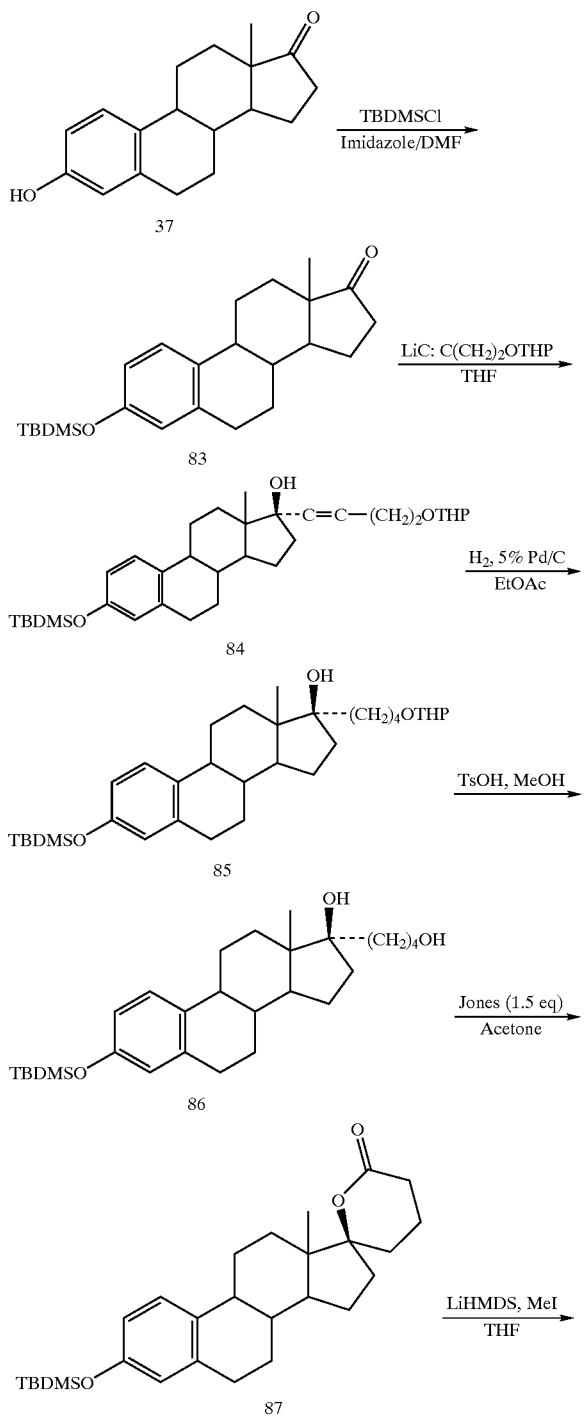

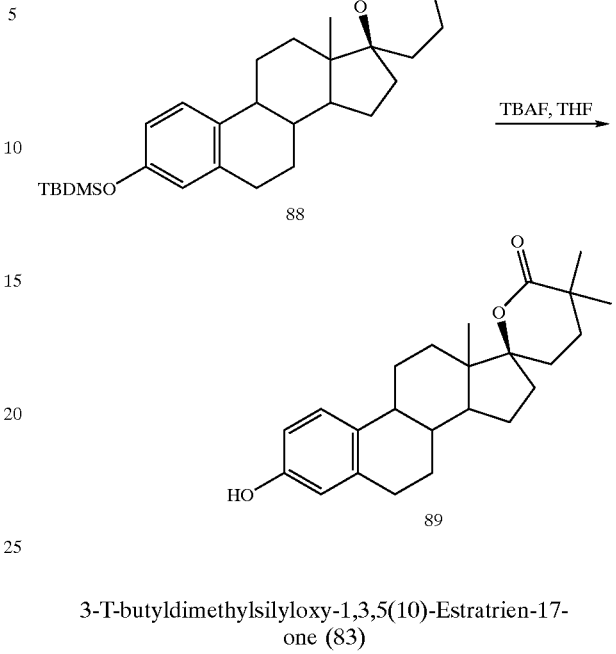

3-T-butyldimethylsilyloxy-1,3,5(10)-Estratrien-17-one (83)

The ether was prepared from estrone (37) following the method described Pelletier et al. (Steroids 59: 536–547, 1994).

3-T-butyldimethylsilyloxy-17β-hydroxy-17α-{4'-(2''-tetrahydro-2''H-pyranyl)butyn-1'-yl}-1,3,5(10)-estratriene (84)

To a solution of HC≡C(CH$_2$)$_2$OTHP (18.3 mL, 117 mmol) in dry THF (600 mL) at 0° C., was added dropwise n-butyllithium (43.7 mL, 109 mmol) and the mixture was stirred for 90 min. The mixture was cooled to −78° C. and a solution of TBDMSestrone 37 (15 g, 39 mmol) in THF (500 mL) was added dropwise. Then, the reaction mixture was allowed to come to room temperature and left stirring for a period of 15 h. Solvents were evaporated to the half volume and 200 mL of water was added. The mixture was extracted with EtOAc (3×200 mL), the organic layer was washed with brine, dried (MgSO$_4$) and evaporated to dryness. The residue was purified over silica gel column chromatography with hexanes/EtOAc (9/1) as an eluent to furnish 15.1 g (72%) of the product; IR (NaCl cm$^{-1}$) δ 432, 2934, 2858, 1607, 1495, 1287, 1256, 1033, 958, 839; $^1$H NMR (300 MHz, CDCl$_3$) δ 7.12 (d, 1H, J=8.4 Hz), 6.62 (dd, 1H, J=2.4, 8.4 Hz), 6.54 (d, 1H, J=2.2 Hz), 4.66 (br.s., 1H), 3.89–3.79 (m, 2H), 3.56–3.50 (m, 2H), 2.79 (br.s., 2H), 2.56 (t, 2H, J=7.0 Hz), 2.35–2.17 (m, 3H), 2.07–1.23 (m, 17H), 0.98 (s, 9H), 0.87 (s, 3H, 18-Me), 0.19 (s, 6H); $^{13}$C NMR (75 MHz, CDCl$_3$) δ 153.3, 137.8, 133.0, 126.1, 119.9, 117.1, 98.7, 84.7, 83.2, 80.0, 65.8, 62.1, 49.5, 47.2, 43.7, 39.4, 39.0, 32.9, 30.6, 29.7, 27.3, 26.4, 25.7, 25.4, 22.8, 20.3, 19.3, 18.1, 12.8, −4.4.

3-T-butyldimethylsilyloxy 17β-Hydroxy-17α-{4'-(2''-tetrahydro-2''H-pyranyl)butan-1'-yl}-1,3,5(10)-estratriene (85)

5% Palladium on activated carbon (1.5 g, 10% wt) was added to a solution of the alkyne 84 (15.1 g, 28 mmol) in EtOAc (500 mL) at room temperature. The flask was purged with $H_2$ three times (vacuum followed by $H_2$) and left stirring under 1 atm pressure of $H_2$. The reaction was followed by TLC. After a period of 3 h, the mixture was filtered over a plug of celite and the solvent was removed under reduced pressure. The crude product was used in the next step without further purification; IR (NaCl, cm$^{-1}$) δ 474, 2935, 2858, 1607, 1570, 1496, 1471, 1286, 1257, 1156, 1137, 1119, 1033, 954, 839, 780; $^1$H NMR (300 MHz, CDCl$_3$) δ 7.12 (d, 1H, J=8.4 Hz), 6.62 (dd, 1H, J=2.1, 8.4 Hz), 6.55 (s, 1H), 4.59 (br.s., 1H), 3.92–3.73 (m, 2H), 3.55–3.38 (m, 2H), 2.82–2.77 (m, 2H), 2.30–1.33 (m, 26H), 0.97 (s, 9H), 0.90 (s, 3H, 18-Me), 0.18 (s, 6H); $^{13}$C NMR (75 MHz, CDCl$_3$) δ 153.27, 137.81, 133.08, 126.02, 119.87, 117.06, (98.90, 98.84), 83.38, 67.61, 62.33, 49.50, 46.67, 43.81, 39.58, 36.35, 34.28, 31.60, 30.75, 30.36, 29.62, 27.51, 26.26, 25.67, 25.47, 23.37, 20.45, 19.66, 18.12, 14.35, −4.43.

3-T-butyldimethylsilyloxy 17β-Hydroxy-17α-(4'-hydroxybutan-1'-yl)-1,3,5(10)-estratriene (86)

To a solution of the THP ether 85 (15.1 g, 28 mmol) in MeOH (400 mL), was added p-toluenesulfonic acid monohydrate (150 mg, 0.8 mmol) and the reaction was stirred over a period of 5 h. A saturated solution of NaHCO$_3$ (100 mL) was added and volume of solvent was reduced to half on a rotary evaporator. The mixture was extracted with CH$_2$Cl$_2$, the organic phase was washed with brine, dried (MgSO$_4$) and evaporated to dryness. The crude product was used in the next step without purification; IR (NaCl, cm$^{-1}$) 3356, 2931, 2858, 1608, 1496, 1471, 1286, 1256, 954, 839, 780; $^1$H NMR (300 MHz, CDCl$_3$) δ 7.12 (d, 1H, J=8.5 Hz), 6.61 (dd, 1H, J=2.5, 8.5 Hz), 6.55 (s, 1H), 3.69 (br.d, 2H, J=5.2 Hz), 2.82–2.78 (m, 2H), 2.35–2.26 (m, 1H), 2.20–1.94 (m, 2H), 1.90–1.81 (m, 1H), 1.62–1.22 (m, 17H), 0.98 (s, 9H), 0.90 (s, 3H, 18-Me), 0.19 (s, 6H); $^{13}$C NMR (75 MHz, CDCl$_3$) δ 153.27, 137.81, 133.05, 126.02, 119.89, 117.09, 83.59, 62.56, 49.50, 46.69, 48.81, 39.58, 35.98, 34.32, 33.20, 31.61, 29.62, 27.51, 26.26, 25.68, 23.37, 19.74, 18.14, 14.36, −4.40.

3-T-butyldimethylsilyloxy-1,3,5(10)-estratrien-17(R)-spiro-2'-(6'-oxo) tetrahydropyran (87)

To a solution of the diol 86 (12.5 g, 27 mmol) in reagent (15.1 mL, 41 mmol). The reaction was stirred for 30 min. 2-Propanol (100 mL) was added, followed by of a saturated solution of NaHCO$_3$ (200 mL). The volume of solvents was reduced to half by evaporation and the mixture was extracted with EtOAc. The organic phase was washed with brine, dried (MgSO$_4$) and concentrated under reduced pressure. The residue was purified a silica gel column chromatography with hexanes/acetone (6/1) to afford 8.6 g of the lactone. (68% yield for 3 steps); IR (NaCl, cm$^{-1}$): 2960, 2930, 2857, 1732, 1607, 1496, 1284, 1264, 1244, 1037, 958, 840; $^1$H NMR (300 MHz, CDCl$_3$) δ 7.11 (d, 1H, J=8.4 Hz), 6.61 (dd, 1H, J=2.3, 8.4 Hz), 6.56 (s, 1H), 2.85–2.79 (m, 2H), 2.58–2.39 (m, 2H), 2.38–2.25 (m, 1H), 2.21–2.10 (m, 1H), 2.03–1.27 (m, 15H), 1.02 (s, 3H, 18-Me), 0.97 (s, 9H), 0.18 (s, 6H); $^{13}$C NMR (75 MHz, CDCl$_3$) δ 172.00, 153.36, 137.63, 132.62, 126.02, 119.92, 117.19, 93.25, 48.88, 47.26, 43.68, 39.05, 33.98, 31.96, 29.50, 29.48, 27.94, 27.46, 25.98, 25.67, 23.48, 18.12, 15.87, 14.30, −4.43.

3-T-butyldimethylsilyloxy-1,3,5(10)-estratrien-17(R)-spiro-2'-(5'-5'-dimethyl-6'-oxo) tetrahydropyran(88)

In a dry 1L flask under argon, was dissolved the lactone 87 (8.6 g, 19 mmol) in dry THF (300 mL), and cooled to 0° C. A 1M solution of LiHMDS (47.3 mL, 47.3 mmol) was added dropwise. The mixture was stirred 15 min at 0° C. and cooled to −78° C. and then methyl iodide (5.9 mL, 79 mmol) was added. The reaction was stirred 1 h at this temperature and then allowed to warm to room temperature over a period of 2 h. A saturated solution of NH$_4$Cl (200 mL) was added and the mixture was extracted with EtOAc. The organic layer was washed with a saturated solution of Na$_2$S$_2$O$_3$, brine, dried (MgSO$_4$) and concentrated under reduced pressure. The residue was purified by column chromatography with hexanes/acetone (5/1) as an eluent to afford 7.4 g (81%) of the dimethyl compound; IR (NaCl, cm$^{-1}$) 2954, 2930, 2858, 1725, 1496, 1287, 1258, 1150, 1137, 956, 840; $^1$H NMR (300 MHz, CDCl$_3$) δ 7.11 (d, 1H, J=8.5 Hz), 6.62 (dd, 1H, J=2.4, 8.5 Hz), 6.55 (d, 1H, J=2.1 Hz), 2.81–2.78 (m, 2H), 2.36–2.28 (m, 1H), 2.20–1.38 (m, 16H), 1.28 (s, 3H), 1.27 (s, 3H), 1.02 (s, 3H, 18-Me), 0.97 (s, 9H), 0.18 (s, 6H); $^{13}$C NMR (75 MHz, CDCl$_3$) δ 177.79, 153.33, 137.62, 132.62, 125.99, 119.90, 117.14, 93.66, 48.67, 47.24, 43.65, 39.06, 37.74, 34.79, 31.96, 31.56, 29.50, 27.73, 27.61, 27.42, 26.01, 25.65, 25.55, 23.26, 18.11, 14.42, −4.43.

1,3,5(10)-Estratrien-3-ol-17(R)-spiro-2'-(5',5'-dimethyl-6'-oxo) Tetrahydropyran (89)

To a solution of the silyl ether 88 (7.1 g, 14.7 mmol) in THF (300 mL) at 0° C., was added dropwise a 1M solution of TBAF (17.6 mL, 17.6 mmol) and the reaction was stirred for 15 min. Ice water (200 mL) was added to precipitate the compound. The flask was placed on a retary evaporator to reduce the volume of THF, and then placed on an ice bath. The precipitate was collected by filtration, washed with cold water and dried in an oven (30° C.) over a period of 24 h to furnish 5.4 g (100%) of the 3-OH compound; IR (NaCl, cm$^{-1}$): 3357, 2932, 2871, 1695, 1287, 1158; $^1$H NMR (300 MHz, CDCl$_3$) δ 7.14 (d, 1H, J=8.4 Hz), 6.63 (dd, 1H, J=2.6, 8.4 Hz), 6.55 (d, 1H, J=2.6 Hz), 4.62 (br.s, 1H, OH), 2.81–2.79 (m, 2H), 2.38–2.29 (m, 1H), 2.20–1.81 (m, 5H), 1.76–1.31 (m, 11H), 1.29 (s, 3H), 1.28 (s, 3H), 1.01 (s, 3H, 18-Me); $^{13}$C NMR (75 MHz, CDCl$_3$) δ 178.06, 153.52, 138.08, 132.19, 126.42, 115.26, 112.74, 93.80, 48.69, 47.29, 43.65, 39.14, 37.81, 34.84, 31.98, 31.61, 29.53, 27.76, 27.64, 27.39, 26.12, 25.59, 23.29, 14.43.

Example 21

Synthesis of 3-Hydroxy-1,3,5(10)-estratrien-17(R)-spiro-2'-(5',5'-dimethyl-6'-oxo)tetrahydropyran-3-derivatives These syntheses are described in Scheme 18.

Scheme 18

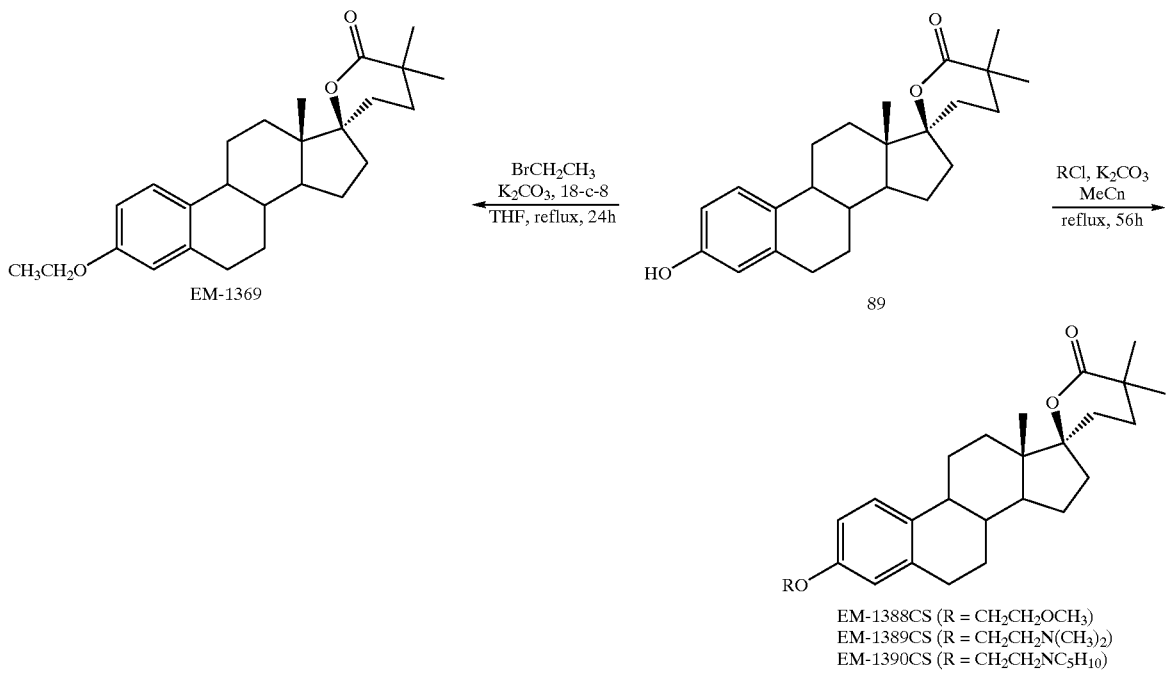

Example 21A

Synthesis of 3-Ethoxy-1,3,5(10)-estratrien-17(R)-spiro-2'-(5',5'-dimethyl-6'-oxo)-tetrahydropyran (EM-1369)

To a solution of lactone 89 (50 mg, 0.136 mmol) in anhydrous THF (10 ml) and under argon was added $K_2CO_3$ (26 mg, 0.190 mmol), 18-crown-6 (14 mg, 0.054 mmol) and bromoethane (303 μl, 4.08 mmol). The solution was refluxed for 24 h. Then water (10 ml) was added and the product was extracted with ethyl acetate (2×20 ml), washed with brine, and dried with $MgSO_4$. After evaporation of solvent, the crude product was purified by flash chromatography on silica gel using ethyl acetate/hexanes (1:9) as eluent to give the pure EM-1369. White solid; 59% yield; IR (film NaCl) υ 2930, 2872, 1732, 1608, 1573, 1500, 1477, 1455, 1385, 1309, 1236, 1149, 1137, 1114, 1051, 1017; $^1$H NMR (300 MHz, CDCl$_3$) δ 1.02 (s, 3H, 18-CH$_3$), 1.28 (2s, 6H, 2×CH$_3$), 1.30 to 2.36 (m, 17H), 1.39 (t, J=7.0 Hz, 3H, CH$_3$CH$_2$O), 2.84 (m, 2H, 6-CH$_2$), 4.00 (q, J=7.0 Hz, 2H, CH$_3$CH$_2$O), 6.62 (d, J=2.5 Hz, 1H, 4-CH), 6.70 (dd, J$_1$=2.5 Hz and J$_2$=8.5 Hz, 1H, 2-CH), 7.19 (d, J=8.5 Hz, 1H, 1-CH); $^{13}$C NMR (75 MHz, CDCl$_3$) δ 14.44, 14.91, 23.30, 25.61, 26.11, 27.48, 27.66, 27.77, 29.73, 31.63, 32.01, 34.85, 37.80, 39.17, 43.69, 47.30, 48.71, 63.31, 93.70, 112.05, 114.50, 126.21, 132.10, 137.76, 156.88, 177.85; HRMS calculated for C$_{26}$H$_{37}$O$_3$ (M$^+$+H): 397.27426, found: 397.27520.

Example 21B

Typical Procedure for the Synthesis of EM-1368-CS, EM-1389-CS, and EM-1390-CS To a solution of lactone 89 (0.20 mmol) in anhydrous acetonitrile (20 ml) and under argon was added $K_2CO_3$ (0.20 mmol). The appropriate electrophile (16.0 mmol) (chloroethylmethylether, 2-dimethylaminoethylchloride.HCl, and 1-(2-chloro-ethyl)-piperidine.HCl). The solution was refluxed for 56 h. The acetonitrile was evaporated to dryness and ethyl acetate (40 ml) was then added. The organic phase was washed with water, brine, and dried with $MgSO_4$ to gave the crude products which were purified by flash chromatography on silica gel using, as eluent, ethyl acetate/hexanes (1:9) for EM-1368CS and CH$_2$Cl$_2$/Et$_3$N (95.5:0.5) for EM-1389CS and EM-1390CS.

3-Methoxyethoxy-1,3,5(10)-estratrien-17(R)-spiro-2'-(5',5'-dimethyl-6'-oxo)-tetrahydropyran (EM-1368-CS)

White solid; 74% yield; IR (film NaCl) υ 2930, 2873, 1722, 1609, 1574, 1499, 1455, 1385, 1309, 1237, 1201, 1135, 1064, 1032, 1017; $^1$H NMR (300 MHz, CDCl$_3$) δ 1.02 (s, 3H, 18-CH$_3$), 1.28 (2s, 6H, 2×CH$_3$), 1.30 to 2.35 (m, 17H), 2.85 (m, 2H, 6-CH$_2$), 3.44 (s, 3H, OCH$_3$), 3.73 (t, J=4.7 Hz, 2H, CH$_3$OCH$_2$CH$_2$O ), 4.09 (t, J=4.7 Hz, 2H, CH$_3$OCH$_2$CH$_2$O), 6.66 (d, J=2.5 Hz, 1H, 4-CH), 6.73 (dd, J$_1$=2.5 Hz and J$_2$=8.6 Hz, 1H, 2-CH), 7.19 (d, J=8.6 Hz, 1H, 1-CH); $^{13}$C NMR (75 MHz, CDCl$_3$) δ 14.44, 23.29, 25.61, 26.09, 27.45, 27.66, 27.76, 29.71, 31.62, 31.99, 34.85, 37.79, 39.14, 43.67, 47.29, 48.70, 59.16, 67.20, 71.12, 93.70, 112.16, 114.67, 126.21, 132.49, 137.78, 156.72, 177.85; HRMS calculated for C$_{27}$H$_{39}$O$_4$ (M$^+$+H): 427.28482, found: 427.28690.

3-(N,N-dimethylaminoethyl)-1,3,5(10)-estratrien-17 (R)-spiro-2'-(5',5'-dimethyl-6'-oxo)-tetrahydropyran (EM-1389-CS)

White solid; 40% yield; IR (film NaCl) υ 2936, 2871, 2819, 2770, 1723, 1609, 1575, 1499, 1456, 1385, 1309, 1290, 1256, 1238, 1202, 1149, 1032; $^1$H NMR (300 MHz, CDCl$_3$) δ 1.01 (s, 3H, 18-CH$_3$), 1.28 (2s, 6H, 2×CH$_3$), 1.30 to 2.20 (m, 17H), 6H, (CH$_3$)$_2$N), 2.71 (t, J=5.8 Hz, 2H, NCH$_2$CH$_2$O ), 2.83 (m, 2H, 6-CH$_2$), 4.04 (t, J=5.8 Hz, 2H, NCH$_2$CH$_2$O), 6.65 (d, J=2.4 Hz, 1H, 4-CH), 6.73 (dd, J$_1$=2.7

Hz and J₂=8.6 Hz, 1H, 2-CH), 7.19 (d, J=8.6 Hz, 1H, 1-CH); $^{13}$C NMR (75 MHz, CDCl₃) δ 14.45, 23.30, 25.62, 26.11, 27.46, 27.67, 27.77, 29.73, 31.64, 32.01, 34.86, 37.79, 39.16, 43.70, 45.87, 47.30, 48.72, 58.35, 65.92, 93.71, 112.13, 114.59, 126.21, 132.34, 137.79, 156.79, 177.85; HRMS calculated for $C_{28}H_{42}O_3N$ (M$^+$+H): 440.31647, found: 440.31520.

3-(N-piperidyl-ethyl)-1,3,5(10)-estratrien-17(R)-spiro-2'-(5',5'-dimethyl-6'-oxo)-tetrahydropyran (EM-1390-CS)

White solid; 69% yield; IR (film NaCl) υ 2933, 2871, 2783, 1724, 1609, 1574, 1499, 1455, 1385, 1308, 1290, 1256, 1236, 1202, 1148, 1136, 1033; $^1$H NMR (300 MHz, CDCl₃) δ 1.01 (s, 3H, 18-CH₃), 1.28 (2s, 6H, 2×CH₃), 1.30 to 2.40 (m, 17H), 2.50 (m, 4H, (CH₂)₂N), 2.76 (t, J=6.2 Hz, 2H, NCH₂CH₂O), 2.84 (m, 2H, 6-CH₂), 4.08 (t, J=6.2 Hz, 2H, NCH₂CH₂O), 6.63 (d, J=2.6 Hz, 1H, 4-CH), 6.71 (dd, J₁=2.6 Hz and J₂=8.6 Hz, 1H, 2-CH), 7.18 (d, J=8.6 Hz, 1H, 1-CH); $^{13}$C NMR (75 MHz, CDCl₃) δ 14.46, 23.31, 24.18, 25.63, 25.92, 26.13, 27.47, 27.68, 27.79, 29.74, 31.65, 32.02, 34.87, 37.81, 39.17, 43.71, 47.32, 48.73, 55.00, 57.98, 65.83, 93.70, 112.14, 114.60, 126.23, 132.32, 137.81, 156.72, 177.87; HRMS calculated for $C_{31}H_{46}O_3N$ (M$^+$+H): 480.34778, found: 480.34550.

Example 22

Synthesis of 2-Chloro-1,3,5(10)-estratrien-17-spiro-δ-lactone Derivatives

These syntheses are described in Scheme 19.

Scheme 19

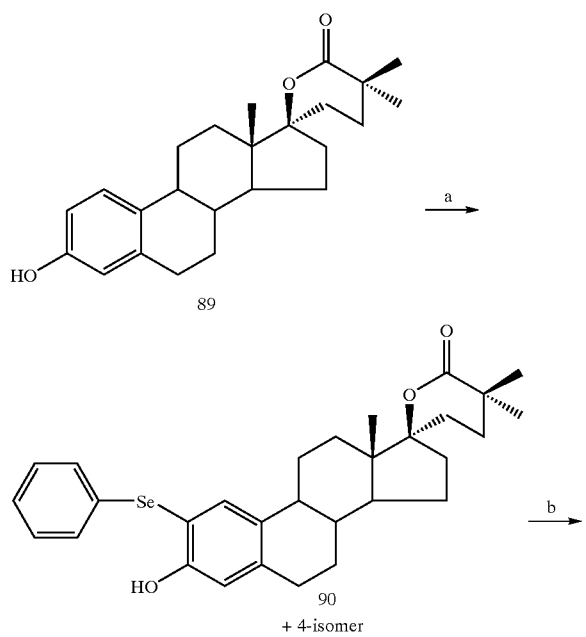

+ 4-isomer

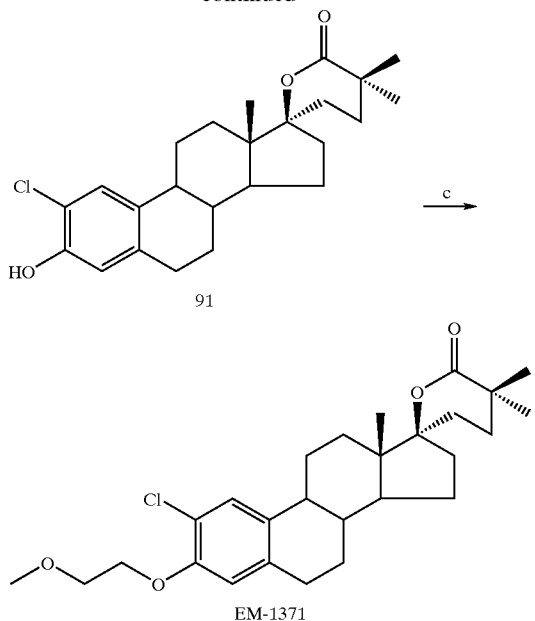

EM-1371 a. PhSeCl, CHCl₃ b. NCS, CHCl₃ c. Cs₂CO₃, CH₃OCH₂CH₂Cl, CH₃CN, NaI

Example 22A

3-Hydroxy-2-phenylselenenyl-1,3,5(10)-estratrien-17(R)-spiro-2'-(5',5'-dimethyl-6'-oxo)tetrahydropyran (90)

A solution of 3-hydroxy-1,3,5(10)-estratrien-17(R)-spiro-2'-(5',5'-dimethyl-6'-oxo)tetrahydropyran (89) (406 mg, 1.10 mmol) and phenylselenenyl chloride (253 mg, 1.32 mmol) in dry CHCl₃ (24 mL) under Ar (g) was stirred at 0° C. for 1 h then at room temperature overnight. The resulting yellow solution was poured onto ice/H₂O then extracted with CH₂Cl₂ (3×). The combined organic phase was dried (cotton plug) then rotary evaporated to give a crude foamy solid. Purification by flash chromatography (SiO₂) using 1:9 EtOAc/Hexanes as eluent gave compound 90 (353 mg, 61%) with the 4-isomer (86 mg, 15%). Compound 90: [α]$^{25}_D$ +77.7° (c 1.14, CHCl₃); IR ν 3366, 3050, 2965, 2928, 2869, 1709, 1603, 1576, 1550, 1458, 1438, 1384, 1349, 1310, 1294, 1262, 1202, 1157, 1141, 1114, 1065, 1017, 984, 892, 845, 736, 689, 665, 593, 555, 498, 460 cm$^{-1}$; $^1$H NMR(CDCl₃) δ 1.02 (3H, s), 1.27(9) (3H, s), 1.28(4) (3H, s), 1.27–1.80 (11H, m), 1.88–2.28 (6H, m), 2.87 (2H, t, J=4.8 Hz), 6.24 (1H, s, OH), 6.80 (1H, s), 7.21 (5H, br s), 7.52 (1H, s); $^{13}$C NMR(CDCl₃) δ 14.4, 23.3, 25.5, 26.1, 27.2, 27.6, 27.7, 29.5, 31.5, 31.8, 34.7, 37.7, 38.9, 43.4, 47.2, 48.6, 93.6, 111.6, 114.7, 126.5, 129.2(6), 129.3(4), 131.2, 133.3, 134.7, 141.4, 154.4, 177.8.

Example 22B

2-Chloro-3-hydroxy-1,3,5(10)-estratrien-17(R)-spiro-2'-(5',5'-dimethyl-6'-oxo)tetrahydropyran (91)

A solution of compound 90 (347 mg, 0.66 mmol) and N-chlorosuccinimide (177 mg, 1.33 mmol) in dry CHCl₃ (30 mL)under Ar(g) at 0° C. were stirred for 30 min. The solution was poured onto ice/H₂O then was extracted with CH₂Cl₂ (3×). The combined organic phase was dried (cotton plug) then rotary evaporated to give a crude solid. Purification by flash chromatography (SiO$_2$) using 1:9 EtOAc/Hexanes as eluent gave compound 91 (104 mg, 39%) as a white solid. $^1$H NMR (CDCl$_3$) δ 1.01 (3H, s), 1.28 (6H, s), 1.25–1.75 (11H, m), 1.85–2.28 (6H, m), 2.80 (2H, dd, J'=8.7 Hz, J"=3.9 Hz), 5.39 (1H, br s, OH), 6.73 (1H, s), 7.19 (1H, s); $^{13}$C NMR(CDCl$_3$) δ 14.4, 23.3, 25.6, 26.1, 27.2, 27.7, 27.8, 29.1, 31.6, 31.9, 34.8, 37.8, 38.8, 43.5, 47.3, 48.6, 93.6, 116.0, 117.1, 125.6, 133.5, 137.2, 149.0, 177.8.

Example 22C

2-Chloro-3-methyloxyethyloxy-1,3,5(10)-estratrien-17(R)-spiro-2'-(5',5'-dimethyl-6'-oxo) tetrahydropyran (EM-1371)

A mixture of compound 91 (95 mg, 0.24 mmol), Cs$_2$CO$_3$ (230 mg, 0.70 mmol) 2-chloroethylmethyl ether (1.72 mL, 1.78 g, 18.86 mmol) and NaI (4 mg, 0.02 mmol) in acetonitrile (45 mL) were refluxed for 4 h. The solvent was rotary evaporated and the residue was taken into H$_2$O/CH$_2$Cl$_2$. The aqueous phase was extracted with CH$_2$Cl$_2$ (3×). The combined organic phase was dried (MgSO$_4$), filtered then rotary evaporated. The crude solid was purified by flash chromatography (SiO$_2$) using 1:9 to 2:8 EtOAc/Hexanes as eluent to give EM-1371 (73 mg, 67%) as a white solid. IR ν 2982, 2963, 2927, 2880, 1718, 1654, 1598, 1499, 1458, 1397, 1387, 1364, 1323, 1307, 1286, 1259, 1247, 1210, 1151, 1125, 1059, 1032, 1018, 987, 928, 885, 866, 738, 669 cm$^{-1}$; $^1$H NMR (CDCl$_3$) δ 1.02 (3H, s), 1.28 (6H, s), 1.29–1.75 (11H, m), 1.85–2.35 (6H, m), 2.80 (2H, br t, J=5.0 Hz), 3.48 (3H, s), 3.78 (2H, t, J=5.2 Hz), 4.14 (2H, t, J=5.2 Hz), 6.66 (1H, s), 7.25 (1H, s); $^{13}$C NMR(CDCl$_3$) δ 14.4, 23.2, 25.5, 26.0, 27.2, 27.6, 27.7, 29.3, 31.5, 31.9, 34.7, 37.7, 38.7, 43.4, 47.2, 48.5, 59.3, 68.9, 70.8, 93.5, 114.5, 120.3, 127.0, 133.7, 136.1, 152.1, 177.7.

Example 23

3-Hydroxy-2,4-dihalo-1,3,5(10)-estratrien-17-spiro-(dimethyl-δ-lactone) Derivatives These syntheses are described in Scheme 20.

Scheme 20

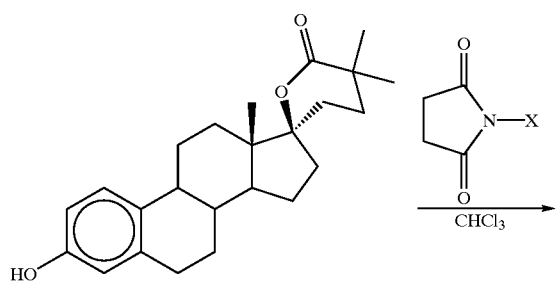

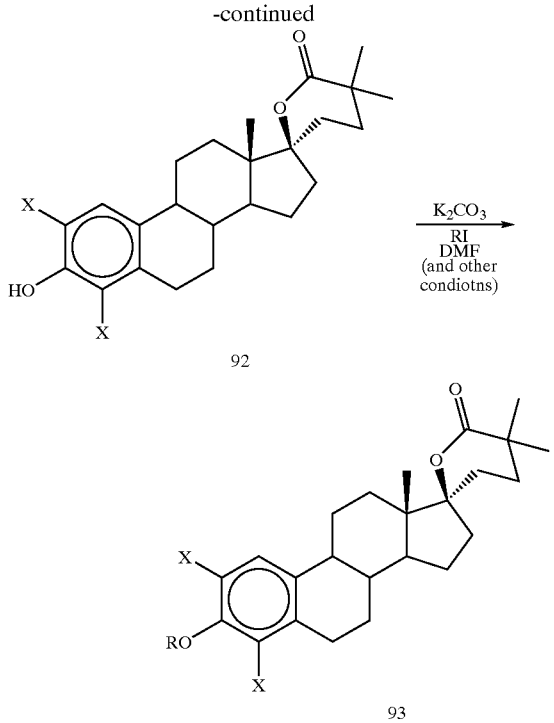

Example 23A 2,4-Dihalo-3-hydroxy-1,3,5(10)-estratrien-17(R)-spiro-2'-(5',5'-dimethyl-6'-oxo)tetrahydropyran (92)

Under argon atmosphere, a solution of 3-hydroxy-1,3,5 (10)-estratriene-17(R)-spiro-2'-(5',5'-dimethyl-6'-oxo) tetrahydropyran (89) and N-halosuccinimide (2 equiv) in anhydrous chloroform (1.3% W/V) was stirred at room temperature for 1.5 h. The reaction mixture was diluted with dichloromethane, washed with brine, dried over magnesium sulfate, filtered, and evaporated. The crude mixture was purified by flash chromatography (hexanes-ethyl acetate 32-1 to hexanes-ethyl acetate 9-1) to provide compound 92 (e.g., EM-1382-CS, X=Br, 62%); IR (NaCl) δ 3197, 2936, 2872, 1694, 1466, 1387, 1297, 1154 cm$^{-1}$; $^1$H NMR (300 MHz, CDCl$_3$) δ 1.01 (s, 3H), 1.29 (s, 6H), 1.35–2.35 (m, 17H), 2.65 (m, 1H), 2.88 (dd, J=6.1 and 18.0 Hz, 1H), 5.83 (s, 1H), 7.40 (s, 1H); $^{13}$C NMR (75 MHz, CDCl$_3$) δ 14.35, 23.25, 25.55, 26.29, 27.39, 27.69, 27.76, 30.98, 31.58, 31.77, 34.76, 37.80, 38.12, 43.59, 47.11, 48.50, 93.44, 106.36, 113.21, 128.45, 135.23, 136.51, 147.17, 177.75.

Example 23B

3-Substituted-2,4-dihalo-1,3,5(10)-estratrien-17(R)-spiro-2'-(5',5'-dimethyl-6'-oxo)tetrahydropyran (93)

Method A: Under argon atmosphere, a solution of compound 92, anhydrous potassium carbonate (1.2 equiv) and alkyliodide (2.0 equiv) in dimethylformamide (3.3% W/V) was stirred at 30° C. for 1 h. The reaction mixture was cooled at room temperature, quenched with saturated ammonium chloride, and extracted with ethyl acetate. The organic phase was quenched with brine, dried over magnesium sulfate, filtered, and evaporated. The crude mixture was purified by flash chromatography (hexanes-ethyl acetate 49-1 to hexanes-ethyl acetate 19-1) to provide compound 93 (e.g., EM-1385-CS, X=Br, R=Me, 78%): IR (NaCl) 2935, 2870, 1720, 1462, 1384, 1298, 1150 cm$^{-1}$; $^1$H NMR (300 MHz, CDCl$_3$) δ 1.01 (s, 3H), 1.29 (s, 6H), 1.30–2.35 (m, 17H), 2.68 (m, 1H), 2.88 (dd, J=5.6 and 18.2 Hz, 1H), 3.86 (s, 3H), 7.45 (s, 1H); $^{13}$C NMR (75 MHz, CDCl$_3$) δ 14.36, 23.28, 25.59, 26.24, 27.45, 27.72, 27.80, 31.07, 31.62, 31.84, 34.79, 37.84, 37.99, 43.87, 47.11, 48.63, 60.38, 93.45, 114.48, 121.45, 129.07, 137.31, 139.26, 151.96, 177.75.

Method B: Under argon atmosphere, a solution of compound 92, triphenylphosphine (6 equiv) and alcohol (6 equiv) in THF (1.5% W/V) was cooled at 0° C. and treated with diethyl azodicarboxylate (6 equiv). The solution was warmed at room temperature, stirred for 2 h, and evaporated. The crude mixture was purified by flash chromatography (hexanes-ethyl acetate 19-1) to provide compound 93 (e.g., EM-1387, X=Br, R=allyl, 72%): IR (neat) 2937, 2871, 1722, 1453, 1386 cm$^{-1}$; $^1$H NMR (300 MHz, CDCl$_3$) δ 1.01 (s, 3H), 1.28 (s, 6H), 1.30–2.35 (m, 17H), 2.68 (m, 1H), 2.88 (dd, J=5.8 and 18.0 Hz, 1H), 4.50 (d, J=5.6 Hz, 2H), 5.30 (dd, J=1.3 and 10.3 Hz, 1H), 5.46 (dd, J=1.3 and 17.0 Hz, 1H), 6.18 (m, 1H), 7.45 (s, 1H); $^{13}$C NMR (75 MHz, CDCl$_3$) δ 14.35, 23.26, 25.56, 26.20, 27.42, 27.69, 27.77, 31.09, 31.59, 31.81, 34.76, 37.81, 37.93, 43.84, 47.08, 48.60, 73.79, 93.42, 114.76, 118.41, 121.73, 129.04, 133.20, 137.24, 139.21, 150.86, 177.72.

Example 24

Synthesis of 2-Fluoro-1,3,5(10)-estratrien-17-dimethyl-δ-lactone Derivatives

These syntheses are described in Scheme 21.

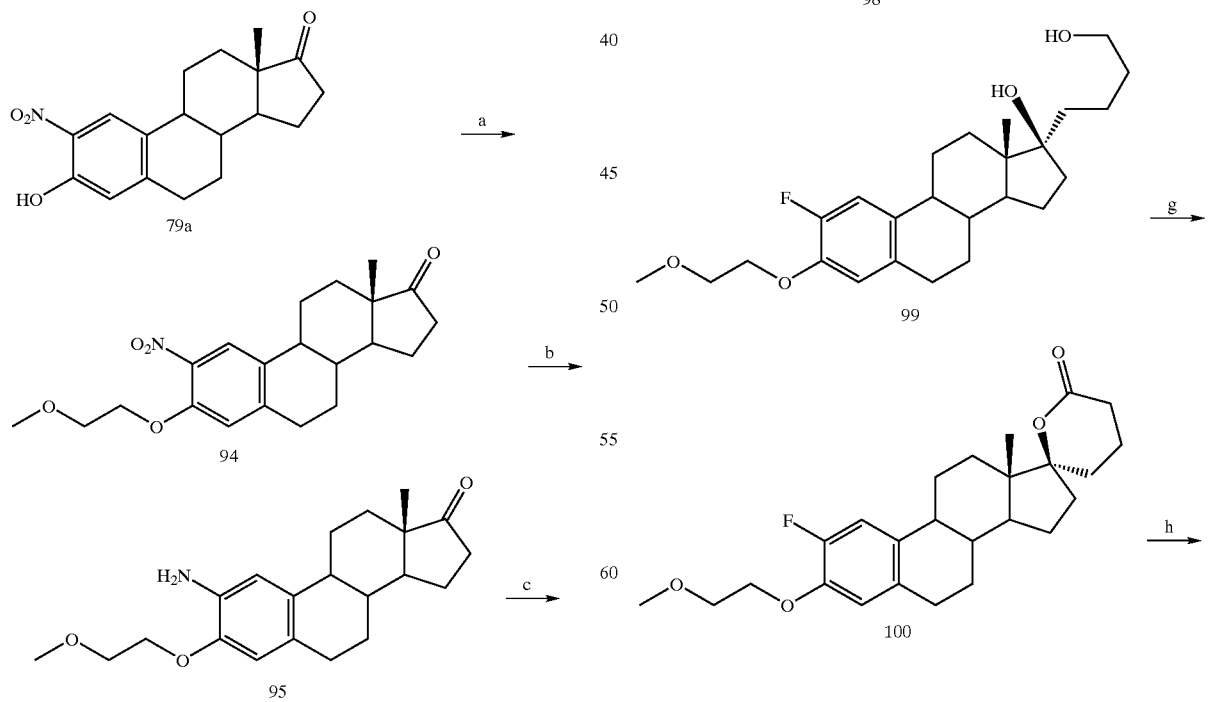

177

-continued

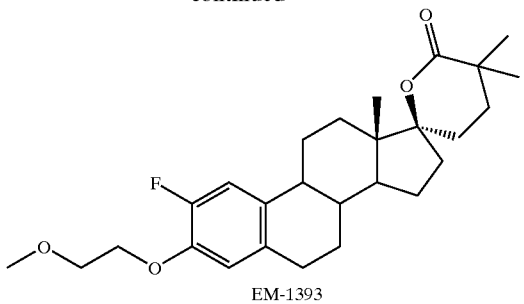

EM-1393 a. K₂CO₃, NaI, CH₃OCH₂CH₂Cl, CH₃CN, Δ;
b. Na₂S₂O₄, NaOH, acetone, H₂O;
c. BF₃—OEt₂, t-BuONO, CH₂Cl₂;
d. HCC(CH₂)₂OTHP, MeLi;
e. H₂, Pd/CaCO₃, MeOH;
f. PTSA, MeOH;
g. Jones' reagent;
h. LiHMDS, MeLi, THF, -60° C.

Example 24A

2-Nitro-3-methyloxyethyloxy-1,3,5(10)-estratrien-17-one (94)

A mixture of compound 79a (905 mg, 2.87 mmol), $K_2CO_3$ (793 mg, 5.74 mmol), 2-chloroethylmethyl ether (17 mL, 18 g, 189 mmol) and NaI (43 mg, 0.29 mmol) in acetonitrile (60 mL) were refluxed for 24 h. The solvent was rotary evaporated and the residue was taken into $H_2O$/EtOAc. The aqueous phase was extracted with EtOAc (3×). The combined organic phase was washed with brine, dried ($MgSO_4$), filtered then rotary evaporated. The crude solid was purified by flash chromatography ($SiO_2$) using 1:9 to 2:8 EtOAc/Hexanes as eluent to give recovery of the starting material (416 mg, 46%) and the title compound (520 mg, 49%) as a yellow solid. $[\alpha]^{25}_D$ +135.8° (c 1.28, $CHCl_3$); IR ν 3448 (w), 2930, 2890, 1737 (CO), 1617, 1568, 1518, 1498, 1454, 1409, 1373, 1351, 1339, 1287, 1194,1129, 1070, 1031, 1006, 960, 916, 895, 874, 833, 795, 758, 733, 669, 594, 588 $cm^{-1}$; $^1H$ NMR ($CDCl_3$) δ 0.91 (3H, s), 1.42–1.66 (6H, m), 1.95–2.42 (6H, m), 2.51 (1H, dd, J=18.9 Hz, J'=8.9 Hz), 2.92 (2H, br t, J=9.5 Hz), 3.45 (3H, s), 3.78 (2H, t, J=5.1 Hz), 4.20 (2H, t, J=4.8 Hz), 6.80 (1H, s), 7.79 (1H, s); $^{13}C$ NMR ($CDCl_3$) δ 13.8, 21.5, 25.7, 26.0, 29.7, 31.3, 35.7, 37.8, 43.5, 47.8, 50.2, 59.4, 69.7, 70.7, 115.4, 122.9, 132.9, 137.9, 144.1, 150.4, 220.1.

Example 24B

2-Amino-3-methyloxyethyloxy-1,3,5(10)-estratrien-17-one (95)

To a refluxing solution of compound 94 (506 mg, 1.35 mmol) in acetone (120 mL), $H_2O$ (24 mL) and aqueous 1 M NaOH (24 mL, 24.0 mmol) was portionwise added with care solid $Na_2S_2O_4$ (3.89 g, 18.97 mmol). The reflux was continued for 2 h then the acetone was removed under vacuum. More $H_2O$ (50 mL) was added and the aqueous phase was extracted with $CH_2Cl_2$ (4×). The organic phase was dried ($MgSO_4$), filtered then rotary evaporated. The crude solid was purified by flash chromatography ($SiO_2$) using 3:7 to 1:1 EtOAc/Hexanes as eluent to give compound 95 (228 mg, 49%) as a foamy solid. $^1H$ NMR ($CDCl_3$) δ 0.88 (3H, s), 1.37–2.78 (14H, m), 3.41 (3H, s), 3.71 (2H, t, J=5.0 Hz), 4.09 (2H, 2.9 Hz), 6.52 (1H, s), 6.65 (1H, s).

Example 24C

2-Fluoro-3-methyloxyethyloxy-1,3,5(10)-estratrien-17-one (96)

To neat $BF_3$-$Et_2O$ (126 μL, 141 mg, 1.00 mmol) at -15° C. under Ar (g) was added a solution of compound 95 (228 mg, 0.66 mmol) in dry $CH_2Cl_2$ (4 mL) followed by the dropwise addition t-butyl nitrite (95 μL, 82 mg, 0.80 mmol). This solution was stirred at -15° C. for 10 min then at 0° C. for 1.5 h. Pentane (16 mL) was added to the cold solution and a red gummy solid precipitated. The solvent was decanted and the residue was rinced with cold $Et_2O$ (5 mL). The residue was dried under vacuum to give a foamy orange-red solid. This solid was heated under vacuum with a heatgum for 5 min. The residue was purified by flash chromatography ($SiO_2$) using 3:7 to 1:1 EtOAc/Hexanes as eluent to give compound 96 (32 mg, 14%) as a solid. $^1H$ NMR ($CDCl_3$) δ 0.90 (3H, s), 1.25–1.64 (m, 6H), 1.92–2.29 (6H, m), 2.50 (1H, dd, J=18.9 Hz, 8.9 Hz), 2.82 (2H, dd, J=8.4 Hz, J'=3.5 Hz), 3.45 (3H, s), 3.75 (2H, t, J=4.7 Hz), 4.15 (2H, t, J=4.5 Hz), 6.71 (1H, d, J=8.7 Hz), 6.98 (1H, d, J=13.2 Hz); $^{13}C$ NMR($CDCl_3$) δ 13.8, 21.5, 25.9, 26.5, 29.0, 29.7, 31.5, 35.8, 38.0, 43.9, 47.9, 50.3, 59.2, 69.2, 71.0, 113.1 (d, J=18.7 Hz), 116.1, 132.6 (d, J=87.0 Hz), 144.5, 149.5, 152.7, 220.6.

Example 24D

2-Fluoro-17β-hydroxy-3-methyloxyethyloxy-17α-(4'-(2"-tetrahydro-2"H-pyranyloxy)-butynyl)-1,3,5 (10)-estratriene (97)

To a stirred solution of 2-(3-butynyloxy)tetrahydro-2H-pyran (58 μL, 57 mg, 0.37 mmol) in dry THF (4 mL) at -30° C. under Ar(g) was dropwise added MeLi (1.4 M in $Et_2O$, 5.39 mL, 7.55 mmol). The solution was stirred at room temperature for 25 min. then cooled down to -30° C. A solution of compound 96 (32 mg, 0.09 mmol) in dry THF (4 mL) was added and the solution was stirred for a further 1 h. The solution was quenched with ice and aqueous sat. $NaHCO_3$ and extracted with EtOAc. The organic layer was washed with brine, dried ($MgSO_4$), filtered then rotary evaporated to give compound 97 as a crude oil (73 mg). This compound was used without further purification.

Example 24E

2-Fluoro-17β-hydroxy-3-methyloxyethyloxy-17α-(4'-(2"-tetrahydro-2"H-pyranyloxy)-butyl)-1,3,5(10)-estratriene (98)

A mixture of crude compound 97 (73 mg, ~0.09 mmol) and 5% Pd/$CaCO_3$ (35 mg) in MeOH (10 mL) was stirred under $H_2$(g) (balloon) at room temperature for 2 h. The mixture was filtered through celite and the solvent evaporated under vacuum to give compound 98 (52 mg) as a crude oil. This compound was used without further purification.

Example 24F

2-Fluoro-17β-hydroxy-3-methyloxyethyloxy-17α-(4'-hydroxybutyl)-1,3,5(10)-estratriene (99)

Crude compound 98 (52 mg, 0.09 mmol) and PTSA monohydrate (7 mg, 0.04 mmol) were stirred in MeOH (5 mL) at room temperature for 3 h. The solvent was reduced to about 1–2 mL, EtOAc was added, and the organic phase was washed with cold aqueous saturated $NaHCO_3$, $H_2O$, brine and was dried ($MgSO_4$), filtered and then evaporated to give compound 99 (42 mg) as a crude solid. This compound was used without further purification.

Example 24G

2-Fluoro-3-methyloxyethyloxy-1,3,5(10)-estratrien-17(R)-spiro-2'-(6'-oxo)tetrahydropyran (100)

To a stirred solution of crude compound 99 (42 mg, ~0.09 mmol) in acetone (6 mL) at 0° C. was added 1.25 M $H_2CrO_4$ (Jones' reagent, 326 μL, 0.4 mmol). The solution was stirred for 20 min. then more 1.25 M H$_2$CrO$_4$ (Jones' reagent, 326 μL, 0.4 mmol) was added. After 20 min, iso-propanol (1 mL) was added and the solution was stirred for a further 10 min. The precipitated formed was decanted and washed with acetone (4×). The acetone volume was reduced to about 2 mL and was then poured onto cold aqueous saturated NaHCO$_3$ with the help of EtOAc. The organic phase was washed with H$_2$O, brine, dried (MgSO$_4$), filtered and then evaporated to give compound 100 (33 mg) as a crude solid. This compound was used without further purification. $^1$H NMR (CDCl$_3$) δ 1.01 (3H, s), 1.24–2.60 (19H, m), 2.78 (2H, br s), 3.45 (3H, s), 3.74 (2H, dd, J=5.0 Hz, J'=4.5 Hz), 4.14 (2H, dd, J=5.0 Hz, J'=4.5 Hz), 6.69 (1H, d, J=8.7 Hz), 6.97 (1H, d, J=13.2 Hz); $^{13}$C NMR (CDCl$_3$) δ 14.3, 15.9, 23.4, 26.0, 27.4, 27.9, 29.0, 29.5, 31.9, 34.0, 38.7, 43.6, 47.2, 48.8, 59.2, 69.2, 71.0, 93.2, 113.1 (d, J=18.6 Hz), 116.1, 132.0, 133.3, 144.4, 151.1 (d, $J_{CF}$=243.4 Hz), 172.0.

Example 24H

2-Fluoro-3-methyloxyethyloxy-1,3,5(10)-estratrien-17(R)-spiro-2'-(5',5'-dimethyl-6'-oxo) tetrahydropyran (EM-1393)

To a stirred solution of compound 100 (33 mg, ~0.08 mmol) in dry THF (3 mL) at 0° C. under Ar(g) was dropwise added HMDSLi (1.0 M in THF, 198 μL, 0.20 mmol). After 25 min, the solution was cooled down to −60° C. and MeI (99 μL, 225 mg, 1.58 mmol) was added. The solution temperature was allowed to slowly rise from −60 to 0° C. over 40 min. The reaction was quenched with aqueous NH$_4$Cl, extracted with EtOAc (4×), dried (MgSO$_4$), filtered and then evaporated. The crude compound was purified on silica gel using 1:9 EtOAc/Hexanes as eluent to give EM-1393 (8 mg, 19% yield from compound 96, 5 steps) as a solid. IR (ν) 2924, 2871, 2832, 1722 (CO), 1620, 1586, 1513, 1454, 1384, 1357, 1306, 1290, 1268, 1201, 1149, 1133, 1116, 1032, 1018, 931, 874, 810, 789, 722 cm$^{-1}$; $^1$H NMR (CDCl$_3$) δ 1.02 (3H, s), 1.28(0) (3H, s), 1.28(3) (3H, s), 1.29–2.30 (17H, m), 2.80 (2H, br s), 3.45 (3H, s), 3.75 (2H, t, J=4.8 Hz), 4.15 (2H, dd, J=5.0 Hz, J'=4.6 Hz), 6.69 (1H, d, J=8.6 Hz), 6.98 (1H, d, J=13.2 Hz); $^{13}$C NMR (CDCl$_3$) δ 14.4, 23.3, 25.6, 26.1, 27.4, 27.6, 27.8, 29.1, 29.7, 31.6, 34.9, 37.8, 38.8, 43.6, 47.3, 48.6, 59.2, 69.2, 71.0, 93.6, 113.1 (d, J=17.7 Hz), 116.1, 132.1, 133.4, 144.4, 151.1 (d, J=248.6 Hz), 177.8.

Example 25

Synthesis of 3-Methylthioethyloxy-1,3,5(10)-estratrien-δ-lactone

These syntheses are described in Scheme 22.

Scheme 22

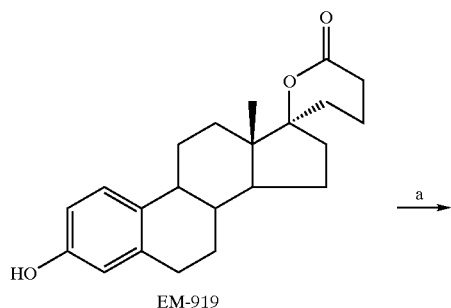

EM-919

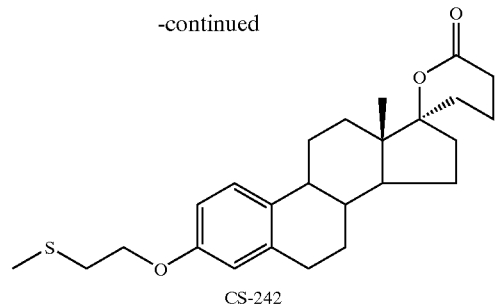

CS-242 a. K$_2$CO$_3$, ClCH$_2$CH$_2$SCH$_3$, DMF, reflux

Example 25A

3-Methylthioethyloxy-1,3,5(10)-estratrien-17(R)-spiro-2'-(6'-oxo) Tetrahydropyran (CS-242)

To a solution of 1,3,5(10)-estratrien-3-ol-17(R)-spiro-2' (6'-oxo)tetrahydropyran (EM-919, 40 mg, 0.117 mmol) in anhydrous acetonitrile (20 mL) at room temperature under Ar(g) was added K$_2$CO$_3$ (16 mg, 0.117 mmol) and chloroethylmethyl sulfide (39 mg, 35 mL, 0.350 mmol). The solution was refluxing for 44 h. The acetonitrile solution was evaporated to dryness and ethyl acetate (40 mL) was then added. The organic phase was washed with water, brine and dried with MgSO$_4$ to gave crude product (49 mg). Purification by flash chromatography on silica gel (SiO$_2$, 3 g) using ethyl acetate/hexanes (2:8) as eluent gave desired product (35 mg, 70%). IR (ν) 2921, 1727, 1608, 1576, 1499, 1466, 1438, 1382, 1348, 1330, 1310, 1280, 1236, 1187, 1159, 1100, 1067, 1036, 992, 931, 914, 860, 818, 731 cm$^{-1}$; $^1$H NMR(CDCl$_3$) δ 1.01 (3H, s), 1.25–2.57 (19H, m), 2.20 (3H, s) 2.85 (4H, t, J=6.88 Hz), 4.12 (2H, t, J=6.74 Hz), 6.62 (1H, d, J=2.49 Hz), 6.71 (1H, dd, J1=2.58 Hz J2=5.89 Hz), 7.19 (1H, d, J=8.54 Hz); $^{13}$C NMR(CDCl$_3$) δ 14.8, 15.9, 16.2, 23.5, 26.1, 27.5, 28.0, 29.5, 29.7, 32.0, 33.1, 34.0, 39.1, 43.7, 47.3, 48.9, 67.4, 93.3, 112.1, 114.6, 126.3, 132.6, 137.9, 156.5, 172.1 ppm. HRMS: FAB M/S [M]+ calculated for C$_{25}$H$_{35}$O$_3$S: 415.23068, found 415.23250.

Example 26

Synthesis of 3-Fluoro-1,3,5(10)estratrien-17-spiro (dimethyl-δ-lactone) Derivatives These syntheses are described in Scheme 22.

Scheme 22

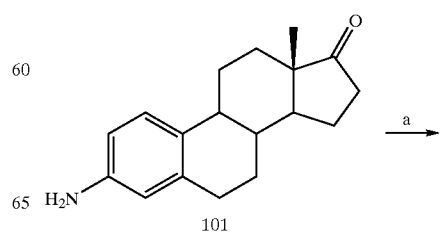

101

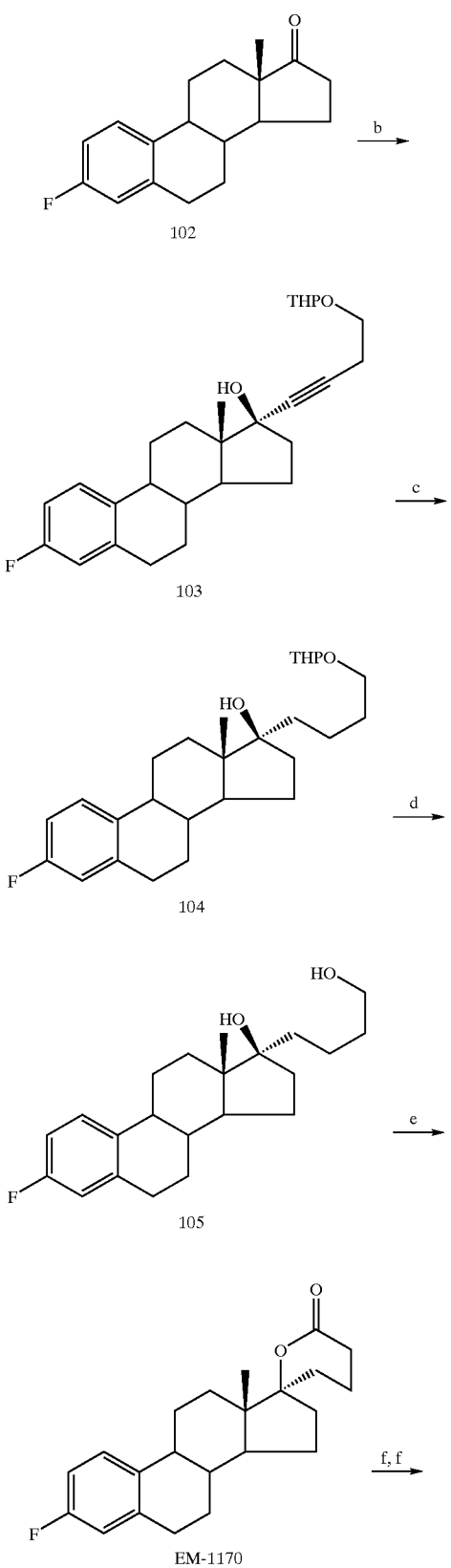

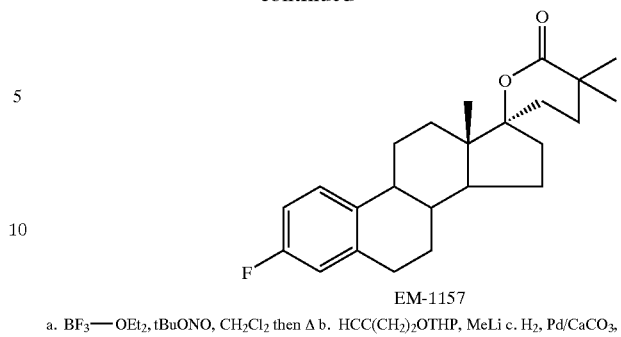

EM-1157 a. BF₃—OEt₂, tBuONO, CH₂Cl₂ then Δ b. HCC(CH₂)₂OTHP, MeLi c. H₂, Pd/CaCO₃, MeOH
d. PTSA, MeOH e. Jones' reagent f. LDA, MeI

Example 26A

2-Amino-1,3,5(10)-estratriene (101)

The title compound was synthesized from estrone according to the procedure reported by Morrow and Hofer (J. Med. Chem. 9, 249–51, 1966).

Example 26B

3-Fluoro-1,3,5(10)-estratriene (102)

3-Fluoroestrone was synthesized from 2-aminoestrone by adapting the procedure reported by Doyle and Bryker (J. Org. Chem. 44, 1572–1574, 1979) for the synthesis of arenediaxonium tetrafluoroborate salts from aromatic amines. The procedure is as followed: To neat stirred boron trifluoride etherate (642 μL, 719 mg, 5.07 mmol) at −15° C. under Ar (g) was added a solution of 3-aminoestrone (101) (910 mg, 3.38 mmol) in dry CH₂Cl₂ (10 mL). After 15 min, a solution of t-butylnitrite (482 μL, 418 mg, 4.05 mmol) in dry CH₂Cl₂ (5 mL) was dropwise added. The now dark brown solution was stirred at −15° C. for 15 min, then at 0° C. for 30 min. Pentane was added to the solution and a gummy solid precipitated. The solvent was decanted and the residue was dried under vacuum to give a crude light brown solid. The neat solid was heated under vacuum at 70–80° C. in an oil bath for 15 min to give a crude orange solid. Purification by flash chromatography on SiO₂ using 1:9 EtOAc/Hexanes gave 3-fluoroestrone (102) as a white solid (437 mg, 47%). M.p. 178° C.; $[\alpha]^{25}_D$ +152.0° (c 1.03, CDCl₃); IR (ν) 3044, 3039, 2928, 1740 (CO), 1611, 1585, 1495, 1474, 1458, 1428, 1405, 1377, 1340, 1272, 1245, 1230, 1212, 1148, 1094, 1084, 1053, 1008, 908, 889, 817, 784, 718, 704, 642, 620, 580, 564, 467 cm⁻¹; ¹H NMR (CDCl₃) δ 0.92 (3H, s), 1.37–1.70 (6H, m), 1.93–2.44 (6H, m), 2.52 (1H, dd, J=18.8 Hz, J'=9.0 Hz), 2.91 (2H, dd, J=8.4 Hz, J'=3.8 Hz), 6.82 (2H, dq, J=8.3 Hz, J'=2.8 Hz), 7.23 (1H, dd, J=8.5 Hz, J'=5.8 Hz); ¹³C NMR (CDCl₃) δ 13.8, 21.6, 25.9, 26.3, 29.5, 31.5, 35.9, 38.1, 44.0, 47.9, 50.4, 112.5 (d, J=21.6 Hz), 115.1 (d, J=19.7 Hz), 126.8 (d, J=7.5 Hz), 135.3, 138.7, 161.0 (d, J=244.3 Hz), 220.7.

Example 26C

3-Fluoro-17β-hydroxy-17α-(4'-(2"-tetrahydro-2"H-pyranyloxy-1'-butynyl)-1,3,5(10)-estratriene (103)

To a stirred solution of 2-(3-butynyloxy)tetrahydro-2H-pyran (1.21 mL, 1.199 g, 7.77 mmol) in dry THF (45 mL)

at −30° C. under Ar(g) was dropwise added MeLi (1.4 M in Et$_2$O, 5.39 mL, 7.55 mmol). After 30 min., a solution of 3-fluoroestrone (102) in dry THF was added and the solution was stirred for a further 2 h. The solution was quenched with ice and aqueous sat NaHCO$_3$ and extracted with EtOAc. The organic layer was washed with H$_2$O, brine, dried (MgSO$_4$), filtered then rotary evaporated to give a crude orange oil. Purification by flash chromatography on silica gel using EtOAc/Hexanes (1:9→2:8→3:7) gave pure compound 103 (789 mg, 83%) as a solid. [α]$^{25}_D$ −4.7° (c 1.14, CDCl$_3$); IR (ν) 3432 (br, OH), 2937, 2870, 1611, 1589, 1495, 1458, 1438, 1420, 1380, 1354, 1285, 1233, 1201, 1183, 1122, 1073, 1032, 970, 911, 870, 846, 815, 783, 728, 692, 563, 466 cm$^{-1}$; $^1$H NMR (CDCl$_3$) δ 0.87 (3H, s), 1.25–2.05 (17H, m), 2.22–2.36 (3H, m), 2.56 (2H, t, J=7.0 Hz), 2.84 (2H, br t, J=4.8 Hz), 3.49–3.59 (2H, m), 3.79–3.88 (2H, m), 4.66 (1H, br s), 6.80 (2H, dq, J=9.8 Hz, J'=2.8 Hz), 7.24 (1H, dd, J=8.4 Hz, J'=5.8 Hz); $^{13}$C NMR (CDCl$_3$) δ 12.7, 19.1, 20.2, 22.7, 25.3, 26.3, 26.9, 29.5, 30.4, 32.7, 38.9, 39.1, 43.5, 46.9, 49.3, 61.8, 65.7, 79.6, 82.9, 84.6, 98.4, 112.1 (d, J=20.9 Hz), 114.9 (d, J=20.6 Hz), 126.6 (d, J=8.5 Hz), 135.7, 138.7 (d, J=6.7 Hz), 160.7 (d, J=244.8 Hz).

Example 26D

3-Fluoro-17β-hydroxyl-17α-(4'-(2"-tetrahydro-2"H-pyranyloxy-1'-butyl)-1,3,5(10)-estratriene (104)

A suspension of compound 103 (720 mg, 1.69 mmol) and 5% Pd/CaCO$_3$ (123 mg) in MeOH (40 mL) was stirred under H$_2$(g) atmosphere (balloon) at room temperature for 2 h. The mixture was filtered through celite and the solvent rotary evaporated to give compound 104 (692 mg, 95%) as a solid. This compound was used without further purification for the next step. [α]$^{25}_D$ +28.8° (c 0.59, CDCl$_3$); IR (ν) 3464 (br w, OH), 2938, 2870, 1611, 1588, 1494, 1453, 1440, 1380, 1271,1252, 1234, 1200, 1142, 1119, 1076,1024, 989, 971, 930, 910, 868, 815, 782, 731 cm$^{-1}$; $^1$H NMR (CDCl$_3$) δ 0.91 (3H, s), 1.31–2.35 (20H, m), 2.84 (2H, br t, J=4.8 Hz), 3.43–3.52 (2H, m), 3.78–3.88 (2H, m), 6.80 (2H, dq, J=8.3 Hz, J'=2.7 Hz), 7.23 (1H, dd, J=8.4 Hz, J'=6.1 Hz) ppm; $^{13}$C NMR (CDCl$_3$) δ 14.4, 19.7, 20.5, 23.4, 25.5, 26.3, 27.3, 29.7, 30.4, 30.8, 31.6, 34.3, 36.4, 39.2, 39.4, 43.8, 46.7, 62.4, 67.7, 83.4, 98.4 (d, J=4.5 Hz), 112.3 (d, J=21.0 Hz), 115.0 (d, J=20.3 Hz), 126.7 (d, J=8.1 Hz), 136.0,138.9 (d, J=6.6 Hz), 160.9 (d, J=244.1 Hz).

Example 26E

3-Fluoro-17β-hydroxyl-17α-(4'-hydroxybutyl)-1,3,5(10)-estratriene (105)

A solution of compound 104 (692 mg, 1.61 mmol), PTSA monohydrate (31 mg, 0.16 mmol) in MeOH was stirred overnight at room temperature. The volume of solvent was reduced to about 10 mL and EtOAc (125 mL) was added. This solution was washed with aqueous saturated NaHCO$_3$, H$_2$O, brine, dried (MgSO$_4$), filtered then rotary evaporated to give a crude solid. Purification on silica gel (3:7 to 1:1 EtOAc/Hexanes) gave compound 105 (469 mg, 84%) as a solid. [α]$^{25}_D$ +42.6° (c 1.07, CDCl$_3$); IR (ν) 3362 (br s, OH), 2933, 2866, 1740 (w), 1611, 1589, 1495, 1458, 1420, 1376, 1303, 1271, 1236, 1144, 1036, 1008, 931, 912, 870, 816, 783, 728, 562, 468 cm$^{-1}$; $^1$H NMR (CDCl$_3$) δ 0.91 (3H, s), 1.25–1.65 (17H, m), 1.85–2.35 (4H, m), 2.85 (2H, br t, J=4.6 Hz), 3.70 (2H, br t, J=5.9 Hz), 6.81(2H, dq, J=8.4 Hz, J'=1.1 Hz), 7.22 (1H, dd, J=8.4 Hz, J'=6.0 Hz); $^{13}$C NMR (CDCl$_3$) δ 14.3, 19.8, 23.4, 26.3, 27.3, 29.6, 31.6, 33.3, 34.4, 36.1, 39.4, 43.8, 46.7, 49.5, 62.7, 83.5, 112.3 (d, J=19.9 Hz), 115.1 (d, J=20.5 Hz), 126.7 (d, J=8.1 Hz), 135.9, 138.9 (d, J=6.9 Hz), 160.9 (d, J=243.8 Hz).

Example 26F

3-Fluoro-1,3,5(10)-estratrien-17(R)-spiro-2'-(6'-oxo)tetrahydropyran (EM-1170)

To a stirred solution of compound 105 (410 mg, 1.18 mmol) in acetone (40 mL) at 0° C. was added Jones' reagent (1.25 M, 1.04 mL, 1.30 mmol). The solution was stirred for 15 min. then more Jones' reagent (1.25 M, 1.04 mL, 1.30 mmil) was added. After 50 min., the excess reagent was quenched with isopropanol and the solution was stirred for a further 10 min. The precipitate was filtered throuch celite and the acetone rotary evaporated. The residue was taken in EtOAc and the solution was washed with aqueous saturated NaHCO$_3$, H$_2$O, brine, dried (MgSO$_4$), filtered, then rotary evaporated to give a crude solid. Purification on silica gel (2:8→3:7 EtOAC/Hexanes) gave EM-1170 (298 mg, 72%) as a solid. [α]$^{25}_D$ +47.0° (c 1.09, CDCl$_3$); IR (ν) δ 435, 3040, 2955, 2933, 2906, 2879, 2836, 2815, 1885, 1736 (CO), 1611, 1586, 1494, 1467, 1435, 1419, 1383, 1366, 1356, 1328, 1312, 1290, 1263, 1232, 1182, 1140, 1103, 1067, 1026, 990, 964, 933, 912, 861, 822, 782, 718, 670, 636, 584, 563, 536, 508 cm$^{-1}$; $^1$H NMR (CDCl$_3$) δ 1.02 (3H, s), 1.23–2.58 (19H, m), 2.85 (2H, br t, J=5.2 Hz), 6.80 (2H, dq, J=8.4 Hz, J'=2.7), 7.23 (1H, dd, J=8.4 Hz, J'=6.0 Hz); $^{13}$C NMR (CDCl$_3$) δ 14.2, 15.7, 23.4, 25.9, 27.1, 27.8, 29.4, 31.8, 33.8, 38.7, 43.5, 47.1, 48.7, 93.1, 112.2 (d, J=20.5 Hz), 114.9 (d, J=20.1 Hz), 126.6 (d, J=8.5 Hz), 135.4, 138.6 (d, J=6.7 Hz), 160.8 (d, J=243.8 Hz), 171.9.

Example 26G

3-Fluoro-1,3,5(10)-estratrien-17(R)-spiro-2'-(5',5'-dimethyl-6'-oxo)tetrahydropyran (EM-1157)

LDA was prepared as follows. To a stirred solution of diisopropylamine (501 μL, 386 mg, 3.82 mmol) in dry THF (20 mL) at −78° C. under Ar(g) was dropwide added n-BuLi (1.6 M in Hexane, 2.38 mL, 3.82 mmol). The solution was stirred at room temperature for 30 min then was cooled down to −78° C. for the addition of a solution of EM-1170 (218 mg, 0.64 mmol) in dry THF (15 mL). The solution was then stirred at room temperature for 1H. then cooled down to −78° C. MeI (476 μL, 1.084 g, 0.64 mmol)was added and the solution was stirred at −78° C. for 5 h and was allowed to rise to room temperature overnight. The reaction was quenched with ice/H$_2$O, extracted with EtOAc, washed with aqeous saturated NH$_4$Cl, 1M aqueous Na$_2$SO$_3$, H$_2$O, brine, dried (MgSO$_4$), filtered then rotary evaporated to give a crude solid. Purification on silica gel (1:9 EtOAc/Hexanes) gave EM-1157 (40 mg, 17%) as a solid. [α]$^{25}_D$ +43.3° (c 1.09, CHCl$_3$); IR (ν) 3430, 2969, 2941, 2867, 1734(CO), 1492, 1458, 1387, 1306, 1235, 1201, 1148, 1132, 1062, 1032, 1017, 979, 915, 874, 818, 785, 727, 597, 580, 567, 530, 508 cm$^{-1}$; $^1$H NMR (CDCl$_3$) δ 1.02 (3H, s), 1.28 (3H, s), 1.28 (3H, s), 1.29–1.74 (10H, m), 1.83–2.36 (7H, m), 2.85 (2H, t, J=5.1 Hz), 6.80 (2H, dq, J=8.6 Hz, J'=2.7 Hz), 7.22 (1H, dd, J=8.6 Hz, J'=6.2 Hz); $^{13}$C NMR (CDCl$_3$) δ 14.4, 23.3, 25.6, 26.1, 27.2, 27.7, 27.8, 29.5, 31.6, 31.9, 34.8, 37.8, 38.9, 43.7, 47.2, 48.7, 93.6, 112.3 (d, J=19.9 Hz), 115.1 (d, J=19.5 Hz), 126.7 (d, J=8.4 Hz), 135.5, 138.7 (d, J=6.8 Hz), 160.9 (d, J=244.2 Hz), 177.8.

Example 27

3-Sulfonyl derivatives of 1,3,5(10)-estratrien-17-spiro-(dimethyl δ-lactone)

These syntheses are described in Scheme 23.

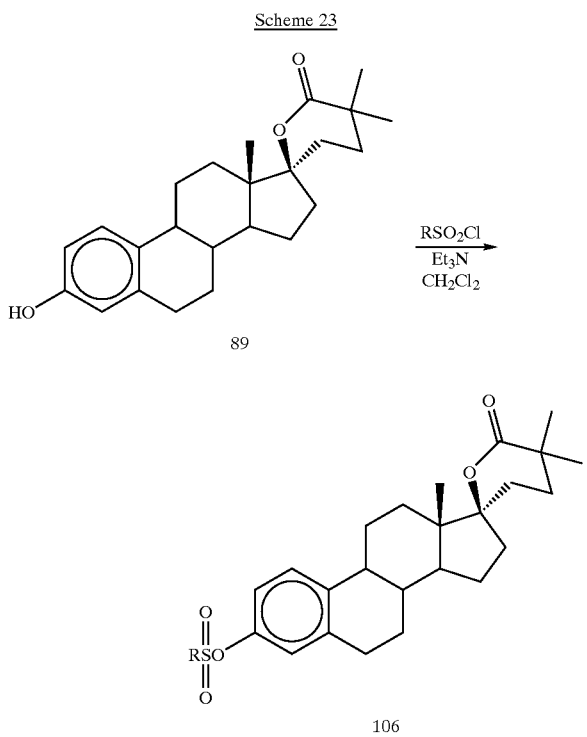

Example 27A

3-Alkylsulfonyloxy-1,3,5(10)-estratrien-17(R)-spiro-2'-(5',5'-dimethyl-6'-oxo)tetrahydropyran (106).

A solution of compound 89 in dichloromethane (3.0% W/V) was treated with alkylsulfonyl chloride (1.1 equiv) and triethylamine (1.5 equiv), and stirred for 2 h. The reaction mixture was quenched with distilled water and diluted with dichloromethane. The organic phase was washed with brine and 5% sodium bicarbonate, dried over magnesium sulfate, filtered, and evaporated. The crude mixture was purified by flash chromatography (hexanes-ethyl acetate 49-1 to hexanes-ethyl acetate 9-1) and trituration (hexanes-acetone 19-1) to provide compound 106 (e.g., EM-1364-CS, R=Et, 90%): IR (CHCl$_3$) ν 3025, 2944, 2874, 1708, 1605, 1492, 1366, 1213, 1136 cm$^{-1}$; $^1$H NMR (300 MHz, CDCl$_3$) δ 1.02 (s, 3H), 1.28 (s, 3H), 1.29 (s, 3H), 1.30–1.80 (m, 13H), 1.80–2.05 (m, 5H), 2.18 (m, 1H), 2.34 (m, 1H), 2.88 (m, 2H), 3.26 (q, J=14.8 Hz, 2H), 6.99–7.05 (m, 2H), 7.30 (d, J=8.5 Hz, 1H); $^{13}$C NMR (75 Hz, CDCl$_3$) δ 8.23, 14.41, 23.29, 25.58, 25.92, 27.67, 27.76, 29.46, 31.61, 31.93, 34.79, 37.80, 38.68, 43.81, 44.89, 47.20, 48.72, 93.53, 118.89, 121.90, 126.77, 138.84, 139.13, 146.99, 177.76.

Example 28

3-Carbonyl substituted 1,3,5(10)-estratrien-17-spiro-(dimethyl-δ-lactone)

These syntheses are described in Scheme 24.

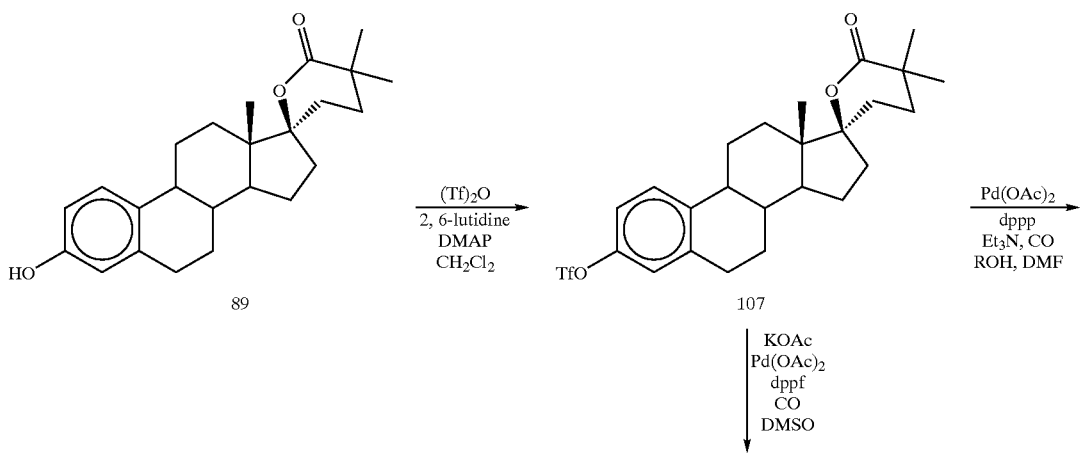

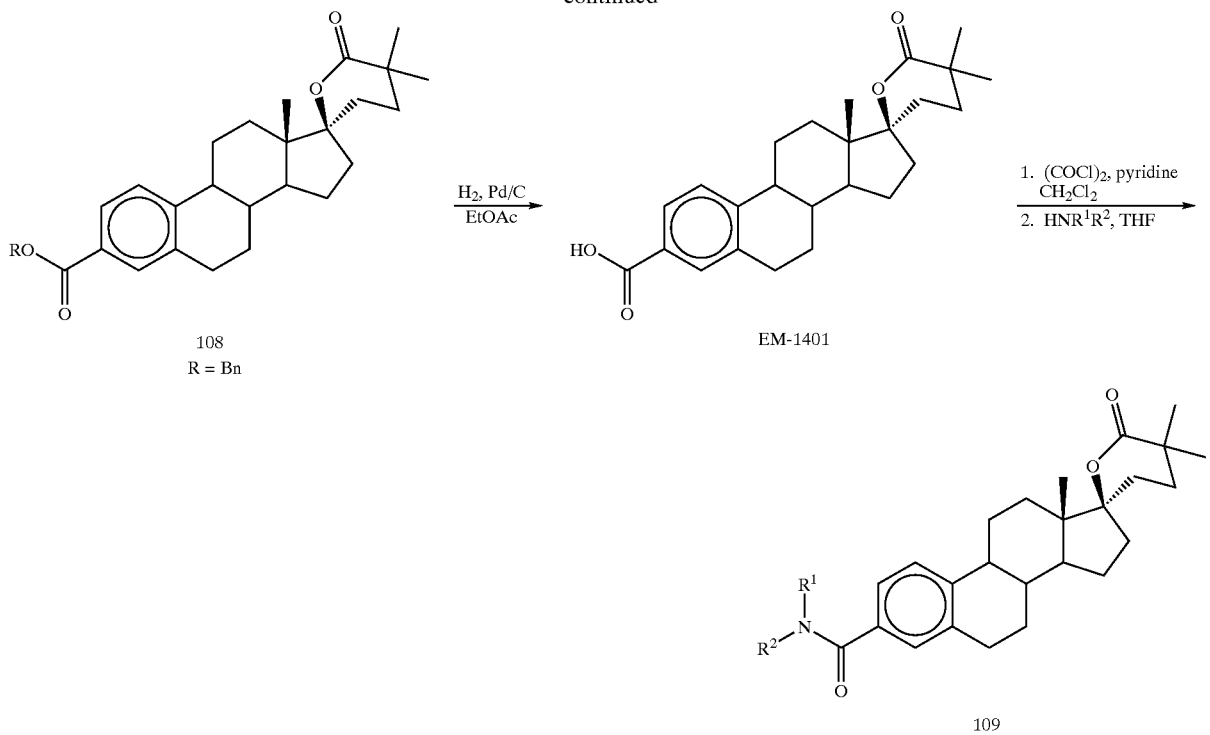

Example 28A

3-Trifluoromethanesulfonyloxy-1,3,5(10)-estratrien-17(R)-spiro-2'-(5',5'-dimethyl-6'-oxo)tetrahydropyran (107)

Under argon atmosphere, a solution of compound 89 (500 mg, 1.35 mmol), 2,6-lutidine (0.355 mL, 3.05 mmol) and 4-dimethylaminopyridine (33 mg, 0.27 mmol) in dry dichloromethane (25 mL) was cooled at 0° C., treated with trifluoromethanesulfonic anhydride (0.308 mL, 1.83 mmol) and stirred for 45 min. The reaction mixture was quenched with water and extracted with dichloromethane. The organic phase was washed with 2% hydrochloric acid, saturated sodium bicarbonate and water, dried over magnesium sulfate, filtered, and evaporated. The crude oil was purified by flash chromatography (hexanes-ethyl acetate 49-1 to hexanes-ethyl acetate 4-1) to provide trifluoromethanesulfonate 107 (EM-1399) (540 mg, 80%): IR (CHCl$_3$) 2957, 2872, 1711, 1490, 1426, 1248, 1214, 1141, 926, 846, 621 cm$^{-1}$; $^1$H NMR (300 MHz, CDCl$_3$) δ 1.03 (s, 3H), 1.28 (s, 3H), 1.29 (s, 3H), 1.35–2.40 (m, 17H), 2.88 (m, 2H), 6.98 (s, 1H), 7.02 (d, J=8 Hz, 1H), 7.33 (d, J=8.7 Hz, 1H); $^{13}$C NMR (75 MHz, CDCl$_3$) δ 14.32, 23.22, 25.48, 25.80, 26.89, 27.57, 27.68, 29.37, 31.49, 31.80, 34.69, 37.72, 38.46, 43.66, 47.10, 48.59, 93.43, 116.54, 118.08, 120.80, 121.07, 127.05, 139.31, 140.43, 147.46, 177.70.

Example 28B

3-Carboxy-1,3,5(10)-estratrien-17(R)-spiro-2'-(5',5'-dimethyl-6'-oxo)tetrahydropyran (EM-1401)

Method A: A mixture of compound 107 (560 mg, 1.12 mmol), potassium acetate (440 mg, 4.48 mmol), palladium acetate (12.6 mg, 0.056 mmol), and 1,1'-bis(diphenylphosphino)ferrocene (125 mg, 0.255 mmol) in dimethyl sulfoxide (20 mL) was purged with carbon monoxide for 20 min and stirred over under a carbon monoxide balloon at 80° C. over a 3 h period. The reaction mixture was diluted with 0.5 N hydrochloric acid and extracted with dichloromethane. The organic phase was washed with water, dried over magnesium sulfate, filtered, and evaporated. The reaction mixture was purified by flash chromatography (dichloromethane-methanol 19-1 to dichloromethane-methanol 4-1) to provide the carboxylic acid EM-1401 (300 mg, 68%): IR (KBr) 2937, 2872, 1718, 1676, 1388, 1314, 1230, 1180, 1160 cm$^{-1}$; $^1$H NMR (300 MHz, CDCl$_3$+CD$_3$OD) δ 0.75 (s, 3H), 1.01 (s, 6H), 1.10–2.17 (m, 17H), 2.65 (m, 2H), 7.09 (d, J=8.1 Hz, 1H), 7.48 (s, 1H), 7.51 (d, J=8.5 Hz, 1H); $^{13}$C NMR (75 MHz, CDCl$_3$+CD$_3$OD) δ 13.71, 22.75, 24.98, 25.27, 26.65, 26.87, 28.76, 30.84, 31.46, 34.21, 37.33, 38.22, 43.84, 46.74, 93.92, 124.84, 126.52, 127.32, 129.91, 136.31, 144.94, 168.70, 178.97.

Example 28C

3-Alkoxycarbonyl-1,3,5(10)-estratrien-17(R)-spiro-2'-(5',5'-dimethyl-6'-oxo)tetrahydropyran (108)

A mixture of compound 107, triethylamine (3.25 equiv), palladium acetate (0.07 equiv), 1,3-bis(diphenylphosphino)propane (0.06 equiv), and alcohol (1.5 equiv to large excess) in DMF (10% W/V) was purged with carbon monoxide for 20 min and stirred under a carbon monoxide balloon at 90° C. over a 16 h period. The reaction mixture was cooled at room temperature, diluted with water and extracted with dichloromethane. The organic phase was washed with brine, dried over magnesium sulfate, filtered, and evaporated. The reaction mixture was purified by 3 flash chromatographies (2 times with benzene-acetone 4-1 and hexanes-ethyl acetate 7-3) to provide compound 108 (e.g., EM-1398, R=benzyl, 70%): IR (CHCl$_3$) 2938, 1716, 1293, 1262, 1177, 1152, 1130, 1109, 732 cm$^{-1}$; $^1$H NMR (300 MHz, CDCl$_3$) δ 1.02 (s, 3H), 1.28 (s, 3H), 1.29 (s, 3H), 1.34–1.41 (m, 17H), 2.91

(m, 2H), 5.35 (s, 2H), 7.33–7.45 (m, 6H), 7.79 (s, 1H), 7.83 (d, J=8.1 Hz, 1H); $^{13}$C NMR (75 MHz, CDCl$_3$) δ 14.39, 23.28, 25.55, 25.74, 27.14, 27.64, 27.75, 29.25, 31.56, 31.93, 34.75, 37.77, 38.56, 44.34, 47.16, 48.82, 66.42, 93.50, 125.34, 126.90, 127.45, 128.05, 128.10, 128.52, 130.23, 136.22, 136.81, 145.49, 166.55, 177.75.

Example 28D 3-Carboxy-1,3,5(10)-estratrien-17(R)-spiro-2'-(5',5'-dimethyl-6'-oxo)tetrahydropyran (EM-1401)

Method B: A mixture of compound 108 (350 mg, 0.72 mmol) and 10% palladium on activated carbon (50 mg) in ethyl acetate (40 mL) was stirred under an hydrogen balloon over a 3 h period. The reaction mixture was filtered on celite and evaporated. The crude mixture was purified by flash chromatography (dichloromethane-THF 19-1 to dichloromethane-THF 3-1) to provide the carboxylic acid EM-1401 (240 mg, 84%). A sample was recrystallized in methanol-THF (the characterization was described previously).

Example 28E

3-Carboxamido-1,3,5(10)-estratrien-17(R)-spiro-2'-(5',5'-dimethyl-6'-oxo)tetrahydropyran (109)

Under argon atmosphere, a solution of EM-1401 and pyridine (15 equiv) in dry dichloromethane (1.6% W/V) was cooled at 0° C., treated with oxalyl chloride (6 equiv) and stirred for 0.5 h. The reaction mixture was allowed to reach room temperature and stirred over a 4 h period. The reaction mixture was evaporated, dissolved in dry THF (1.6% W/V), cooled at 0° C., treated with 10 equiv of amine and stirred for 15 min. The reaction mixture was quenched with water, extracted with dichloromethane, dried over magnesium sulfate, filtered, and evaporated. The crude mixture was purified by flash chromatography (hexanes-acetone 19-1 to hexanes-acetone 3-2) to provide compound 109 (e.g., EM-1404, R$^1$=R$^2$=H, 65%): IR (CHCl$_3$) 3433, 3350, 2941, 2873, 1702, 1664, 1611, 1388, 1310, 1159 cm$^{-1}$; $^1$H NMR (300 MHz, CDCl$_3$+CD$_3$OD) δ 0.73 (s, 3H), 0.99 (s, 6H), 1.10–2.16 (m, 17H), 2.64 (m, 2H), 7.08 (d, J=8.0 Hz, 1H), 7.30 (s, 1H), 7.32 (d, J>9 Hz, 1H); $^{13}$C NMR (75 MHz, CDCl$_3$+CD$_3$OD) δ 13.69, 22.72, 24.96, 25.27, 26.64, 26.84, 28.78, 29.09, 30.81, 31.44, 34.19, 37.31, 38.27, 43.72, 46.74, 93.92, 124.20, 124.93, 127.70, 130.00, 136.45, 143.88, 170.63, 178.96.

Example 29

Synthesis of 2-Carboxy/alkoxycarbonyl/carboxamide-3-alkoxy-1,3,5(10)-estratrien-17spiro-(dimethyl-δ-lactone) Derivatives These syntheses are described in Scheme 25.

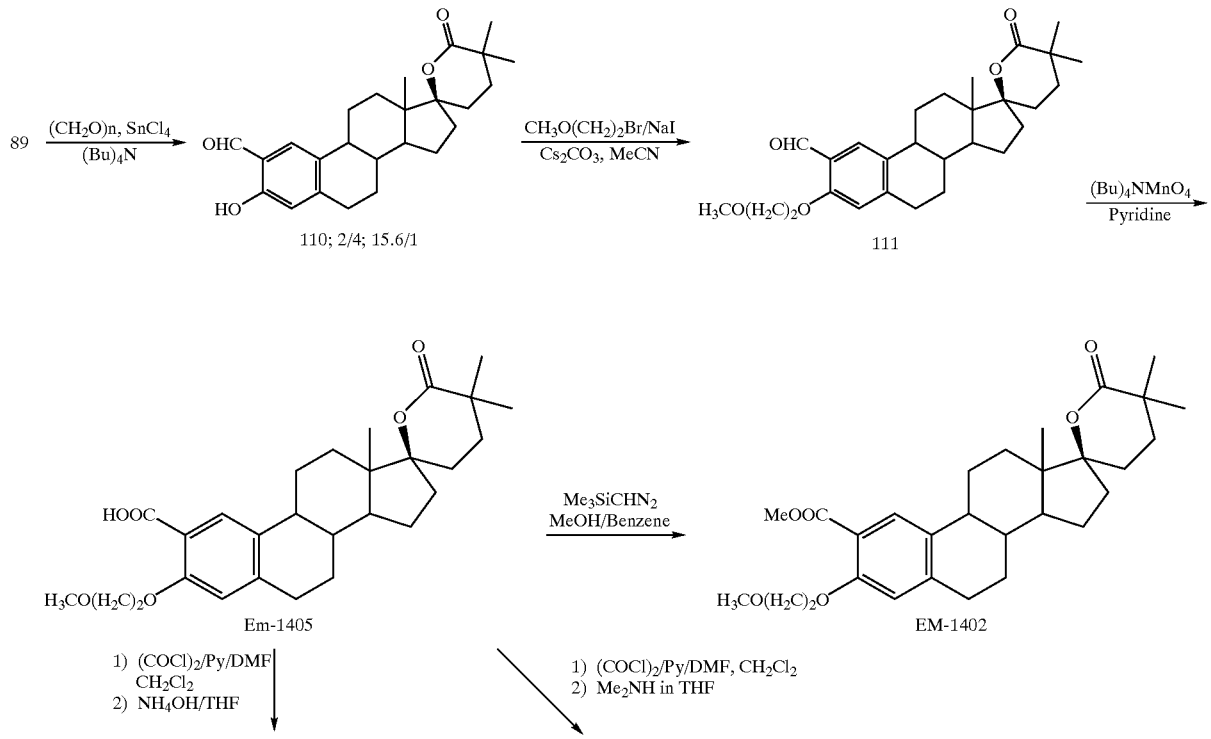

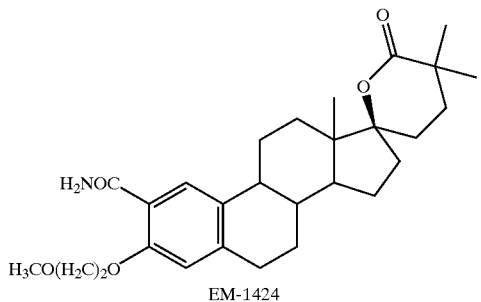

EM-1424

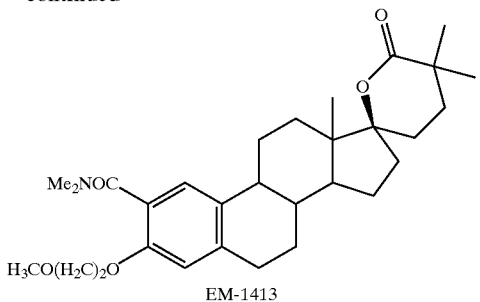

EM-1413

2-Formyl-1,3,5(10)-estratrien-3-ol-17(R)-spiro-2'-(5',5'-dimethyl-6'-oxo)tetrahydropyran (110)

Lactone 89 (1.0 g, 2.72 mmol) was dissolved in dry 1,2-dichloroethane (9 mL) under argon atmosphere. SnCl$_4$ (0.16 mL, 1.37 mmol) and Bu$_3$N (0.52 mL, 2.18 mmol) were added successively. The mixture was stirred at room temperature for 20 min. Formaldehyde (0.23 g, 7.84 mmol) was added and the mixture was stirred at reflux for 6h. The reaction mixture was poured into aq acid (pH=2) and, was extracted with CH$_2$Cl$_2$. The organic layers were washed with brine solution, dried (Na$_2$SO$_4$) filtered and concentrated in vacuo. The crude product was purified by flash chromatography on silica gel, eluting with (95:5 to 80:20) hexanes-acetone to yield 0.74 g (69%) of the product; IR (NaCl cm$^{-1}$): 3164, 2937, 2872, 1716, 1652, 1571, 1487, 1466, 1386, 1298, 1152, 1017, 914, 731; $^1$H NMR (CDCl$_3$) 1.00 (s, 3H), 1.26 (s, 6H) 1.23–2.40 (m, 17H), 2.80–2.90 (m, 2H), 6.66 (s, 1H), 7.39 (s, 1H), 9.79 (s, 1H), 10.77 (s, 1H); $^{13}$C NMR (CDCl$_3$) δ 14.3, 23.2, 25.4, 25.9, 26.8, 27.6, 27.7, 30.0, 31.4, 31.6, 34.6, 37.7, 38.6, 42.9, 47.0, 48.5, 93.4, 116.9, 118.9, 130.3, 132.2, 147.8, 159.2, 177.7, 196.0.

2-Formyl-3-(2"-methoxyethyloxy)-1,3,5(10)-estratrien-17(R)-spiro-2'-(5',5'-dimethyl-6'-oxo) tetrahydropyran (111)

To a solution of aldehyde 110 (0.74 g, 1.87 mmol) in CH$_3$CN (19 mL), Cs$_2$CO$_3$ (0.96 g, 2.95 mmol), NaI (55 mg, 0.37 mmol) and 2-chloroethyl methyl ether (0.86 mL, 9.42 mmol) were added, and the mixture was stirred at reflux for 20 h. The reaction mixture was quenched with brine solution, and was extracted with CH$_2$Cl$_2$. The organic layers were dried (Na$_2$SO$_4$) filtered and evaporated to crude product, which was purified by flash column chromatography (CH$_2$Cl$_2$: Acetone, 95:5) to give 0.62 g (73%) of the desired compound; IR (NaCl, cm$^{-1}$): 2942, 2879, 1714, 1675, 1609, 1459, 1394, 1308, 1269, 1152, 874; $^1$H NMR (CDCl$_3$) δ 1.01 (s, 3H), 1.28 (s, 6H) 1.25–2.20 (m, 16H), 2.35–2.45 (m, 1H), 2.85–2.95 (m, 2H), 3.45 (s, 3H), 3.79 (t, 2H, J=4.7 Hz), 4.20 (t, 2H, J=4.6 Hz), 6.68 (s, 1H), 7.76 (s, 1H), 10.45 (s, 1H); $^{13}$C NMR (CDCl$_3$) δ 14.4, 23.3, 25.6, 26.0, 27.1, 27.7, 27.8, 30.4, 31.6, 31.9, 34.9, 37.8, 38.9, 43.4, 47.3, 48.7, 59.4, 68.3, 70.9, 93.6, 113.0, 123.0, 125.2, 133.1, 146.0, 159.2, 177.8, 189.6.

2-Carboxy-3-(2"-methoxyethyloxy)-1,3,5(10)-estratrien-17(R)-spiro-2'-(5',5'-dimethyl-6'-oxo) tetrahydropyran (EM-1405)

The aldehyde (130 mg, 0.29 mmol) was solubilized in pyridine (4 mL) and n-Bu$_4$NMnO$_4$ (140 mg, 2 eq., 0.38 mmol) (prepared by mixing the aquous solution of KMnO$_4$ and n-Bu$_4$NBr in water and filtering the precipitate) was added to the above solution. After 16 h the mixture was poured in a solution of 300 mg of NaHSO$_3$ in 30 ml of 1 N HCl. The final product was then extracted with ethyl acetate and dried (Na$_2$SO$_4$). Evaporation of solvents under vacuum gave 140 mg of a semi-solid mixture, which was purified on C$_{18}$ reverse phase gel using MeCN:MeOH:H$_2$O in a proportion of 35:35:30 and then 40:35:25 to give the acid (44 mg, 32%); IR (KBr, cm$^{-1}$) 3274, 2944, 2890, 1723, 1613, 1422; $^1$H NMR(CDCl$_3$) δ 10.96 (bs, 1H), 8.08 (s, 1H), 6.73 (s, 1H), 4.32 (t, 2H, J=5.2 Hz), 3.78 (t, 2H, J=4.4 Hz), 3.45 (s, 3H), 2.87–2.88 (m, 2H), 1.28 (s, 6H), 1.02 (s, 3H); $^{13}$C NMR (CDCl$_3$) δ 177.7, 165.7, 155.2, 144.6, 134.6, 130, 115.7, 113.6, 93.5, 69.9, 69.2, 59.1, 48.6, 47.2, 43.4, 38.7, 37.7, 34.8, 31.7, 31.5, 29.9, 27.7, 27.6, 26.9, 25.9, 25.5, 23.2, 14.4.

2-Carbomethoxy-3-(2"-methoxyethyloxy)-1,3,5(10)-estratrien 17(R)-spiro-2'-(5',5'-dimethyl-6'-oxo) tetrahydropyran (EM-1402)

The acid EM-1405 (44 mg, 0.094 mmol) was solubilized in a mixture of ahydrous methanol (2 mL) and anhydrous benzene (4 mL). Then, a 2M solution of TMSCHN$_2$ (250 µL, 0.5 mmol, 5 eq.) in hexane was added and the mixture was stirred for 4 h at room temperature. The solvants were removed under vacuum and the oil was purified on silica gel column using acetone:hexanes as an eluent to give the methyl ester (32 mg, 70%); IR (KBr, cm$^{-1}$) 2941, 2813, 1716, 1611, 1271; $^1$H NMR (CDCl$_3$) δ 7.73 (s, 1H), 6.69 (s, 1H), 4.15 (t, 2H, J=4.8 Hz), 3.86 (s, 3H, J=4.5 Hz), 3.79 (t, 2H), 3.47 (s, 3H), 2.82–2.90 (m, 2H), 1.28 (s, 6H), 1.02 (s, 3H); $^{13}$C NMR (CDCl$_3$) δ 177.7, 166.8, 156.5, 142.8, 132.5, 128.8, 118.0, 114.6, 93.5, 71.0, 69.1, 59.3, 51.7, 48.6, 47.2, 43.4, 38.9, 37.7, 34.7, 31.8, 31.5, 29.8, 27.7, 27.6, 27.1, 25.9, 25.5, 23.2, 14.4.

2-Dimethylcarbamoyl-3-(2"-methoxyethyloxy) 1,3,5 (10)-estratrien 17(R)-spiro-2'-(5',5'-dimethyl-6'-oxo) tetrahydropyran (EM-1413)

To a solution of the acid EM-1405 (50 mg, 0.11 mmol) in anhydrous CH$_2$Cl$_2$ (5 mL) at 0° C., were added pyridine (40 µL, 0.49 mmol) oxalyl chloride (30 µL, 0.34 mmol) and DMF (10 µL, 0.13 mmol). The mixture was allowed to warm to room temperature and stirred over a period of 3 h. The volatiles were removed under vacuum. The dry residue was dissolved in anhydrous CH$_2$Cl$_2$ (10 mL) under argon and cooled to 0° C. A 2M solution of dimethylamine (1 mL, 2.1 mmol) in THF was added and the temperature was raised to 25° C., and the mixture was stirred for 1 h. The reaction mixture was diluted with CH$_2$Cl$_2$, washed with brine, dried (MgSO$_4$) and concentrated to dryness. The residue was purified by silica gel column chromatography with hexanes/acetone (7/3) to afford 35 mg (70%) of the dimethylamide.

IR (NaCl, cm$^{-1}$): 2927, 2871, 1719, 1630, 1148,1134; $^1$H NMR (300 MHz, CDCl$_3$) δ 7.18 (s, 1H), 6.59 (s, 1H), 4.09 (m, 2H), 3.69 (m, 2H), 3.41 (s, 3H), 3.09 (s, 3H), 2.88 (s, 3H), 2.87–2.80 (m, 2H), 2.35–2.22 (m, 1H), 1.98–1.80 (m, 3H), 1.77–1.31 (m, 13H), 1.28 (s, 6H, 2×CH$_3$), 0.88 (s, 3H, 18-Me); $^{13}$C NMR (75 MHz, CDCl$_3$) δ 177.8, 169.7, 152.4, 138.9, 133.1, 125.3, 124.4, 112.7, 93.6, 71.0, 68.2, 59.2, 48.7, 47.3, 43.6, 39.0, 38.3, 37.8, 34.9, 34.7, 31.9, 31.6, 29.8, 27.8, 27.6, 27.4, 26.0, 25.6, 23.3, 14.4.

2-Carbamoyl-3-(2"-methoxyethyloxy)-1,3,5(10)-estratrien 17(R)-spiro-2'-(5',5'-dimethyl-6'-oxo)tetrahydropyran (EM-1424)

The acid of EM-1405 (0.11 mmol) was dissolved in a mixture of CH$_2$Cl$_2$ (5 mL) and THF (5 mL) and cooled to 0° C. 28% of Aq. ammonium hydroxide (260 μL, 23 mmol) was added, and the mixture was allowed to warm to room temperature and stirred over a period of 3 h. The reaction mixture was then diluted with CH$_2$Cl$_2$, washed with brine, dried (MgSO$_4$) and concentrated under reduced pressure. The residue was purified by silica gel column chromatography with hexanes/acetone (6/4) to afford 27 mg (45%) of the amide; IR (NaCl, cm$^{-1}$): 3446, 3335, 3178, 2926, 2872, 1717, 1664, 1589, 1427, 1151, 1134; $^1$H NMR (300 MHz, CDCl$_3$) δ 8.11 (s, 1H), 7.98 (br.s, 1H), 6.67 (s, 1H), 5.64 (br.s, 1H), 4.23–4.20 (m, 2H), 3.79–3.76 (m, 2H), 3.42 (s, 3H), 2.89–2.86 (m, 2H), 2.52–2.45 (m, 1H), 2.16–1.30 (m, 16H), 1.28 (s, 6H, 2×CH$_3$), 1.01 (s, 3H, 18-Me); $^{13}$C NMR (75 MHz, CDCl$_3$) δ 177.8, 167.2, 154.9, 142.5, 133.5, 129.6, 118.9, 113.3, 93.6, 70.5, 68.1, 58.9, 48.7, 47.3, 43.6, 39.0, 37.8, 34.9, 31.9, 31.6, 29.8, 27.8, 27.7, 27.1, 26.1, 25.6, 23.3, 14.4.

Example 30

3-Hydroxy derivatives of 2-cyano-1,3,5(10)-estratrien-17-spiro-(dimethyl-δ-lactone)

These syntheses are described in Scheme 26.

Scheme 26

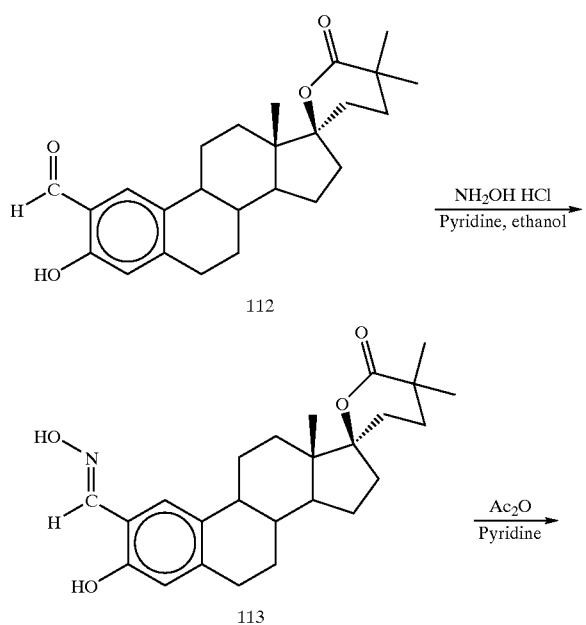

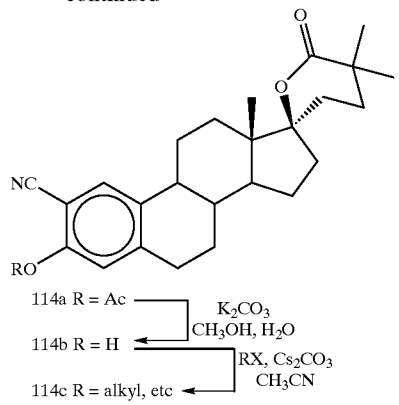

Example 30A

2-Oximino-1,3,5(10)-estratrien-3-ol-17(R)-spiro-2'-(5',5'-dimethyl-6'-oxo)tetrahydropyran (113)

Under argon atmosphere, a solution of compound 112 (215 mg, 0.54 mmol) in anhydrous ethanol-pyridine 1-1 (4 mL) was treated with hydroxylamine hydrochloride (56.6 mg, 0.814 mmol) and stirred at room temperature for 25 min. The reaction mixture was evaporated, diluted with water, and extracted 3 times with dichloromethane. The combined organic phase was washed with brine, dried over sodium sulfate, filtered, and evaporated to provide the oxime 113 (217 mg, 98%): $^1$H NMR (300 MHz, CDCl$_3$) δ 1.02 (s, 3H), 1.29 (s, 6H), 1.43–1.70 (m, 10H), 1.89–2.12 (m, 6H), 2.22–2.37 (m, 1H), 2.80–2.87 (m, 2H), 6.69 (s, 1H), 7.05 (s, 1H), 8.15 (broad s, 1H), 8.20 (s, 1H), 9.61 (s, 1H).

Example 30B

3-Acetoxy-2-cyano-1,3,5(10)-estratrien-17(R)-spiro-2'-(5',5'-dimethyl-6'-oxo)tetrahydropyran (114a)

A solution of compound 113 (180 mg, 0.44 mmol) and acetic anhydride (125 μL, 1.32 mmol) in pyridine (3.5 mL) was refluxed for 1 h. The reaction mixture was evaporated, diluted with dichloromethane, and washed 3 times with water, 1 time with saturated sodium bicarbonate and 1 time with brine. The organic phase was dried over magnesium sulfate, filtered, and evaporated. The crude mixture was purified by flash chromatography (dichloromethane to dichloromethane-ethyl acetate 19-1) to provide acetate 114a (145 mg, 76%): IR (CHCl$_3$) 2933, 2872, 2229, 1773, 1718, 1613, 1494, 1183 cm$^{-1}$; $^1$H NMR (300 MHz, CDCl$_3$) δ 1.02 (s, 3H), 1.28 (s, 6H), 1.34–1.89 (m, 11H), 1.94–2.33 (m, 6H), 2.37 (s, 3H), 2.89–2.94 (m, 2H), 6.95 (s, 1H), 7.55 (s, 1H).

Example 30C

2-Cyano-1,3,5(10)-estratrien-3-ol-17(R)-spiro-2'-(5',5'-dimethyl-6'-oxo)tetrahydropyran (114b)

A solution of compound 114a (135 mg, 0.34 mmol) in methanol (10 mL) was treated with 10% potassium carbonate (1 mL) and stirred 30 min. The reaction mixture was acidified to pH 2 with 1 N hydrochloric acid and extracted 3 times with dichloromethane. The combined organic phase was washed with water, saturated sodium bicarbonate, and brine, dried over magnesium sulfate, filtered, and evaporated. The crude phenol 114b (115 mg, 85%) was directly used for the next step: ¹H NMR (300 MHz, CDCl₃) δ 0.97 (s, 3H), 1.29 (s, 6H), 1.26–2.14 (m, 16H), 2.21–2.28 (m, 1H), 2.82–2.86 (m, 2H), 6.69 (s, 1H), 6.91 (s, 1H), 7.35 (s, 1H).

Example 30D

3-Alkyloxy-2-cyano-1,3,5(10)-estratrien-17(R)-spiro-2'-(5',5'-dimethyl-6'-oxo)tetrahydropyran (114c)

Under argon atmosphere, a suspension of compound 114b, alkyl iodide (5 equiv) and cesium carbonate (1.5 equiv) in anhydrous acetonitrile (1% W/V) was stirred for 16 h with refluxing condition if necessary. The reaction mixture was quenched with brine and extracted 3 times with dichloromethane. The combined organic phase was washed with brine, dried over magnesium sulfate, filtered, and evaporated. The crude mixture was purified by flash chromatography (dichloromethane to dichloromethane-ethyl acetate 10-1) and recrystallization (methanol) to provide compound 114c (e.g., EM-1396, R=(CH₂)₂OCH₃, 75%): IR (CHCl₃) 3013, 2941, 2881, 2229, 1710, 1610, 1500, 1304, 1136 cm⁻¹; ¹H NMR (300 MHz, CDCl₃) δ 1.01 (s, 3H), 1.28 (s, 6H), 1.20–1.75 (m, 10H), 1.80–2.20 (m, 6H), 2.20–2.35 (m, 1H), 2.80–2.95 (m, 2H), 3.47 (s, 3H), 3.79 (t, J=4.8 Hz, 2H), 4.17 (t, J=4.8 Hz, 2H), 6.67 (s, 1H), 7.44 (s, 1H); ¹³C NMR (75 MHz, CDCl₃) δ 14.41, 23.25, 25.58, 25.90, 26.96, 27.66, 27.74, 30.24, 31.59, 31.78, 34.79, 37.80, 38.68, 43.16, 47.20, 48.60, 59.55, 68.78, 70.71, 93.43, 99.55, 112.80, 116.98, 130.72, 133.31, 144.09, 158.29, 177.70.

Example 31

Synthesis of 1,3,5(10)-Estratrien-6-one-17-spiro-(dimethyl-δ-lactones)

These syntheses are described in Schemes 27 and 28.

Scheme 27

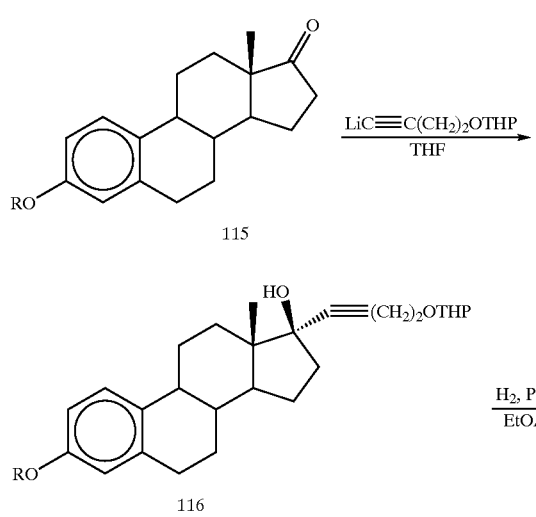

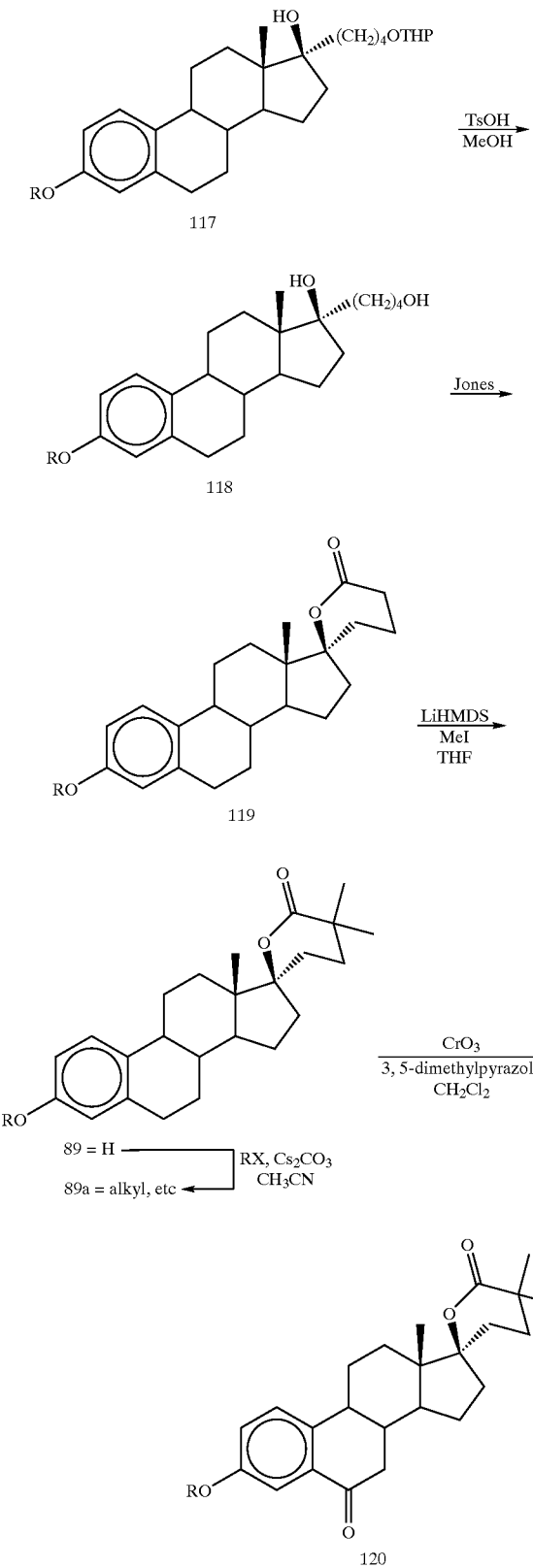

Scheme 28

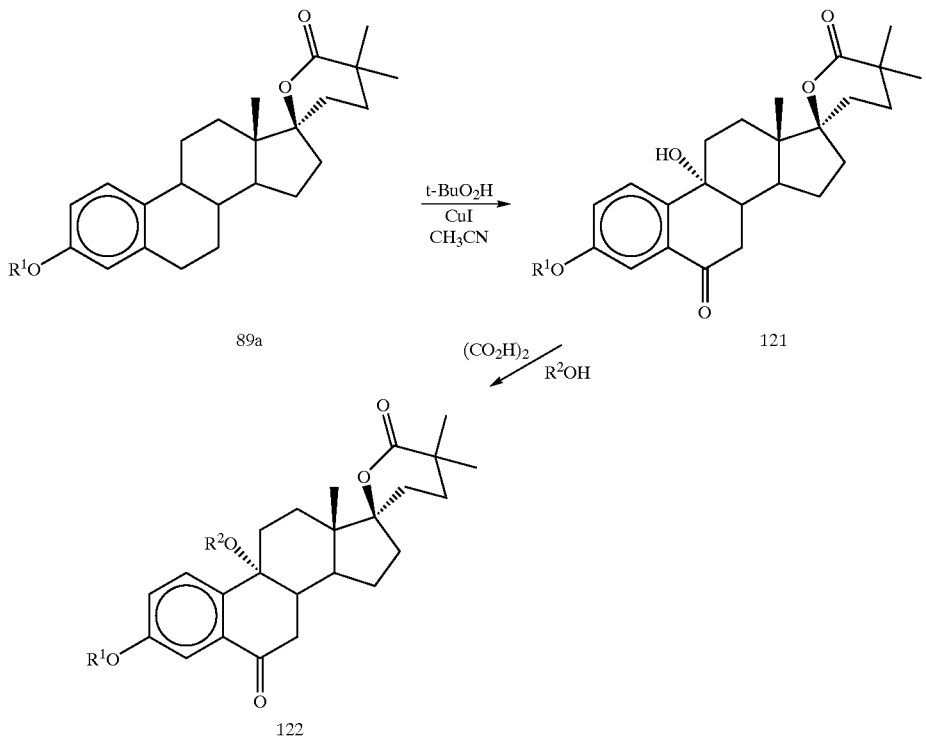

Example 31A

3-Alkoxy-1,3,5(10)-estratrien-6-one-17(R)-spiro-2'-(5',5'-dimethyl-6'-oxo)tetrahydropyran (120)

Under argon atmosphere, a solution of chromium (VI) oxide (10 equiv) in anhydrous dichloromethane (22% W/V) was treated with 3,5-dimethylpyrazole (10 equiv), cooled at −20° C., and stirred 20 min. The reaction mixture was treated with a cool solution (−20° C.) of 3-alkoxy-1,3,5(10)-estratrien-17(R)-spiro-2'-(5',5'-dimethyl-6'-oxo)tetrahydropyran (89a) in anhydrous dichloromethane (29% W/V) and stirred 1.5 h. The reaction mixture was then poured on silica gel and eluted with dichloromethane to dichloromethane-ethyl acetate 3-1. The crude mixture was purified by flash chromatography (hexanes to hexanes-acetone 5-1) to provide compound 120 (e.g., EM-1394, R=Me, 11%): IR (CHCl$_3$) 2990, 2963, 1709, 1678, 1608, 1493, 1217, 1152 cm$^{-1}$; $^1$H NMR (300 MHz, CDCl$_3$) δ 1.03 (s, 3H), 1.29 (s, 6H), 1.47–2.25 (m, 14H), 2.43–2.47 (m, 2), 2.76 (dd, J=2.9 and 16.4 Hz, 1H), 3.85 (s, 3H), 7.11 (dd, J=2.8 and 8.6 Hz, 1H), 7.34 (d, J=8.6 Hz, 1H), 7.56 (d, J=2.8 Hz, 1H); $^{13}$C NMR (75 MHz, CDCl$_3$) δ 14.32, 23.03, 25.37, 25.55, 27.67, 27.76, 31.53, 31.62, 34.61, 37.82, 40.39, 42.65, 44.15, 47.07, 48.61, 55.51, 93.20, 109.69, 121.58, 126.52, 133.29, 139.18, 158.27, 177.60, 197.53.

Example 31B

3-Alkoxy-1,3,5(10)-estratrien-9α-ol-6one-17(R)-spiro-2'-(5',5'-dimethyl-6'-oxo)tetrahydropyran (121)

Under argon atmosphere, compound 89a in acetonitrile (5.5% W/V) was treated with copper iodide (0.01 equiv) and t-butyl hydroperoxide (6.7 equiv), and stirred and heated at 50° C. for 20 h. The reaction mixture was poured into 10% sodium sulfite and extracted with ethyl acetate. The organic phase was washed with saturated sodium bicarbonate, brine and water, dried over magnesium sulfate, filtered, and evaporated. The crude mixture was purified by flash chromatography (hexanes-ethyl acetate 19-1 to hexanes-ethyl acetate 7-3) to provide compound 121 (e.g., EM-1386, R$^1$=CH$_3$, 44%); IR (CHCl$_3$) 3603, 3486, 3012, 2985, 2872, 1710, 1682, 1604, 1494, 1288, 1248, 1144, 1030 cm$^{-1}$; $^1$H NMR (300 MHz, CDCl$_3$) δ 1.04 (s, 3H), 1.29 (s, 6H), 1.40–1.80 (m, 5H), 1.80–2.23 (m, 8H), 2.35 (m, 1H), 2.43 (dd, J=2.5 and J=9.5 Hz, 1H), 2.52 (dd, J=3.7 and 17.6 Hz, 1H), 2.78 (dd, J=8.7 and 12.4 Hz, 1H), 3.86 (s, 3H), 7.13 (dd, J=2.9 and 8.7 Hz, 1H), 7.51 (d, J=8.7 Hz, 1H), 7.56 (d, J=2.9 Hz, 1H); $^{13}$C NMR (75 Hz, CDCl$_3$) δ 13.51, 22.75, 25.75, 27.54, 27.60, 27.70, 31.47, 32.18, 34.75, 37.77, 41.73, 41.96, 46.98, 55.49, 68.96, 93.30, 110.37, 121.24, 125.53, 132.75, 139.96, 159.46, 177.79, 197.85.

Example 31C 3.9α-Dialkoxy-1,3,5(10)-estratrien-6-one-17(R)-spiro-2'-(5',5'-dimethyl-6'-oxo)tetrahydropyran (122)

A solution of compound 121 in methanol (0.8% W/V) was treated with oxalic acid (4 equiv) and a drop of water and refluxed for 0.5 h. The reaction mixture was cooled at room temperature, evaporated and diluted with ethyl acetate. The obtained solution was washed with 5% sodium bicarbonate and brine, dried over magnesium sulfate, filtered, and evaporated. The crude mixture was purified by flash chromatography (hexanes-ethyl acetate 9-1 to hexanes-ethyl acetate 7-3) to provide compound 122 (e.g., R$^1$,R$^2$=CH$_3$, 35%): IR (CHCl$_3$) 2955, 2874, 2824, 1720, 1683, 1604, 1493, 1286, 1268, 1248, 1141 cm$^{-1}$; $^1$H NMR (300 MHz, CDCl$_3$) δ 1.04 (s, 3H), 1.28 (s, 6H), 1.35–2.20 (m, 12H), 2.35 (m, 1H), 2.43

(dd, J=4.6 and 17.9 Hz, 1H), 2.64 (m, 1H), 2.80 (m, 1H), 2.83 (s, 3H), 3.86 (s, 3H), 7.08 (dd, J=2.8 and 8.4 Hz, 1H), 7.39 (d, J=8.4 Hz, 1H), 7.58 (d, J=2.8 Hz, 1H); $^{13}$C NMR (75 MHz, CDCl$_3$) δ 13.79, 22.92, 24.48, 25.81, 27.37, 27.71, 27.77, 31.50, 34.74, 37.29, 37.82, 42.02, 42.74, 46.84, 49.27, 55.52, 72.96, 93.34, 110.89, 119.61, 127.56, 133.75, 136.72, 159.54, 177.79, 198.26.

Example 32

2,3-Oximino-1,3,5(10)-estratrien-17-spiro-(dimethyl-δ-lactone)

This synthesis is described in Scheme 29.

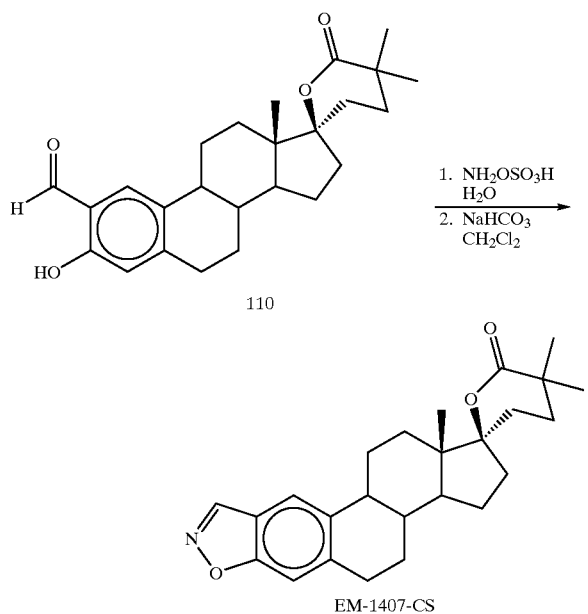

Example 32A

Synthesis of 1,3,5(10)-estratrien-(2,3-oximino)-17 (R)-spiro-2'-(5',5'-dimethyl-6'-oxo)tetrahydropyran (EM-1407-CS)

A solution of hydroxylamine-O-sulfonic acid (14 mg, 0.12 mmol) and sodium sulfate (2 mg, 0.014 mmol) in methanol-water 2-1 (1.5 mL) was treated with compound 110 (40 mg, 0.10 mmol) and stirred for 30 min. The reaction mixture was diluted with water (5 mL) and dichloromethane (5 mL), cooled at −10° C., vigorously stirred for 15 min, treated with sodium bicarbonate (17 mg, 0.20 mmol), and stirred for 30 min. The reaction mixture was allowed to reach room temperature and stirred for 1 h. The two phases were separated, then the aqueous phase was extracted 4 times with dichloromethane. The combined organic phase was dried over magnesium sulfate, filtered, and evaporated. The crude mixture was purified by flash chromatography (hexanes to hexanes-acetone 19-1) to provide the 1,2-benzisoxazole EM-1407-CS (30 mg, 77%): IR (CHCl$_3$) 3013, 2937, 2872, 1708, 1625, 1507, 1299, 1153, 1017 cm$^{-1}$; $^1$H NMR (300 MHz, CDCl$_3$) δ 1.03 (s, 3H), 1.29 (s, 6H), 1.30–180 (m, 1OH), 1.80–2.20 (m, 5H), 2.20–2.45 (m, 2H), 3.01–3.06 (m, 2H), 7.32 (s, 1H), 7.61 (s, 1H), 8.6 (s, 1H); $^{13}$C NMR (75 MHz, CDCl$_3$) δ 14.41, 23.38, 25.59, 26.11, 27.10, 27.67, 27.78, 30.15, 31.59, 31.84, 34.78, 37.81, 38.76, 43.71, 47.20, 49.00, 93.52, 108.70, 117.57, 119.62, 137.00, 140.62, 146.02, 160.96, 177.78.

Example 33

Synthesis of 2-Methyl/2-trifluoromethyl-3-alkoxy-1,3,5(10)-estratrien-17-spiro-(dimethyl-δ-lactone) Derivatives These syntheses are described in Schemes 30 and 31.

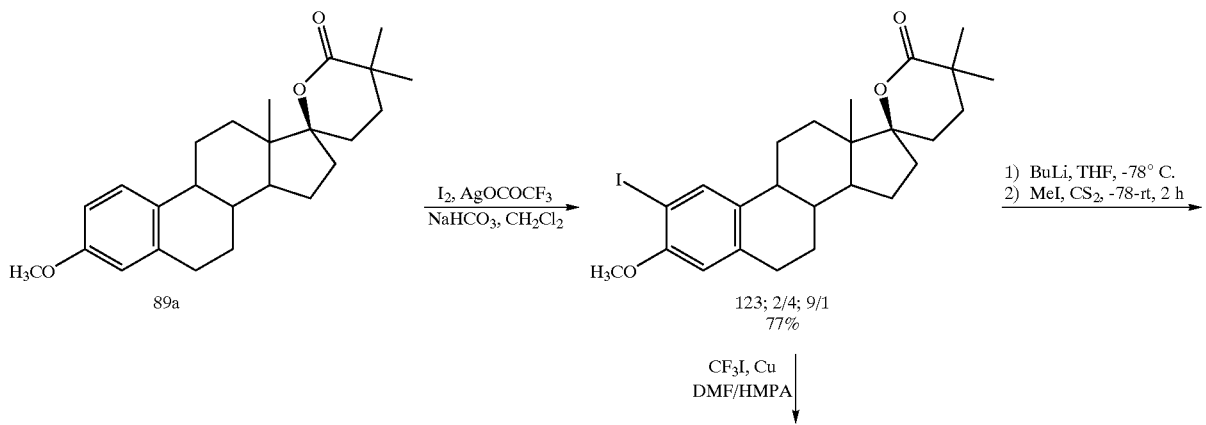

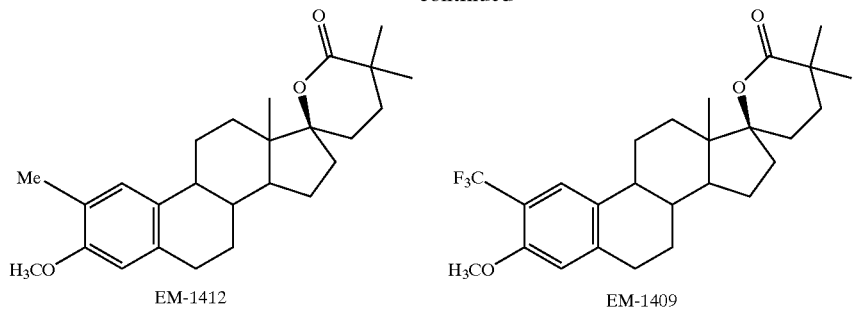
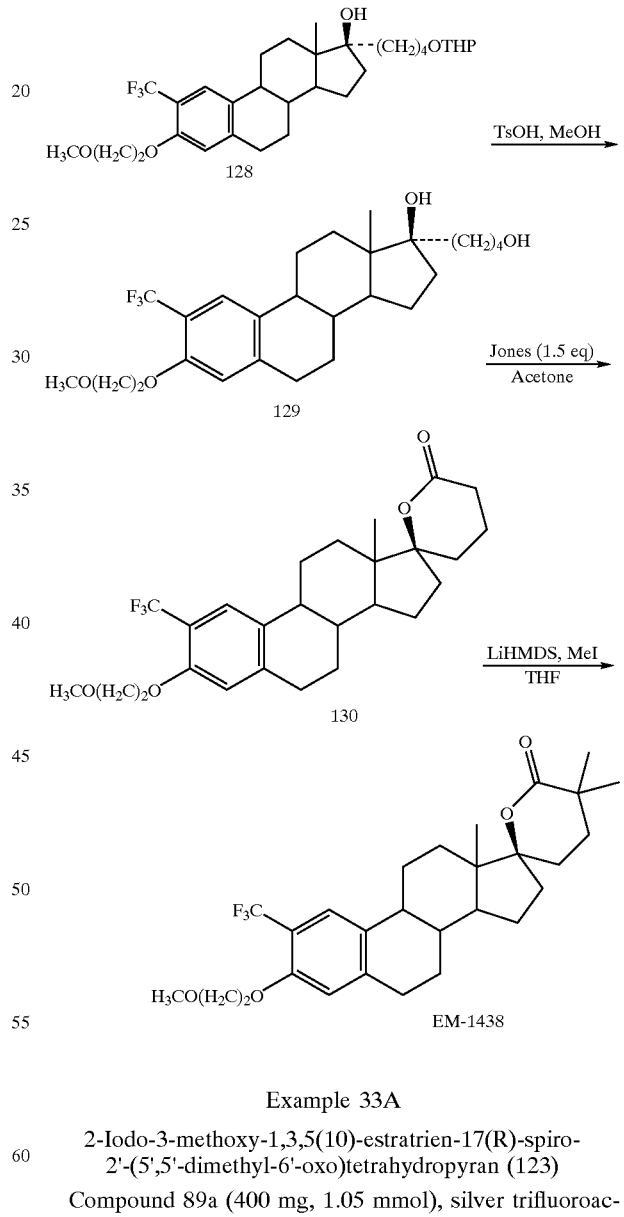
Example 33A
2-Iodo-3-methoxy-1,3,5(10)-estratrien-17(R)-spiro-2'-(5',5'-dimethyl-6'-oxo)tetrahydropyran (123)
Compound 89a (400 mg, 1.05 mmol), silver trifluoroacetate (254 mg, 1.15 mmol) and sodium bicarbonate (439 mg, 5.23 mmol) were mixed in dichloromethane (4 mL) at −30° C. Crushed iodine (278 mg 1.10 mmol) was added and the resulting mixture was stirred vigorously for 1 h during which the red color completely disappeared. The reaction mixture was then filtered and washed with dichloromethane (50 mL), and concentrated. The residue was purified by chromatography on silica gel using hexanes/ethyl acetate (80/20) to afford 412 mg (77%) of the 2-iodo compound as a white solid along with 10% of the 4-iodo compound; IR (KBr, cml): 2955, 1712,1461,1288, 1140; $^1$H NMR (300 MHz, CDCl$_3$) δ 1.0 (s, 3H), 1.25–1.78 (m, 10H), 1.28 (s, 6H), 1.82–2.40 (m, 7H), 2.80–2.84 (m, 2H), 3.83 (s, 3H), 6.54 (s, 1H), 7.63 (s, 1H); $^{13}$C NMR (75 MHz, CDCl$_3$) δ 14.4, 23.3, 25.6, 26.11, 27.3, 27.7, 27.8, 29.6, 31.6, 31.8, 34.8, 37.8, 38.9, 43.3, 47.2, 48.6, 56.3, 82.6, 93.5, 111.4, 134.6, 136.3, 138.2, 156.0, 177.8.

Example 33B

3-Methoxy-2-methyl-1,3,5(10)-estratrien-17(R)-spiro-2'-(5',5'-dimethyl-6'-oxo)tetrahydropyran (EM-1412)

The 2-iodoestrone derivative 123 (300 mg, 0.590 mmol) was dissolved in anhydrous THF (4 mL) and then cooled to −78° C. A 1.6 M solution of BuLi in hexane (390 μL, 0.620 mmol) was added following after 10 min., iodomethane (180 μL, 2.95 mmol) and after 5 min., carbon disulfide (39 μL, 0.65 mmol). The resulting mixture was stirred at −78° C. for 1 h then warmed to room temperature. After 1 h, the solvent was removed and the residue was purified by column chromatography using hexanes/ethyl acetate (85/15) to give a white solid (104 mg, 44%). IR (KBr, cm$^{-1}$): 2932, 1718, 1507, 1202, 1154; $^1$H NMR (300 MHz, CDCl$_3$) δ 1.02 (s, 3H), 1.20–1.80 (m, 10H), 1.29 (s, 6H), 1.80–2.20 (m, 6 H), 2.18 (s, 3H), 2.30–2.40 (m, 1H), 2.75–2.90 (m, 2H), 3.79 (s, 3H), 6.55 (s, 1 H), 7.05 (s, 1H); $^{13}$C NMR (75 MHz, CDCl$_3$) δ 14.4, 15.9, 23.3, 25.6, 26.2, 27.6, 27.6, 27.8, 29.6, 31.6, 32.1, 34.8, 37.8, 39.3, 43.6, 47.3, 48.7, 55.3, 93.7, 110.4, 123.8, 127.6, 131.4, 134.8, 155.7, 177.9.

Example 33C

3-Methoxy-2-trifluoromethyl-1,3,5(10)-estratrien-17 (R)-spiro-2'-(5',5'-dimethyl-6'-oxo)tetrahydropyran (EM-1409)

A pressure reaction bottle was charged with activated copper powder (90 mg, 1.4 mmol), as a suspension in DMF (1 mL) and HMPA (0.8 mL). 2-Iodoestrone derivative 123 (180 mg, 0.354 mmol) was added and the resulting mixture was cooled to −78° C., and an excess of trifluoromethyl iodide was condensed. The pressure bottle was tightly closed and warmed to 130° C. Stirring was maintained for 20 h. The mixture was cooled to room temperature and filtered on silica gel, and washed with a mixture of 25 mL of dichloromethane and 75 mL of ethyl acetate. Evaporation of solvents and column chromatography using hexanes/ ethyl acetate (80/20) gave a white solid (104 mg, 65%); IR (KBr, cm$^{-1}$): 2938, 1713, 1623, 1509, 1299, 1120; $^1$H NMR (300 MHz, CDCl$_3$) δ 1.02 (s, 3H),1.25–1.80 (m, 10H), 1.29 (s, 3H), 1.80–2.25 (m, 6H), 2.34–2.42 (m, 1H), 2.80–2.96 (m, 2H), 3.86 (s, 3H), 6.70 (s, 1H), 7.45 (s, 1H). $^{13}$C NMR (75 MHz, CDCl$_3$) δ 14.4, 23.2, 25.5, 26.0, 27.1, 27.6, 27.7, 29.8, 31.5, 31.9, 34.7, 37.7, 38.9, 43.3, 47.2, 48.5, 93.5, 112.3, 116.0 (q, $J_{C-F}$=31 Hz), 123.9 (q, $J_{C-F}$=272 Hz), 123.9 (d, $J_{C-F}$=6Hz), 131.7, 142.3,155.2, 177.8, 196.7.

Example 33D 3-(2'-Methoxyethoxy)-1,3,5(10)-estratrien-17-one (124)

A mixture of estrone (10 g; 37 mmol), NaI (1.1 g, 7.4 mmol), Cs$_2$CO$_3$ (18.08 g; 55.5 mmol) and Br(CH$_2$)$_2$OCH$_3$ (15 mL; 156 mmol) in CH$_3$CN (200 mL) was refluxed for 1 h. The mixture was filtered over silica gel and washed successively with CH$_2$Cl$_2$ and EtOAc to give the ether (12.1 g; 99.4%); $^1$H NMR (300 MHz, CDCl$_3$) δ 7.23 (d, 1H, J=8.6 Hz), 6.75 (dd, 1H, J=2.6, 8.6 Hz), 6.72 (s, 1H), 4.1 (t, 2H, J=4.4 Hz), 3.74(t, 2H, J=3.7 Hz), 3.44 (s, 3H), 2.87 (dd, 2H, J=4.25, 8.5 Hz), 2.48 (dd, 1H, J=8.4, 18.7 Hz), 0.91 (s, 3H).

Example 33E

2-Iodo-3-(2'-methoxyethyl)-1,3,5(10)-estratrien-17-one (125)

The iodo compound was prepared in 73.5% yield (3.04 g) by following the method, described above; $^1$H NMR (300 MHz, CDCl$_3$) δ 7.64 (s, 1H), 6.57 (s, 1H), 4.12 (t, 2H, J=5.1 Hz), 3.8 (t, 2H, J=4.9 Hz), 3.5 (s, 3H), 2.85 (dd, 2H, J=3.9, 8.5 Hz), 2.5 (dd, 1H, 8.8, 18.8 Hz), 0.90 (s, 3H).

Example 33F 3-(2'-Methoxyethoxy)-2-trifluoromethyl-1,3,5(10)-estratrien-17-one (126)

Was prepared in 66.6% yield (581 mg) by the method, described above; $^1$H NMR (300 MHz, CDCl$_3$) δ 7.45 (s, 1H), 6.72 (s, 1H), 4.15 (t, 2H, J=5.1 Hz), 3.77 (t, 2H, J=5.1 Hz), 3.45 (s, 3H), 2.91 (m, 2H), 2.5 (dd, 1H, 8.9, 18.8 Hz), 0.91 (s, 3H).

Example 33G

17β-Hydroxy3-(2'-methoxyethoxy)-17α-{4'-(2"-tetrahydro-2"H-pyranyl)butyn-1'-yl}-2-trifluoromethyl-1,3,5(10)-estratriene (127)

Was prepared in 63% yield (523 mg) by the method, described above; $^1$H NMR (300 MHz, CDCl$_3$) δ 7.42 (s, 1H), 6.67 (s, 1H), 4.64 (bs, 1H), 4.11 (t, 2H, J=4.5 Hz), 3.84–3.75 (m, 2H), 3.73 (t, 2H, J=4.7 Hz), 3.54–3.46 (m, 3H), 3.41 (s, 3H), 2.82 (bs, 2H), 2.71 (bs, 1H), 2.52 (t, 2H, 6.8 Hz), 0.81 (s, 3H).

Example 33H

17β-Hydroxy-3-(2'-methoxyethoxy)-17α-{4'-(2"-tetrahydro-2"H-pyranyl)butan-1'-yl}-2-trifluoromethyl-1,3,5(10)-estratriene (128)

Was prepared (the crude; 455 mg) by the method, described above; $^1$H NMR (300 MHz, CDCl$_3$) δ 7.44 (s, 1H), 6.7 (s, 1H), 4.59 (bs, 1H), 4.14 (t, 2H, J=5.1 Hz), 3.90–3.80 (m, 2H), 3.76 (t, 2H, J=5 Hz), 3.52–3.43 (m, 2H), 3.45 (s, 3H), 2.87–2.85 (m, 2H), 0.89 (s, 3H).

Example 33I

17β-Hydroxy-3-(2'-methoxyethoxy)-17α-(4'-hydroxybutan-1'-yl)-2-trifluoromethyl-1,3,5(10)-estratriene 17(129)

Was prepared (the crude; 386 mg) by the method described above; $^1$H NMR (300 MHz, CDCl$_3$) δ 7.44 (s, 1H), 6.7 (s, 1H), 4.14 (t, 2H, J=4.9 Hz), 3.77 (t, 2H, J=5.1 Hz), 3.70 (t, 2H, J=5.8 Hz), 3.46 (s, 3H), 2.86 (m, 2H), 0.90 (s, 3H).

Example 33J 3-(2'-Methoxyethoxy)-2-trifluoromethyl-1,3,5(10)-estratrien 17(R)-spiro-2'-(5',5'-dimethyl-6'-oxo) tetrahydropyran (130)

Was prepared in 59% yield (for 3 steps) by the method, described above; $^1$H NMR (300 MHz, CDCl$_3$) δ 7.44 (s, 1H), 6.7 (s, 1H), 4.14 (t, 2H, J=4.2 Hz), 3.77 (t, 2H, J=5.1 Hz), 3.45 (s, 3H), 2.91–2.90 (m, 2H), 1.02 (s, 3H).

Example 33H 3-(2'-Methoxyethoxy)-2-trifluoromethyl-1,3,5(10)-estratrien-17(R)-spiro-2'-(5',5'-dimethyl-6'-oxo) tetrahydropyran (EM-1438)

Was prepared in 88.7% yield by the method described above; IR (KBr, cm$^{-1}$), 3419, 2988, 2939, 2879, 2818, 1718, 1622, 1508, 1298, 1154, 1052; $^1$H NMR (300 MHz, CDCl$_3$) δ 7.43 (s, 1H), 6.7 (s, 1H), 4.13 (t, 2H, J=5.2 Hz), 3.76 (t, 2H, J=4.77 Hz), 3.44 (s, 3H), 2.87 (m, 2H), 2.36–3.32 (m, 1H), 1.27 (s, 6H), 1.01 (s, 3H); $^{13}$C NMR (75 MHz, CDCl$_3$) δ 177.7, 154.5, 142.2, 132.1, 123.9 (d, j$_{C-F}$=5.3 Hz), 123.8 (q, J$_{C-F}$=272 Hz), 116.6 (q, J$_{C-F}$=31 Hz), 113.7, 93.5, 70.8, 68.8, 59.3, 48.6, 47.2, 43.3, 38.9, 37.8, 34.8, 31.8, 31.6, 29.8, 27.7, 27.6, 27.1, 26.0, 25.5, 23.2, 14.4.

Example 34

Synthesis of 1,3,5(10)-estratrien-17-spiro-(diethyl-δ-lactone) Derivatives

These synthesis are described in Scheme 32.

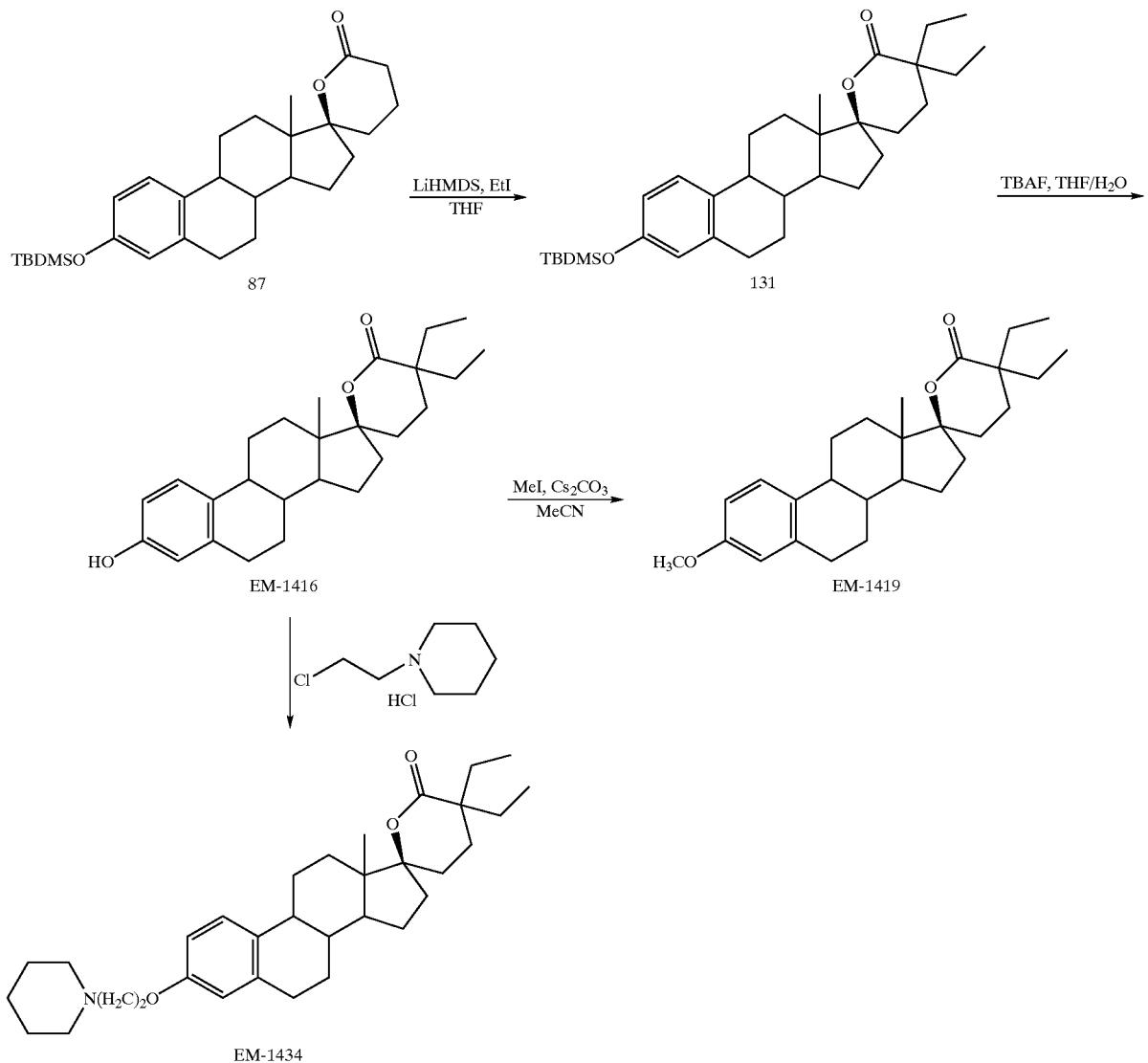

Scheme 32

Example 34A

3-T-butyldimethylsilyloxy-1,3,5(10)-estratrien-17(R)-spiro-2'-(5',5'-diethyl-6'-oxo)tetrahydropyran (131)

In a dry 25 mL flask under argon the lactone 87 (200 mg, 0.44 mmol) in THF (5 mL) was charged and cooled to 0° C. LiHMDS (1.1 mL, 1.1 mmol) was added dropwise. The mixture was stirred 15 minutes at 0° C. and the cooled to −78° C. Ethyl iodide (176 μL, 2.2 mmol) was added, and stirred 1 h at this temperature, and then allowed to warm to room temperature over a period of 2 h. A saturated solution of NH$_4$Cl (5 mL) was added and the mixture was extracted with CH$_2$Cl$_2$. The organic layer was washed with a saturated solution of Na$_2$S$_2$O$_3$ and brine, dried (MgSO$_4$), and concentrated under reduced pressure. The residue was purified by silica gel column chromatography with hexanes/acetone (9/1) as an eluent to afford 193 mg (86%) of diethyl compound; IR (NaCl, cm$^{-1}$): 2933, 2857, 1719, 1496, 1259, 1143, 957, 839; $^1$H NMR (300 MHz, CDCl$_3$) δ 7.11 (d, 1H, 1=8.4Hz), 6.62 (dd, 1H, J=2.1, 8.4Hz), 6.56 (s, 1H), 2.81–2.78 (m, 2H), 2.36–2.25 (m, 1H), 2.19–1.22 (m, 20H), 1.02 (s, 3H, 18-Me), 0.98 (s, 9H), 0.90 (app.q, 6H, J=7.5Hz), 0.19 (s, 6H); $^{13}$C NMR (75 MHz, CDCl$_3$) δ 176.6, 153.3, 137.6, 132.6, 125.9, 119.8, 117.1, 93.0, 48.6, 47.2, 45.3, 43.6, 39.0, 34.5, 31.9, 30.5, 29.5, 27.4, 25.9, 25.6, 24.3, 23.4, 18.1, 14.3, 8.2, −4.5.

Example 34B

1,3,5(10)-Estratrien-3-ol-17(R)-spiro-2'-(5',5'-diethyl-6'-oxo)tetrahydropyran (EM-1416)

The silyl ether (193 mg, 0.38 mmol) was treated with a 1M solution of TBAF (455 μL) to give the hydroxy compound (143 mg, 95%); IR (NaCl, cm$^{-1}$): 3349, 2967, 2930, 2878, 1696, 1682, 1503, 1454, 1146, 910, 732; $^1$H NMR (300 MHz, CDCl$_3$) δ 7.10 (d, 1H, J=8.4Hz), 6.76 (s, 1H, OH), 6.66 (d, 1H, J=8.4 Hz), 6.60 (s, 1H), 2.82–2.77 (m, 2H), 2.36–2.28 (m, 1H), 2.17–1.22 (m, 20H), 0.98 (s, 3H, 18-Me), 0.91 (app.q, 6H, J=7.6 Hz); $^{13}$C NMR (75 MHz, CDCl$_3$) δ 177.8, 154.0, 137.6, 137.6, 131.4, 126.1, 115.3, 112.9, 93.5, 48.5, 47.2, 45.4, 43.5, 39.1, 34.5, 31.9, 31.7, 30.6, 29.4, 27.3, 26.0, 25.6, 24.1, 23.3, 14.2, 8.7.

Example 34C

3-Methoxy-1,3,5(10)-estratrien-17(R)-spiro-2'-(5',5'-diethyl-6'-oxo)tetrahydropyran (EM-1419)

To the alcohol (19 mg, 0.063 nmmol) and Cs$_2$CO$_3$ (31 mg, 0.094 mmol) in acetonitrile (2 mL), was added MeI (40 μL, 0.63 mmol) at room temperature. after 1 h, another MeI (40 μL) was added. The solution was diluted with CH$_2$Cl$_2$, washed with a 10% aq HCl and brine, dried (MgSO$_4$), and concentrated under reduced pressure. The residue was purified by silica gel column chromatography with hexanes/ EtOAc (9/1) to afford 19 mg (97%) of the 3-methoxy compound; IR (NaCl, cm$^{-1}$): 2935, 2877, 1718, 1500, 1462, 1256, 1142, 1037, 731; $^1$H NMR (300 MHz, CDCl$_3$) δ 7.20 (d, 1H, J=8.6 Hz), 6.71 (dd, 1H, J=2.8, 8.6 Hz), 6.63 (d, 1H, J=2.4 Hz), 3.78 (s, 3H), 2.87–2.84 (m, 2H), 2.35–2.31 (m, 1H), 2.17–1.26 (m, 20H), 1.02 (s, 3H, 18-Me), 0.90 (app.q, 6H, J=7.5 Hz); $^{13}$C NMR (75 MHz, CDCl$_3$) δ 176.6, 157.5, 137.8, 132.2, 126.2, 113.8, 111.5, 93.0, 55.2, 48.7, 47.2, 45.4, 43.7, 39.1, 34.6, 31.9, 30.6, 29.7, 27.5, 26.1, 25.7, 24.4, 23.4, 14.4, 8.7.

Example 34D

3-[2'-(N-piperidinyl)ethyl]oxy-1,3,5(10)-estratrien-17(R)-spiro-2'-(5',5'-dimethyl-6'-oxo)tetrahydropyran (EM-1434)

The mixture of alcohol EM-1416 (60 mg, 0.15 mmol), K$_2$CO$_3$ (668 mg, 4.8 mmol) and 1-(2-chloroethyl)-piperidine monohydrochloride (834 mg, 4.5 mmol) in acetonitrile (25 mL) was refluxed for a period of 15 h. The pH was adjusted to a neutral with a 10% aq HCl and then, the mixture was extracted with EtOAc, washed with brine, dried (MgSO$_4$) and concentrated under reduced pressure. The residue was purified by silica gel column chromatography with hexanes/acetone (5/1) to afford 35 mg (46%) of compound; IR (NaCl, cm$^{-1}$): 2934, 1719, 1499, 1256, 1142, 1037; $^1$H NMR (300 MHz, CDCl$_3$): 7.18 (d, 1H, J=8.6 Hz), 6.70 (dd, 1H, J=2.6, 8.6 Hz), 6.63 (d, 1H, J=2.3 Hz), 4.07 (t, 2H, J=6.0 Hz), 2.87–2.81 (m, 2H), 2.75 (t, 2H, J=6.0 Hz), 2.51–2.48(m, 4H), 2.34–2.30 (m, 1H), 2.17–1.25 (m, 26H), 1.01 (s, 3H, 18-Me), 0.90 (app.q, 6H, J=7.5 Hz); $^{13}$C NMR (75 MHz, CDCl$_3$) δ 176.7, 156.7, 137.8, 132.3, 126.2, 114.6, 112.1, 93.0, 65.8, 57.9, 54.9, 48.6, 47.2, 45.4, 43.6, 39.1, 34.6, 31.9, 30.6, 29.7, 27.5, 26.1, 25.9, 25.7, 24.4, 24.2, 23.2, 14.4, 8.7.

Example 35

Synthesis of 1,3,5(10)-Estratrien-17-spiro-(5"-ally/5"-methoxycarbonyl/4"-methyl)-δ-lactone and Lactenone

These syntheses are described in Scheme 33

Scheme 33

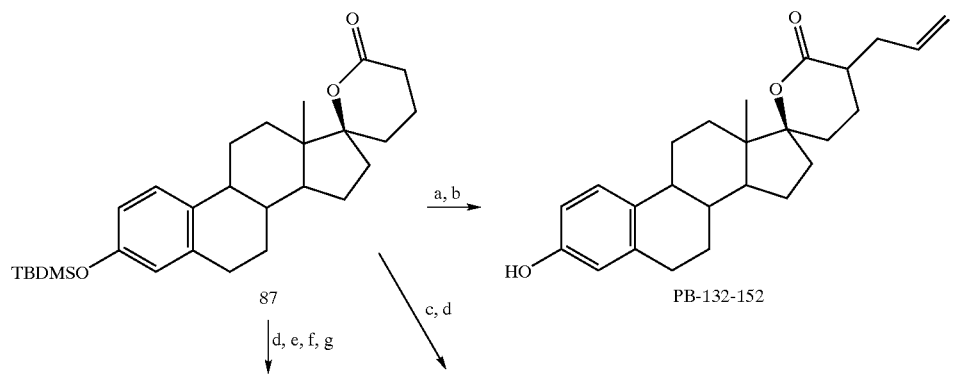

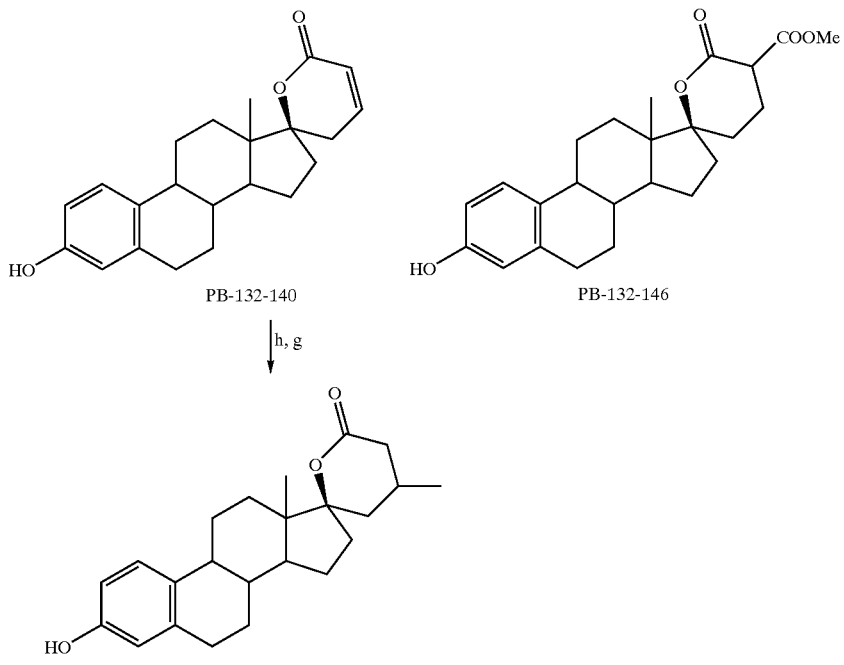

a: NH(isopropyl)₂, nBuLi, HMPA, THF, CH₂=CH—CH₂Br, -78° C. ⟶ room temperature
b: 1M Bu₄NF, 2h, room temperature.
c: NH(isopropyl)₂, nBuLi, HMPA, THF, NC COOCH₃, -78° C.
d: NH(isopropyl)₂, nBuLi, THF, 0° C.
e: PhSeCl, -78° C. ⟶ room temperature
f: H₂O₂, CH₂Cl₂, room temperature.
g: 1M Bu₄NF, 0° C.
h: CuCN, Et₂O, room temperature, CH₃I.

Example 35A

3-Hydroxy-1,3,5(10)-estratrien-17(R)-spiro-2'-(4',5'-dihydro-6'-oxo)-pyran

To a solution of 1.6 mmol of LDA in 20 mL of dry THF was added 380 mg (0.837 mmol) of lactone 87 in 20 mL of dry THF at 0° C. and the mixture was stirred for 30 min. Then, the temperature was dropped to −78° C. and 248 mg (1.29 mmol) of PhSeCl was added. The solution was stirred overnight and let warm to room temperature. The reaction mixture was quenched with water and extracted with EtOAc. The organic phase was washed with water and dried over MgSO₄. After evaporation of solvent, the crude compound was dissolved in 10 mL of CH₂Cl₂ and 0.5 mL of H₂O₂ (30% w/v). After 30 min at room temperature, water was added, and aqueous phase extracted with CH₂Cl₂. The organic phase was washed with water and dried over MgSO₄. The crude compound was purified by flash chromatography with hexanes/EtOAc (95:5) as eluent to give 133 mg (35%) of 3-(tert-butyldimethylsilyloxy)-1,3,5(10)-estratrien-17(R)-spiro-2'-(4',5'-dihydro-6'-oxo)-tetrahydropyran. White solid; IR ν (KBr): 1722 (C=O, lactone); ¹H NMR (CDCl₃) δ 0.18 (s, 6H, Si(CH₃)₂), 0.97 (s, 9H, SiC(CH₃)₃), 1.01 (s, 3H, 18-CH₃), 2.81 (m, 2H, 6-CH₂), 6.03 (d, J₁=9.8 Hz, 1H, 3'-CH), 6.55 (d, 1H, J=2.1 Hz, 4-CH), 6.60 (dd, J₁=2.5 Hz and J₂=8.5 Hz, 2H, 2-CH), 6.80 (m, 1H, 2'-CH), 7.09 (d, J=8.4 Hz, 1H, 1-CH); ¹³C NMR (CDCl₃) δ −4.42 (Si(CH₂)₂), 14.06 (C-18), 22.94 (C-15), 25.68 (SiC(CH₃)₃), 26.23 (C-11), 27.42 (C-7), 29.49 (C-6), 31.35 (C-12), 34.26 (C-16), 36.13 (C-2'), 38.98 (C-8), 43.63 (C-9), 47.22 (C-13), 49.17 (C-14), 91.91 (C-17), 117.22 (C-2), 119.95 (C-4), 121.54 (C-1'), 126.01 (C-1), 132.44 (C-10), 137.59 (C-5), 144.21 (C-3'), 154.41 (C-3), 164.56 (C=O, lactone).

The TBDMS group of the above compound (133 mg, 0.294 mmol) was cleaved at 0° C. using 0.16 mL of 1 M Bu₄NF solution in THF (0.16 mmol). After evaporation of solvent, the crude compound was purified by flash chromatography with hexanes/EtOAc (7:3) as eluent to give 97 mg (97%) of 3-hydroxy-1,3,5(10)-estratrien-17(R)-spiro-2'-(4',5'-dihydro-6'-oxo)pyran (PB-132-140). White solid; IR ν (KBr): 3235 (OH, phenol), 1691 (C=O, lactone); ¹H NMR (CDCl₃ 90% and CD₃OD 10%) δ 0.84 (s, 3H, 18-CH₃), 2.62 (m, 2H, 6-CH₂), 5.86 (d, J₁=9.9 Hz, 1H, 3'-CH), 6.40 (d, 1H, J=2.2 Hz, 4-CH), 6.45 (dd, J₁=x Hz and J₂=x Hz, 2H, 2-CH), 6.75 (m, 1H, 2'-CH), 6.93 (d, J=8.4 Hz, 1H, 1-CH); ¹³C NMR (CDCl₃ 90% and CD₃OD 10%) δ 13.73 (C-18), 22.66 (C-15), 26.09 (C-11), 27.17(C-7), 29.29 (C-6), 31.12 (C-12), 34.05 (C-16), 35.84 (C-1), 38.91 (C-8), 43.34 (C-9), 47.82 (C-13), under solvent pics (C-14), 92.15 (C-17), 112.58 (C-2), 115.02 (C-4), 120.82 (C-2'), 126.00 (C-1), 130.80 (C-10), 137.56 (C-5), 145.09 (C-3), 154.28 (C-3), 165.36 (C=O, lactone). EI-HRMS: calcd for C₂₁H₂₆O₃ (M⁺) 338.18820, found 338.18638

Example 35B

3-Hydroxy-1,3,5(10)-estratrien-17(R)-spiro-2'-(4'-methyl-6'-oxo)tetrahydropyran (PB-132-142)

To a solution of 24 mg (0.271 mmol) of CuCN in 5 mL of dry Et₂O at room temperature was added 0.377 mL (0.528 mmol) of CH₃I. After 30 min, a solution of 30 mg (0.066 mmol) of TBDMS-derivative of compound PB-132-140 in dry $Et_2O$ was added at −78° C. The solution was stirred overnight and let reheat to room temperature. The solution was then quenched at −20° C. with aqueous $NH_4Cl$ and extracted with EtOAc. The organic phase was washed with water and dried over $MgSO_4$. The crude compound was purified by flash chromatography with hexanes/EtOAc (9:1) as eluent to give 24 mg (78%) of intermediate compound. As described above the TBDMS group of this later compound was cleaved using 0.07 mL of 1 M $Bu_4NF$ solution in THF (0.07 mmol) at 0° C. After evaporation of solvent, the crude compound was purified by flash chromatography with hexanes/EtOAc (7:3) as eluent to give 17 mg (73% two steps) of p-methylated lactone PB-132-142. White solid; IR ν (film): 3330 (OH, phenol), 1694 (C=O, lactone); $^1$H NMR ($CDCl_3$) δ 0.99 (s, 3H, 18-$CH_3$), 1.04 (d, J =6.2 Hz, 3H, $CH_3$ of lactone ring), 2.56 (dm, J=13.9 Hz, 1H), 2.80 (m, 2H, 6-$CH_2$), 6.58 ($S_{app}$, 1H, 4-CH), 6.63 (dd, $J_1$=8.4 Hz and $J_2$=2.5 Hz, 1H, 2-CH), 7.12 (d, J=8.4 Hz, 1H, 1-CH); $^{13}$C NMR ($CDCl_3$) δ 14.78 (C-18), 21.76 (C-1'), 22.90 (C-15), 25.05 (C-3'), 26.22 (C-11), 27.36 (C-7), 29.55 (C-6), 29.67 ($CH_3$ of lactone), 33.21 (C-12), 38.28 (C-16), 39.25 (C-8), 40.19 (C-2'), 43.45 (C-9), 48.14 (C-13), 49.37 (C-14), 93.63 (C-17), 112.82 (C-2), 115.31 (C4), 126.37 (C-1), 131.87 (C-10), 138.01 (C-5), 153.73 (C-3), 172.23 (C=O, lactone). EI-HRMS: calcd for $C_{23}H_{30}O_3$ ($M^+$) 354.21948, found 354.21791.

Example 35C

3-Hydroxy-1,3,5(10)-estratrien-17(R)-2'-(5'-allyl-6'-oxo)tetrahydropyran (PB-132-152)

The allylation of lactone 87 (50 mg, 0.11 mmol) was conducted at −78° C. with LDA (0.45 mmol), HMPA (0.12 mmol) and allylbromide (0.72 mmol). The mixture was stirred overnight and let warm to room temperature. Without purification the crude lactone was treated for 2 h with a solution in THF of 0.12 ml of 1 M $Bu_4NF$ (0.12 mmol). Then, the crude allyl derivative was purified by flash chromatography with hexanes/EtOAc (9:1) as eluent to give 33 mg (79% two step) of allyl-lactone PB-132-152. White solid; IR ν (film): 3348 (OH, phenol), 1699 (C=O, lactone); $^1$H NMR ($CDCl_3$) δ 1.00 (s, 3H, 18-$CH_3$), 2.82 (m, 2H, 6-$CH_2$), 5.09 (d, J=8.8 Hz, 1H, $CH_2CH=CH_2$), 5.11 (d, J=19.6 Hz, 1H, $CH_2CH=CH_2$), 5.79 (m, 1H, $CH_2CH=CH_2$), 6.57 (d, J=2.5 Hz, 1H, 4-CH), 6.64 (dd, $J_1$=8.4 Hz and $J_2$=2.5 Hz, 1H, 2-CH), 7.13 (d, J=8.4 Hz, 1H, 1-CH); $^{13}$C NMR ($CDCl_3$) δ 14.34 (C-18), 20.25, 21.30 (C-2'), 21.63, 23.40 and 23.58 (C-15), 25.61, 26.09 (C-11), 27.28, 27.40, 28.27 (C-1'), 29.53 (C-6), 29.67 (C-1"), 31.95 (C-12), 34.00 (C-3'), 34.50 (C-16), 35.96, 38.13, 39.12 (C-8), 40.50, 43.63 (C-9), 47.22 (C-13), 48.62 and 48.76 (C-14), 92.85 and 93.57 (C-17), 112.81 (C-2), 115.30 (C-4), 117.35 and 117.63 (C-2"), 126.35 (C-1), 131.91 (C-10), 135.04 and 135.29 (C-3"), 137.96 (C-5), 153.78 (C-3), 173.87 and 174.79 (C=O, lactone).

Example 35D

3-Hydroxy-1,3,5(10)-estratrien-17(R)-2'-(5'-methoxycarbonyl-6'-oxo)tetrahydropyran (PB-132-146)

At 0° C., a solution of lactone 87 (50 mg, 0.11 mmol) in dry THF was added to 0.41 mmol of LDA and the mixture was cooled to −78° C. Then, HMPA (20 μL, 0.12 mmol) and $NCCOOCH_3$ (31 μL, 0.45 mmol) were added. Without purification the crude lactone was treated for 2 h with a solution in THF of 0.13 ml of 1 M $Bu_4NF$ (0.13 mmol). The crude phenol was purified by flash chromatography with hexanes/EtOAc (6:4) as eluent to give 32 mg (73% two steps) of methoxycarbonyl-lactone PB-132-146. White solid; IR ν (film): 3372 (OH, phenol), 1744, 1720, 1710 (C=O, lactone and $COOCH_3$); $^1$H NMR ($CDCl_3$) δ 1.02 (s, 3H, 18-$CH_3$), 2.82 (m, 2H, 6-$CH_2$), 3.46 (dd, $J_1$=7.5 Hz and $J_2$=10.7 Hz, 0.5H, CH of lactone), 3.54 (dd, $J_1$=5.9 Hz and $J_2$=7.8 Hz, 0.5H, CH of lactone), 3.79 and 3.80 (2s, 3H, $COOCH_3$), 6.57 ($s_{app}$, 1H, 4-CH), 6.63 (dd, $J_1$=8.1 Hz and $J_2$=2.2 Hz, 1H, 2-CH), 7.13 (d, J=8.4 Hz, 1H, 1-CH); $^{13}$C NMR ($CDCl_3$) δ 14.33 (C-18), 20.00 and 20.68 (C-2'), 23.46 (C-15), 26.02 (C-11), 26.26 (C-1'*), 27.39 (C-7), 29.52 (C-6), 29.68, 31.85 and 31.97 (C-12), 34.03 and 34.34 (C-16), 39.10 (C-8), 43.61 (C-9), 46.30, 47.43 and 47.93 (C-13), 48.72 and 48.83 (C-14), 52.79 (COO$CH_3$), 94.36 and 94.55 (C-17), 112.79 (C-2), 115.28 (C-4), 126.40 (C-1), 131.99 (C-10), 138.01 (C-5), 153.62 (C-3), 167.28 and 167.94 ($C$OO$CH_3$), 169.93 (C=O, lactone); EI-HRMS: calcd for $C_{24}H_{30}O_5$ ($M^+$) 398.20932, found 398.21077.

SYNTHESIS OF PREFERRED TYPE 3 17β-HSD INHIBITORS

Example 36

Example 36A

Syntheses of 3-thio-3-deoxy Estrone Derivatives

General procedure for 3-alkylation of 3-thio-3-deoxy-estrone

To a solution of 3-thio-3-deoxyestrone in DMF under Ar(g) was added 1.05 molar equivalent of NaH (60% in oil) at 0° C. After 1 h, 1.2 molar equivalent of the appropriate alkyl halide chain was added and the solution was stirred at room temperature overnight. The solution was poured onto cold water then was extracted with EtOAc. The organic phase was washed with brine, dried with $MgSO_4$, filtered then evaporated under reduced pressure to give the crude product which was purified by flash chromatography on $SiO_2$ using a mixture of EtOAc/Hexanes.

3-Methoxymethylthio-Estra-1,3,5(10)-trien-17-one (EM-1064)

Using 3-thioestrone (600 mg, 2.1 mmol) and chloromethyl methyl ether (202 mg, 2.51 mmol) to give EM-1064 as white solid (488 mg, 72%), Mp: 55° C., $[\alpha]^{25}_D$+88.9° (c1.6, $CH_2Cl_2$); IR: 2929, 2820, 2249, 1970, 1738, 1594, 1557, 1485, 1453, 1404, 1373, 1305, 1259, 1182, 1083, 1052, 1008, 951, 898, 860, 820, 777, 732, 693, 679, 582, 559, 483 $cm^{-1}$; $^1$H NMR($CDCl_3$) δ 0.91 (3H, s), 1.43–1.63 (6H, m), 1.95–2.49 (7H, m), 2.90 (2H,dd, J1=4.6 Hz, J2=4.0 Hz), 3.43 (3H,s), 4.93 (2H,s), 7.21–7.26 (3H,m). $^{13}$C NMR ($CDCl_3$) δ 13.8, 21.6, 25.7, 26.4, 29.3, 31.6, 35.9, 38.1, 44.3, 48.0, 50.5, 56.0, 76.6, 126.0, 128.0, 131.0, 132.5, 137.4, 138.7, 220.8. HRMS: 330.16534 $C_{20}H_{26}O_2S$.

3-Methylthioethylthio-Estra-1,3,5(10)-trien-17-one (EM-1065)

Using 3-thioestrone (406 mg, 1.4 mmol) and 2-chloroethyl methyl sulfide (188 mg, 1.7 mmol) to give EM-1065 as a white solid (187 mg, 37%), Mp: 74° C., $[\alpha]^{25}_D$ −58.2° (c2.0, $CH_2Cl_2$); IR: 2927, 2859, 2247, 1737, 1593, 1556, 1484, 1453, 1436, 1404, 1373, 1339, 1260, 1202, 1120, 1082, 1051, 1007, 964, 912, 859, 821, 777, 733, 646, 581, 559 cm$^{-1}$; $^1$H NMR(CDCl$_3$) δ 0.91 (3H, s), 1.44–1.63 (6H, m), 1.95–2.55 (7H, m), 2.13 (3H, s), 2.70 (2H, dd, J$_1$=1.9 Hz, J$_2$=4.4 Hz), 2.89 (2H, dd, J1=4.7 Hz, J2=4.0 Hz), 3.08 (2H, dd, J$_1$=4.9Hz, J$_2$=5.5 Hz), 7.12 (1H, d, J=6.7 Hz), 7.16 (1H, s), 7.22 (1H, d, J=8.2 Hz). $^{13}$C NMR(CDCl$_3$) δ 13.8, 15.5, 21.6, 25.7, 26.4, 29.3, 31.6, 33.7, 35.8, 38.1, 44.2, 48.0, 50.5, 126.1, 127.6, 130.7, 132.2, 137.5, 138.5, 220.7 ppm. HRMS: 360.15817 (C$_{21}$H$_{28}$OS$_2$).

Example 36B

Synthesis of Estrone Derivatives.

3-Methylthiomethyloxy-1,3,5(10)-estratrien-17-one (EM-1066)

To a solution of estrone (2.0 g, 7.39 mmol) in anhydrous DMF under Ar (g), was added NaH (60% in oil, 0.26g, 11.0 mmol). After the evolution of hydrogen had ceased, the solution was cooled in an ice bath for the addition of CH$_3$SCH$_2$Cl (3.56 g, 36.9 mmol, 3.08 mL) and DMAP (0.09 g, 7.0 mmol). The solution was stirred in a cold room (4° C.) for 16 hours. The reaction was stopped with cold water, extracted with ethyl acetate, wash with water and brine, dry over MgSO$_4$, filtered and concentrated under reduce pressure. The crude extract was purified by flash chromatography on silica gel column and eluted with EtOAc:hexanes (1:9), to give EM-1066 (0.7 g, 30%) as a white solide; Rf 0.5 (3:7 EtOAc/Hexanes); M.p.65° C.; [α]$_D^{26}$ +116.40 (c 1.06, CHCl$_3$); IR (v) 2919, 2864, 1735, 1604, 1577, 1497, 1448, 1375, 1282, 1255, 1211, 1151, 1051, 989, 885, 823, 787, 739,640–690, 579 cm$^{-1}$; $^1$H NMR δ 2.24 (3H, s, CH$_3$—S), 5.12 (2H, s, S—CH$_2$—O), 7.21 (1H, d, J=2.8 Hz, 1'-CH), 6.76 (2H, dd, j$_1$=2.8 Hz and J$_2$=8.6 Hz, 2'-CH), 6.70 (1H, d, J=8.0 Hz, 4'-CH).

Example 36C

3-Methyloxymethyloxy-1,3,5(10)-estratrien-17-one (EM-1070)

To a solution of estrone (55 mg, 0.203 mmole) in anhydrous dichloromethane (20 mL) under Ar (g) was added diisopropylethylamine (580.5 µL, 3.33 mmole). The solution was cooled down to 0° C. and chloromethylmethylether (110 µL, 1.45 mmole) was added. The solution was refluxed lightly overnight after which was added aqueous 1M HCl (40 mL). The solution was extracted 2 times with dichloromethane, washed with brine, dried with magnesium sulfate, filtered and concentrated in vacuo. The yellow solid was purified on silica gel (20 g, 1:9 ethyl acetate/hexanes) to give EM-1070 as yellowish crystals (62 mg, 96%). m.p.; [α]D$^{25}$ +103.9° (c 1.12, CDCl$_3$); IR (NaCl) 2926, 1737 (s,C=O), 1669, 1498, 1243, 1152, 1077, 1006 cm$^{-1}$; $^1$H NMR (CDCl$_3$) δ 0.91 (3H,s, 18-CH3), 1.25–1.78 (6H, m), 1.90–2.38 (5H, m), 2.40–2.55 (2H, m), 2.89 (2H, m, 6-CH$_2$), 3.48 (3H, s, CH$_3$O), 5.15 (2H, s, CH3OC<u>H</u>$_2$), 6.79 (1H, d, J=2.4 Hz, 4-CH), 6.84 (1H, dd, J$_1$=8.4Hz and J$_2$=2.6Hz, 2-CH), 7.21 (1H, d, J=8.6 Hz, 1-CH).

Example 36D

3-Ethyloxyethyloxy-1,3,5(10)-estratrien-17-one (EM-1071)

To a solution of estrone (495 mg, 1.83 mmole) in anhydrous acetonitrile (150 mL) under Ar (g) was added dry potassium carbonate (291 mg, 2.11 mmole) and 2-chloroethylethylether (2.6 mL, 23.77 mmole). The solution was refluxed for 36 hours then concentrated and ethyl acetate (175 mL) was added. The solution was washed with water (2 times), with brine (2 times), dried with magnesium sulfate, filtered and then concentrated in vacuo. The white solid was purified on RP-18 (40–63 µm) gel (40 g, 100% methanol) to give EM-1071 as white crystals (588 mg, 94%). m.p.; [α]D$^{25}$ +129.6° (c 3.06, CDCl$_3$); IR (NaCl) 2928, 2867, 1739 (s,C=O), 1609, 1574, 1499, 1454, 1373, 1310, 1281, 1255, 1158, 1122, 1064, 1007, 957, 924, 875, 818, 781, 650, 581 cm$^{-1}$; $^1$H NMR (CDCl$_3$) δ 0.91 (3H,s, 18-CH3), 1.24 (3H, t, J=6.7 Hz, C<u>H</u>$_3$CH$_2$), 1.24–1.78 (6H, m), 1.90–2.38 (5H, m). 2.40–2.55 (2H, m), 2.88 m, 6-CH2), 3.60 (2H, q, J=7.2 Hz, CH$_3$C<u>H</u>$_2$), 3.78 (2H, t, J=5.2 Hz, C<u>H</u>$_2$CH2O), 4.10 (2H, t, J=4.8 Hz, CH$_2$OPh), 6.68 (1H, d, J=2.5Hz, 4-CH), 6.74 (1H, dd, J$_1$=8.5 Hz and J$_2$=2.7 Hz, 2-CH), 7.19 (1H, d, J=8.6Hz, 1-CH).

Example 36E

3-Methyloxyethyloxy-1,3,5(10)-estratrien-17-one (EM-1073)

To a solution of estrone (502 mg, 1.86 mmole) in anhydrous acetonitrile (250 mL) under Ar (g) was added potassium carbonate (547 mg, 3.96 mmole) and 2-chloroethylmethylether (16.6 mL, 182 mmole). The solution was refluxed for 72 hours, concentrated and ethyl acetate (175 mL) was added. The solution was washed with water (2 times) with brine (2 times), dried with magnesium sulfate, filtered and then concentrated in vacuo. The brownish powder was purified on silica gel (40 g, 1:15 ethyl acetate/hexanes) to give EM-1073 as white crystals (232 mg, 38%). m.p.; [α]D$^{25}$ +134.0° (c 1.06, CHCl$_3$); IR (NaCl) 2927, 2872, 1738 (s,C=O), 1609, 1574, 1499, 1454, 1406, 1372, 1338, 1311, 1281, 1256, 1198, 1158, 1128, 1065, 1036, 1007, 954, 868, 818, 781 cm$^{-1}$; $^1$H NMR (CDCl$_3$) δ 0.90 (3H,s, 18-CH$_3$), 1.25–1.78 (6H, m), 1.90–2.38 (5H, m). 2.40–2.55 (2H, m), 2.87 (2H, m, 6-CH$_2$), 3.44 (3H, s, CH$_3$O), 3.73 (2H, t, J=5.1 Hz, CH$_3$OC<u>H</u>$_2$), 4.09 (2H, t, J=4.4 Hz, CH$_2$OPh), 6.68 (1H, d, J=2.8 Hz, 4-CH), 6.74 (1H, dd, J$_1$=8.5 Hz and J$_2$=2.8 Hz, 2-CH), 7.19 (1H, d, J=8.6 Hz, 1-CH).

Example 36F

3-Butyloxy-1,3,5(10)-estratrien-17-one (EM-1074)

To a solution of estrone (508 mg, 1,88 mmole) in anhydrous dimethylformamide (75 mL) under Ar (g) was added 60% sodium hydride in oil (89 mg, 2.23 mmole). After the evolution of hydrogen had ceased bromobutane (596 µL, 5.55 mmole) was added. The reaction mixture was keep at 80° C. overnight after which was added 10g of ice. The solution was extracted 3 times with ethyl acetate, washed 4 times with brine, dried with magnesium sulfate, filtered and then concentrated in vacuo. The yellowish solid was purified on silica gel (40 g, 1:9 ethyl acetate/hexanes) to give EM-1074 as white crystals (559 mg, 91%). m.p.; [α]D$^{25}$ +138.5° (c 0.53, CHCl$_3$); IR (NaCl) 3448, 2960, 2936, 2867, 1735 (s,C=O), 1612, 1571, 1493, 1474, 1439, 1390, 1349, 1280, 1257, 1222, 1185, 1156, 1115, 1055, 1007, 969, 918, 872, 821, 782, 738, 657,581 cm$^{-1}$; $^1$H NMR (CDCl$_3$) δ 0.90 (3H, s, 18-CH3), 0.96 (3H, t, J=7.3 Hz, C<u>H</u>$_3$CH$_2$), 1.18–1.78 (10H, m), 1.90–2.30 (5H, m). 2.36–2.55 (2H, m), 2.88 (2H, m, 6-CH$_2$), 3.93 (2H, t, J=6.6 Hz, CH$_2$O), 6.64 (1H, s, 4-CH), 6.70 (1H, d, J=8.5 Hz, 2-CH), 7.18 (1H, d, J=8.6 Hz, 1-CH).

Example 37

Synthesis of Androstane Derivatives

These syntheses are described in Scheme 34.

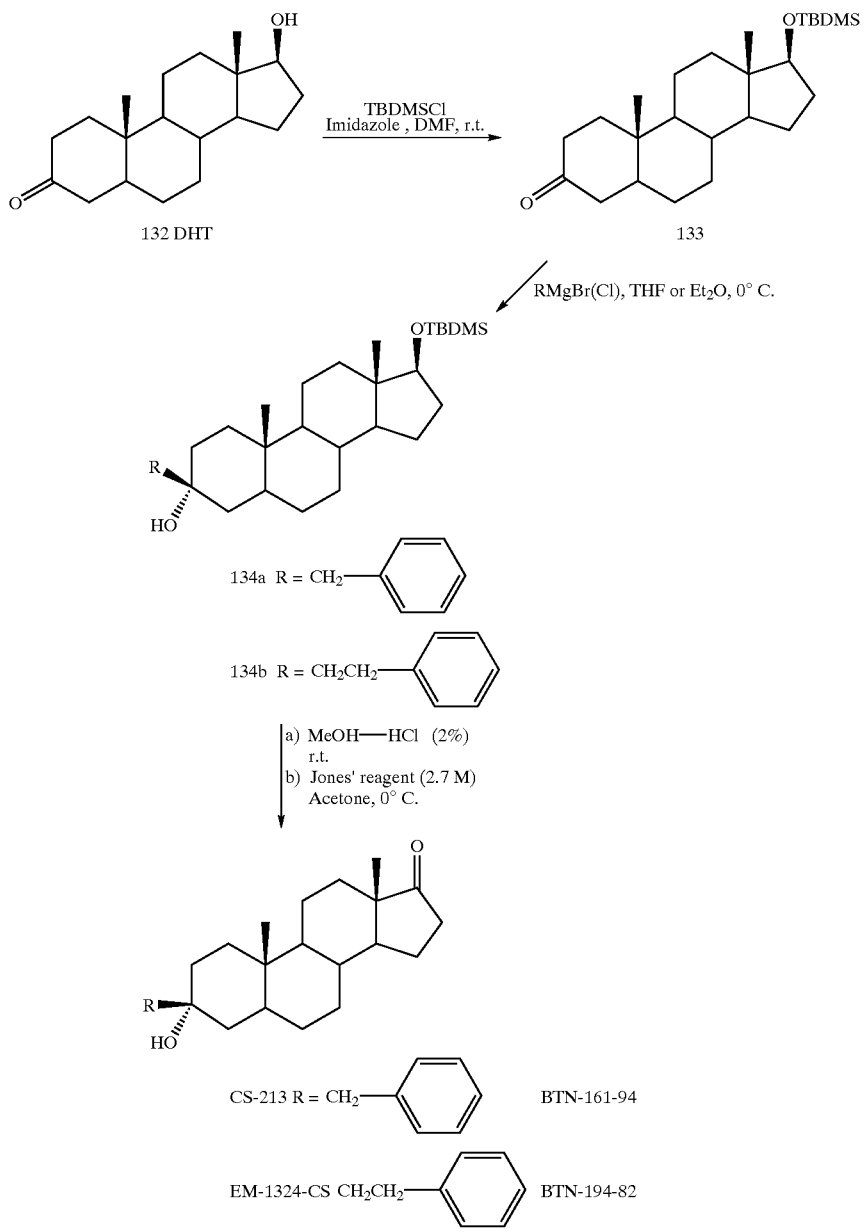

Scheme 34

Example 37A

Protection of the 17β-alcohol with TBDMS

To a solution of dihydrotestosterone (DHT, 132) (5 g, 17.2 mmol) in DMF was added imidazole (6 eq.) and TBDMSCl (5 eq.). The reaction was stirred overnight at room temperature. The mixture was poured onto ice and filtered. The resulting white precipitate was washed with water, dried over phosphorous pentoxide under reduced pressure for 24 h. A 85 to 90% yield was obtained.

17β-[(Tert-butyldimethylsilyl)oxy]-5α-androstane-3-one (133)

White solid; IR (KBr) ν 1719 (C=O, ketone); $^1$H NMR (CDCl$_3$) δ −0.001 and 0.005 (s, 6H, Si(CH$_3$)$_2$), 0.71 (s, 3H, CH$_3$-18), 0.87 (s, 9H, SiC(CH$_3$)$_3$), 1.01 (s, 3H, CH$_3$-19), 3.54 (t, J=8.2 Hz, 1H, CH-17); $^{13}$C NMR (CDCl$_3$) δ −4.80 and −4.47, 11.41, 11.52, 18.11, 21.13, 23.56, 25.87, 28.98, 30.94, 31.36, 35.54, 35.78, 37.13, 38.21, 38.65, 43.36, 44.74, 46.84, 50.55, 54.15, 81.79, 212.03.

Example 37B

Alkylation of the Carbonyl at Position 3

To a solution of compound 133 (500 mg, 1.23 mmol) in dry THF (100 mL) at 0° C. was added dropwise 3 eq. of commercially available Grignard's reagent, in dry THF. The mixture was allowed to react for 3 h at 0° C., then left over night at room temperature. A solution of saturated $NH_4Cl$ was added and the crude product was extracted with EtOAc. The organic phase was washed with a saturated NaCl solution, dried over $MgSO_4$ and evaporated under reduced pressure. The 3β-alkylated stereoisomer was easily separated from the 3α-alkylated stereoisomer by flash chromatography on silica gel, using a mixture of hexanes and ethyl acetate as eluent. When the Grignard's reagent was generated in situ as in the case of ethylphenyl magnesium bromide, 5 eq. was prepared, by a well-known procedure, using the corresponding bromide, activated magnesium and iodide. The steroid was then dissolved in dry diethyl ether and added dropwise to the solution of reagent. The yields obtained were around 60% for the two stereoisomers.

3β-Benzyl-17β[(tert-butyldimethylsilyl)oxy]-3α-hydroxy-5α-androstane (134a)

White solid (24%); IR (KBr) ν 3585 and 3460 (OH, alcohol); $^1$H NMR ($CDCl_3$) δ 0.002 and 0.009 (s, 6H, $Si(CH_3)_2$), 0.69 (s, 3H, $CH_3$-18), 0.75 (s, 3H, $CH_3$-19), 0.88 (s, 9H, $SiC(CH_3)_3$), 2.71 (s, 2H, $CH_2Ph$), 3.54 (t, J=8.2 Hz, 1H, CH-17), 7.20 to 7.34 (5H, Ph); $^{13}$C NMR ($CDCl_3$) δ −4.82 and −4.50($SiC(CH_3)_3$), 11.25, 11.40, 18.08, 20.62, 23.50, 25.85, 28.41, 30.91, 31.62, 33.27, 33.81, 35.60, 35.84, 37.19, 40.10, 40.84, 43.30, 50.43, 50.69, 54.43, 71.22, 81.82 (C-17), 126.37, 128.09 (2x), 130.56 (2x), 137.06.

3α-hydroxy-3β-(phenylethyl)-17β[(tert-butyldimethylsilyl)oxy]-5α-androstane (134b)

White solid (38%); IR (film) ν 3447 (OH, alcohol); $^1$H NMR ($CDCl_3$) δ 0.018 and 0.025 (s, 6H, $Si(CH_3)_2$), 0.71 (s, 3H, $CH_3$-18), 0.78 (s, 3H, $CH_3$-19), 0.89 (s, 9H, $SiC(CH_3)_3$), 2.73 (m, 2H, $Ph-CH_2$), 3.56 (t, J=8.1 Hz, 1H, CH-17), 7.18 to 7.31 (5H, Ph); $^{13}$C NMR ($CDCl_3$) δ −4.77 and −4.46 ($Si(CH_3)_3$), 11.28, 11.44, 18.12 ($SiC(CH_3)_3$), 20.67, 23.54, 25.89 ($SiC(CH_3)_3$), 28.52, 29.60, 30.97, 31.66, 33.31, 33.92, 35.66, 36.04, 37.25, 40.03, 41.05, 43.35, 46.47, 50.76, 54.55, 71.50 (C-3), 81.86 (C-17), 125.68, 128.38 (4x), 142.82.

Example 37C

Procedure for Hydrolysis of TBDMS Group and Oxidation of the Resulting Alcohol The silylated ether was dissolved in a methanolic solution of HCl (2%, v/v) and the resulting mixture was stirred at room temperature for 3h. Water was then added and MeOH evaporated under vacuum. The resulting white precipitate was submitted to Jones' oxidation without purification. To a stirred solution of crude alcohol in acetone at 0° C., Jones' reagent (2.7M chromic acid solution) was added dropwise. After 30 to 45 minutes, the reaction was completed. Isopropanol and water were added and acetone was removed in vacuo. The remaining aqueous layer was extracted with EtOAc. The combined organic phases were washed with brine, dried over $MgSO_4$, filtered and evaporated under reduced pressure. The purification was done on silica gel, using HPLC grade solvents, EtOAc and hexanes as eluents.

3β-benzyl-3α-Hydroxy-5α-androstane-17-one (CS-213)

White solid (88% for the two steps); IR (KBr) ν 3408 (OH, alcohol), 1732 (C=O, ketone); $^1$H NMR ($CDCl_3$) δ 8 0.75 (s, 3H, $CH_3$-19), 0.84 (s, 3H, $CH_3$-18), 2.69 (s, 2H, $CH_2Ph$), 7.18 to 7.32 (5H, Ph); $^{13}$C NMR ($CDCl_3$) δ 11.18, 13.78, 20.20, 21.71, 28.16, 30.79, 31.52, 33.18, 33.70, 35.64, 35.79, 35.88, 39.97, 40.69, 47.75, 50.39, 51.41, 54.22, 71.12, 126.40, 128.09 (2x), 130.51 (2x), 136.93, 221.27

3α-hydroxy-3β-phenylethyl-5α-androstane-17-one (EM-1324-CS)

White solid (82% for the two steps); IR (film) ν 3486 (OH, alcohol), 1737 (C=O, ketone); $^1$H NMR ($CDCl_3$) 8 0.79 (s, 3H, $CH_3$-19), 0.86 (s, 3H, $CH_3$-18), 2.7 (m, 2H, $Ph-CH_2$), 7.18 to 7.30 (5H, Ph); $^{13}$C NMR ($CDCl_3$) δ 11.21, 13.82, 20.26, 21.76, 28.26, 29.54, 30.87, 31.58, 33.27, 33.80, 35.10, 35.84, 36.07, 39.89, 40.90, 46.43, 47.80, 51.49, 54.35, 71.42, 125.69, 128.31 (2x), 128.39 (2x), 142.70, 221.31.

PHARMACEUTICAL COMPOSITION EXAMPLES

Set forth below, by way of example and not of limitation, are several pharmaceutical compositions utilizing a preferred active compound EM-1404. Other compounds of the invention or combination thereof, may be used in place of (or in addition to) EM-1404. The concentration of active ingredient may be varied over a wide range as discussed herein. The amounts and types of other ingredients that may be included are well known in the art.

Example A

Composition Suitable for Injection

| Ingredient | Weight % (by weight of total composition) |
| --- | --- |
| EM-1404 | 0.4 |
| Ethanol | 6.4 |
| NaCl | 0.8 |
| Water | 91.5 |
| Benzyl alcohol | 0.9 |

Example B

Composition Suitable for Use as Topical Lotion

| Ingredient | Weight % (by weight of total composition) |
| --- | --- |
| EM-1404 | 1.0 |
| Ethanol | 70.0 |
| Propylene glycol | 29.0 |

Example C

Composition Suitable for Use as Topical Gel

| Ingredient | Weight % (by weight of total composition) |
|---|---|
| EM-1404 | 1.0 |
| Krucel | 1.5 |
| Ethanol | 70.0 |
| Propylene glycol | 27.5 |

Example D

Tablet

| Ingredient | Weight % (by weight of total composition) |
|---|---|
| EM-1404 | 1.0 |
| Gelatin | 5.0 |
| Lactose | 67.5 |
| Starch | 26.5 |

Example E

Gelatin Capsule

| Ingredient | Weight % (by weight of total composition) |
|---|---|
| EM-1404 | 2.0 |
| Lactose hydrous | 80.0 |
| Starch | 4.8 |
| Cellulose microcrystalline | 12.8 |
| Magnesium stearate | 0.4 |

Example F

Composition Suitable for Use as Topical Gel

| Ingredient | Weight % (by weight of total composition) |
|---|---|
| EM-1404 | 1.0 |
| Ethanol | 4.0 |
| Polyethylene glycol | 4.0 |
| Gelatin | 1.0 |
| NaCl | 0.9 |
| Benzyl alcohol | 1.0 |
| Water USP | 88.1 |

Other inhibitors of type 5 17β-hydroxysteroid dehydrogenase may be substituted for EM-1404 in the above formulations, as may an inhibitor of type 3 17β-hydroxysteroid dehydrogenase. Both type 3 and type 5 may be included together, in which case the combined weight percent of the two is preferably double that of EM-1404 alone, with a corresponding reduction in the weight of the most prevalent excipient (e.g., water lactose, ethanol or the like).

The invention has been described in terms of preferred embodiments and examples, but is not limited thereby.

Those of skill in the art will readily recognize the broader applicability and scope of the invention which is limited only by the patent claims herein.

What is claimed is:

1. An inhibitor of type 5 17β-hydroxysteroid dehydrogenase having the molecular structure:

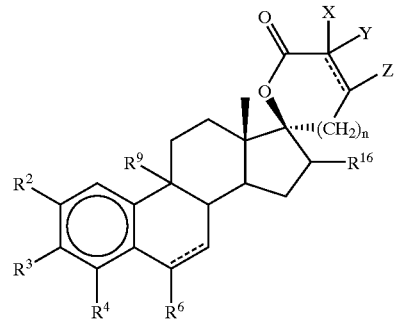

wherein n is an integer from 1–2;

wherein the dotted lines are optional pi bonds;

wherein X and Y are independently selected from the group consisting of $^-$H, $(C_1-C_3)$alkyl, $(C_2-C_3)$ alkenyl, and methoxycarbonyl;

wherein Z is selected from the group consisting of —H and $(C_1-C_3)$alkyl;

wherein $R^3$ is selected from the group consisting of hydrogen, acyl, carboxyl, alkoxycarbonyl, substituted or unsubstituted carboxamide, cyano, alkoxy, alkoxyalkoxy, alkythioalkoxy, acyloxy; hydroxy, halo, —O—SO$_2$R$^a$ (R$^a$ being selected from the group consisting of $C_1-C_6$ alkyl and $C_6-C_{10}$ aryl), and together with $R^2$ is: —CH=N—O—;

wherein $R^2$ is selected from the group consisting of hydrogen, amido, acyloxy, carboxyl, carboxamide, alkoxycarbonyl, cyano, halo, nitro, $C_1-C_8$ alkyl, and $CF_3$ and together with $R^3$ is: —CH=N—O—;

wherein $R^4$ is hydrogen or halo;

wherein $R^6$ is selected from the group consisting of hydrogen and oxo;

wherein $R^9$ is $^-$H or $^-$OH.

provided that X, Y, and Z are not all hydrogen; and $R^3$ is not hydroxyl or alkoxy when $R^2$, $R^4$, $R^6$ and $R^9$ are all hydrogen atoms.

2. The inhibitor of claim 1, wherein $R^3$ is carboxyl unsubstituted carboxamide or alkoxyl.

3. The inhibitor of claim 1, wherein at least one of X, Y or Z is methyl.

4. The inhibitor of claim 1, wherein both X and Y are methyl.

5. The inhibitor of claim 1, wherein n=1.

6. The inhibitor of claim 1, wherein $R^6$ is oxo.

7. The inhibitor of claim 1, wherein $R^3$ is carboxamide.

8. An inhibitor of type 5 17β-hydroxysteroid dehydrogenase having a molecular structure selected from the group consisting of:

EM-1401
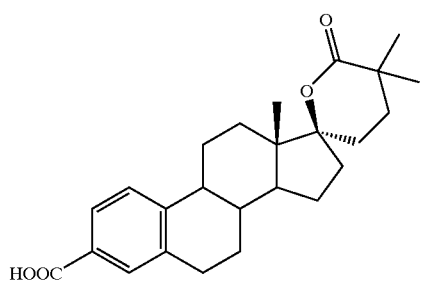
EM-1404
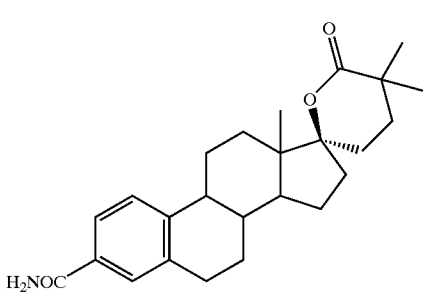
EM-1394
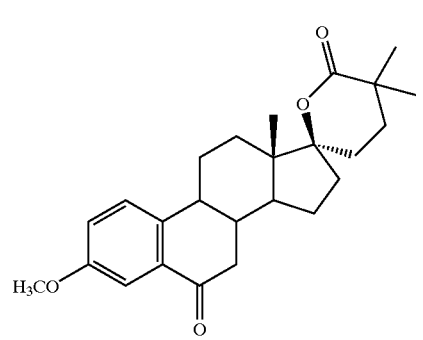
EM-1424
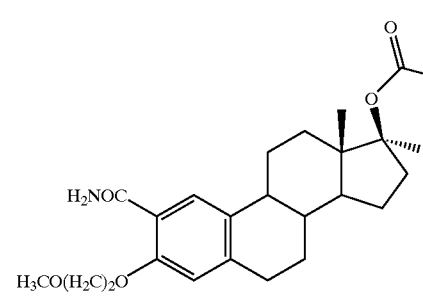
EM-1157-CS
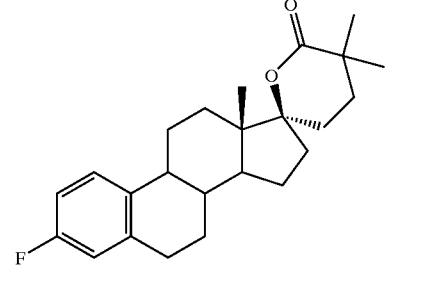
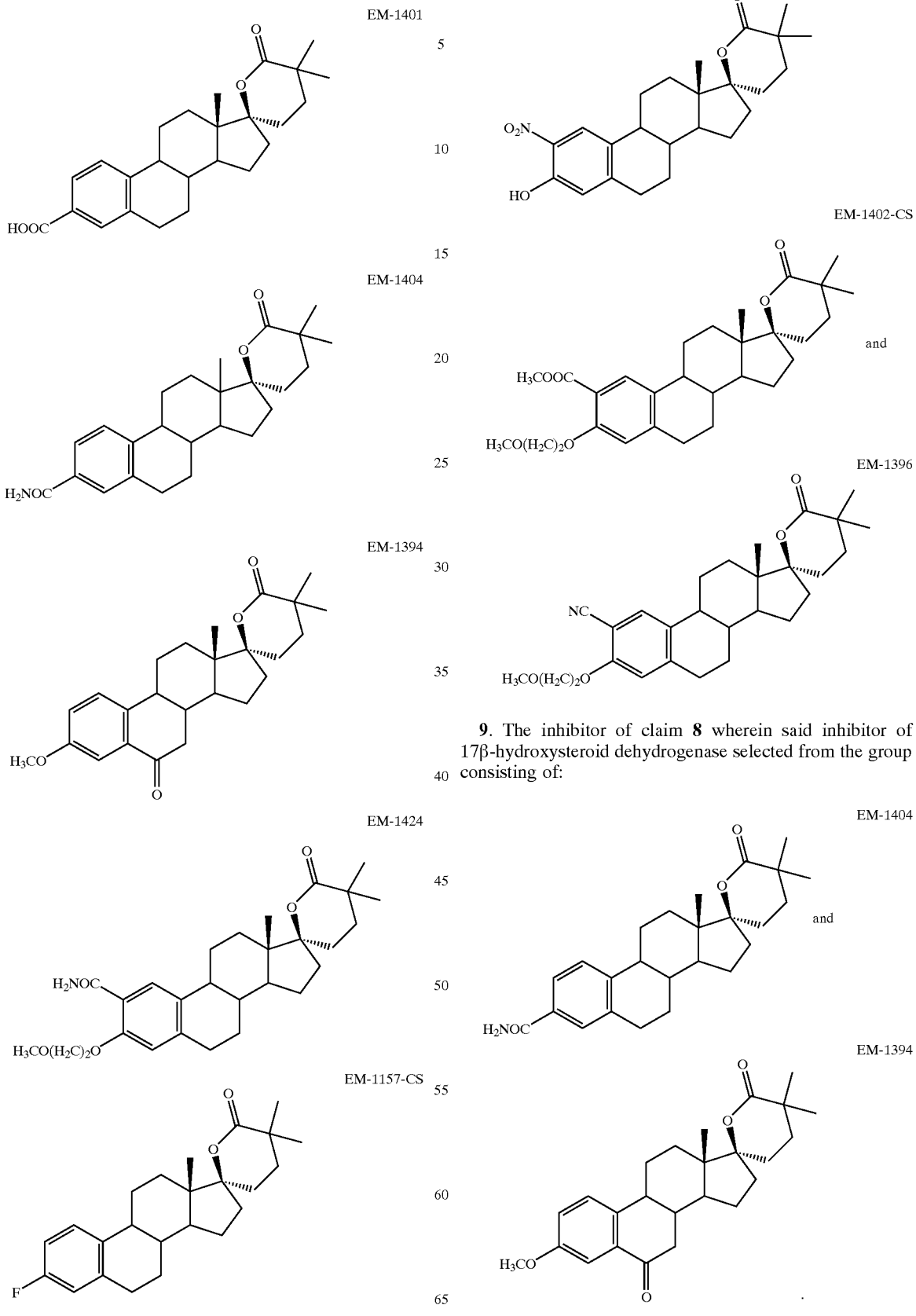
9. The inhibitor of claim 8 wherein said inhibitor of 17β-hydroxysteroid dehydrogenase selected from the group consisting of:

10. A pharmaceutical composition comprising a pharmaceutically acceptable diluent or carrier and a therapeutically acceptable amount of an inhibitor of type 5 17b-hydroxysteroid dehydrogenase having the molecular structure:

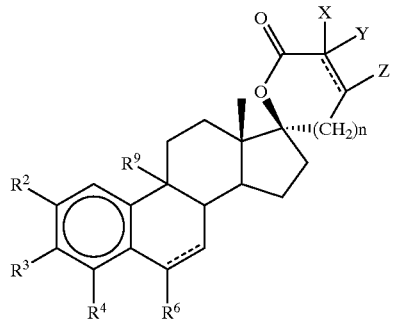

wherein n is an integer from 1–2;
wherein the dotted lines are optional pi bonds;
wherein X and Y are independently selected from the group consisting of $^-$H, $(C_1–C_3)$alkyl, $(C_2–C_3)$ alkenyl, and methoxycarbonyl;
wherein Z is selected from the group consisting of —H and $(C_1–C_3)$alkyl;
wherein $R^3$ is selected from the group consisting of hydrogen acyl, carboxyl, alkoxycarbonyl, substituted or unsubstituted carboxamide, cyano, alkoxy, alkoxyalkoxy, alkythioalkoxy, acyloxy; hydroxy, halo, —O—SO$_2$R$^a$ (R$^a$ being selected from the group consisting of $C_1–C_6$ alkyl and $C_6–C_{10}$ aryl), and together with $R^2$ is: —CH=N—O—;
wherein $R^2$ is selected from the group consisting of hydrogen, amido, acyloxy, carboxyl, carboxamide, alkoxycarbonyl, cyano, halo, nitro, $C_1–C_8$ alkyl, and $CF_3$ and together with $R^3$ is: —CH=N—O—;
wherein $R^4$ is hydrogen or halo;
wherein $R^6$ is selected from the group consisting of hydrogen and oxo;
wherein $R^9$ is $^-$H or $^-$OH;
provided that X, Y, and Z are not all hydrogen; and
$R^3$ is not hydroxyl or alkoxy when $R^2$, $R^4$, $R^6$ and $R^9$ are all hydorgen atoms.

11. The pharmaceutical composition of claim 10, wherein $R^3$ is alkoxyalkoxy.

12. The pharmaceutical composition of claim 10, herein $R^3$ is carboxyl or alkoxyl.

13. The pharmaceutical composition of claim 10, wherein at least one of X, Y or Z is methyl.

14. The pharmaceutical composition of claim 10, wherein both X and Y are methyl.

15. The pharmaceutical composition of claim 10, wherein $R^6$ is oxo.

16. The pharmaceutical composition of claim 10, wherein $R^3$ carboxamide.

17. A pharmaceutical composition comprising a pharmaceutically acceptable diluent or carrier and a therapeutically acceptable amount of an inhibitor of type 5 17β-hydroxysteroid dehydrogenase having a molecular structure selected from the group consisting of:

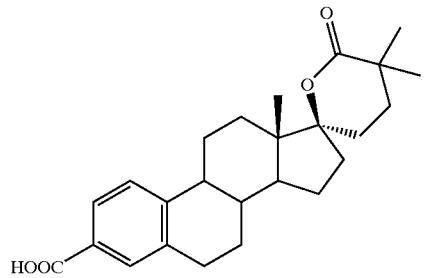

EM-1401

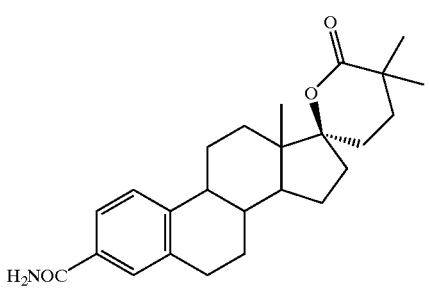

EM-1404

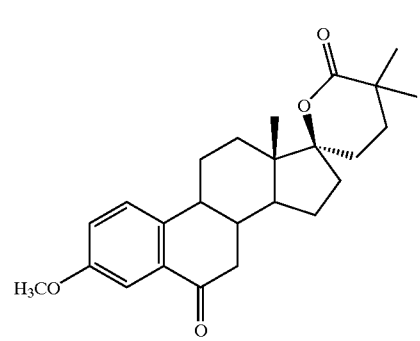

EM-1394

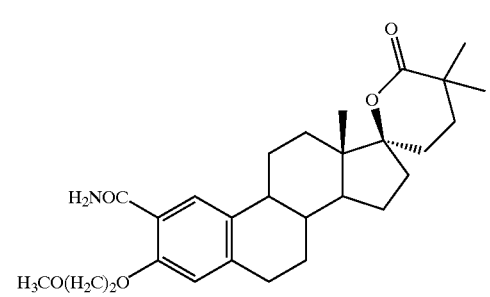

EM-1424

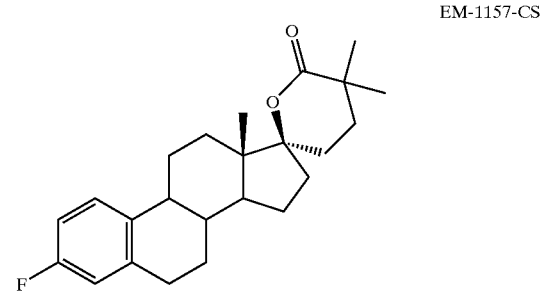

EM-1157-CS

-continued
EM-1125
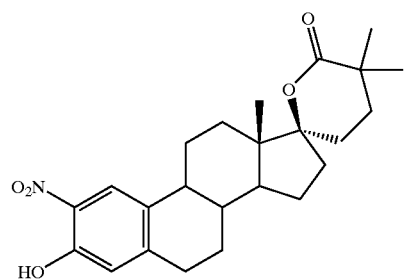
EM-1402-CS
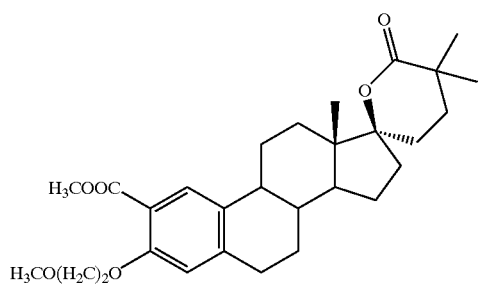
and
EM-1396
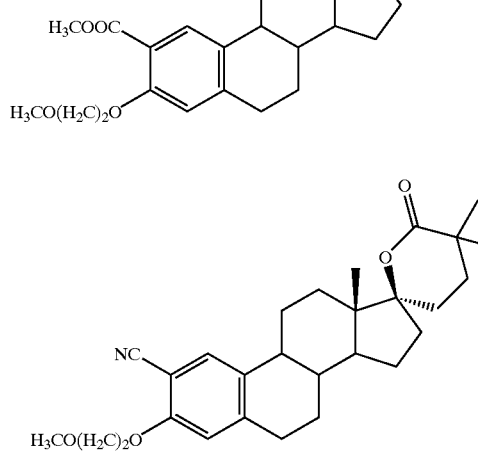
18. The pharmaceutical composition of claim 17 wherein said inhibitor of 17β-hydroxysteroid dehydrogenase is selected from the group consisting of:
EM-1404
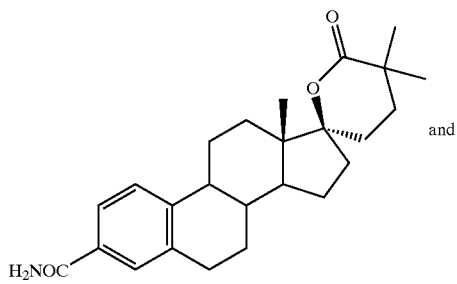
and
EM-1394
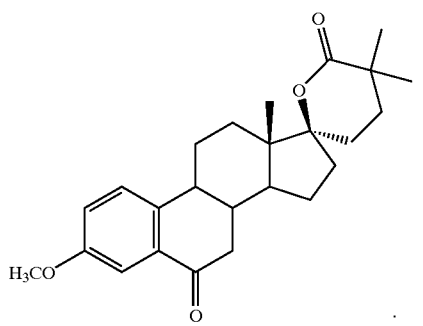
* * * * *